US008323950B2

(12) United States Patent
Burk et al.

(10) Patent No.: US 8,323,950 B2
(45) Date of Patent: *Dec. 4, 2012

(54) METHODS AND ORGANISMS FOR UTILIZING SYNTHESIS GAS OR OTHER GASEOUS CARBON SOURCES AND METHANOL

(75) Inventors: Mark J. Burk, San Diego, CA (US); Christophe H. Schilling, San Diego, CA (US); Anthony P. Burgard, Bellefonte, PA (US); John D. Trawick, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/106,764

(22) Filed: May 12, 2011

(65) Prior Publication Data
US 2011/0223637 A1  Sep. 15, 2011

Related U.S. Application Data

(63) Continuation of application No. 12/863,978, filed as application No. PCT/US2009/031737 on Jan. 22, 2009.

(60) Provisional application No. 61/022,804, filed on Jan. 22, 2008, provisional application No. 61/059,256, filed on Jun. 5, 2008.

(51) Int. Cl.
*C12N 1/20* (2006.01)
*C12N 1/00* (2006.01)
*C12P 19/60* (2006.01)
*C12P 19/32* (2006.01)
*C12P 11/00* (2006.01)
*C12P 7/26* (2006.01)
*C12P 5/02* (2006.01)
*C07H 21/04* (2006.01)

(52) U.S. Cl. ......... 435/252.3; 435/75; 435/92; 435/130; 435/148; 435/167; 435/243; 536/23.2

(58) Field of Classification Search .................. None
See application file for complete search history.

(56) References Cited

U.S. PATENT DOCUMENTS

| | | | |
|---|---|---|---|
| 3,513,209 A | 5/1970 | Clement | |
| 3,912,586 A | 10/1975 | Kaneyuki et al. | |
| 3,965,182 A | 6/1976 | Worrel | |
| 4,048,196 A | 9/1977 | Broecker et al. | |
| 4,082,788 A | 4/1978 | Mims | |
| 4,190,495 A | 2/1980 | Curtiss | |
| 4,301,077 A | 11/1981 | Pesa et al. | |
| 4,624,920 A | 11/1986 | Inoue et al. | |
| 4,652,685 A | 3/1987 | Cawse et al. | |
| 4,871,667 A | 10/1989 | Imada et al. | |
| 5,079,143 A | 1/1992 | Klein et al. | |
| 5,143,833 A | 9/1992 | Datta | |
| 5,143,834 A | 9/1992 | Glassner et al. | |
| 5,168,055 A | 12/1992 | Datta et al. | |
| 5,173,429 A | 12/1992 | Gaddy et al. | |
| 5,182,199 A | 1/1993 | Hartley | |
| 5,192,673 A | 3/1993 | Jain et al. | |
| 5,403,721 A | 4/1995 | Ward, Jr. et al. | |
| 5,413,922 A | 5/1995 | Matsuyama et al. | |
| 5,416,020 A | 5/1995 | Severson et al. | |
| 5,457,040 A | 10/1995 | Jarry et al. | |
| 5,478,952 A | 12/1995 | Schwartz | |
| 5,487,987 A | 1/1996 | Frost et al. | |
| 5,504,004 A | 4/1996 | Guettler et al. | |
| 5,512,465 A | 4/1996 | Matsuyama et al. | |
| 5,521,075 A | 5/1996 | Guettler et al. | |
| 5,573,931 A | 11/1996 | Guettler et al. | |
| 5,616,496 A | 4/1997 | Frost et al. | |
| 5,686,276 A | 11/1997 | Lafend et al. | |

(Continued)

FOREIGN PATENT DOCUMENTS
CN  1 358 841  7/2002
(Continued)

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Abadjieva et al., "The Yeast ARG7 Gene Product is Autoproteolyzed to Two Subunit Peptides, Yielding Active Ornithine Acetyltransferase," *J. Biol. Chem.* 275(15):11361-11367 (2000).

(Continued)

*Primary Examiner* — Anand Desai
*Assistant Examiner* — Iqbal H Chowdhury
(74) *Attorney, Agent, or Firm* — Jones Day

(57) ABSTRACT

The invention provides a non-naturally occurring microbial organism having an acetyl-CoA pathway and the capability of utilizing syngas or syngas and methanol. In one embodiment, the invention provides a non-naturally occurring microorganism, comprising one or more exogenous proteins conferring to the microorganism a pathway to convert CO, $CO_2$ and/or $H_2$ to acetyl-coenzyme A (acetyl-CoA), methyl tetrahydrofolate (methyl-THF) or other desired products, wherein the microorganism lacks the ability to convert CO or $CO_2$ and $H_2$ to acetyl-CoA or methyl-THF in the absence of the one or more exogenous proteins. For example, the microbial organism can contain at least one exogenous nucleic acid encoding an enzyme or protein in an acetyl-CoA pathway. The microbial organism is capable of utilizing synthesis gases comprising CO, $CO_2$ and/or $H_2$, alone or in combination with methanol, to produce acetyl-CoA. The invention additionally provides a method for producing acetyl-CoA, for example, by culturing an acetyl-CoA producing microbial organism, where the microbial organism expresses at least one exogenous nucleic acid encoding an acetyl-CoA pathway enzyme or protein in a sufficient amount to produce acetyl-CoA, under conditions and for a sufficient period of time to produce acetyl-CoA.

20 Claims, 15 Drawing Sheets

U.S. PATENT DOCUMENTS

| | | | |
|---|---|---|---|
| 5,700,934 | A | 12/1997 | Wolters et al. |
| 5,770,435 | A | 6/1998 | Donnelly et al. |
| 5,807,722 | A | 9/1998 | Gaddy et al. |
| 5,869,301 | A | 2/1999 | Nghiem et al. |
| 5,908,924 | A | 6/1999 | Burdette et al. |
| 5,958,745 | A | 9/1999 | Gruys et al. |
| 6,117,658 | A | 9/2000 | Dennis et al. |
| 6,133,014 | A | 10/2000 | Mukouyama et al. |
| 6,136,577 | A | 10/2000 | Gaddy et al. |
| 6,159,738 | A | 12/2000 | Donnelly et al. |
| 6,194,572 | B1 | 2/2001 | Buijs et al. |
| 6,214,592 | B1 | 4/2001 | Crouzet et al. |
| 6,274,790 | B1 | 8/2001 | Kunst et al. |
| 6,280,986 | B1 | 8/2001 | Hespell et al. |
| RE37,393 | E | 9/2001 | Donnelly et al. |
| 6,340,581 | B1 | 1/2002 | Gaddy et al. |
| 6,353,100 | B1 | 3/2002 | Guit et al. |
| 6,432,686 | B1 | 8/2002 | Bulthuis et al. |
| 6,448,061 | B1 | 9/2002 | Pan et al. |
| 6,455,284 | B1 | 9/2002 | Gokarn et al. |
| 6,485,947 | B1 | 11/2002 | Rajgarhia et al. |
| 6,660,857 | B2 | 12/2003 | Agterberg et al. |
| 6,686,194 | B1 | 2/2004 | Mutzel et al. |
| 6,686,310 | B1 | 2/2004 | Kourtakis et al. |
| 6,743,610 | B2 | 6/2004 | Donnelly et al. |
| 6,838,276 | B2 | 1/2005 | Falco et al. |
| 6,852,517 | B1 | 2/2005 | Suthers et al. |
| 7,127,379 | B2 | 10/2006 | Palsson et al. |
| 7,186,541 | B2 | 3/2007 | Gokarn et al. |
| 7,223,567 | B2 | 5/2007 | Ka-Yiu et al. |
| 7,241,594 | B2 | 7/2007 | Lee et al. |
| 7,244,610 | B2 | 7/2007 | San et al. |
| 7,256,016 | B2 | 8/2007 | San et al. |
| 7,262,046 | B2 | 8/2007 | Ka-Yiu et al. |
| 7,285,402 | B2 | 10/2007 | Gaddy et al. |
| 7,309,597 | B2 | 12/2007 | Liao et al. |
| 7,371,558 | B2 | 5/2008 | Cervin et al. |
| 7,393,676 | B2 | 7/2008 | Gorkarn et al. |
| 7,432,091 | B2 | 10/2008 | Yukawa et al. |
| 7,491,520 | B2 | 2/2009 | Raemakers-Franken et al. |
| 7,569,380 | B2 | 8/2009 | San et al. |
| 7,803,589 | B2 * | 9/2010 | Burk et al. ............ 435/183 |
| 7,947,483 | B2 | 5/2011 | Burgard et al. |
| 2002/0012939 | A1 | 1/2002 | Palsson |
| 2002/0040123 | A1 | 4/2002 | Patil et al. |
| 2002/0106358 | A1 | 8/2002 | Hopwood et al. |
| 2002/0168654 | A1 | 11/2002 | Maranas et al. |
| 2003/0028915 | A1 | 2/2003 | Tilton et al. |
| 2003/0032153 | A1 | 2/2003 | Yamamoto et al. |
| 2003/0059792 | A1 | 3/2003 | Palsson et al. |
| 2003/0087381 | A1 | 5/2003 | Gokarn |
| 2003/0113886 | A1 | 6/2003 | Brzostowicz et al. |
| 2003/0182678 | A1 | 9/2003 | Mitsky et al. |
| 2003/0224363 | A1 | 12/2003 | Park et al. |
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2004/0096946 | A1 | 5/2004 | Kealey et al. |
| 2004/0152159 | A1 | 8/2004 | Causey et al. |
| 2005/0042736 | A1 | 2/2005 | San et al. |
| 2005/0079482 | A1 | 4/2005 | Maranas et al. |
| 2005/0250135 | A1 | 11/2005 | Klaenhammer et al. |
| 2005/0287655 | A1 | 12/2005 | Tabata et al. |
| 2006/0035348 | A1 | 2/2006 | Gulevich et al. |
| 2006/0073577 | A1 | 4/2006 | Ka-Yiu et al. |
| 2006/0099578 | A1 | 5/2006 | Wallace et al. |
| 2006/0110810 | A1 | 5/2006 | Rajgarhia et al. |
| 2006/0172399 | A1 | 8/2006 | Nomoto et al. |
| 2006/0281156 | A1 | 12/2006 | Aoyama et al. |
| 2007/0042476 | A1 | 2/2007 | Lee et al. |
| 2007/0072279 | A1 | 3/2007 | Meynial-Salles et al. |
| 2007/0087425 | A1 | 4/2007 | Ohto |
| 2007/0092957 | A1 | 4/2007 | Donaldson et al. |
| 2007/0111294 | A1 | 5/2007 | Burgard et al. |
| 2007/0117191 | A1 | 5/2007 | Kamachi et al. |
| 2007/0184539 | A1 | 8/2007 | San et al. |
| 2007/0190605 | A1 | 8/2007 | Bessler et al. |
| 2007/0259410 | A1 | 11/2007 | Donaldson et al. |
| 2008/0138870 | A1 | 6/2008 | Bramucci et al. |
| 2008/0171371 | A1 | 7/2008 | Yukawa et al. |
| 2008/0182308 | A1 | 7/2008 | Donaldson et al. |
| 2008/0274522 | A1 | 11/2008 | Bramucci et al. |
| 2008/0293125 | A1 | 11/2008 | Subbian et al. |
| 2009/0047718 | A1 | 2/2009 | Blaschek et al. |
| 2009/0068207 | A1 | 3/2009 | Breitbart et al. |
| 2009/0075351 | A1 | 3/2009 | Burk et al. |
| 2009/0191593 | A1 | 7/2009 | Burk et al. |
| 2009/0305364 | A1 | 12/2009 | Burgard et al. |
| 2010/0009419 | A1 | 1/2010 | Burk et al. |
| 2010/0099925 | A1 | 4/2010 | Kharas |
| 2010/0168481 | A1 | 7/2010 | Farmer et al. |
| 2010/0304453 | A1 | 12/2010 | Trawick et al. |
| 2011/0045575 | A1 | 2/2011 | Van Dien et al. |
| 2011/0129904 | A1 | 6/2011 | Burgard et al. |
| 2011/0196180 | A1 | 8/2011 | Alibhai et al. |

FOREIGN PATENT DOCUMENTS

| | | |
|---|---|---|
| EP | 0 494 078 | 7/1992 |
| EP | 1 075 482 A1 | 2/2001 |
| EP | 1 473 368 | 11/2004 |
| EP | 1 647 594 A1 | 4/2006 |
| EP | 2 017 344 | 1/2009 |
| GB | 1230276 | 4/1971 |
| GB | 1314126 | 4/1973 |
| GB | 1344557 | 1/1974 |
| GB | 1512751 | 6/1978 |
| JP | 50 006776 | 1/1975 |
| WO | WO 82/03854 | 11/1982 |
| WO | WO 91/13997 | 9/1991 |
| WO | WO 99/06532 | 2/1999 |
| WO | WO 99/58686 | 11/1999 |
| WO | WO 01/16346 | 3/2001 |
| WO | WO 02/42418 | 5/2002 |
| WO | WO 02/055995 | 7/2002 |
| WO | WO 02/090312 | 11/2002 |
| WO | WO 03/010322 | 2/2003 |
| WO | WO 03/106691 | 12/2003 |
| WO | WO 03/106998 | 12/2003 |
| WO | WO 2004/062763 A2 | 7/2004 |
| WO | WO 2005/026338 | 3/2005 |
| WO | WO 2005/047498 | 5/2005 |
| WO | WO 2005/068643 | 7/2005 |
| WO | WO 2006/028063 | 3/2006 |
| WO | WO 2006/031424 | 3/2006 |
| WO | WO 2006/034156 | 3/2006 |
| WO | WO 2007/001982 | 1/2007 |
| WO | WO 2007/030830 | 3/2007 |
| WO | WO 2007/050671 A2 | 5/2007 |
| WO | WO 2007/141208 | 12/2007 |
| WO | WO 2008/018930 | 2/2008 |
| WO | WO 2008/024023 | 2/2008 |
| WO | WO 2008/027742 | 3/2008 |
| WO | WO 2008/115840 | 3/2008 |
| WO | WO 2008/080124 | 7/2008 |
| WO | WO 2008/089102 A2 | 7/2008 |
| WO | WO 2008/131286 | 10/2008 |
| WO | WO 2008/137403 | 11/2008 |
| WO | WO 2008/152016 | 12/2008 |
| WO | WO 2009/013160 A2 | 1/2009 |
| WO | WO 2009/014437 | 1/2009 |
| WO | WO 2009/023493 | 2/2009 |
| WO | WO 2009/031766 | 3/2009 |
| WO | WO 2009/049274 A2 | 4/2009 |
| WO | WO 2009/094485 A1 | 7/2009 |
| WO | WO 2009/103026 | 8/2009 |
| WO | WO 2009/111513 A1 | 9/2009 |
| WO | WO 2009/113853 | 9/2009 |
| WO | WO 2009/113855 | 9/2009 |
| WO | WO 2009/131040 | 10/2009 |
| WO | WO 2010/023206 A1 | 3/2010 |

OTHER PUBLICATIONS

Abe et al., "Discovery of amide (peptide) bond synthetic activity in Acyl-CoA synthetase," *J. Biol. Chem.* 283(17):11312-11321 (2008).

Aberhart and Hsu, "Stereospecific hydrogen loss in the conversion of [$2^H_7$] isobutyrate to β-hydroxyisobutyrate in *Pseudomonas putida*.

The stereochemistry of β-hydroxyisobutyrate dehydrogenase," *J. Chem. Soc.* [Perkin1] 6:1404-1406 (1979).

Abiko et al., "Localization of NAD-isocitrate dehydrogenase and glutamate dehydrogenase in rice roots: candidates for providing carbon skeletons to NADH-glutamate synthase," *Plant Cell Physiol.* 46:1724-1734 (2005).

Abo-Dalo et al., "A novel member of the GCN5-related N-acetyltransferase superfamily from *Caenorhabditis elegans* preferentially catalyses the N-acetylation of thialysine [S-(2-aminoethyl)-L-cysteine]," *Biochem. J.* 384:129-137 (2004).

Adams and Kletzin, "Oxidoreductase-type enzymes and redox proteins involved in fermentative metabolisms of hyperthermophilic Archaea," *Adv. Protein Chem.* 48:101-180 (1996).

Aevarsson et al., "Crystal structure of 2-oxoisovalerate and dehydrogenase and the architecture of 2-oxo acid dehydrogenase multienzyme complexes," *Nat. Struct. Biol.* 6:785-792 (1999).

Agnihotri and Liu, "Enoyl-CoA Hydratase: Reaction, Mechanism, and Inhibition," *Bioorg. Med. Chem.* 11(1):9-20 (2003).

Ahmed and Lewis, "Fermentation of Biomass-Generated Synthesis Gas: Effects of Nitric Oxide," *Biotechol. Bioeng.* 97:1080-1086 (2007).

Ahmed et al., "Effects of biomass-generated producer gas constituents on cell growth, product distribution and hydrogenase activity of *Clostridium carboxidivorans* P7$^T$," *Biomass Bioenergy* 30(7):665-672 (2006).

Akashi et al., "Molecular and biochemical Characterization of 2-Hydroxyisoflavanone Dehydratase. Involvement of Carboxylesterase-Like Proteins in Leguminous Isoflavone Biosynthesis," *Plant. Physiol.* 137:882-891 (2005).

Akatsuka et al., "The *Serratia marcescens* bioH gene encodes an esterase," *Gene* 302(1-2):185-192 (2003).

Akhtar and Jones, "Construction of a synthetic YdbK-dependent pyruvate:$H_2$ pathway in *Escherichia coli* BL21(DE3)," *Metab. Eng.* 11(3):139-147 (2009).

Alam et al., "Anaerobic Fermentation Balance of *Escherichia coli* as Observed by In Vivo Nuclear Magnetic Resonance Spectroscopy," *J. Bacteriol.* 171(11):6213-6217 (1989).

Alber et al., "3-Hydroxypropionyl-Coenzyme A synthetase from *Metallosphaera sedula*, an enzyme involved in autotrophic $CO_2$ fixation," *J. Bacteriol.* 190:1383-1389 (2008).

Alber et al., "Malonyl-Coenzyme A reductase in the modified 3-hydroxypropionate cycle for autotrophic carbon fixation in archaeal *Metallosphaera* and *Sulfolobus* spp.," *J. Bacteriol.* 188(24):8551-8559 (2006).

Alber et al., "Propionyl-Coenzyme A synthase from Chloroflexus aurantiacus, a key enzyme of the 3-hydroxypropionate cycle for autotrophic $CO_2$ fixation," *J. Biol. Chem.* 277:12137-12143 (2002).

Alber et al., "Study of an alternate glyoxylate cycle for acetate assimilation by *Rhodobacter sphaeroides*," *Mol. Microbiol.* 61(2):297-309 (2006).

Alberty, Biochemical thermodynamics. *Biochim. Biophys. Acta* 1207:1-11 (1994).

Aldor and Keasling, "Metabolic engineering of poly(3-hydroxybutyrate-co-3-hydroxyvalerate) composition in recombinant *Salmonella enterica* serovar typhimurium," *Biotechnol. Bioeng.* 76(2):108-114 (2001).

Aldor et al., "Metabolic Engineering of a Novel Propionate-Independent Pathway for the Production of Poly(3-Hydroxybutyrate-co-3-Hydroxyvalerate) in Recombinant *Salmonella enterica* Serovar Typhimurium," *Appl. Environ. Microbiol.* 68(8):3848-3854 (2002).

Aldrich Catalog, Sigma-Aldrich Company, Milwaukee, WI, p. 481 (2002).

Aldrich et al., "Cloning and complete nucleotide sequence determination of the catB gene encoding cis,cis-muconate lactonizing enzyme," *Gene* 52:185-195 (1987).

Alexeeva et al., "Requirement of ArcA for redox regulation in *Escherichia coli* under microaerobic but not anaerobic or aerobic conditions," *J. Bacteriol.* 185(1):204-209 (2003).

Alexson et al., "NADH-sensitive propionyl-CoA hydrolase in brown-adipose-tissue mitochondria of the rat," *Biochim. Biophys. Acta* 1005(1):13-19 (1989).

Alhapel et al., "Molecular and functional analysis of nicotinate catabolism in *Eubacterium barkeri*," *Proc. Natl. Acad. Sci. U.S.A.* 103(33):12341-12346 (2006).

Alper et al., "Construction of lycopene-overproducing *E. coli* strains by combining systematic and combinatorial gene knockout targets," *Nat. Biotechnol.* 23(5):612-616 (2005).

Alper et al., "Identifying gene targets for the metabolic engineering of lycopene biosynthesis in *Escherichi coli*," *Metab. Eng.* 7(3):155-164 (2005).

Alper et al., "Engineering yeast transcription machinery for improved ethanol tolerance and production," *Science* 314(5805):1565-1568 (2006).

Altamirano et al., "Decoupling cell growth and product formation in Chinese hamster ovary cells throguh metabolic control," *Biotechnol. Bioeng.* 76(4):351-360 (2001).

Altmiller and Wanger, "Purification and properties of dihydroxy acid dehydratase from soluble and mitochondrial fractions of *Neurospora crassa*," *Arch. Biochem. Biophys.* 138:160-170 (1970).

Amann et al., "Tightly regulated tac promoter vectors useful for the expression of unfused and fused proteins in *Escherichia coli*," *Gene* 69:301-315 (1988).

Andersen and Hansen, "Cloning of the lysA gene from *Mycobacterium tuberculosis*," *Gene* 124(1):105-109 (1993).

Andersen et al., "A gene duplication led to specialized γ-aminobutyrate and β-alanine aminotransferase in yeast," *FEBS J.* 274:1804-1817 (2007).

Anderson and Dawes, "Occurrence, metabolism, metabolic role, and industrial uses of bacterial polyhydroxyalkanoates," *Microbiol. Rev.* 54(4):450-472 (1990).

Anderson et al., "Evaluation of 5-enolpyruvoylshikimate-3-phosphate synthase substrate and inhibitor binding by stopped-flow and equilibrium fluorescence measurements," *Biochemistry* 27:1604-1610 (1988).

Andersson et al., "Effect of different carbon sources on the production of succinic acid using metabolically engineered *Escherichia coli*," *Biotechnol. Prog.* 23(2):381-388 (2007).

Andreesen and Ljungdahl, "Formate Dehydrogenase of *Clostridium thermoaceticum*: Incorporation of Selenium-75, and the Effects of Selenite, Molybate, and Tungstate on the Enzyme," *J. Bacteriol.* 116(2):867-873 (1973).

Aneja and Charles, "Poly-3-hydroxybutyrate degradation in Rhizobium (Sinorhizobium) meliloti: isolation and characterization of a gene encoding 3-hydroxybutyrate dehydrogenase," *J. Bacteriol.* 181(3):849-857 (1999).

Angrand et al., "Simplified generation of targeting constructs using ET recombination," *Nucleic Acids Res.* 27(17):e16 (1999).

Ansorge and Kula, "Production of Recombinant L-Leucine Dehydrogenase from *Bacillus cereus* in Pilot Scale Using the Runaway Replication System *E. coli*[pIET98]," *Biotechnol. Bioeng.* 68:557-562 (2000).

Aoshima and Igarashi, "A novel biotin protein required for reductive carboxylation of 2-oxoglutarate by isocitrate dehydrogenase in Hydrogenobacter thermophilus TK-6," *Mol. Microbiol.* 51(3):791-798 (2004).

Aoshima and Igarshi, "Nondecarboxylating and decarboxylating isocitrate dehydrogenases: oxalosuccinate reductase as an ancestral form of isocitrate dehydrogenase," *J. Bacteriol.* 190(6):2050-2055 (2008).

Aoshima et al., "A novel enzyme, citryl-CoA lyase, catalysing the second step of the citrate cleavage reaction in Hydrogenobacter thermophilus TK-6," *Mol. Microbiol.* 52(3):763-770 (2004).

Aoshima et al., "A novel enzyme, citryl-CoA synthetase, catalysing the first step of the citrate cleavage reaction in Hydrogenobacter thermophilus TK-6," *Mol. Microbiol.* 52(3):751-761 (2004).

Aoshima et al., "A novel oxalosuccinate-forming enzyme involved in the reductive carboxylation of 2-oxoglutarate in Hydrogenobacter thermophilus TK-6," *Mol. Microbiol.* 62(3):748-759 (2006).

Aoshima, "Novel enzyme reactions related to the tricarboxylic acid cycle: phylogenetic/functional implications and biotechnological applications," *Appl. Microbiol. Biotechnol.* 75(2):249-255 (2007).

Aragon and Lowenstein, "A survey of Enzymes Which Generate or Use Acetoacetyl Thioesters in Rat Liver," *J. Biol. Chem.* 258(8):4725-4733 (1983).

Arendsen et al., "Nitrate-Dependent Regulation of Acetate Biosynthesis and Nitrate Respiration by clostridium thermoaceticum," *J. Bacteriol.* 181:1489-1495 (1999).

Argyrou and Blanchard, "Kinetic and chemical mechanism of Mycobacterium tuberculosis 1-deoxy-D-xylulose-5-phosphate isomeroreductase," *Biochemistry* 43:4375-4384 (2004).

Arikawa et al., "Soluble fumarate reductase isoenzymes from *Saccharomyces cerevisiae* are required for anaerobic growth," *FEMS Microbiol. Lett.* 165:111-116 (1998).

Aristidou et al., "Metabolic Engineering of *Escherichia coli* to Enhance Recombinant Protein Production through Acetate Reduction," *Biotechnol. Prog.* 11(4):475-478 (1995).

Aristidou et al., "Metabolic flux analysis of *Escherichia coli* expressing the *Bacillus subtilis* Acetolactate Synthase in Batch and Continuous Cultures," *Biotechnol. Bioeng.* 63(6):737-749 (1999).

Armstrong et al., "Steroselectivity and sterospecificity of the α,β-dihydroxyacid dehydratase from *Salmonella typhimurium*," *Biochim. Biophys. Acta* 498:282-293 (1977).

Arps et al., "Genetics of serine pathway enzymes in Methylobacterium extorquens AM1: phosphoenolpyruvate carboxylase and malyl Coenzyme A lyase," *J. Bacteriol.* 175:3776-3783 (1993).

Asano and Kato, "Crystalline 3-methylaspartase from a facultative anaerobe, *Escherichia coli* strain YG1002," *FEMS Microbiol. Lett.* 118(3):255-258 (1994).

Asano et al., "Alteration of substrate specificity of aspartase by directed evolution," *Biomol. Eng.* 22(1-3):95-101 (2005).

Asanuma et al., "Characterization and transcription of the genes encoding enzymes involved in butyrate production in *Butyrivibrio fibrisolvens*," *Curr. Microbiol.* 45:203-207 (2003).

Asuncion et al., "Overexpression, purification, crystallization and data collection of 3-methylaspartase from Clostridium tetanomorphum," *Acta. Crystallogr. D. Biol. Crystallogr.* 57(Pt 5):731-733 (2001).

Asuncion et al., "The structure of 3-methylaspartase from Clostridium tetanomorphum functions via the common enolase chemical step," *J. Biol. Chem.* 277(10):8306-8311 (2002).

Atsumi et al., "Metabolic engineering of *Escherichia coli* for 1-butanol production," *Metab. Eng.* 10(6):305-311 (2007).

Atsumi et al., "Non-fermentative pathways for synthesis of branched-chain higher alcohols as biofuels," *Nature* 451(7174):86-89 (2008).

Atteia et al., "Pyruvate formate-lyase and a novel route of eukaryotic ATP synthesis in *Chlamydomonas mitochondria*," *J. Biol. Chem.* 281:9909-9918 (2006).

Auerbach et al., "Lactate dehydrogenase from the hyperthermophilic bacterium thermotoga maritima: the crystal structure at 2.1 Å resolution reveals strategies for intrinsic protein stabilization," *Structure* 6:769-781 (1998).

Baba et al., "Construction of *Escherichia coli* K-12 in-frame, single-gene knockout mutants: the Keio collection," *Mol. Syst. Biol.* 2:2006.0008 (2006).

Bachmann and Townsend, "β-Lactam-Lactamsynthetase: a new biosynthetic enzyme," *Proc. Natl. Acad. Sci. U.S.A.* 95(16):9082-9086 (1998).

Bai et al., "Lewis-acid assisted cross metathesis of acrylonitrile with functionalized olefins catalyzed by phosphine-free ruthenium carbene complex," *Org. Biomol. Chem.* 3:4139-4142 (2005).

Bailey et al., "Identification, cloning, purification, and enzymatic characterization of Mycobacterium tuberculosis 1-deoxy-D-xylulose 5-phosphate synthase," *Glycobiology* 12:813-820 (2002).

Baird et al., "Enzymes involved in acetoacetate formation in various bovine tissues," *Biochem. J.* 117(4):703-709 (1970).

Baker and van der Drift, "Purification and properties of L-erythro-3,5-diaminohexanoate dehydrogenase from Clostridium sticklandii," *Biochemistry* 13(2):292-299 (1974).

Baker et al., "Purification and properties of L-erythro-3,5-diaminohexanoate dehydrogenase from a lysine-fermenting Clostridium," *J. Biol. Chem.* 247:7724-7734 (1972).

Bakker et al., "Stoichiometry and compartmentation of NADH metabolism in *Saccharomyces cerevisiae*," *FEMS Microbiol. Rev.* 25:15-37 (2001).

Banerji et al., "The cloning and characterization of the arom gene of *Pneumocystis carinii*," *J. Gen. Microbiol.* 139:2901-2914 (1993).

Barber et al., "Structure and regulation of acetyl-CoA carboxylase genes of metazoa," *Biochimica. Biophysica. Acta* 1733:1-28 (2005).

Barker and Frost, "Microbial synthesis of *p*-hydroxybenzoic acid from glucose," *Biotechnol. Bioeng.* 76:376-390 (2001).

Barker et al., "Butyryl-CoA:Acetoacetate CoA-transferase from Lysine-fermenting Clostridium," *J. Biol. Chem.* 253(4):1219-1225 (1978).

Barker et al., "Pathway of Lysine Degradation in *Fusobacterium nucleatum*," *J. Bacteriol.* 152(1):201-207 (1982).

Barrick et al., "Quantitative analysis of ribosome binding sites in *E. coli*," *Nucleic Acids Res.* 22(7):1287-1295 (1994).

Barrowman et al., "Immunological comparison of microbial TPP-dependent non-oxidative α-keto acid decarboxylase," *FEMS Microbiol. Lett.* 34:57-60 (1986).

Barthelmebs et al., "Expression of *Escherichia coli* of Native and chimeric Phenolic Acid Decarboxylases with Modified Enzymatic Activities and Method for Screening Recombinant *E. coli* Strains Expressing These Enzymes," *Appl. Environ. Microbiol.* 67:1063-1069 (2001).

Barthelmebs et al., "Inducible metabolism of phenolic acids in *Pedicoccus pentosaecus* is encoded by an autoregulated operon which involves a new class of negative transcriptional regulator," *J. Bacteriol.* 182:6724-6731 (2000).

Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.* 172(12):7035-7042 (1990).

Basset et al., "Folate synthesis in plants: the p-aminobenzoate branch is initiated by a bifunctional PabA-PabB protein that is targeted to plastids," *Proc. Natl. Acad. Sci. U.S.A* 101:1496-1501 (2004).

Battaile et al., "Structures of isobutyryl-CoA dehydrogenase and enzyme-product complex: Comparison with isovaleryl- and short-chain acyl-CoA dehydrogenases," *J. Biol. Chem.* 279:16526-16534 (2004).

Baudin et al., "A simple and efficient method for direct gene deletion in *Saccharomyces cerevisiae*," *Nucleic Acids Res.* 21(14):3329-3330 (1993).

Bauer et al., "Improved Expression of Human Interleukin-2 in High-Cell-Density Fermentor Cultures of *Escherichia coli* K-12 by a Phosphotransacetylase Mutant," *Appl. Environ. Microbiol.* 56:1296-1302 (1990).

Beatrix et al., "The biotin-dependent sodium ion pump glutaconyl-CoA decarboxylase from *Fusobactevium nucleatum* (subsp. *nucleatum*). Comparison with the glutaconyl-CoA decarboxylases from gram-positive bacteria," *Arch. Microbiol.* 154(4):362-369 (1990).

Beckers et al., "Large-scale mutational analysis for the annotation of the mouse genome," *Curr. Opin. Chem. Biol.* 6:17-23 (2001).

Benner et al., "Stereospecificity and sterochemical infidelity of acetoacetate decarboxylase (AAD)," *J. Am. Chem. So.* 103:993-994 (1981).

Benning et al., "New reactions in the crotonase superfamily: Structure of methylmalonyl CoA decarboxylase from *Escherichia coli*," *Biochemistry* 39:4630-4639 (2000).

Berg et al., "A 3-Hydroxypropionate/4-Hydroxybutyrate Autotrophic Carbon Dioxide Assimilation Pathway in Archaea," *Science* 318(5857) 1782-1786 (2007).

Bergquist and Gibbs, "Degenerate oligonucleotide gene shuffling," *Meth. Mol. Biol.* 352:191-204 (2007).

Bergquist et al., "Degenerate oligonucleotide gene shuffling (DOGS) and random drift mutagenesis (RNDM): Two complementary techniques for enzyme evolution," *Biomol. Eng.* 22:63-72 (2005).

Berkovitch et al., "A locking mechanism preventing radical damage in the absence of substrate, as revealed by the x-ray structure of lysine 5,6-aminomutase," *Proc. Natl. Acad. Sci. U.S.A.* 101:15870-15875 (2004).

Berman and Magasanik, "The pathway of myo-inositol degradation in Aerobacter aerogenes," *J. Biol. Chem.* 241(4):800-806 (1966).

Bermejo et al., "Expression of *Clostridium acetobutylicum* ATCC 824 Genes in *Escherichia coli* for Acetone Production and Acetate Detoxification," *Appl. Environ. Microbiol.* 64(3):1079-1085 (1998).

Berrios-Rivera et al., "Metabolic Engineering of *Escherichia coli*: Increase of NADH Availability by Overexpressing an $NAD^+$-Dependent Formate Dehydrogenase," *Metab Eng.* 4(3):217-229 (2002).

Berthold et al., "Structure of the branched-chain keto acid decarboxylase (KdcA) from *Lactococcus lacti* prvides insights into structural basis for the chemoselective enantioselective carboligation reaction," *Acta. Crystallogr. D. Biol. Crystallogr.* 63(Pt 12):1217-1224 (2007).

Biellmann et al., "Aspartate-β-semialdehyde dehydrogenase from *Escherichia coli*. Purification and general properties," *Eur. J. Biochem.* 104(1):53-58 (1980).

Binieda et al., "Purification, characterization, DNA sequence and cloning of a pimeloyl-CoA synthetase from *Pseudomonas mendocina* 35," *Biochem. J.* 340:793-801 (1999).

Binstock and Schulz, "Fatty acid oxidation complex from *Escherichia coli*," *Methods Enzymol.* 71(Pt C):403-411 (1981).

Birch et al., "Cloning, sequencing, and expression of the gene encoding methylmalonyl-Coenzyme A mutase from *Streptomyces cinnamonensis*," *J. Bacteriol.* 175(11):3511-3519 (1993).

Birrer et al., "Electro-transformation of *Clostridium beijerinckii* NRRL B-592 with shuttle plasmid pHR106 and recombinant derivatives," *Appl. Microbiol. Biotechnol.* 41(1):32-38 (1994).

Bisswanger, "Substrate specificity of the Pyruvate Dehydrogenase Complex from *Escherichia coli*," *J. Biol. Chem.* 256(2):815-822 (1981).

Blanco et al., "Critical catalytic functional groups in the mechanism of aspartate-β-semialdehyde dehydrogenase," *Acta. Crystallogr. D. Biol. Crystallogr.* 60(Pt 10):1808-1815 (2004).

Blanco et al., "The role of substrate-binding groups in the mechanism of aspartate-β-semialdehyde dehydrogenase," *Acta. Crystallogr. D. Biol. Crystallogr.* 60(Pt 8):1388-1395 (2004).

Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem.* 123(3):563-569 (1982).

Blazquez et al., "Identification and analysis of a glutaryl-CoA dehydrogenase-encoding gene and its cognate transcriptional regulator from *Azoarcus* sp. CIB," *Environ. Microbiol.* 10(2):474-482 (2008).

Blombach et al., "*Corynebacterium glutamicum* tailored for high-yield L-valine production," *Appl. Microbiol. Biotechnol.* 79(3):471-479 (2008).

Blomqvist et al., "Characterization of the genes of the 2,3-butanediol operons from *Klebsiella terrigena* and *Enterobacter aerogenes*," *J. Bacteriol.* 175:1392-1404 (1993).

Bobik and Rasche, "HPLC assay for methylmalonyl-CoA epimerase," *Anal. Bioanal. Chem.* 375(3):344-349 (2003).

Bobik and Rasche, "Identification of the human methylmalonyl-CoA racemase gene based on the analysis of prokaryotic gene arrangements. Implications for decoding the human genome," *J. Biol. Chem.* 276(40):37194-37198 (2001).

Bobik et al., "Propanediol Utilization Genes (pdu) of *Salmonella typhimurium*: Three Genes for the Propanediol Dehydratase," *J. Bacteriol.* 179(21):6633-6639 (1997).

Bock et al., "Purification and characterization of two extremely thermostable enzymes, phosphate acetyltransferase and acetate kinase, from the hyperthermophilic eubacterium Thermotoga maritima," *J. Bacteriol.* 181:1861-1867 (1999).

Boiangiu et al., "Sodium Ion Pumps and Hydrogen Production in Glutamate Fermenting Anaerobic Bacteria," *J. Mol. Microbiol. Biotechnol.* 10:105-119 (2005).

Boles et al., "Characterization of a glucose-repressed pyruvate kinase (Pyk2p) in *Saccharomyces cerevisiae* that is catalytically insensitive to fructose-1,6-bisphosphate," *J. Bacteriol.* 179:2987-2993 (1997).

Bonnarme et al., "Itaconate biosynthesis in *Aspergillus terreus*," *J. Bacteriol.* 177(12):3573-3578 (1995).

Bonner and Bloch, "Purification and properties of fatty acyl thioesterase I from *Escherichia coli*," *J. Biol. Chem.* 247(10):3123-3133 (1972).

Boronin et al., "Plasmids specifying ε-caprolactam degradation in Pseudomonas strains," *FEMS Microbiol Lett.* 22(3):167-170 (1984).

Bose et al., "Genetic analysis of the methanol- and methylamine-specific methyltransferase 2 genes of *Methanosarcina acetivorans* C2A," *J. Bacteriol.* 190(11):4017-4026 (2008).

Bott et al., "Methylmalonyl-CoA decarboxylase from *Propionigenium modestum*. Cloning and sequencing of the structural genes and purification of the enzyme complex," *Eur. J. Biochem.* 250:590-599 (1997).

Botting et al., "Substrate Specificity of the 3-Methylaspartate Ammonia-Lyase Reactin: Observation of Differential relative Reaction Rates for Substrate-Product Pairs," *Biochemistry* 27:2953-2955 (1988).

Bottomley et al., "Cloning, sequencing, expression, purification and preliminary characterization of type II dehydroquinase from *Helicobacter pylori*," *Biochem. J.* 319:559-565 (1996).

Bower et al., "Cloning, sequencing, and characterization of the *Bacillus subtilis* biotin biosynthetic operon," *J. Bacteriol.* 178(14):4122-4130 (1996).

Boylan and Dekker, "L-Threonine Dehydrogenase of *Escherichia coli* K-12," *Biochem. Biophys. Res. Commun.* 85(1):190-197 (1978).

Boynton et al., "Cloning, sequencing, and expression of clustered genes encoding β-hydroxybutyryl-Coenzyme A (CoA) dehydrogenase, crotonase, and butyryl-CoA dehydrogenase from *Clostridium acetobutylicum* ATCC 824," *J. Bacteriol.* 178(11):3015-3024 (1996).

Brachmann et al., "Designer deletion strains derived from *Saccharomyces cerevisiae* S288C: a useful set of strains and plasmids for PCR-mediated gene disruption and other applications," *Yeast* 14(2):115-132 (1998).

Bradford, "A rapid and sensitive method for the quantitation of microgram quantities of protein utilizing the principle of protein-dye binding," *Anal. Biochem.* 72:248-254 (1976).

Branlant, "Nucleotide sequence of *Escherichia coli* gap gene. Different evolutionary behavior of the $NAD^+$-binding domain and of the catalytic domain of D-glyceraldehyde-3-phosphate dehydrogenase," *Eur. J. Biochem.* 150:61-66 (1985).

Bräsen and Schönheit, "Unusual ADP-forming acetyl-Coenzyme A synthetases from the mesophilic halophilic euryarchaeon *Haloarcula marismortui* and from the hyperthermophilic crenarchaeon *Pyrobaculum aerophilum*," *Arch. Microbiol.* 182(4):277-287 (2004).

Braune et al., "The sodium ion translocating glutaconyl-CoA decarboxylase from *Acidaminococcus fermentans*: cloning and function on the genes forming a second operon," *Mol. Microbiol.* 31(2):473-487 (1999).

Bravo et al., "Reliable, sensitive, rapid and quantitative enzyme-based assay for gamma-hydroxybutyric acid (GHB)," *J. Forensic Sci.* 49:379-387 (2004).

Bredwell et al., "Reactor Design Issues for Synthesis-Gas Fermentations," *Biotechnol. Prog.* 15(5):834-844 (1999).

Breese et al., "Genes coding for the benzoyl-CoA pathway of anaerobic aromatic metabolism in the bacterium *Thauera aromatica*," *Eur. J. Biochem.* 256(1):148-154 (1998).

Breitkruez et al., "A novel γ-hydroxybutyrate dehydrogenase: Identification and expression of an *Arabidopsis* cDNA and potential role under oxygen deficiency," *J. Biol. Chem.* 278:41552-41556 (2003).

Bremer, "Pyruvate Dehydrogenase, Substrate Specificity and Product Inhibition," *Eur. J. Biochem.* 8:535-540 (1969).

Brey et al., "Cloning of multiple genes involved with cobalamin (Vitamin $B_{12}$) biosynthesis in *Bacillus megaterium*," *J. Bacteriol.* 167:623-630 (1986).

Bro et al., "In silico aided metabloic engineering of *Saccharomyces cerevisiae* for improved bioethanol production," *Metab. Eng.* 8(2):102-111 (2006).

Brooke et al., "GAMS: A User's Guide. GAMS Development Corporation," (1998).

Broun et al., "Catalytic plasticity of fatty acid modification enzymes underlying chemical diversity of plant lipids," *Science* 282:1315-1317 (1998).

Brown et al., "A role for *pabAB*, a p-aminobenzoate synthase gene of *Streptomyces venezuelae* ISP5230, in chloramphenicol biosynthesis," *Microbiol.* 142 (Pt 6):1345-1355 (1996).

Brown et al., "Comparative structural analysis and kinetic properties of lactate dehydrogenases from the four species of human malarial parasites," *Biochemistry* 43:6219-6229 (2004).

Browner et al., "Sequence analysis, biogenesis, and mitochondrial import of the α-subunit of rat liver propionyl-CoA carboxylase," *J. Biol. Chem.* 264:12680-12685 (1989).

Bu and Tobin, "The exon-intron organization of the genes (GAD1 and GAD2) encoding two human glutamate decarboxylases ($GAD_{67}$ and $GAD_{65}$) suggests that they derive from a common ancestral GAD," *Genomics* 21:222-228 (1994).

Bu et al., "Two human glutamate decarboxylases, 65-kDa GAD and 67-kDa GAD, are each encoded by a single gene," *Proc. Natl. Acad. Sci. U.S.A.* 89:2115-2119 (1992).

Buchanan et al., "An extremely thermostable aldolase from *Sulfolobus solfataricus* with specificity for non-phosphorylated substrates," *Biochem. J.* 343:563-570 (1999).

Buck et al., "Primary structure of the succinyl-CoA synthetase of *Escherichia coli*," *Biochem.* 24(22):6245-6252 (1985).

Buckel and Barker, "Two pathways of glutamate fermentation by anaerobic bacteria," *J. Bacteriol.* 117(3):1248-1260 (1974).

Buckel and Golding, "Radical enzymes in anaerobes," *Annu. Rev. Microbiol.* 60:27-49 (2006).

Buckel and Golding, "Radical species in the catalytic pathways of enzymes from anaerobes," *FEMS Microbiol. Rev.* 22(5):523-541 (1999).

Buckel et al., "ATP-Driven electron transfer in enzymatic radical reactions," *Curr. Opin. Chem. Biol.* 8:462-467 (2004).

Buckel et al., "Glutaconate CoA-Transferase from *Acidaminococcus fermentans*," *Eur. J. Biochem.* 118:315-321 (1981).

Buckel et al., "Radical-mediated dehydration reactions in anaerobic bacteria," *Biol. Chem.* 386:951-959 (2005).

Buckel, "Sodium ion-translocating decarboxylases," *Biochimica. Biophysica. Acta* 1505:15-27 (2001).

Bueding and Yale, "Production of α-methylbutyric acid by bacteria-free *Ascaris lumbricoides*," *J. Biol. Chem.* 193:411-423 (1951).

Bühler and Simon, "On the kinetics and mechanism of enoate reductase," *Hoppe Seylers Z. Physiol. Chem.* 363(6):609-625 (1982).

Bunch et al., "The *IdhA* gene encoding the fermentative lactate dehydrogenase of *Escherichia coli*," *Microbiol.* 143:187-195 (1997).

Burgard and Maranas, "Probing the performance limits of the *Escherichia coli* metabolic network subject to gene additions or deletions," *Biotechnol. Bioeng.* 74:364-375 (2001).

Burgard et al., "Minimal Reaction Sets for *Escherichia coli* Metabolism under Different Growth Requirements and Uptake Environments," *Biotechnol. Prog.* 17:791-797 (2001).

Burgard et al., "Optknock: a bilevel programming framework for identifying gene knockout strategies for microbial strain optimization," *Biotechnol. Bioeng.* 84(6):647-657 (2003).

Burke et al., "The Isolation, Characterization, and Sequence of the Pyruvate Kinase Gene of *Saccharomyces cerevisiae*," *J. Biol. Chem.* 258(4):2193-2201 (1983).

Burks et al., "Stereochemical and Isotopic Labeling Studies of 2-Oxo-hept-4-ene-1,7-dioate Hydratase: Evidence for an Enzyme-Catalyzed Ketonization Step in the Hydration Reaction," *J. Am. Chem. Soc.* 120(31):7665-7675 (1998).

Buu et al., "Functional characterization and localization of acetyl-CoA hydrolase, Ach1p, in *Saccharomyces cerevisiae*," *J. Biol. Chem.* 278:17203-17209 (2003).

Buzenet et al., "Purification and properties of 4-Aminobutyrate 2-Ketoglutarate Aminotransferase From Pig Liver," *Biochimica. Biophysica. Acta* 522:400-411 (1978).

Byrnes et al., "Thermodynamics of reactions catalyzed by anthranilate synthase," *Biophys. Chem.* 84:45-64 (2000).

Cahyanto et al., "Regulation of aspartokinase, asparate semialdehyde dehydrogenase, dihydrodipicolinate synthease and dihydropdipicolinate reductase in *Lactobacillus plantarum*," *Microbiology.* 152 (Pt 1): 105-112 (2006).

Caldovic and Tuchman, "N-Acetylglutamate and its changing role through evolution," *Biochem. J.* 372:279-290 (2003).

Calhoun et al., "Threonine deaminase from *Eschericiha coli.* I. Purification and properties," *J. Biol. Chem.* 248(10):3511-3516 (1973).

Camara et al., "Characterization of a Gene Cluster Involved in 4-Chlorocatechol Degradation by *Pseudomonas reinekei* MT1," *J. Bacteriol.* 191(15):4905-4915 (2009).

Campbell and Cronan, Jr., "The enigmatic *Escherichia coli* fadE gene is yafH," *J. Bacteriol.* 184(13):3759-3764 (2002).

Campbell et al., "A complete shikimate pathway in Toxoplasma gondii: an ancient eukaryotic innovation," *Int. J. Parasitol.* 34:5-13 (2004).

Campbell et al., "A new *Escherichia coli* metabolic competency: growth on fatty acids by a novel anaerobic β-oxidation pathway," *Mol. Microbiol.* 47(3):793-805 (2003).

Canovas et al., "Characterization of the genes for the biosynthesis of the compatible solute ecotine in the moderately haliphilic bacterium *Halomonas elongate* DSM 3043," *Syst. Appl. Microbiol.* 21:487-497 (1998).

Cao et al., "Simultaneous Production and recovery of Fumaric Acid from Immobilized *Rhizopus oryzae* with a Rotary biofilm Contactor and an Adsorption Column," *Appl. Environ. Microbiol.* 62(8):2926-2931 (1996).

Carlini et al., "Guerbet condensation of methanol with n-propanol to isobutyl alcohol over heterogeneous copper chromite/Mg—Al mixed oxides catalysts," *J. Mol. Catal. A. Chem.* 220:215-220 (2004).

Carlini et al., "Selective synthesis of isobutanol by means of the Guerbet reaction Part 3: Methanol/n-propanol condensation by using bifunctional catalytic systems based on nickel, rhodium and ruthenium species with basic components," *J. Mol. Catal. A. Chem.* 206:409-418 (2003).

Carlini et al., "Selective synthesis of isobutanol by means of the Guebet reaction Part 1. Methanol/n-propanol condensation by using copper based catalytic systems," *J. Mol. Catal. A. Chem.* 184:273-280 (2002).

Carlini et al., "Selective synthesis of isobutanol by means of the Guerbet reaction Part 2. Reaction of methanol/ethanol and methanol/ethanol/n-propanol mixtures over copper based MeONa catalytic systems," *J. Mol. Catal. A. Chem.* 200:137-146 (2003).

Carpenter et al., "Structure of dehydroquinate synthase reveals an active site capable of multistep catalysis," *Nature* 394:299-302 (1998).

Carretero-Paulet et al., "Expression and molecular analysis of the *Arabidopsis* DXR gene encoding1-deoxy-D-xylulose 5-phosphate reductoisomerase, the firszt committed enzyme of the 2-*C*-methyl-D-erythritiol 4-phosphate pathway," *Plant Physiol.* 129:1581-1591 (2002).

Carta et al., "Production of fumaric acid by fermentation of enzymatic hydrolysates derived from *Cassava bagasse*," *Biores. Tech.* 68:23-28 (1999).

Cary et al., "Cloning and Expression of *Clostridium acetobutylicum* ATCC 824 Acetoacetyl-Coenzyme A:Acetate/Butyrate:Coenzyme A-Transferase in *Escherichia coli*," *App. Environ. Microbiol.* 56(6):1576-1583 (1990).

Cary et al., "Cloning and expression of *Clostridium acetobutylicum* phosphotransbutyrylase and butyrate kinase genes in *Escherichia coli*," *J. Bacteriol.* 170(10):4613-4618 (1988).

Casero and Pegg, "Spermidine/spermine $N^1$-acetyltransferase—the turning point in polyamine metabolism," *FASEB J.* 7:653-661 (1993).

Caspi et al., "MetaCyc: a multiorganism database of metabolic pathways and enzymes," *Nucleic Acids Res.* 34(Database issue):D511-D516 (2006).

Cavin et al., "Gene cloning, transcriptional analysis, purification, and characterization of phenolic acid decarboxylase from *Bacillus subtilis*," *Appl. Environ. Microbiol.* 64(4):1466-1471 (1998).

Cha and Bruce, "Stereo- and regiospecific cis,cis-muconate cycloisomerization by *Rhodococcus rhodochrous* N75," *FEMS Microbiol. Lett.* 224:29-34 (2003).

Cha and Parks, Jr., "Succinic Thiokinase. I. Purification of the Enzyme from Pig Heart," *J. Biol. Chem.* 239:1961-1967 (1964).

Chandra et al. "Pyruvate decarboxylase: a key enzyme for the oxidative metabolism of lactic acid by *Acetobacter pasteurianus*," *Arch. Microbiol.* 176:443-451 (2001).

Chang et al., "p-Aminobenzoic acid and chloramphenicol biosynthesis in *Streptomyces venezuelae*: gene sets for a key enzyme, 4-amino-4-deoxychorismate synthase," *Microbiology* 147:2113-2126 (2001).

Chang et al., "Effects of deletions at the carboxyl terminus of *Zymomonas mobilis* pyruvate decarboxylase on the kinetic properties and substrate specificity," *Biochemistry* 39(31):9430-9437 (2000).

Chao and Ramsdell, "The effects of wall populations on coexistence of bacteria in the liquid phase of chemostat cultures," *J. Gen. Microbiol.* 131(5):1229-1236 (1985).

Chaparro-Riggers et al., "Comparison of Three Enoate Reductases and their Potential Use for Biotransformations," *Adv. Synth. Catal.* 349:1521-1531 (2007).

Charles et al., "The isolation and nucleotide sequence of the complex AROM locus of *Aspergillus nidulans*," *Nucleic Acids Res.* 14:2201-2213 (1986).

Charrier et al., "A novel class of CoA-transferase involved in short-chain fatty acid metabolism in butyrate-producing human colonic bacteria," *Microbiology* 152:179-185 (2006).

Chatterjee et al., "A general model for selectively in olefin cross methathesis," *J. Am. Chem. Soc.* 125(37):11360-11370 (2003).

Chatterjee et al., "Mutation of the ptsG Gene Results in Increased Production of Succinate in Fermentation of Glucose by *Escherichia coli*," *Appl. Env. Microbiol.* 67:148-154 (2001).

Chaudhuri et al., "Identification of the active-site lysine residues of two biosynthetic 3-dehydroquinases," *Biochem. J.* 275:1-6 (1991).

Chen and Hiu, "Acetone-Butanol-Isopropanol Production by *Clostridium beijerinckii* (Synonym, Clostridium Butylicum)," *Biotechnology Letters* 8(5):371-376 (1986).

Chen et al., "A novel lysine 2,3-aminomutase encoded by the yodO gene of *Bacillus subtilis*: characterization and the observation of organic radical intermediates," *Biochem. J.* 348:539-549 (2000).

Chen et al., "Cloning, Sequencing, Heterologous Expression, Purification, and Characterization of Adenosylcobalamin-dependent D-Ornithine Aminomutase from *Clostridium sticklandii*," *J. Biol. Chem.* 276:44744-44750 (2001).

Chen et al., "The control region of the pdu/cob regulon in *Salmonella typhimurium*," *J. Bacteriol.* 176:5474-5482 (1994).

Cheng et al., "Genetic Analysis of a Gene Cluser for Cyclohexanol Oxidation in *Acinetobacter* sp. Strain SE19 by In Vitro Transportation," *J. Bacteriol.* 182(17):4744-4751 (2000).

Cheng et al., "Mammalian Wax Biosynthesis. I. Identification of two fatty acyl-Coenzyme A reductases with different substrate specificities and tissue distributions," *J. Biol. Chem.* 279(36):37789-37797 (2004).

Cheng et al., "Mammalian Wax Biosynthesis. II. Expression cloning of wax synthase cDNAs encoding a member of the acyltransferase enzyme family," *J. Biol. Chem.* 279(36):37798-37807 (2004).

Cheng et al., "Structural basis for shikimate-binding specificity of Helicobacter pylori shikimate kinase," *J. Bacteriol.* 187:8156-8163 (2005).

Chicco et al., "Regulation of Gene Expression of Branched-chain Keto Acid Dehydrogenase Complex in Primary Cultured Hepatocytes by Dexamethasone and a cAMP Analog," *J. Biol. Chem.* 269(30):19427-19434 (1994).

Chirpich et al., "Lysine 2,3-Aminomutase. Purification and Properties of Pyridoxal Phosphate and S-Adenosylmethionine-Activated Enzyme," *J. Biol. Chem.* 245(7):1778-1789 (1970).

Cho et al., "Critical residues for the Coenzyme specificity of NAD$^+$-dependent 15-hydroxyprostaglandin dehydrogenase," *Arch. Biochem. Biophys.* 419:139-146 (2003).

Choi et al, "Olefin Metathesis Involving Ruthenium Enoic Carbene Complexes," *J. Am. Chem. Soc.* 123(42):10417-10418 (2001).

Choi et al., "Enhanced production of cis,cis-muconate in a cell-recycle bioreactor," *J. Ferment. Bioeng.* 84:70-76 (1997).

Choi-Rhee and Cronan, "The biotin carboxylase-biotin carboxyl carrier protein complex of *Escherichia coli* acetyl-CoA carboxylase," *J. Biol. Chem.* 278:30806-30812 (2003).

Chopra et al., "Expression, purification, and biochemical characterization of *Mycobacterium tuberculosis* aspartate decarboxylase, PanD," *Protein Expr. Purif.* 25:533-540 (2002).

Chou et al., "Effect of Modulated Glucose Uptake on High-Level Recombinant Protein Production in a Dense *Escherichia coli* Culture," *Biotechnol. Prog.* 10:644-647 (1994).

Chowdhury et al., "3-Hydroxyisobutyrate dehydrogenase from *Pseudomonas putida* E23: purification and characterization," *Biosci. Biotechnol. Biochem.* 60(12):2043-2047 (1996).

Chowdhury et al., "Cloning and overexpression of the 3-hydroxyisobutyrate dehydrogenase gene from *Pseudomonas putida* E23," *Biosci. Biotechnol. Biochem.* 67(2):438-441 (2003).

Christenson et al., "Kinetic analysis of the 4-methylideneimidazole-5-one-containing tyrosine aminomutase in enediyne antitumor antibiotic C-1027 biosynthesis," *Biochemistry* 42:12708-12718 (2003).

Chuakrut et al., "Characterization of a bifunctional archael acyl Coenzyme A carboxylase," *J. Bacteriol.* 185:938-947 (2003).

Clark and Ljungdahl, "Purification and properties of 5,10-methylenetetrahydrofolate reductase from *Clostridium formicoaceticum*," *Methods Enzymol.* 122:392-399 (1986).

Clark and Ljungdahl, "Purification and Properties of 5,10-Methylenetetrahydrofolate Reductase, an Iron-sulfur Flavoprotein from *Clostridium formicoaceticum*," *J. Biol. Chem.* 259(17)10845-10849 (1984).

Clark et al., "Mutants of *Escherichia coli* defective in acid fermentation," *Appl. Biochem. Biotechnol.* 17:163-173 (1988).

Clark, Progress Report for Department of Energy Grant DE-FG02-88ER13941, "Regulation of Alcohol Fermentation in *Escherichia coli*," pp. 1-7 for the period: Jul. 1991-Jun. 1994.

Clarke et al., "Rational construction of a 2-Hydroxyacid Dehydrogenase With New Substrate Specificity," *Biochem. Bioghys. Res. Commun.* 148:15-23 (1987).

Clausen et al., "PAD1 encodes phenylarcrylic acid decarboxylase which confers resistance to cinnamic acid in *Saccharomyces cerevisiae*," *Gene* 142:107-112 (1994).

Coco et al., "DNA shuffling method for generating highly recombined genes and evolved enzymes," *Nat. Biotechnol.* 19:354-359 (2001).

Coggins et al., "The arom multifunctional enzyme from *Neurospora crassa*," *Methods Enzymol.* 142:325-341 (1987).

Colby and Chen, "Purification and properties of 3-hydroxybutyryl-Coenzyme A dehydrogenase from *Clostridium beijerinckii* ("*Clostridium butylicum*") NRRL B593," *Appl. Environ. Microbiol.* 58:3297-3302 (1992).

Coleman, "Expression of a glutamate decarboxylase homologue is required for normal oxidative stress tolerance in *Saccharomyces cerevisiae*," *J. Biol. Chem.* 276:244-250. (2001).

Conrad et al., "D- and L-Isoleucine Metabolism and Regulation of Their Pathways in *Pseudomonas Putida*," *J. Bacteriol.* 118(1):103-111 (1974).

Cooper, "Glutamate-γ-aminobutyrate transaminase," *Methods Enzymol.* 113:80-82 (1985).

Corthesy-Theulaz et al., "Cloning and Characterization of *Helicobacter pylori* Succinyl CoA:Acetoacetate CoA-transferase, a Novel Prokaryotic Member of the CoA-transferase Family," *J. Biol. Chem.* 272(41):25659-25667 (1997).

Couturier et al., "A Cyclometalated Aryloxy(chloro)neopentylidenetungsten Complex: A Highly Active and Stereoselective Catalyst for the Metathesis of cis- and trans-2-Pentene, Norbornene, 1-Methyl-norbornene, and Ethyl Oleate," *Angew. Chem Int. Ed. Engl.* 31(5):628-631 (1992).

Cox et al., "Development of a metabolic network design and optimization framework incorporating implementation constraints: A succinate production case study," *Metab. Eng.* 8(1):46-57 (2006).

Craney et al., "A synthetic luxCDABE gene cluster optimized for expression in high-GC bacteria," *Nucleic Acids Res.* 35(6):e46 (2007).

Cukalovic et al., "Feasibility of production method for succinic acid derivatives: a marriage of renewable resources and chemical technology," *Biofuels Bioprod. Bioref.* 2:505-529 (2008).

Cunningham et al., "Transcriptional regulation of the aconitase genes (acnA and acnB) of *Escherichia coli*," *Microbiology* 143(Pt 12):3795-3805 (1997).

Dai et al., "Highly Selective Diels-Alder Reactions of directly Connected Enzyme Dienphiles," *J. Am. Chem. Soc.* 129:645-657 (2007).

Dakoji et al., "Studies on the inactivation of bovine liver enoyl-CoA hydratase by (methylenecyclopropyl)formyl-CoA: elucidation of the inactivation mechanism and identification of cysteine-114 as the entrapped nucleophile," *J. Am. Chem. Soc.* 123(4):9749-9759 (2001).

Dal et al., "Transcriptional Organization of Genes for Protocatechuate and quinate Degradation from *Acinetobacter* sp. Strain ADP1," *Appl. Environ. Microbiol.* 71(2):1025-1034 (2005).

Dangel et al., "Anaerobic metabolism of cyclohexanol by denitrifying bacteria," *Arch. Microbiol.* 150(4):358-362 (1988).
Dangel et al., "Enzyme reactions involved in anaerobic cyclohexanol metabolism by a dentitrifying *Psedomonas* species," *Arch. Microbiol.* 152:273-279 (1989).
D'Ari and Rabinowitz, "Purification Characterization, cloning, and Amino Acid Sequence of the Bifunctional Enzyme 5,10-Methylenetetrahydrofolate Dehydrogenase/5,10-Methenyltetrahydrofolate Cyclohydrolase from *Escherichia coli*," *J. Biol. Chem.* 266(35):23953-23958 (1991).
Das et al., "Characterization of a corrinoid protein involved in the C1 metabolism of strict anaerobic bacterium *Moorella thermoacetica*," *Proteins* 67(1):167-176 (2007).
Datar et al., "Fermentation of biomass-generated producer gas to ethanol," *Biotechnol. Bioeng.* 86(5):587-594 (2004).
Datsenko et al., "One-step inactivation of chromosomal genes in *Escherichia coli* K-12 using PCR products," *Proc. Natl. Acad. Sci. U.S.A.* 97:6640-6645 (2000).
Datta et al., "Covalent structure of biodegradative threonine dehydratase of *Escherichi coli*: homology with other dehydratases," *Proc. Natl. Acad. Sci. U.S.A.* 84(2):393-397 (1987).
Davey and Trudgill, "The metabolism of trans-cyclohexan-1,2-diol by an Acinetobacter species," *Eur. J. Biochem.* 74(1):115-127 (1977).
Davids et al, "Characterization of the *N*-acetyltransferases respectively responsible for arylalkylamine and diamine acetylation in *Ascaris suum*," *Mol. Biochem. Parasitol.* 64(2):341-344 (1994).
Davie et al., "Expression and assembly of a functional E1 component ($\alpha_2\beta_2$) of mammalian branched-chain $\alpha$-ketoacid dehydrogenase complex in *Escherichia coli*," *J. Biol. Chem.* 267:16601-16606 (1992).
De Biase et al., "Isolation, overexpression, and biochemical characterization of the two isoforms of glutamic acid decarboxylase from *Escherichia coli*," *Protein Expr. Purif.* 8:430-438 (1996).
de Bok et al., "Two W-containing formate dehydrogenases ($CO_2$-reductases) involving syntrophic propionate oxidation by *Syntrophobacter fumaroxidans*," *Eur. J. Biochem.* 270:2476-2485 (2003).
de Crecy et al., "Development of a novel continuous culture device for experimental evolution of bacterial populations," *Appl. Microbiol. Biotechnol.* 77(2): 489-496 (2007).
de la Torre et al., "Identification and functional analysis of a prokaryotic-type aspartate aminotransferase: implications for plant amino acid metabolism," *Plant. J.* 46(3):414-425 (2006).
de Mata and Rabinowitz, "Formyl-methenyl-methylenetetrahydrofolate synthetase (combined) from yeast. Biochemical characterization of the protein from an ADE3 mutant lacking the formyltetrahydrofolate synthetase function," *J. Biol Chem.* 255:2569-2577 (1980).
de Mendonca et al., "Functional characterization by genetic complementation of aroB-encoded dehydroquinate synthase from *Mycobacterium tuberculosis* H37Rv and its heterologous expression and purification," *J. Bacteriol.* 189:6246-6252 (2007).
de Smidt et al., "The alcohol dehydrogenases of *Saccharomyces cerevisiae*: a comprehensive review," *FEMS Yeast Rev.* 7:967-978 (2008).
Deana, "Substrate specificity of a dicarboxyl-CoA: dicarboxylic acid Coenzyme A transferase from rat liver mitochondria," *Biochem. Int.* 26(4):767-773 (1992).
DeFeyter and Pittard, "Purification and properties of shikimate kinase II from *Escherichia coli* K-12," *J. Bacteriol.* 165:331-333 (1986).
Del Campillo-Campbell et al., "Biotin-requiring Mutants of *Escherichia coli* K-12," *J. Bacteriol.* 94(6):2065-2066 (1967).
Deno, "The Diels-Alder Reaction with $\alpha, \beta, \gamma, \delta$-Unsaturated Acids," *J. Am. Chem. Soc.* 72:4057-4059 (1950).
Department of Energy, "Top value added chemicals from biomass. Volume I—Results of Screening for Potential Candidates from Sugars and Synthesis Gas," *Biomass*, Aug. 2004.
Desvaux, "*Clostridium cellulolyticum*: model organism of mesophilic cellulolytic clostridia," *FEMS Microbiol. Rev.* 29(4):741-764 (2005).
Devos et al., "Practical limits of function prediction," *Proteins* 41:98-107 (2000).

Di Gennaro, "Styrene lower catabolic pathway in *Pseudomonas fluorescens* ST: identification and characterization of genes for phenylacetic acid degradation," *Arch. Microbiol.* 188(2):117-125 (2007).
Diao et al., "Crystal structure of butyrate kinase 2 from *Thermotoga maritima*, a member of the ASKHA superfamily of phosphotransferases," *J. Bacteriol.* 191:2521-2529 (2009).
Diao et al., "Crystallization of the butyrate kinase 2 from *Thermotoga maritima* mediated by vapor diffusion of acetic acid," *Acta. Crystallogr. D. Biol. Crystallogr.* 59(Pt 6):1100-1102 (2003).
Dias et al., "Well-Defined Ruthenium Olefin Metathesis Catalyst: Mechanism and Activity," *J. Am. Chem. Soc.* 119(17):3887-3897 (1997).
Diaz et al., "Gene cloning, heterologous overexpression and optimized refolding of the NAD-glutamate dehydrogenase from *Haloferax mediterranei*," *Extremophiles* 10:105-115 (2006).
Diderichsen et al., "Cloning of aldB, Which Encodes $\alpha$-Acetolactate Decarboxylase, an Exoenzyme from *Bacillus brevis*," *J. Bacteriol.* 172(8):4315-4321 (1990).
Dittrich et al., "Redistribution of Metabolic Fluxes in the Central Aerobic Metabolic Pathway of *E. coli* Mutant Strains with Deletion of the *ackA-pta* and *poxB* Pathways for the Synthesis of Isoamyl Acetate," *Biotechnol Prog.* 21(2):627-631 (2005).
Do et al., "Engineering *Escherichia coli* for fermentative dihydrogen production: potential role of NADH-ferredoxin oxidoreductase from the hydrogenosome of anaerobic protozoa," *Appl. Biochem. Biotechnol.* 153(1-3):21-33 (2009).
Do et al., "Growth of rhodospirillum rubrum on synthesis gas: conversion of CO to $H_2$ and Poly-$\beta$-hydroxyalkanoate," *Biotechnol. Bioeng.* 97(2):279-286 (2007).
Dobbek et al., "Crystal structure of a carbon monoxide dehydrogenase reveals a [Ni-4Fe-5S] cluster," *Science* 293(5533):1281-1285 (2001).
Dombek and Ingram, "Ethanol production during batch fermentation with *Saccharomyces cerevisiae*: Changes in glycolytic enzymes and internal pH," *Appl. Environ. Microbiol.* 53:1286-1291 (1987).
Donnelly and Cooper, "Succinic semialdehyde dehydrogenases of *Escherichia coli*: Their role in the degradation of p-hydroxyphenylacetate and $\gamma$-aminobutyrate," *Eur. J. Biochem.* 113:555-561 (1981).
Donnelly and Cooper, "Two succinic semialdehyde dehydrogenases are induced when *Escherichia coli* K-12 Is grown on $\gamma$-aminobutyrate," *J. Bacteriol.* 145:1425-1427 (1981).
Donnelly et al., "A novel fermentation pathway in an *Escherichia coli* mutant producing succinic acid, acetic acid, and ethanol," *App. Biochem. Biotech.* 70-72:187-198 (1998).
Doten et al., "Cloning and Genetic Organization of the pca Gene cluster from *Acinetobacter calcoaceticus*," *J. Bacteriol.* 169(7):3168-3174 (1987).
Doyle et al., "Structural Basis for a Change in substrate Specificity: Crystal Structure of S113E Isocitrate Dehydrogenase in a Complex with Isopropylmalate, $Mg^{2+}$ and NAPD," *Biochemistry* 40:4234-4241 (2001).
Drake and Daniel, "Physiology of the thermophilic acetogen *Moorella thermoacetica*," *Res. Microbiol.* 155(10):869-883 (2004).
Drake, "Acetogenesis, acetogenic bacteria, and the acetyl-CoA "Wood/Ljungdahl" pathway: past and current perspectives," in *Acetogenesis*, H. L. Drake, (ed.), Chapman & Hall, New York, p. 3-60 (1994).
Drake, "Demonstration of hydrogenase in extracts of the homoacetate-fermenting bacterium *Clostridium thermoaceticum*," *J. Bacteriol.* 150(2):702-709 (1982).
Draths and Frost, "Environmentally compatible synthesis of adipic acid from D-glucose," *J. Am. Chem. Soc.* 116:399-400 (1994).
Drevland et al., "Enzymology and Evolution of the Pyruvate Pathway to 2-Oxobutyrate in *Methanocaldococcus jannachii*," *J. Bacteriol.* 189(12):4391-4400 (2007).
Drewke et al., "4-O-Phosphoryl-L-threonine, a substrate of the pdxC(serC) gene product involved in vitamin $B_6$ biosynthesis," *FEBS Lett.* 390:179-182 (1996).
Drewke et al., "Ethanol formation in adh) mutants reveals the existence of a novel acetaldehyde-reducing activity in *Saccharomyces cerevisiae*," *J. Bacteriol.* 172:3909-3917 (1990).

Driscoll and Taber, "Sequence Organization and Regulation of the *Bacillus subtilis* menBE Operon," *J. Bacteriol.* 174(15):5063-5071 (1992).

Drummond and Stern, "Enzymes of ketone body metabolism. II. Properties of an acetoacetate-synthesizing enzyme prepared from ox liver," *J. Biol. Chem.* 235:318-325 (1960).

Du et al., "Succinic acid production from wheat using a biorefining strategy," *Appl. Microbiol. Biotechnol.* 76:1263-1270 (2007).

Duarte et al., "Reconstruction and validation of *Saccharomyces cerevisiae* iND750, a fully compartmentalized genome-scale metabolic model," *Genome Res.* 14(7):1298-1309 (2004).

Duckworth et al., "The Binding of Reduced Nicotinamide Adenine Dinucleotide to Citrate Synthase of *Escherichia coli* K12," *Biochemistry* 15(1):108-114 (1976).

Duncan et al., "The pentafunctional arom enzyme of *Saccharomyces cerevisiae* is a mosaic of monofunctional domains," *Biochem. J.* 246:375-386 (1987).

Duncan et al., "Acetate utilization and butyryl Coenzyme A (CoA):acetate-CoA transferase in butyrate-producing bacteria from the human large intestine," *Appl. Environ. Microbiol.* 68(10):5186-5190 (2002).

Duncombe and Frerman, "Molecular and catalytic properties of the acetoacetyl-Coenzyme A thiolase of *Escherichia coli*," *Arch. Biochem. Biophys.* 176(1):159-170 (1976).

Duran et al., "Characterization of cDNA clones for the 2-methyl branched-chain enoyl-CoA reductase. An enzyme involved in branched-chain fatty acid synthesis in anerobic mitochondria of the parasitic nematode *Ascaris suum*," *J. Biol. Chem.* 268(30):22391-22396 (1993).

Durner et al., "Accumulation of Poly[(R)-3-Hydroxyalkanoates] *Pseudomonas oleovorans* during Growth with Octanoate in continuous culture at Different Dilution Rates," *Appl. Environ. Microbiol.* 66(8):3408-3414 (2000).

Durre and Bahl, "Microbial Production of Acetone/Butanol/Isopropanol," In Biotechnology vol. 6: "Products of Primary Metabolism", Second edition pp. 229-268, M. Roehr, ed. Published jointly by: VCH Verlagsgesellschaft mbH, Weinheim, Federal Republic of Germany and VCH Publishers Inc., New York, Ny (1996).

Dürre et al., "Solventogenic enzymes of *Clostridium acetobutylicum*: catalytic properties, genetic organization, and transcriptional regulation," *FEMS Microbiol. Rev.* 17:251-262 (1995).

Dürre, "Biobutanol: an attractive biofuel," Biotechnol. J. 2(12):1525-1534 (2007).

Dürre, "New insights and novel developments in clostridial acetone/butanol/isopropanol fermentation," *Appl. Microbiol. Biotechnol.* 49:639-648 (1998).

Dusch et al., "Expression of the *Corynebacterium glutamicum* panD gene encoding L-aspartate-α-decarboxylase leads to pantothenate overproduction in *Escherichia coli*," *Appl. Environ. Microbiol.* 65(4)1530-1539 (1999).

Dutscho et al., "Cloning and sequencing of the genes of 2-hydoxyglutaryl-CoA dehydratase from *Acidaminococcus fermentans*," *Eur. J. Biochem.* 181(3):741-746 (1989).

Dwiarti et al., "Purification and characterization of cis-aconitic acid decarboxylase from *Aspergillus terreus* TN484-M1," *J. Biosci Bioeng.* 94(1):29-33 (2002).

Dwyer et al., "Proton Abstraction reaction, Steady-State kinetics, and Oxidation-Reduction Potential of Human Glutaryl-CoA Dehydrogenase," *Biochemistry* 39:11488-11499 (2000).

Dykhuizen, "Chemostats used for studying natural selection and adaptive evolution," *Methods. Enzymol.* 224:613-631 (1993).

Eberhard and Gerlt, "Evolution of Function in the Crotonase Superfamily: The Stereochemical course of the Reaction catalyzed by 2-Ketocyclohexanecarboxyl-CoA Hydrolase," *J. Am. Chem. Soc.* 126:7188-7189 (2004).

Edegger et al., "Biocatalytic deuterium- and hydrogen-transfer using over-expressed ADH-'A': enhanced steroselectivity and $^2$H-labeled chiral alcohols," *Chem. Commun.* 22:2402-2404 (2006).

Eden et al., "Involvement of branched-chain amino acid aminotransferases in the production of fusel alcohols during fermentation in yeast," *Appl. Microbiol. Biotechnol.* 55:296-300 (2001).

Edwards and Palsson, "Metabolic flux balance analysis and the in silico analysis of *Escherichia coli* K-12 gene deletions," *BMC Bioinform.* 1:1 (2000).

Edwards and Palsson, "Systems properties of the Haemophilus influenzae Rd metabolic genotype," *J. Biol. Chem.* 274(25):17410-17416 (1999).

Edwards and Palsson, "The *Escherichia coli* MG1655 in silico Metabolic Genotype: Its Definition, Characteristics, and Capabilities," *Proc. Natl. Acad. Sci. U.S.A.* 97(10):5528-5533 (2000).

Edwards et al., "Metabolic modelling of microbes: the flux-balance approach," *Environ. Microbiol.* 4(3):133-140 (2002).

Edwards et al., "In Silico Predictions of *Escherichia coli* metabolic capabilities are Consistent with Experimental Data," *Nat. Biotechnol.* 19(2):125-130 (2001).

Efe et al., "Options for biochemical production of 4-hydroxybutyrate and its lactone as a substitute for petrochemical production," *Biotechnol. Bioeng.* 99:1392-1406 (2008).

Egland et al., "A cluster of bacterial genes for anaerobic benzene ring biodegradation," *Proc. Natl. Acad. Sci. U.S.A.* 94:6484-6489 (1997).

Eikmanns et al., "The phosphoenolpyruvate carboxylase gene of *Corynebacterium glutamicum*: Molecular cloning, nucleotide sequence, and expression." *Mol. Gen. Genet.* 218:330-339 (1989).

Elshahed et al., "Metabolism of Benzoate, Cyclohex-1-ene Carboxylate, and Cyclohexane Carboxylate by "*Syntrophus aciditrophicus*" Strain SB in Syntrophic Association with $H_2$-Using Microorganisms," *Appl. Environ. Microbiol.* 67(4):1728-1738 (2001).

Engel, "Butyryl-CoA Dehydrogenase from *Megasphaera elsdenii*," *Methods Enzymol.* 71:359-366 (1981).

Enomoto et al., "Cloning and sequencing of the gene encoding the soluble fumarate reductase from *Saccharomyces cerevisiae*," *DNA Res.* 3:263-267 (1996).

Ensign and Ludden, "Characterization of the CO Oxidation/$H_2$ Evolution System of *Rhodospirillum rubrum*. Role of a 22-kDa iron-sulfur protein in mediating electron transfer between carbon monoxide dehydrogenase and hydrogenase," *J. Biol. Chem.* 266(27)18395-18403 (1991).

Estévez et al., "X-ray crystallographic and kinetic correlation of a clinically observed human fumarase mutation," *Protein Sci.* 11(6):1552-1557 (2002).

Eulberg et al., "Characterization of a protocatechuate catabolic gene cluster from *Rhodococcus opacus* 1CP: evidence for a merged enzyme with 4-carboxymuconolactone-cecarboxylating and 3-oxoadipate enol-lactone-hydrolyzing activity," *J. Bacteriol.* 180:1072-1081 (1998).

Evans et al., "[$^{13}$C]propionate oxidatin in wild-type and citrate synthase mutant *Escherichia coli*: evidence for multiple pathways of propionate utilization," *Biochem. J.* 291(Pt 3):927-932 (1993).

Ezeji et al., "Butanol fermentation research: upstream and downstream manipulations," *Chem. Rec.* 4(5):305-314 (2004).

Faehnle et al., "A New Branch in the Family: Structure of Aspartate-β-semialdehyde Dehydrogenase from *Methanococcus jannaschii*," *J. Mol. Biol.* 353:1055-1068 (2005).

Feist et al., "The growing scope of applications of genome-scale metabolic reconstructions using *Escherichia coli*," *Nat. Biotechnol.* 26(6):659-667 (2008).

Feldberg and Datta, "L-threonine deaminase of *Rhodospirillum rubrum*. Purification and characterization," *Eur. J. Biochem.* 21(3):438-446 (1971).

Fell and Small, "Fat Synthesis in Adipose Tissue. An Examination of Stoichiometric Constraints," *Biochem. J.* 238(3):781-786 (1986).

Fernandez-Canon and Penalva, "Characterization of a fungal maleylacetoacetate isomerase gene and indentification of its human homologue," *J. Biol. Chem.* 273:329-337 (1998).

Fernandez-Valverde et al., "Purification of *Pseudomonas putida* Acyl Coenzyme A Ligase Active with a Range of aliphatic and Aromatic substrates," *Appl. Environ. Microbiol.* 59(4):1149-1154 (1993).

Fischer and Sauer, "Metabolic flux profiling of *Escherichi coli* mutants in central carbon metabolism using GC-MS," *Eur. J. Biochem.* 270(5):880-891 (2003).

Fish and Blumenthal, "2-Keto-3-deoxy-D-glucarate aldolase," *Methods Enzymol.* 9:529-534 (1966).

Fishbein and Bessman, "Purification and properties of an enzyme in human blood and rat liver microsomes catalyzing the formation and hydrolysis of γ-lactones. I. Tissue localization, stoichiometry, specificity, distinction from esterase," *J. Biol. Chem.* 241:4835-4841 (1966).

Fishbein and Bessman, "Purification and properties of an enzyme in human blood and rat liver microsomes catalyzing the formation and hydrolysis of γ-lactones. II. Metal ion effects, kinetics, and equilibria," *J. Biol. Chem.* 241:4842-4847 (1966).

Fitzgerald and Flanagan, "Characterization and sequence analysis of the human ornithine decarboxylase gene," *DNA* 8:(9):623-634 (1989).

Flint et al., "The role and properties of the iron-sulfur cluster in *Escherichia coli* dihydroxy-acid dehydratase," *J. Biol. Chem.* 268:14732-14742 (1993).

Flint, "Initial kinetic and mechanistic characterization of *Escherichia coli* fumarase A," *Arch. Biochem. Biophys.* 311(2):509-516 (1994).

Fochi, "Selective catalytic dehydrogenation of 1,4-cyclohexadiene to benzene. 1. Radical anions derived from stransition-metal arene complexes as promoters," *Organometallics* 7:2255-2256 (1988).

Fomine and Tlenkopatchev, "Cross-methathesis of dimethyl maleate and ethylene catalyzed by second generation ruthenium carbene complexes: B3LYP and MPW1K comparison study," *J. Org. Chem.* 691:5189-5196 (2006).

Fong and Palsson, "Metabolic gene-deletion strains of *Escherichia coli* evolve to computationally predicted growth phenotypes," *Nat. Genet.* 36(10):1056-1058 (2004).

Fong et al., "Description and Interpretation of Adaptive Evolution of *Escherichia coli* K-12 MG1655 by Using a Genome-Scale in Silico Metabolic Model," *J. Bacteriol.* 185(21):6400-6408 (2003).

Fong et al., "In Silico design and adaptive evolution of *Escherichia coli* for production of lactic acid," *Biotechnol. Bioeng.* 91(5):643-648 (2005).

Fonknechten et al., "A conserved gene cluster rules anaerobic oxidative degradation of L-ornithine," *J. Bacteriol.* 191(9):3162-3167 (2009).

Fontaine et al., "Molecular charcterization and transcriptional analysis of adhE2, the gene encoding the NADH-dependent aldehyde/alcohol dehydrogenase responsible for butanol production in alcohologenic cultures of *Clostridium acetobutylicum* ATCC 824," *J. Bacteriol.* 184:821-830 (2002).

Fontaine et al., "A New Type of Glucose Fermentation by *Clostridium thermoaceticum* N.Sp.," *J. Bacteriol.* 43(6):701-715 (1942).

Ford et al., "Molecular properties of the lyst[1+] gene and the regulation of α-aminoadipate reductase in *Schizosaccharomyces pombe*," *Curr. Genet.* 28:131-137 (1995).

Forouhar et al., "Structural and Functional Evidence for *Bacillus subtilis* PaiA as a Novel $N^1$-Spermidine/spermine Acetyltransferase," *J. Biol. Chem.* 280(48):40328-40336 (2005).

Forster et al., "Genome-scale reconstruction of the *Saccharomyces cerevisiae* metabolic network," *Genome Res.* 13(2):244-253 (2003).

Fox et al., "Characterization of the region encoding the CO-induced hydrogenase of *Rhodospirillum rubrum*," *J. Bacteriol.* 178(21):6200-6208 (1996).

Freiberg et al., "Identification and characterization of the first class of potent bacterial acetyl-CoA carboxylase inhibitors with antibacterial activity," *J. Biol. Chem.* 279:26066-26073 (2004).

Freidrich et al., "The complete stereochemistry of the enzymatic dehydration of 4-hydroxybutyryl Coenzyme A to crontonyl Coenzyme A," *Angew. Chem. Int. Ed.* 47:3254-3257 (2008).

Frerman and Duncombe, "Studies on the subunits of *Escherichia coli* Coenzyme A transferase. Reconstitution of an active enzyme," *Biochim. Biophys. Acta* 580(2):289-297 (1979).

Fries et al., "Reaction Mechanism of the heterotetrameric ($\alpha_2\beta_2$) E1 Component of 2-Oxo Acid Dehydrogenase Multienzyme Complexes," *Biochemistry* 42:6996-7002 (2003).

Frost and Draths, "Synthesis of adipic acid from biomass-derived carbon sources," *Biotechnol Adv.* 15(1):294 (1997).

Frost et al., "Dehydroquinate synthase from *Escherichia coli*: purification, cloning, and construction of overproducers of the enzyme," *Biochemistry* 23:4470-4475 (1984).

Frost, "Redefining chemical manufacture. Replacing petroleum with plant-derived feedstocks," *Ind. Biotechnol.* 1(1):23-24 (2005).

Fu et al., "Crystal structures of human glutaryl-CoA dehydrogenase with and without an alternate substrate: structural bases of dehydrogenation and decarboxylation reactions," *Biochemistry* 43(30):9674-9684 (2004).

Fujii et al., "Characterization of L-lysine 6-aminotransferase and its structural gene from *Flavobacterium lutescens* IFO3084," *J. Biochem.* 128:391-397 (2000).

Fujii et al., "Error-prone rolling circle amplification: the simplest random mutagenesis protocol," *Nat. Protoc.* 1:2493-2497 (2006).

Fujii et al., "One-step random mutagenesis by error-prone rolling circle amplification," *Nucleic Acids Res.* 32:e145 (2004).

Fujii, T. et al. "Molecular Cloning, Sequence Analysis, and Expression of the Yeast Alcohol *Acetyltransferase* Gene," *Appl. Environ. Microbiol.* 60:2786-2792 (1994).

Fujishiro et al., "Crystallization and Some Properties of Acetylpolyamine Amidohydrolase From *Mycoplana bullata*," *Biochem. Biophys. Res. Commun.* 157(3):1169-1174 (1988).

Fujita et al., "Novel Substrate Specificity of Designer 3-Isopropylmalate Dehydrogenase Derived from *Thermus thermophilus* HB8," *Biosci. Biotechnol. Biochem.* 65(12):2695-2700 (2001).

Fukao et al., "Succinyl-CoA:3-ketoacid CoA transferase (SCOT): cloning of the human SCOT gene, tertiary structural modeling of the human SCOT monomer, and characterization of three pathogenic mutations," *Genomics* 68:144-151 (2000).

Fukuda and Wakagi, "Substrate recognition by 2-oxoacid:ferredoxin oxidoreductase from *Sulfolobus* sp. Strain 7," *Biochim. Biophys. Acta* 1597:74-80 (2002).

Fukuda et al., "Role of a highly conserved YPITP motif in 2-oxoacid:ferredoxin oxidoreductase Heterologous expression of the gene from *Sulfolobus* sp. Strain 7, and characterization of the recombinant and variant enzymes," *Eur. J. Biochem.* 268:5639-5646 (2001).

Fukui et al., "Engineering of *Ralstonia eutropha* for production of poly(3-hydroxybutyrate-co-3-hydroxyhexanoate) from fructose and solid-state properties of the copolymer," *Biomacromolecules* 3(3):618-624 (2002).

Fukumura et al, "Hydrolysis of cyclic and linear oligomers of 6-aminocaproic acid by a bacterial cell extract," *J. Biochem.* 59(6):531-536 (1966).

Fukumura et al., "Purification and properties of a novel enzyme, L-α-amino-ε-caprolactamase from *Cryptococcus laurentii*," *FEBS Lett.* 89(2):298-300 (1978).

Fuller and Leadlay, "Proton transfer in methylmalonyl-CoA epimerase from *Propionibacterium shermanii*. The reaction of (2R)-methylmalonyl-CoA in tritiated water," *Biochem. J.* 213(3):643-650 (1983).

Furdui and Ragsdale, "The role of pyruvate ferredoxin oxidoreductase in pyruvate synthesis during autotrophic growth by the Wood-Ljungdahl pathway," *J. Biol. Chem.* 275(37):28494-28499 (2000).

Furukawa et al., "Increased alcohol acetyltransferase activity by inositol limitation in *Saccharomyces cerevisiae* in sake mash," *J. Biosci. Bioeng.* 96(4):380-386 (2003).

Galagan et al., "The genome of *M. acetivorans* reveals extensive metabolic and physiological diversity," *Genome Res.* 12(4):532-542 (2002).

Gallagher et al., "The crystal structure of chorismate lyase shows a new fold and a tightly retained product," *Proteins* 44:304-311 (2001).

Gangloff et al., "Molecular cloning of the Yeast Mitochondrial Aconitase Gene (ACO1) and Evidence of a Synergistic Regulation of Expression by Glucose plus Glutamate," *Mol. Cell. Biol.* 10(7):3551-3561 (1990).

Garras et al., "Subcellular localisation and induction of NADH-sensitive acetyl-CoA hydrolase and propionyl-CoA hydrolase activities in rat liver under lipogenic conditions after treatment with sulfur-substituted fatty acids," *Biochim. Biophys Acta* 1255(2):154-160 (1995).

Garvie, "Bacterial lactate dehydrogenases," *Microbiol. Rev.* 44:106-139 (1980).

Gay et al., "Cloning Structural Gene sacB, Which Codes for Exoenzyme Levansucrase of *Bacillus subtilis*: Expression of the Gene in *Escherichia coli*," *J. Bacteriol.* 153(3):1424-1431 (1983).

Genda et al., "Purification and characterization of fumarase from *Corynebacterium glutamicum*," *Biosci. Biotechnol. Biochem.* 70:1102-1109 (2006).

Gerhardt et al. "Fermentation of 4-aminobutyrate by *Clostridium aminobutyricum*: cloning of two genes involved in the formation dehydration of 4-hydroxybutyrl-CoA," *Arch. Microbiol.* 174:189-199 (2000).

Gerischer and Dürre, "mRNA Analysis of the *adc* Gene Region of *Clostridium acetobutylicum* during the Shift to Solventogenesis," *J. Bacteriol.* 174(2):426-433 (1992).

Gescher et al., "Genes coding for a new pathway of aerobic benzoate metabolism in *Azoarcus evansii*," *J Bacteriol.* 184(22):6301-6315 (2002).

Giaever et al., "Functional profiling of the *Saccharomyces cerevisiae* genome," *Nature* 418(6896):387-391 (2002).

Gibbs et al., "Degenerate olignucleotide gene shuffling (DOGS): a method for enhancing the frequence of recombination with family shuffling," *Gene* 271:13-20 (2001).

Gibson (née Thomas) et al., "Cross metathesis of the amino acid homoallylglycine," *Chem. Commun.* 1107-1108 (1997).

Gibson and McAlister-Henn, "Physical and genetic interactions of cytosolic malate dehydrogenase with other gluconeogenic enzymes," *J. Biol. Chem.* 278:25628-25636 (2003).

Giesel and Simon, "On the occurrence of enoate reductase and 2-oxo-carboxylate reductase in clostridia and some observations on the amino acid fermentation by *Peptostreptococcus anaerobius*," *Arch. Microbiol.* 135(1):51-57 (1983).

Gillyon et al., "Putrescine Breakdown in the Yeast *Candida boidinii*: Subcellular Location of Some of the Enzymes Involved and Properties of Two Acetamidoaldehyde Dehydrogenases," *J. of Gen. Microbiol.* 133:2477-2485 (1987).

Glasemacher et al., "Purification and properties of acetyl-CoA synthetase (ADP-forming), an archael enzyme of acetate formation and ATP synthesis, from the hyperthermophile *Pyrococcus furiosus*," *Eur. J. Biochem.* 244:561-567 (1997).

Göbel et al., "Degradation of Aromatics and Chloroaromatics by *Pseudomonas* sp. Strain B13: Cloning, Characterization, and analysis of Sequences Encoding 3-Oxoadipate:Succinyl-Coenzyme A (CoA) Transferase and 3-oxoaipyl-CoA Thiolase," *J. Bacteriol.* 184(1):216-223 (2002).

Goda et al., "Cloning, sequencing, and expression in *Escherichia coli* of the *Clostridium tetanomorphum* gene encoding β-methylaspartase and characterization of the recombinant protein," *Biochemistry* 31(44):10747-10756 (1992).

Gokarn et al., "Expression of pyruvate carboxylase enhances succinate production in *Escherichia coli* without affecting glucose uptake," *Biotechnol. Lett.* 20:795-798 (1998).

Gokarn et al., "Metabolic Analysis of *Escherichia coli* in the Presence and Absence of the Carboxylating Enzymes Phosphoenolpyruvate Carboxylase and Pyruvate Carboxylase," *Appl. Environ. Microbiol.* 66:1844-1850 (2000).

Gokarn, et al., "The physiological effects and metabolic alterations caused by the expression of *Rhizobium etli* pyruvate carboxylase in *Escherichia coli*," *Appl. Microbiol. Biotechnol.* 56(1-2):188-195 (2001).

Gokulan et al., "Crystal structure of *Mycobacterium tuberculosis* diaminipimelate decarboxylase, an essential enzyme in bacterial lysine biosynthesis," *J. Biol. Chem.* 278(20):18588-18596 (2003).

Goldberg et al., "Improved Conversion of Fumarate to Succinate by *Escherichia coli* Strains Amplified for Fumarate Reductase," *Appl. Environ. Microbiol.* 45:1838-1847 (1983).

Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).

González and Robb, "Genetic analysis of *Carboxydothermus hydrogenoformans* carbon monoxide dehydrogenase genes cooF and cooS," *FEMS Microbiol. Lett.* 191(2):243-247 (2000).

Gonzalez et al., "Characterization of a (2R,3R)-2,3-Butanediol Dehydrogenase as the *Saccharomyces cerevisiae* YAL060W Gene Product," *J. Biol. Chem.* 275(46):35876-35885 (2000).

Gonzalez-Pajuelo et al., "Metabolic engineering of *Clostridium acetobutylicum* for the industrial production of 1,3-propanediol from glycerol," *Met. Eng.* 7:329-336 (2005).

Gordon and Doelle, "Purification, properties and immunological relationship of L(+)-lactate dehydrogenase from *Lactobacillus casei*," *Eur. J. Biochem.* 67:543-555 (1976).

Goupil et al., "Imbalance of Leucine Flux in *Lactococcus lactis* and Its Use for the Isolation of Diacetyl-Overproducing Strains," *Appl. Environ. Microbiol.* 62(7):2636-2640 (1996).

Goupil-Feuillerat et al., "Transcriptional and Translational Regulation of α-Acetolactate Decarboxylase of *Lactococcus lactis* subsp. *Lactis*," *J. Bacteriol.* 182(19):5399-5408 (2000).

Gourley et al., "The two types of 3-dehydroquinase have distinct structures but catalyze the same overall reaction," *Nat. Struct. Biol.* 6:521-525 (1999).

Grant and Patel. "The non-oxidative decarboxylation of p-hydroxybenzoic acid, gentisic acid, protocatechuic acid and gallic acid by *Klebsiella aerogenes* (*Aerobacter aerogenes*)," *Antonie Van Leeuwenhoek* 35:325-343 (1969).

Green and Bennett, "Genetic manipulation of acid and solvent formation in *Clostridium acetobutylicum* ATCC 824," *Biotechnol. Bioeng.* 58(2-3):215-221 (1998).

Green and Nichols, "p-Aminobenzoate biosynthesis in *Escherichia coli*. Purification of aminodeoxychorismate lyase and cloning of pabC," *J. Biol. Chem.* 266:12971-12975 (1991).

Green et al., "Catabolism of α-ketoglutarate by a sucA mutant of *Bradyrhizobium japonicum*: evidence for an alternative tricarboxylic acid cycle," *J. Bacteriol.* 182:2838-2844 (2000).

Green et al., "Characterization and sequence of *Escherichia coli* pabC, the gene encoding aminodeoxychorismate lyase, a pyridoxal phosphate-containing enzyme," *J. Bacteriol.* 174:5317-5323 (1992).

Grethlein and Jain, "Bioprocessing of coal-derived synthesis gases by anaerobic bacteria," *Trends Biotech.* 10:418-423 (1992).

Grolle et al., "Isolation of the dxr gene of *Zymomonas mobilis* and characterization of the 1-deoxy-D-xylulose 5-phosphate reductoisomerase," *FEMS Microbiol. Lett.* 191:131-137 (2000).

Grubbs, "Olefin Meethathesis," *Tetrahedron* 60:7117-7140 (2004).

Gu et al., "Crystal structure of shikimate kinase from *Mycobacterium tuberculosis* reveals the dynamic role of the LID domain in catalysis," *J. Mol. Biol.* 319:779-789 (2002).

Gueldener et al., "A second set of *loxP* marker cassettes for Cre-mediated multiple gene knockouts in budding yeast," *Nucleic Acids Res.* 30(6):e23 (2002).

Guerra et al., "Role of transmembrane segment M8 in the biogenesis and function of yeast plasma-membrane $H^+$-ATPase," *Biochim. Biophys. Acta* 1768:2383-2392 (2007).

Guest et al., "The fumarase genes of *Escherichia coli*: location of the fumB gene and discovery of a new gene (fumC)," *J. Gen. Microbiol.* 131(11):2971-2984 (1985).

Guettler et al., "*Actinobacillus succinogenes* sp. nov., a novel succinic-acid-producing strain from the bovine rumen," *Int. J. Syst. Bacteriol.* 49:207-216 (1999).

Guirard and Snell, "Purification and properties of ornithine decarboxylase from *Lactobacillus* sp. 30a," *J. Biol. Chem.* 255:5960-5964 (1980).

Guo and Bhattacharjee, "Posttranslational activation, site-directed mutation and phylogenetic analyses of the lysine biosynthesis enzymes α-aminoadipate reductase Lys1p (AAR) and the phosphopantetheinyl transferase Lys7p (PPTase) from *Schizosaccharomyces pombe*," *Yeast* 21:1279-1288 (2004).

Guo and Bhattacharjee, "Site-directed mutational analysis of the novel catalytic domains of α-aminoadipate reductase (Lys2p) from *Candida albicans*," *Mol. Gen. Gemonics* 269:271-279 (2003).

Guterman et al., "Generation of phenylpropanoid pathway-derived volatiles in transgenic plants: rose alcohol acetyltransferase produces phenylethyl acetate and benzyl acetate in petunia flowers," *Plant Mol. Biol.* 60(4):555-563 (2006).

Gutierrez et al., "A mutant D-amino acid aminotransferase with broad substrate specificity: construction by replacement of the interdoman loop Pro119-Arg120-Pro121 by Gly-Gly-Gly," *Protein Eng.* 11:53-58 (1998).

Gutknecht et al., "The dihydroxyacetone kinase of *Escherichia coli* utilizes a phosphoprotein instead of ATP as phosphoryl donor," *EMBO J.* 20(10):2480-2486 (2001).

Guyer et al., "Identification of a sex-factor-affinity site in *E. coli* as γδ," *Cold Spring Harbor Symp. Quant. Biol.* 45:135-140 (1981).

Guzman et al., "Tight regulation, modulation, and high-level expression by vectors containing the arabinose $P_{BAD}$ promoter," *J. Bacteriol.* 177:4121-4130 (1995).

Haarasilta and Oura, "On the activity and regulation of anaplerotic and gluconeogenetic enzymes during the growth process of baker's yeast. The biphasic growth," *Eur. J. Biochem.* 52:1-7 (1975).

Hadfield et al., "Active Site Analysis of the Potential Antimicrobial Target Aspartate Semialdehyde Dehydrogenase," *Biochemistry* 40:14475-14483 (2001).

Hadfield et al., "Structure of Aspartate-β-semialdehyde Dehydrogenase from *Escherichia coli*, A Key Enzyme in the Aspartate Family of Amino Acid Biosynthesis," *J. Mol. Biol.* 289:991-1002 (1999).

Hagemeier et al., "Insight into the mechanism of biological methanol activation based on the crystal structure of the methanol-cobalamin methyltransferase complex," *Proc. Natl. Acad. Sci. U.S.A.* 103(50):18917-18922 (2006).

Hahm et al., "Characterization and evaluation of a *pta* (phosphotransacetylase) negative mutant of *Escherichia coli* HB101 as a production host of foreign lipase," *Appl. Microbiol. Biotechnol.* 42:100-107 (1994).

Haller et al., "Discovering new enzymes and metabolic pathways: conversion of succinate to propionate by *Escherichia coli*," *Biochem.* 39(16):4622-4629 (2000).

Hambraeus and Nyberg, "Enzymatic Hydrogenation of trans-2-Nonenal in Barley," *J. Agric. Food Chem.* 53:8714-8721 (2005).

Hamilton-Kemp et al., "Production of the long-chain alcohols octanol, decanol, and dodecanol by *Escherichia coli*," *Curr. Microbiol.* 51:82-86 (2005).

Hammer and Bode, "Purification and characterization of an inducible L-lysine:2-oxoglutarate 6-aminotransferase from *Candida utilis*," *J. Basic Microbiol.* 32:21-27 (1992).

Han et al., "Biochemical characterization and inhibitor discovery of shikimate dehydrogenase from *Helicobacter pylori*," *FEBS J.* 273:4682-4692 (2006).

Hanai et al., "Engineered synthetic pathway for isopropanol production in *Escherichia coli*," *Appl. Environ. Microbiol.* 73(24):7814-7818 (2007).

Hansford, "Control of mitochondrial substrate oxidation," *Curr. Top Bioenergy* 10:217-278 (1980).

Harder, "Anaerobic degradation of cyclohexane-1,2-diol by a new *Azoarcus* species," *Arch. Microbiol.* 168:199-204 (1997).

Hardison et al., "Globin Gene Server: A prototype E-Mail Database Server Featuring Extensive Multiple Alignments and Data Compilation for Electronic Genetic Analysis," *Genomics* 21:344-353 (1994).

Harker and Bramley, "Expression of prokaryotic 1-deoxy-D-xylulose-5-phosphatases in *Escherichia coli* increases carotenoid and ubiquinone biosynthesis," *FEBS Lett.* 448:115-119 (1999).

Harms and Thauer, "Methylcobalamin: Coenzyme M methyltransferase isoenzymes MtaA and MtbA from *Methanosarcina barkeri*. Cloning, sequencing and differential transcription of the encoding genes, and functional overexpression of the mtaA gene in *Escherichia coli*," *Eur. J. Biochem.* 235(3):653-659 (1996).

Harrison and Harwood, "The pimFABCDE operon from *Rhodopseudomonas palustris* mediates dicarboxylic acid degradation and participates in anaerobic benzoate degradation," *Microbiology* 151:727-736 (2005).

Hartel et al., "Purification of glutaryl-CoA dehydrogenase from *Pseudomonas* sp., an enzyme involved in the anaerobic degradation of benzoate," *Arch. Mirobiol.* 159:174-181 (1993).

Harwood and Parales, "The β-ketoadipate pathway and the biology of self-identity," *Annu. Rev. Microbiol.* 50:553-590 (1996).

Harwood et al., "Anaerobic metabolism of aromatic compounds via the benzoyl-CoA pathway," *FEMS Microbiol. Rev.* 22:439-458 (1999).

Harwood et al., "Identification of the pcaRKF Gene cluster from *Pseudomonas putida*: Involvement in Chemotaxis, Biodegradation, and Transport of 4-Hydroxybenzoate," *J. Bacteriol.* 176(21):6479-6488 (1994).

Hasan and Nester, "Dehydroquinate synthase in *Bacillus subtilis*. An enzyme associated with chorismate synthase and flavin reductase," *J. Biol. Chem.* 253:4999-.5004 (1978).

Hasegawa et al., "Transcriptional regulation of ketone body-utilizing enzyme, acetoacetyl-CoA synthetase, by C/EBPα during adipocyte differentiation," *Biochim. Biophys. Acta.* 1779(6-7):414-419 (2008).

Haselbeck and McAlister-Henn, "Isolation, nucleotide sequence, and disruption of the *Saccharomyces cerevisiae* gene encoding mitochondrial NADP(H)-specific isocitrate dehydrogenase," *J. Biol. Chem.* 266(4):2339-2345 (1991).

Hashidoko et al., "Cloning of a DNA fragment carrying the 4-hydroxycinnamate decarboxylase (pofK) gene from *Klebsielss oxytoca* and its constitutive expression in *Escherichia coli* JM109 cells," *Biosci. Biotech. Biochem.* 58(1):217-218 (1994).

Hashimoto et al., "Activation of L-Lysine ε-Dehydrogenase from *Agrobacterium tumefaciens* by Several Amino Acids and Monocarboxylates," *J. Biochem.* 106:76-80 (1989).

Hasson et al., "The crystal structure of benzoylfomate decarboxylase at 1.6 Å resolution: diversity of catalytic residues in thiamin diphosphate-dependent enzymes," *Biochemistry* 37:9918-9930 (1998).

Hatakeyama et al., "Analysis of oxidation sensitivity of maleate cis-trans isomerase from *Serratia marcesens*," *Biosci. Biotechnol. Biochem.* 64:1477-1485 (2000).

Hatakeyama et al., "Gene Cloning and Characterization of Maleate cis-trans Isomerase from *Alcaligenes faecalis*," *Biochem. Biophys. Res. Comm.* 239:74-79 (1997).

Hawes et al., "Primary structure and tissue-specific expression of human β-hydroxyisobutyryl-Coenzyme A hydrolase," *J. Biol. Chem.* 271:26430-26434 (1996).

Hawes et al., "Mammalian 3-hydroxyisobutyrate dehydrogenase," *Methods Enzymol.* 324:218-228 (2000).

Hayashi et al., "Properties of 2-hydroxyglutarate dehydrogenase from *Fusobacterium*," *J. Nihon. Univ. Sch. Dent.* 28(1):12-21 (1986).

Hayden et al., "Glutamate dehydrogenase of *Halobacterium salinarum*: evidence that the gene sequence currently assigned to the NADP$^+$-dependent enzyme is in fact that of the NAD$^+$-dependent glutamate dehydrogenase," *FEMS Microbiol. Lett.* 211:37-41 (2002).

Hayes et al., "Combining computational and experimental screening for rapid optimization of protein properties," *Proc. Natl. Acad. Sci. U.S.A.* 99(25):15926-15931 (2002).

Hayes et al., "The Biofine Process: Production of Levulinic Acid, Furfural and Formic Acid from Lignocellulosic Feedstocks," In *Biorefineries: Industrial Proceses and Products*, Wiley, Weinheim, Germany, 139-164. (2006).

Haywood and Large, "4-Acetamidobutyrate Deacetylase in the Yeast *Candida boidinii* Grown on Putrescine or Spermidine as Sole Nitrogen, Source and Its Probable Role in Polyamine Catabolism," *J. Gen. Microbiol.* 132:7-14 (1986).

Haywood et al., "Characterization of two 3-ketothiolases possessing differing substrate specificities in the polyhydroxyalkanoate synthesizing organism *Alcaligenes eutrophus*," *FEMS Microbiol. Lett.* 52:91-96 (1988).

He and Wiegel. "Purification and characterization of an oxygen-sensitive reversible 4-hydroxybenzoate decarboxylase from *Clostridium hydroxybenzoicum*," *Eur. J. Biochem.* 229:77-82 (1995).

Heidlas and Tress!, "Purification and Properties of two oxidoreductases catalyzing the enantioselective reduction of diacetyl and other diketones from baker's yeast," *Eur. J. Biochem.* 188:165-174 (1990).

Heipieper and Isken, "Ethanol tolerance and membrane fatty acid adaptation in adh multiple and null mutants of *Kluyveromyces lactis*," *Res. Microbiol.* 151:(9):777-784 (2000).

Helin et al., "The refined x-ray structure of muconate lactonizing enzyme from *Pseudomonas putida* PRS2000 at 1.85 Å resolution," *J. Mol. Biol.* 254:918-941 (1995).

Heller et al., "Cloning and expression of the gene for the vitamin $B_{12}$ receptor protein in the outer membrane of *Escherichia coli*," *J. Bacteriol.* 161:896-903 (1985).

Hemschemeier et al., "Biochemical and physiological characterization of the pyruvate formate-lyase Pfl1 of *Chlamydomonas reinhardtii*, a typically bacterial enzyme in eukaryotic alga," *Eukaryot. Cell* 7:518-526 (2008).

Henne et al., "Construction of environmental DNA libraries in *Escherichia coli* and screening for the presence of genes conferring utilization of 4-hydroxybutyrate," *Appl. Environ. Microbiol.* 65(9):3901-3907 (1999).

Hennessy et al., "The reactivity of gamma-hydroxybutyric acid (GHB) and gamma-butyrolactone (GBL) in alcoholic solutions," *J. Forensic. Sci.* 49(6):1220-1229 (2004). (provided electronically by publisher as pp. 1-10).

Henning et al., "Identification of novel benzoylformate decarboxylases by growth selection," *Appl. Environ. Microbiol.* 72:7510-7517 (2006).

Henriksson et al., "The 1.9 Å resolution structure of *Mycobacterium tuberculosis* 1-deoxy-D-xylulose 5-phosphate reductoisomerase, a potential drug target," *Acta. Crystallogr. D. Biol. Crystallogr.* 62(Pt 7):807-813 (2006).

Henstra et al., "Microbiology of synthesis gas fermentation for biofuel production," *Curr. Opin. Biotechnol.* 18:200-206 (2007).

Hermes et al., "Searching sequence space by definably random mutagenesis: Improving the catalytic potency of an enzyme," *Proc. Natl. Acad. Sci U.S.A.* 87:696-700 (1990).

Herrmann et al., "Energy Conservation via Electron-Transferring Flavoprotein in Anaerobic Bacteria," *J. Bacteriol.* 190(3):784-791 (2008).

Herrmann et al., "Two β-alanyl-CoA:ammonia lyases in *Clostridium propionicum*," *FEBS J.* 272:813-821 (2005).

Hespell et al., "Stabilization of *pet* Operon Plasmids and Ethanol Production in *Escherichia coli* Strains Lacking Lactate Dehydrogenase and Pyruvate Formate-Lyase Activities," *Appl. Environ. Microbiol.* 62:4594-4597 (Dec. 1996).

Hesslinger et al., "Novel keto acid formate-lyase and propionate kinase enzymes are components of an anaerobic pathway in *Escherichia coli* that degrades L-threonine to propionate," *Mol. Microbiol.* 27(2):477-492 (1998).

Hester et al., "Purification of active $E1\alpha_2\beta_2$ of *Pseudomonas putida* branched-chain-oxoacid dehydrogenase," *Eur. J. Biochem.* 233:828-836 (1995).

Hetzel et al., "Acryloyl-CoA reductase from clostridium propionicum. An enzyme complex of pripionyl-CoA dehydrogenase and electron-transferring flavoprotein," *Eur. J. Biochem.* 270:902-910 (2003).

Heydari et al., "Highly Stable L-Lysine 6-Dehydrogenase from the thermophile *Geobacillus stearothermophilus* Isolated from a Japanese Hot Spring: characterization, Gene Cloning and sequencing, and Expression," *Appl. Environ. Microbiol.* 70(2):937-942 (2004).

Hibbert et al., "Directed evolution of biocatalytic processes," *Biomol. Eng.* 22:11-19 (2005).

Highbarger et al., "Mechanism of the reaction catalyzed by acetoacetate decarboxylase. Importance of lysine 116 in determining the $pK_a$ of active-site lysine 115," *Biochemistry* 35(1):41-46 (1996).

Hijarrubia et al., "Domain Structure Characterization of the Multifunctional α-Aminoadipate Reductase from *Penicillium chrysogenum* by Limited Proteolysis," *J. Biol. Chem.* 278(10):8250-8256 (2003).

Hill et al., "PCR based gene engineering of the Vibrio harveyi lux operon and the *Escherichia coli* trp operon provides for biochemically functional native and fused gene products," *Mol. Gen. Genet.* 226:41-48 (1991).

Hillmer and Gottschalk, "Particulate Nature of Enzymes Involved in the Fermentation of Ethanol and Acetate by *Clostridium kluyveri*," *FEBS Lett.* 21(3):351-354 (1974).

Hillmer and Gottschalk, "Solubilization and partial characterization of particulate dehydrogenases from *Clostridium kluyveri*," *Biochim. Biophys. Acta* 334:12-23 (1974).

Hirano et al., "Purification and characerization of the Alcohol Dehydrogenase with a Broad Substrate Specificy Originated from 2-Phenylethanol-Assimilating *Brevibacterium* sp. KU 1309," *J. Biosci. Bioeng.* 100(3): 318-322 (2005).

Hirata et al., "Stereochemistry of reduction of the endocyclic double bond of (-)-carvone with the enzyme preparation from cultured cells of *Nicotiana tabacum*," *Phytochemistry* 28(12):3331-3333 (1989).

Hiser et al., "ERG10 from *Saccharomyces cerevisiae* encodes acetoacetyl-CoA thiolase," *J. Biol. Chem.* 269:31383-31389 (1994).

Ho et al., "Regulation of serine biosynthesis in Arabidopsis. Crucial role of plastidic 3-phosphoglycerate dehydrogenase in non-photosynthetic tissues," *J. Biol. Chem.* 274:397-402 (1999).

Hoang et al., "A broad-host-range Flp-FRT recombination system for site-specific excision of chromosomally-located DNA sequences: application for isolation of unmarked *Pseudomonas aeruginosa* mutants," *Gene* 212(1):77-86 (1998).

Hoffmann and Dimroth, "Sterochemistry of the methylmalonyl-CoA decarboxylation reaction," *FEBS Lett.* 220:121-125 (1987).

Hoffmeister et al., "Mitochondrial trans-2-enoyl-CoA reductase of wax ester fermentation from *Euglena gracilis* defines a new family of enzymes involved in lipid synthesis," *Biol. Chem.* 280(6):4329-4338 (2005).

Hofmeister and Buckel, "(R)-lactyl-CoA dehydratase from *Clostridium propionicum*. Stereochemistry of the dehydration of (R)-2-hydroxybutyryl-CoA to crotonly-CoA," *Eur. J. Biochem.* 206(2):547-552 (1992).

Hofmeister et al., "Cloning and expression of the two genes coding for L-serine dehydratase from *Peptostreptococcus asaccharolyticus*: relationship of the iron-sulfur protein to both L-serine dehydratases from *Escherichia coli*," *J. Bacteriol.* 179(15):4937-4941 (1997).

Hogan et al., "Improved Specificity toward Substrates with Positively Charged Side chains by Site-Directed Mutagenesis of the L-Lactate Dehydrogenase of *Bacillus stearothermophilus*," *Biochemistry* 34:4225-4230 (1995).

Holloway and Marsh, "Adenosylcobalamin-dependent glutamate mutase from *Clostridium tetanomorphum*. Overexpression in *Escherichia coli*, purification, and characterization of the recombinant enzyme," *J. Biol. Chem.* 269(32):20425-20430 (1994).

Holms, "The central metabolic pathways in *Escherichia coli*: relationship between flux and control at a branch point, efficiency of conversion to biomass, and excretion of acetate," *Curr. Top Cell. Regul.* 28:69-105 (1986).

Hong and Lee, "Metabolic flux analysis for succinic acid production by recombinant *Escherichia coli* with amplified malic enzyme activity," *Biotechnol. Bioeng.* 74(2):89-95 (2001).

Hong and Lee, "Enhanced Production of Succinic Acid by Metabolically Engineered *Escherichia coli* with Amplified Activities of Malic Enzyme and Fumarase," *Biotechnol. Bioprocess. Eng.* 9:4:252-255 (2004).

Hong et al., "The genome sequence of the capnophilic rumen bacterium *Mannheimia succiniciproducens*." *Nat. Biotechnol.* 22(10):1275-1281 (2004).

Hong et al., "Importance of redox balance on the production of succinic acid by metabolically engineered *Escherichia coli*," *Appl. Microbiol. Biotechnol.* 58:286-290 (2002).

Horswill and Escalante-Semerena, "In vitro conversion of propionate to pyruvate by *Salmonella enterica* enzymes: 2-methylcitrate dehydratase (PrpD) and aconitas Enzymes catalyze the conversion of 2-methylcitrate to 2-methylisocitrate," *Biochemistry* 40(15):4703-4713 (2001).

Horton et al., "Heterologous expression of the *Saccharomyces cerevisiae* alcohol acetyltransferase genes in *Clostridium acetobutylicum* and *Escherichia coli* for the production of isoamyl acetate," *J. Ind. Microbiol. Biotechnol.* 30(7):427-432 (2003).

Howard et al., "Titanium Metallacarbene-Metallacylobutane Reactions: Stepwise Metathesis," *J. Am. Chem. Soc.* 102:6876-6878 (1980).

Hsu et al., "Expression of an aromatic-dependent decarboxylase which provides growth-essential $CO_2$ equivalents for the acetogenic (Wood) pathway of *Clostridium thermoaceticum*," *J. Bacteriol.* 172:5901-5907 (1990).

Hu et al., "The catalytic intermediate stabilized by a "down" active site loop for diaminopimelate decarboxylase from *Helicobacter*

*pylori*. Enzymatic characterization with crystal structure analysis," *J. Biol. Chem.* 283(30):21284-21293 (2008).
Huang et al., "Genetic characterization of the resorcinol catabolic pathway in *Corynebacterium glutamicum*," *Appl. Environ. Microbiol.* 72:7238-7245 (2006).
Huang et al., "Purification and characterization of a ferulic acid decarboxylase from *Pseudomonas fluorescens*," *J. Bacteriol.* 176:5912-5918 (1994).
Huang et al., "Identification and characterization of a second butyrate kinase from *Clostridium acetobutylicum* ATCC 824," *J. Mol. Microbiol. Biotechnol.* 2(1):33-38 (2000).
Hübner et al., "The mechanism of substrate activation of pyruvate decarboxylase: A first approach," *Eur. J. Biochem.* 92:175-181 (1978).
Huder and Dimroth, "Sequence of the sodium ion pump methylmalonyl-CoA decarboxylase from *Veillonella parvula*," *J. Biol. Chem.* 268:24564-24571 (1993).
Hughes et al., "Cloning and expression of pca genes from *Pseudomonas putida* in *Escherichia coli*," *J. Gen. Microbiol.* 134:2877-2887 (1988).
Hughes et al., "Evidence for isofunctional enzymes in the degradation of phenol, m- and p-toluate, and p-cresol via catechol meta-cleavage pathways in *Alcaligenes eutrophus*," *J. Bacteriol.* 158(1):79-83 (1984).
Hugler et al., "Malonyl-Coenzyme A Reductase from Chloroflexus aurantiacus, a Key Enzyme of the 3-Hydroxypropionate Cycle for Autotrophic CO2 Fixation," *J. Bacteriol.* 184(9):2404-2410 (2002).
Huh et al., "Global analysis of protein localization in budding yeast," *Nature* 425:686-691 (2003).
Huisman and Lalonde, "Enzyme evolution for chemical process applications," In R.N. Patel (ed.), *Biocatalysis in the pharmaceutical and biotechnology industries*, CRC Press, p. 717-742 (2007).
Huo and Viola, "Substrate Specificity and Identification of Functional Groups of Homoserine Kinase from *Escherichia coli*," *Biochemistry* 35:16180-16185 (1996).
Husain and Steenkamp, "Partial purification and characterization of glutaryl-Coenzyme A dehydrogenase, electron transfer flavoprotein, and electron transfer flavoprotein-Q oxidoreductase from *Paracoccus denitrificans*," *J. Bacteriol.* 163:709-715 (1985).
Hustede et al., "Cloning of poly(3-hydroxybutyric acid) synthase genes of *Rhodobacter sphaeroides* and *Rhodospirillum rubum* and heterologous expression in *Alcaligenes eutrophys*," *FEMS Microbiol. Lett.* 93:285-290 (1992).
Ibarra et al., "*Escherichia coli* K-12 undergoes adaptive evolution to achieve in silico predicted optimal growth," *Nature* 420(6912):186-189 (2002).
Ichikawa et al., "Catalytic reaction of 1,3-butanediol over solid acids," *J. Mol. Catalysis A Chem.* 256:106-112 (2006).
Ichikawa et al., "PIO study on 1,3-butanediol dehydration over $CeO_2$ (1 1 1) surface," *J. Mol. Catalysis A Chem.* 231:181-189 (2005).
Iffland et al., "Directed Molecular Evolution of Cytochrome *c* Peroxidase," *Biochemistry* 39:10790-10798 (2000).
Ikai and Yamamoto, "Identification and analysis of a gene encoding L-2,4-diaminobutyrate:2-ketoglutarate 4-aminotransferase involved in the 1,3-diaminopropane production pathway in *Acinetobacter baummanni*," *J. Bacteriol.* 179:5118-5125 (1997).
Imai and Ohno, "Measurement of yeast intracellular pH by image processing and the change it undergoes during growth phase," *J.Biotechnol.* 38:165-172 (1995).
Ingoldsby et al., "The discovery of four distinct glutamate dehydrogenase genes in a strain of *Halobacterium salinarum*," *Gene* 349:237-244 (2005).
Ingram and Vreeland, "Differential-Effects of Ethanol and Hexanol on the *Escherichia-coli* Cell-Envelope," *J. Bacteriol.* 144:481-488 (1980).
Inui et al., "Occurrence of Oxygen-Sensitive, NADP'-Dependent Pyruvate-Dehydrogenase in Mitochondria of *Euglena-gracilis*," *J. Biochem.* 96:931-934 (1984).
Inui et al., "Pyruvate-NADP$^+$ Oxidoreductase from *Euglena-gracilis*—the Kinetic-Properties of the Enzyme," *Arch. Biochem Bipophys.* 274:434-442 (1989).
Inui et al., "Wax Ester Fermentation in *Euglena-gracilis*," *FEBS Lett.* 150:89-93 (1982).

Inui et al., "Fatty acid synthesis in mitochondria of *Euglena gracilis*," *Euro. J. Biochem.* 142(1):121-126 (1984).
Inui et al., "Production and Composition of Wax Esters by Fermentation of *Euglena gracilis*," *Agr. Biol. Chem.* 47(11):2669-2671 (1983).
Inui et al., "Purification and characterization of pyruvate:NADP$^+$ oxidoreductase in *Euglena gracilis*," *J. Biol. Chem.* 262(19):9130-9135 (1987).
Inui et al., "Pyruvate:NADP$^+$ oxidoreductase from *Euglena gracilis*: mechanism of $O_2$-inactivation of the enzyme and its stability in the aerobe," *Arch. Biochem. Biophys.* 280:292-298 (1990).
Inui et al., "The physiological role of oxygen-sensitive pyruvate dehydrogenase in mitochondrial fatty acid synthesis in *Euglena gracilis*," *Arch. Biochem. Biophys.* 237(2):423-429 (1985).
Ishida et al., "Efficient production of L-Lactic acid by metabolically engineered *Saccharomyces cerevisiae* with a genome-integrated L-lactate dehydrogenase gene," *Appl. Envirom. Microbiol.* 71:1964-1970 (2005).
Ishige et al, "Long-chain aldehyde dehydrogenase that participates in n-alkane utilization and wax ester synthesis in *Acinetobacter* sp. strain M-1," *Appl. Environ. Microbiol.* 66:3481-3486 (2000).
Ishige et al., "Wax ester production from n-alkanes by Acinetobacter sp. strain M-1: ultrastructure of cellular inclusions and role of acyl Coenzyme A reductase," *Appl. Environ. Microbiol.* 68(3):1192-1195 (2002).
Ismaiel et al., "Purification and Characterization of a Primary-Secondary Alcohol Dehydrogenase from Two Strains of *Clostridium beijerinckii*," *J. Bacteriol.* 175(16):5097-5105 (1993).
Ismail et al., "Functional genomics by NMR spectroscopy. Phenylacetate catabolism in *Escherichia coli*," *Eur. J. Biochem.* 270(14):3047-3054 (2005).
Ito and Yanofsky, "Anthranilate synthetase, an enzyme specified by the tryptophan operon of *Escherichia coli*: Comparative studies on the complex and the subunits," *J. Bacteriol.* 97:734-742 (1969).
Ito et al., "Colistin nephrotoxicity: report of a case with light and electron microscopic studies," *Acta. Pathol. Jpn.* 19:55-67 (1969).
Ito et al., "D-3-hydroxybutyrate dehydrogenase from *Pseudomonas fragi*: molecular cloning of the enzyme gene and crystal structure of the enzyme," *J. Mol. Biol.* 355(4):722-733 (2006).
Iverson et al., "Structure of the *Escherichia coli* fumarate reductase respiratory complex," *Science* 284(5422):1961-1966 (1999).
Iwakura et al., "Studies on regulatory functions of malic enzymes. VI. Purification and molecular properties of NADP-linked malic enzyme from *Escherichia coli* W," *J. Biochem.* 85:1355-1365 (1979).
Izard and Blackwell, "Crystal structures of the metal-dependent 2-dehydro-3-deoxy-galacarate aldolase suggest a novel reaction mechanism," *EMBO J.* 19:3849-3856 (2000).
Izumi et al., "Structure and Mechanism of HpcG, a Hydratase in the Homoprotocatechuate Degradation Pathway of *Escherichia coli*," *J. Mol. Biol.* 370:899-911 (2007).
Jacobi et al., "The hyp operon gene products are required for the maturation of catalytically active hydrogenase isoenzymes in *Escherichia coli*," *Arch. Microbiol.* 158(6):444-451 (1992).
Jacques et al., "Characterization of yeast homoserine dehydrogenase, an antifungal target: the invariant histidine 309 is important for enzyme integrity," *Biochem. Biophys. Acta* 1544:28-41 (2001).
Jager and Farber, "Die Alanatreduktion von β-Carbonyl-oxalylsäure-estern," *Chem. Ber.* 92:2492-2499 (1959).
James and Cronan, "Expression of two *Escherichia coli* acetyl-CoA carboxylase subunits is autoregulated," *J. Biol. Chem.* 279:2520-2527 (2004).
James and Viola, "Production and characterization of bifunctional enzymes. Domain swapping to produce new bifunctional enzymes in the aspartate pathway," *Biochemistry* 41(11) 3720-3725 (2002).
Jansen and Wanders, "L-2-hydroxyglutarate dehydrogenase: identification of a novel enzyme activity in rat and human liver. Implications for L-2-hydroxyglutaric academia," *Biochim. Biophys. Acta* 1225(1):53-56 (1993).
Janssen, "Propanol as an end product of theonine fermentation," *Arch. Microbiol.* 182:482-486 (2004).

Jantama et al., "Combining metabolic engineering and metabolic evolution to develop non recombinant strains of *Escherichia coli* C that produce succinate and malate," *Biotechnol. Bioeng.* 99(5):1140-1153 (2008).

Jantama et al., "Eliminating Side Products and Increasing succinate Yields in Engineered Strains of *Escherichia coli* C," *Biotechnol. Bioeng.* 101(5) 881-893 (2008).

Javid-Majd and Blanchard, "Mechanistic Analysis of the argE-Encoded N-Acetylornithine Deacetylase," *Biochemistry* 39:1285-1293 (2000).

Jeng et al., "Ornithine degradation in *Clostridium sticklandii*; pyridoxial phosphate and Coenzyme A dependent thiolytic cleavage of 2-amino-4-ketopentanoate to alanine and acetyl Coenzyme A," *Biochemistry* 13(14):2898-2903 (1974).

Jenkins and Nunn, "Genetic and molecular characterization of the genes involved in short-chain fatty acid degradation in *Escherichia coli*: the ato system," *J. Bacteriol.* 169(1):42-52 (1987).

Jennert et al., "Gene transfer to *Clostridium cellulolyticum* ATCC 35319," *Microbiol.* 146:3071-3080 (2000).

Jenssen et al., "A literature network of human genes for high-throughput analysis of gene expression," *Nat. Gene.* 28:21-28 (2001).

Jeon et al., "Heterologous expression of the alcohol dehydrogenase (adhI) gene from *Geobacillius thermoglucosidasius* strain M10EXG," *J. Biotechnol.* 135:127-133 (2008).

Jewell et al., "Bioconversion of propionic, valeric and 4-hydroxybutyric acids into the corresponding alcohols by *Clostridium acetobutylicum* NRRL 527," *Curr. Microbiol.* 13(4):215-219 (1986).

Jiang et al., "De Novo Computational Design of Retro-Aldol Enzymes," *Science* 319:1387-1391 (2008).

Jin and Sonenshein, "Characterization of the major citrate synthase of *Bacillus subtilis*," *J. Bacteriol.* 178(12):3658-3660 (1996).

Johanson et al., "Strain engineering for steroselective bioreduction of dicarbonyl compounds by yeast reductases," *FEMS Yeast Res.* 5:513-525 (2005).

Johnson et al., "Alteration of a single amino acid changes the substrate specificity of dihydroflavonol 4-reductase," *Plant J.* 25(3):325-333 (2001).

Johnston et al., "Structure of naphthoate synthase (MenB) from *Mycobacterium tuberculosis* in both native and product-bound forms," *Acta. Crystallogr. D. Biol. Crystallogr.* 61(Pt 9):1199-1206 (2005).

Jojima et al., "Production of isopropanol by metabolically engineered *Escherichia coli*," *Appl. Microbiol. Biotechnol.* 77:1219-1224 (2008).

Jones and Woods, "Acetone-butanol fermentation revisited," *Microbiol. Rev.* 50(4):484-524 (1986).

Junker and Ramos, "Involvement of the cis/trans isomerase Cti in solvent resistance of *Pseudomonas putida* DOT-T1E," *J. Bacteriol.* 181:5693-5700 (1999).

Kaclikova et al., "Fumaric acid overproduction in yeast mutants deficient in fumarase," *FEMS Microbiol. Lett.* 91(2):101-106 (1992).

Kahng et al., "Characterization of strain HY99, a novel microorganism capable of aerobic and anaerobic degradation of aniline," *FEMS Microbiol. Lett.* 190:215-221 (2000).

Kai et al., "Phosphoenolpyruvate carboxylase: three-dimensional structure and molecular mechanisms," *Arch. Biochem. Biophys.* 414:170-179 (2003).

Kakimoto et al., "β-aminoisobutyrate-α-ketoglutarate transaminase in relation to β-aminoisobutyric aciduria," *Biochim. Biophys. Acta* 156(2):374-380 (1968).

Kalousek et al., "Isolation and characterization of propionyl-CoA carboxylase from normal human liver. Evidence for a protomeric tetramer of nonidentical subunits," *J. Biol. Chem.* 255:60-65 (1980).

Kalpos, "On the mammalian acetone metabolism: from chemistry to clinical implications," *Biochim. Biophys. Acta* 1621(2):122-139 (2003).

Kalscheuer and Steinbuchel, "A novel bifunctional wax ester synthase/acyl-CoA:diacylglycerol acyltransferase mediates wax ester and triacylglycerol biosynthesis in *Acinetobacter calcoaceticus* ADP1," *J. Biol. Chem.* 278(10):8075-8082 (2003).

Kalscheuer et al., "Analysis of storage lipid accumulation in *Alcanivorax borkumensis*: Evidence for alternative triacylglycerol biosynthesis routes in bacteria," *J. Bacteriol.* 189(3):918-928 (2007).

Kanagawa et al., "Characterization of the 6-aminohexanoate-dimer hydrolase from *Pseudomonas* sp. NK87," *J. Gen. Microbiol.* 139(4):787-795 (1993).

Kanamasa et al., "Cloning and functional characterization of the cis-aconitic acid decarboxylase (CAD) gene from *Aspergillus terreus*," *Appl. Microbiol. Biotechnol.* 80(2):223-229 (2008).

Kanao et al., "Characterization of isocitrate dehydrogenase from the green sulfur bacterium *Chlorbium limicola*. A carbon dioxide-fixing enzyme in the reductive tricarboxylic acid cycle," *Eur. J. Biochem.* 269(7):1926-1931 (2002).

Kanaujia et al., "Cloning, expression, purification, crystallization and preliminary X-ray crystallographic study of DHNA synthetase from *Geobacillus kaustophilus*," *Acta. Crystallogr. Sect. F. Struct. Biol. Cryst. Commun.* 63(Pt 2):103-105 (2007).

Kanehisa and Goto, "KEGG: Kyoto Encyclopedia of Genes and Genomes database," *Nucleic Acids Res.* 28(1):27-30 (2000).

Kapatral et al., "Genome Sequence and Analysis of the Oral Bacterium *Fusobacterium nucleatum* Strain ATCC 25586," *J. Bacteriol.* 184(7):2005-2018 (2002).

Karyakin et al., "Kinetic properties of L-lysine-2-monooxygenase from *Pseufomonas putida* and its application to biosensors for L-lysine," *Prikladnaya Biokhimiya I Mikrobiologiya* 27:825-832 (1991).

Kasberg et al., "Cloning, characterization, and sequence analysis of the clcE gene encoding the maleylacetate reductase of *Pseufomonas* sp. Strain B13," *J. Bacteriol.* 179:3801-3803 (1997).

Kaschabek and Reineke, "Degradation of chloroaromatics: purification and characterization of maleylacetate reductase from *Pseudomonas* sp. Strain B13," *J. Bacteriol.* 175:6075-6081 (1993).

Kaschabek and Reineke, "Maleylacetate reductase of *Pseufomonas* sp. Strain B13: specificity of substrate conversion and halide elimination," *J. Bacteriol.* 177:320-325 (1995).

Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.* 184(1):207-215 (2002).

Kashket and Cao, "Isolation of a Degeneration-Resistant Mutant of *Clostridium acetobutylicum* NCIMB 8052," *Appl. Environ. Microbiol.* 59:4198-4202 (1993).

Kato and Asano, "3-Methylaspartate ammonia-lyase as a marker enzyme of the mesaconate pathway for (S)-glutamate fermentation in Enterobacteriaceae," *Arch Microbiol.* 168(6):457-463 (1997).

Katti et al., "Crystal structure of muconolactone isomerase at 3.3 Å resolution," *J. Mol. Biol.* 205:557-571 (1989).

Katz et al., "Screening of two complementary collections of *Saccharomyces cerevisiae* to identify enzymes involved in stereo-selective reductions of specific carbonyl compounds: an alternative to protein purification," *Enzyme Microb. Technol.* 33:163-172 (2003).

Kawabata et al., "The Effect of Growth Temperature on Wax Ester Content and Composition of *Euglena gracilis*," *J. Gen. Microbiol.* 135: 1461-1467 (1989).

Kazahaya et al, "Aerobic Dissimilation of Glucose by Heterolactic Bacteria III. Aldehyde dehydrogenase and alcohol dehydrogenase of luconostoc mesenteroids," *J. Gen. Appl. Microbiol.* 18(1):43-55 (1972).

Kefala et al., "Cloning, expression, purification, crystallization and preliminary x-ray diffraction analysis of LysA (Rv1293) from *Mycobacterium tuberculosis*," *Acta. Crystallogr. Sect. F. Struct. Biol. Cryst. Commun.* 61(Pt 8):782-784 (2005).

Kellum and Drake, "Effects of cultivation gas phase on hydrogenase of the acetogen *Clostridium thermoaceticum*," *J. Bacteriol.* 160(1):466-469 (1984).

Kenealy et al., "Biochemical Aspects of Fumaric Acid Accumulation by *Rhizopus arrhizus*," *Appl. Environ. Microbiol.* 52:128-133 (1986).

Keng and Viola, "Specificity of Aspartokinase III from *Escherichia coli* and Examination of Important Catalytic Residues," *Arch. Biochem. Biophys.* 335(1):73-81 (1996).

Kenklies et al., "Proline biosynthesis from L-ornithine in *Clostridium sticklandii*: purification of $\Delta^1$-pyrroline-5-carboxylate reductase, and sequence and expression of encoding gene, proC," *Microbiology* 145(Pt 4):819-826 (1999).

Kerby et al., "Carbon Monoxide-Dependent Growth of *Rhodospirillum rubrum*," *J. Bacteriol.* 177:2241-2244 (1995).

Kerby et al., "Genetic and physiological characterization of the *Rhodospirillum rubrum* carbon monoxide dehydrogenase system," *J. Bacteriol.* 174(16):5284-5294 (1992).

Kern et al., "Isoamyl alcohol-induced morphological change in *Saccharomyces cerevisiae* involves increases in mitochondria and cell wall chitin content," *FEMS Yeast Res.* 5:43-49 (2004).

Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).

Khan et al., "Molecular Properties and Enhancement of Thermostability by Random Mutagenesis of Glutamate Dehydrogenase from *Bacillus subtilis*," *Biosci. Biotechnol. Biochem.* 69(10):1861-1870 (2005).

Killenberg-Jabs et al., "Active oligomeric states of pyruvate decarboxylase and their functional characterization," *Eur. J. Biochem.* 268:1698-1704 (2001).

Kim et al, "Effect of Overexpression of *Actinobacillus succinogenes* Phosphoenolpyruvate Carboxykinase on Succinate Production in *Escherichia coli*," *Appl. Env. Microbiol.* 70(2) 1238-1241 (2004).

Kim et al., "2-Hydroxyisocaproyl-CoA dehydratase and its activator from *Clostridium difficile*," *FEBS J.* 272:550-561 (2005).

Kim et al., "Construction of an *Escherichia coli* K-12 Mutant for Homoethanologenic Fermentation of Glucose or Xylose without Foreign Genes," *Appl. Environ. Microbiol.* 73(6):1766-1771 (2007).

Kim et al., "Dehydration of (R)-2-hydroxyacyl-CoA to enoyl-CoA in the fermentation of a-amino acids by anaerobic bacteria," *FEMS Microbiol. Rev.* 28:455-468 (2004).

Kim et al., "Dihydrolipoamide dehydrogenase mutation alters the NADH sensitivity of pyruvate dehydrogenase complex of *Escherichia coli* K-12," *J. Bacteriol.* 190:3851-3858 (2008).

Kim et al., "Studies of the hyperthermophile *Thermotoga maritima* by random sequencing of cDNA and genomic libraries. Identification and sequencing of the *trpEG* (D) operon," *J. Mol. Biol.* 231:960-981 (1993).

Kim, "Purification and Properties of a diamine α-Ketoglutarate Transminase from *Escherichia coli*," *J. Biol. Chem.* 239(3):783-786 (1964).

Kino et al. Synthesis of DL-tryptophan by modified broad specificity amino acid racemase from *Pseudomonas putida* IFO 12996, *Appl. Microbiol. Biotechnol.* 73:1299-1305 (2007).

Kinoshita et al., "Purification and characterization of 6-aminohexanoic-acid-oligomer hydrolase of *Flavobacterium* sp. KI72," *Eur. J. Biochem.* 116(3):547-551 (1981).

Kinoshita, "Purification of two alcohol dehydrogenases from *Zymomonas mobilis* and their properties," *Appl. Microbiol. Biotechnol.* 22:249-254 (1985).

Kisselev L., "Polypeptide release factors in prokaryotes and eukaryotes: same function, different structure," *Structure* 10:8-9 (2002).

Klasson, et al., "Biological conversion of coal and coal-derived synthesis gas," *Fuel* 72(12):1673-1678 (1993).

Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).

Kleanthous et al., "A comparison of the enzymological and biophysical properties of two distinct classes of dehydroquinase enzymes," *Biochem. J.* 282(Pt3):687-695 (1992).

Klyosov, "Kinetics and specificity of human liver aldehyde dehydrogenases toward aliphatic, aromatic, and fused polycyclic aldehydes," *Biochemistry* 35(14):4457-4467 (1996).

Knapp et al., "Crystal Structure of the Truncated Cubic Core component of the *Escherichia coli* 2-Oxoglutarate Dehydrogenase Multienzyme Complex," *J. Mol. Biol.* 280:655-668 (1998).

Knappe and Sawers, "A radical-chemical route to acetyl-CoA: the anaerobically induced pyruvate formate-lyase system of *Escherichia coli*," *FEMS. Microbiol. Rev.* 75:383-398 (1990).

Knappe et al., "Post-translational activation introduces a free radical into pyruvate formate-lyase," *Proc. Natl. Acad. Sci. U.S.A.* 81:1332-1335 (1984).

Knothe, "'Designer' Biodiesel: Optimizing Fatty Ester Composition to Improve Fuel Properties," *Energy Fuels* 22:1358-1364 (2008).

Kobayashi et al., "Physicochemical, catalytic, and immunochemical properties of fumarases crystallized separately from mitochondrial and cytosolic fractions of rat liver," *J. Biochem.* 89(6):1923-1931 (1981).

Koch and Fuchs, "Enzymatic reduction of benzoyl-CoA to alicyclic compounds, a key reaction in anaerobic aromatic metabolism," *Eur. J. Biochem.* 205:195-202 (1992).

Koch et al., "Products of enzymatic reduction of benzoyl-CoA, a key reaction in anaerobic aromatic metabolism," *Eur. J. Biochem.* 211:649-661 (1993).

Koland and Gennis, "Proximity of Reactive Cysteine Residue and Flavin in *Escherichia coli* Pyruvate Oxidase As Estimated by Flourescence Energy Transfer," *Biochemistry* 21:4438-4442 (1982).

Kollmann-Koch et al.,"Nicotinic acid metabolism. Dimethylmaleate hydratase," *Hoppe Seylers Z Physiol Chem.* 365:s.847-857 (1984).

Koo et al., "Cloning and characterization of the bifunctional alcohol/acetaldehyde dehydrogenase gene (adhE) in *Leuconostoc mesenteroides* isolated from kimchi," *Biotechnol. Lett.* 27(7):505-510 (2005).

Korbert et al., "Crystallization of the $NADP^+$-dependent Glutamate Dehydrogenase from *Escherichia coli*," *J. Mol. Biol.* 234:1270-1273 (1993).

Kornberg, "The role and control of the glyoxylate cycle in *Escherichia coli*," *Biochem. J.* 99:1-11 (1966).

Korolev et al., "Autotracing of *Escherichia coli* acetate CoA-transferase α-subunit structure using 3.4 Å MAD and 1.9 Å native data," *Acta. Crystallogr. D. Biol. Crystallogr.* 58(Pt 12):2116-2121 (2002).

Korotkova and Lidstrom, "Connection between poly-β-hydroxybutyrate biosynthesis and growth on $C_1$ and $C_2$ compounds in the methylotroph *Methylobacterium extorquens* AM1," *J. Bacteriol.* 183(3):1038-1046 (2001).

Korotkova and Lidstrom, "MeaB is a component of the methylmalonyl-CoA mutase complex required for protection of the enzyme from inactivation," *J. Biol. Chem.* 279(14):13652-13658 (2004).

Kort et al., "Glutamate dehydrogenase from the hyperthermophilic bacterium *Thermotoga maritima*: molecular characterization and phylogenetic implications," *Extremophiles* 1:52-60 (1997).

Kosaka et al., "Characterization of the sol operon in butanol-hyperproducing *Clostridium saccharoperbutylacetonicum* strain N1-4 and its degeneration mechanism," *Biosci. Biotechnol. Biochem.* 71:58-68 (2007).

Kosjek et al., "Purification and characterization of a chemotolerant alcohol dehydrogenase applicable to coupled redox reactions," *Biotechnol. Bioeng.* 86(1):55-62 (2004).

Kouzarides, "Acetylation: a regulatory modification to rival phosphorylation?" *EMBO J.* 19(6):1176-1179 (2000).

Kovachy et al., "Recognition, Isolation, and Characterization of Rat Liver D-Methylmalonyl Coenzyme A Hydrolase," *J. Biol. Chem.* 258(18):11415-11421 (1983).

Kowalchuk et al., "Contrasting patterns of evolutionary divergence within the *Acinetobacter calcoaceticus* pca operon," *Gene* 146:23-30 (1994).

Kraus et al., "Biosynthesis and mitochondrial processing of the β subunit of propionyl Coenzyme A carboxylase from rat liver," *J. Biol. Chem.* 258:7245-7248 (1983).

Kreimeyer et al., "Identification of the Last Unknown Genes in the Fermentation Pathway of Lysine," *J. Biol. Chem.* 282(10):7191-7197 (2007).

Kress et al., "First direct observation of the simultaneous presence and of the interconversion of chain-propagating metal-carbene and metallacyclobutane complexes in a catalytic olefin metathesis reaction: the ring-opening polymerization of norbornene," *J. Am. Chem. Soc.* 109(3):899-901 (1987).

Kress et al., "Tungsten(VI) and molybdenum(VI) oxo-alkyl species. Their role in the metathesis of olefins," *J. Chem. Soc. Chem. Commun.* 431-432 (1980).

Kretz et al., "Gene site saturation mutagenesis: a comprehensive mutagenesis approach," *Methods Enzymol.* 388:3-11 (2004).

Krieger et al., "Pyruvate decarboxylase from *Kluyveromyces lactis* an enzyme with an extraordinary substrate activation behaviour," *Eur. J. Biochem.* 269:3256-3263 (2002).

Krishna et al., "Enzymatic synthesis of isoamyl acetate using immobilized lipase from *Rhizomucor miehei*," *J. Biotechnol.* 87:193-201 (2001).

Kuchta and Abeles, "Lactate Reduction in *Clostridium propionicum* Purification and properties of lactyl-CoA dehydratase," *J. Biol. Chem.* 260(24):13181-13189 (1985).

Kühnl et al., "Functional analysis of the methylmalonyl-CoA epimerase from *Caenorhabditis elegans*," *FEBS J.* 272(6):1465-1477 (2005).

Kulkarni and Kanekar, "Bioremediation of ε-caprolactum from nylon-6 waste water by use of *Pseudomonas aeruginosa* MCM B-407," *Curr. Microbiol.* 37(3):191-194 (1998).

Kumamaru et al., "Enhanced degradation of polychlorinated biphenyls by directed evolution of biphenyl dioxygenase," *Nat. Biotechnol.* 16:663-666 (1998).

Kumari et al., "Cloning, Characterization, and Functional Expression of acs, the Gene Which Encodes Acetyl Coenzyme A Synthetase in *Escherichia coli*," *J. Bacteriol.* 177(10): 2878-2886 (1995).

Kuntze et al., "6-Oxocyclohex-1-ene-1-carbonyl-Coenzyme A hydrolases from obligately anaerobic bacteria: characterization and indentification of its gene as a functional marker for aromatic compounds degrading anaerobes," *Environ. Microbiol.* 10(6):1547-1556 (2008).

Kurihara et al., "γ-Glutamyputrescine synthetase in the putrescine utilization pathway of *Escherichia coli* K-12," *J. Biol. Chem.* 283(29)19981-19990 (2008).

Kurihara et al., "A Novel Putrescine Utilization Pathway Involves γ-Glutamylated Intermediates of *Escherichia coli* K-12," *J. Biol. Chem.* 280(6):4602-4608 (2005).

Kuznetsova et al., "Enzyme genomics: Application of general enzymatic screens to discover new enzymes," *FEMS Microbiol. Rev.* 29(2):263-279 (2005).

Kwok and Hanson, "GFP-labelled Rubisco and aspartate aminotransferase are present in plastid stromules and traffic between plastids," *J. Exp. Bot.* 55(397):595-604 (2004).

Kwon et al., "Influence of gluconegoenic phosphoenolpyruvate carbosykinase (PCK) expression on succinic acid fermentation in *Escherichi coli* under high bicarbonate condition," *J. Microbiol. Biotechnol.* 16(9):1448-1452 (2006).

Laempe et al., "6-Hydroxycyclohex-1-ene-1-carbonyl-CoA dehydrogenase and 6-oxocyclohex-1-ene-1-carbonyl-CoA hydrolase, enzymes of the benzoyl-CoA pathway of anaerobic aromatic metabolism in the denitrifying bacterium *Thauera aromatica*," *Eur. J. Biochem.* 263(2):420-429 (1999).

Laivenieks et al., "Cloning sequencing, and overexpression of the *Anaerobiospirillum succinicproducens* phosphoenolpyruvate carboxykinase (*pckA*) gene," *Appl. Environ. Microbiol.* 63:2273-2280 (1997).

Lam and Winkler, "Metabolic Relationships between Pyridoxine (Vitamin $B_6$) and Serine Biosynthesis in *Escherichia coli* K-12," *J. Bacteriol.* 171(11):6518-6528 (1990).

Lamas-Maceiras et al., "Amplification and disruption of the phenylacetyl-CoA ligase gene of *Penicillium chrysogenum* encoding an aryl-capping enzyme that supplies phenylacetic acid to the isopenicillin N-acyltransferase," *Biochem. J.* 395(1):147-155 (2006).

Lamed and Zeikus, "Novel NADP-linked alcohol-aldehyde/ketone oxidoreductase in thermophilic ethanologenic bacteria," *Biochem. J.* 195:183-190 (1981).

Lardizabal et al., "Purification of a jojoba embryo wax synthase, cloning of its cDNA, and production of high levels of wax in seeds of transgenic arabidopsis," *Plant Physiol.* 122(3):645-655 (2000).

Lawrence and Roth, "Evolution of Coenzyme $B_{12}$ synthesis among enteric bacteria: evidence for loss and reacquisition of a multigene complex," *Genetics* 142(1):11-24 (1996).

Lawrence and Roth, "The cobalamin (Coenzyme $B_{12}$) biosynthetic genes of *Escherichia coli*," *J. Bacteriol.* 177(22):6371-6380 (1995).

Lebbink et al., "Engineering activity and stability of *Thermotoga maritima* glutamate dehydrogenase I. Introduction of a six-residue ion-pair network in the hinge region," *J. Mol. Biol.* 280:287-296 (1998).

Lebbink et al., "Engineering Activity and Stability of *Thermotoga maritima* glutamate Dehydrogenase. II: construction of a 16-Residue Ion-pair Network at the Subunit Interface," *J. Mol. Biol.* 289:357-369 (1999).

Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).

Lee and Cho, "Identification of essential active-site residues in ornithine decarboxylase of *Nicotiana glutinosa* decarboxylating both L-ornithine and L-lysine," *Biochem. J.* 360:657-665 (2001).

Lee et al., "A new approach to directed gene evolution by recombined extension on truncated templates (RETT)," *J. Molec. Catalysis* 26:119-129 (2003).

Lee et al., "Batch and continuous cultivation of *Anaerobiospirillum succiniciproducens* for the production of succinic acid from whey," *Appl. Microbiol. Biotechnol.* 54(1):23-27 (2000).

Lee et al., "Biological conversion of wood hydrolysate to succinic acid by *Anaerobiospirillum succiniciproducens*," *Biotechnol. Lett.* 25(2):111-114 (2003).

Lee et al., "Biosynthesis of enantiopure (S)-3-hydroxybutyric acid in metabolically engineered *Escherichia coli*," *App. Microbiol. Biotechnol.* 79:633-641 (2008).

Lee et al., "Chaperonin GroESL mediates the protein folding of human liver mitochondrial aldehyde dehydrogenase in *Escherichia coli*," *Biochem. Biophys. Res. Commun.* 298(2):216-224 (2002).

Lee et al., "Cloning and Characterization of *Mannheimia succiniciproducens* MBEL55E Phosphoenolpyruvate Carboxykinase (*pckA*) Gene," *Biotechnol. Bioprocess Eng.* 7:95-99 (2002).

Lee et al., "Fermentative production of chemicals that can be used for polymer synthesis," *Macromol. Biosci.* 4:157-164 (2004).

Lee et al., "Genome-based metabolic engineering of *Mannheimia succiniciproducens* for succinic acid productiion," *Appl. Environ. Microbiol.* 72(3):1939-1948 (2006).

Lee et al., "Isolation and characterization of a new succinic acid-producing bacterium, *Mannheimia succiniciproducens* MBEL55E, from bovine rumen," *Appl. Microbiol. Biotechnol.* 58(5):663-668 (2002).

Lee et al., "Phylogenetic diversity and the structural basis of substrate specificity in the β/α-barrel fold basic amino acid decarboxylases," *J. Biol. Chem.* 282:27115-27125 (2007).

Lee et al., "Metabolic engineering of *Escherichia coli* for enhanced production of succinic acid, based on genome comparison and in silico gene knockout simulation," *Appl Environ Microbiol.* 71(12):7880-7887 (2005).

Lehtio and Goldman, "The pyruvate format lyase family: sequences, structures and activation," *Protein Eng. Des.Sel.* 17:545-552 (2004).

Lehtio et al., "Crystal structure of glycyl radical enzyme from *Archaeoglobus fulgidus*," *J. Mol. Biol.* 357(1):221-235 (2006).

Lei et al., "A shared binding site for $NAD^+$ and Coenzyme A in an acetaldehyde dehydrogenase involved in bacterial degradation of aromatic compounds," *Biochemistry* 47:6870-6882 (2008).

Lemoine et al., "Microcorrespondence: Monofunctional biosynthetic peptidoglycan transglycosylases," *Mol. Microbiol.* 19(3):639-647 (1996).

Lemonnier and Lane, "Expression of the second lysine decarboxylase gene of *Escherichia coli*," *Microbiology* 144(Pt 3):751-760 (1998).

Lenski and Travisano, "Dynamics of adaptation and diversification: a 10,000-generation experiment with bacterial populations," *Proc. Natl. Acad. Sci. U.S.A.* 91(15):6808-6814 (1994).

Leonardo et al., "Anaerobic Regulation of the adhE gene, Encoding the Fermentative Alcohol Dehydrogenase of *Escherichia coli*," *J. Bacteriol.* 175(3):870-878 (1993).

Lepore et al., "The x-ray crystal structure of lysine-2,3-aminomutase from *Clostridium subterminale*," *Proc. Natl. Acad. Sci U.S.A.* 102:13819-13824 (2005).

Leppänen et al., "Pyruvate formate lyase is structurally homologous to type I ribonucleotide reductase," *Structure* 7:733-744 (1999).

Lessner et al., "An unconventional pathway for reduction of $CO_2$ to methane in CO-grown *Methanosarcina acetivorans* revealed by proteomics," *Proc. Natl. Acad. Sci. U.S.A.* 103(47):17921-17926 (2006).

Leutwein and Heider, "Succinyl-CoA(R)-benzylsuccinate CoA-Transferase: an enzyme of the anaerobic toluene catabolic pathway in denitrifying bacteria," *J. Bacteriol.* 183(14):4288-4295 (2001).

Levanon et al., "Effect of Oxygen on the *Escherichia coli* ArcA and FNR Regulation Systems and Metabolic Responses," *Biotechnol. Bioeng.* 89(5):556-564 (2005).

Li and Jordan, "Effects of substitution of tryptophan 412 in the substrate activation pathway of yeast pyruvate decarboxylase," *Biochemistry* 38:10004-10012 (1999).

Li et al., "Properties of Nicotinamide Adenine Dinucleotide Phosphate-Dependent Formate Dehydrogenase from *Clostridium thermoaceticum*," *J. Bacteriol.* 92(2):405-412 (1966).

Li et al., "Purification, crystallization and preliminary crystallographic studies on 2-dehydro-3-deoxygalactarate aldolase from *Leptospira interrogans*," *Acta. Crystallogr. Sect. F. Struct. Biol. Cryst. Commun.* 62(Pt 12):1269-1270 (2006).

Li, Guang-Shan, "Development of a reporter system for the study of gene expression for solvent production in *Clostridium beijerinckii* NRRL B592 and *Clostridium acetobutylicum* ATCC 824," Dissertation, Department of Biochemistry, Virginia Polytechnic Institute and State University (Sep. 1998).

Lian et al., "Stereochemical and Isotopic Labeling Studies of 4-Oxalocrotonate Decarboxylase and Vinylpyruvate hydratase: Analysis and Mechanistic Implications," *J. Am. Chem Soc.* 116:10403-10411 (1994).

Lin et al., "Chemostat culture characterization of *Escherichia coli* mutant strains metabolically engineered for aerobic succinate production: A study of the modified metabolic network based on metabolite profile, enzyme activity, and gene expression profile," *Metab. Eng.* 7(5-6):337-352 (2005).

Lin et al., "Functional Expression of Horseradish Peroxidase in *E. coli* by Directed Evolution," *Biotechnol. Prog.* 15:467-471 (1999).

Lin et al., "Effect of carbon sources differing in oxidation state and transport route on succinate production in metabolically engineered *Escherichia coli*," *J. Ind. Microbiol. Biotechnol.* 32:87-93 (2005).

Lin et al., "Fed-batch culture of a metabolically engineered *Escherichia coli* strain designed for high-level succinate production and yield under aerobic conditions," *Biotechnol. Bioeng.* 90:775-779 (2005).

Lin et al., "Genetic Reconstruction of the Aerobic Central Metabolism in *Escherichia coli* for the Absolute Aerobic Production of Succinate," *Biotechnol. Bioeng.* 89(2):148-156 (2005).

Lin et al., "Increasing the Acetyl-CoA pool in the Presence of Overexpressed Phosphoenolpyruvate Carboxylase or Pyruvate Carboxylase Enhances Succinate Production in *Escherichia coli*," *Biotechnol. Prog.* 20(5):1599-1604 (2004).

Lin et al., "Metabolic engineering of aerobic succinate production systems in *Escherichia coli* to improve process productivity and achieve the maximum theoretical succinate yield," *Metab. Eng.* 7(2):116-127 (2005).

Lin, "Metabolic Network Design and Engineering in *Escherichia coli*" Ph.D. Thesis, Rice University, Dept. of Bioengineering (2005).

Lin, H et al., "Effect of *Sorghum vulgare* phosphoenolpyruvate carboxylase and *Lactococcus lactis* pyruvate carboxylase coexpression on succinate production in mutant strains of *Escherichia coli*," *Appl. Microbiol. Biotechnol.* 67(4): 515-523 (2005).

Lingen et al., "Alteration of the substrate specificity of benzoylformate decarboxylase from *Pseudomonas putida* by directed evolution," *Chembiochem.* 4:721-726 (2003).

Lingen et al., "Improving the carboligase activity of benzoylformate decarboxylase from *Pseudomonas putida* by a combination of directed evolution and site-directed mutagenesis," *Protein Eng.* 15:585-593 (2002).

Link et al., "Methods for generating precise deletions and insertions in the genome of wild-type *Eshcerichia coli*: application to open reading frame characterization," *J. Bacteriol.* 179:6228-6237 (1997).

Liou et al., "*Clostridium carboxidivorans* sp. nov., a solvent-producing *clostridium* isolated from an agricultural settling lagoon, and reclassification of the acetogen *Clostridium scatologenes* strain SL1 as *Clostridium drakei* sp. nov," *Int. J. Syst. Evol. Microbiol.* 55(Pt 5):2085-2091 (2005).

Liu et al., "Kinetic and crystallographic analysis of active site mutants of *Escherichia coli* γ-aminobutyrate aminotransferase," *Biochemistry* 44:(8):2982-2992 (2005).

Liu et al., "Microbial production of R-3-hydroxybutyric acid by recombinant *E. coli* harboring genes of phbA, phbB , and tesB," *Appl. Microbiol. Biotechnol.* 76:811-818 (2007).

Liu et al., "Purification and characterization of ornithine acetyltransferase from *Saccharomyces cerevisiae*," *Eur. J. Biochem.* 228:291-296 (1995).

Liu et al., "Crystal structures of unbound and aminooxyacetate-bound *Escherichia coli* γ-aminobutyrate aminotransferase," *Biochemistry* 43(34):10896-10905 (2004).

Liu et al., "Economical succinic acid production from cane molasses by *Actinobacillus succinogenes*," *Bioresour Technol* 99(6):1736-1742 (2008).

Ljungdahl and Andreesen, "Formate dehydrogenase, a selenium-tungsten enzyme from *Clostridium thermoaceticum*," *Methods Enzymol.* 53:360-372 (1978).

Ljungdahl and Andreesen, "Tungsten, a component of active formate dehydrogenase from *Clostridium thermoacetium*," *FEBS Lett.* 54:279-282 (1975).

Ljungdahl, "The Autotrophic Pathway of Acetate Synthesis in Acetogenic Bacteria," *Ann. Rev. Microbiol.* 40:415-450 (1986).

Lloyd-Jones et al., "Rate Enhancement by Ethylene in the Ru-Catalyzed Ring-Closing Metathesis of Enynes: Evidence for an "Ene-then-Yne" Pathway that Diverts through a Second Catalytic Cycle," *Andew Chem Int Ed.* 44(45):7442-7447 (2005).

Lokanath et al., "Crystal structure of novel NADP-dependent 3-hydroxyisobutyrate dehydrogenase from *Thermus thermophilus* HB8," *J. Mol. Biol.* 352(4):905-917 (2005).

Loke et al., "Active acetyl-CoA synthase from *Clostridium thermoaceticum* obtained by cloning and heterologous expression of acsAB in *Escherichia coli*," *Proc. Natl. Acad. Sci. U.S.A.* 97:12503-12535 (2000).

Longtine et al., "Additional modules for versatile and economical PCR-based gene deletion and modification in *Saccharomyces cerevisiae*," *Yeast* 14(10): 953-961 (1998).

Lopez-Barragan et al., "The bzd gene cluster, coding for anaerobic benzoate catabolism, in *Azoarcus* sp. Strain CIB," *J. Bacteriol.* 186(17):5762-5774 (2004).

Louie and Chan, "Cloning and characterization of the gamma-glutamyl phosphate reductase gene of *Campylobacter jejuni*," *Mol. Gen. Genet.* 240:29-35 (1993).

Louis et al., "Restricted distribution of the butyrate kinase pathway among butyrate-producing bacteria from the human colon," *J. Bacteriol.* 186:2099-2106 (2004).

Lovell et al., "Cloning and expression in *Escherichia coli* of the *Clostridium thermoaceticum* gene encoding thermostable formyltetrahydrofolate synthetase," *Arch. Microbiol.* 149(4):280-285 (1988).

Lovell et al., "Primary structure of the thermostable formyltetrahydrofolate synthetase from *Clostridium thermoaceticum*," *Biochemistry* 20(29):5687-5694 (1990).

Low et al., "Mimicking somatic hypermutation: Affinity maturation of antibodies displayed on baceriophage using a bacterial mutator strain," *J. Mol. Biol.* 260(3):359-368 (1996).

Lu et al., "Controlled Poetntial Enzymology of Methyl Transfer Reactions Involved in Acetyl-CoA Synthesis by CO Dehydrogenase and the Corrinoid/Iron-Sulfur Protein from *Clostridium thermoaceticum*," *J. Biol. Chem.* 265(6):3124-3133 (1990).

Lu et al., "Functional Analysis and Regulation of the Divergent spuABCDEFGH-spuI Operons for Polyamine Uptake and Utilization in *Pseudomonas aeruginosa* PAO1," *J. Bacteriol.* 184(14):3765-3773 (2002).

Lu et al., "Sequence and expression of the gene encoding the corrinoid/iron-sulfur protein from *Clostridium thermoaceticum* and reconstitution of the recombinant protein to full activity," *J. Biol. Chem.* 268(8):5605-5614 (1993).

Luersen, "Leishmania major thialsine Nᵉ-acetyltransferase: Identification of amino acid residues crucial for substrate binding," *FEBS Lett.* 579:5347-5352 (2005).

Luli and Strohl, "Comparison of Growth, Acetate Production, and Acetate Inhibition of *Escherichia coli* Strains in Batch and Fed-Batch Fermentations," *Appl. Environ. Microbiol.* 56:1004-1011 (1990).

Lupa et al., "Distribution of genes encoding the microbial non-oxidative reversible hydroxyarylic acid decarboxylases/phenol carboxylases," *Genomics* 86:342-351 (2005).

Lupa et al., "Properties of the reversible nonoxidative vanillate/4-hydroxybenzoate decarboxylase from *Bacillus subtilis*," *Can. J. Microbiol* 54:75-81 (2008).

Lütke-Eversloh and Steinbüchel, "Biochemical and molecular characterization of a succinate semialdehyde dehydrogenase involved in the catabolism of 4-hydroxybutyric acid in *Ralstonia eutropha*," *FEMS Microbiol. Lett.* 181(1):63-71 (1999).

Lutz and Bujard, "Independent and tight regulation of transcriptional units in *Escherichia coli* via the LacR/O, the TetR/O and AraC/$I_1$-$I_2$ regulatory elements," *Nucleic Acids Res.* 25(6):1203-1210 (1997).

Lutz et al., "Creating multiple-crossover DNA libraries independent of sequence identity," *Proc. Natl. Acad. Sci U.S.A.* 98:11248-11253 (2001).

Lutz et al., "Dissecting the functional program of *Escherichia coli* promoters: the combined mode of action of Lac repressor and AraC activator," *Nucleic Acids Res.* 29(18):3873-3881 (2001).

Lutz et al., "Rapid generation of incremental truncation libraries for protein enginering using α-phosphothioate nucleotides," *Nucleic Acids Res.* 29:E16 (2001).

Lynch et al., "SCALEs: multiscale analysis of library enrichment," *Nat. Methods* 4(1):87-93 (2007).

Lynd et al., "Microbial Cellulose Utilization: Fundamentals and Biotechnology," *Microbiol. Mol. Biol. Rev.* 66:506-577 (2002).

Lynn et al., "Living Ring-Opening Metathesis Polymerization in Aqueous Media Catalyzed by Well-Defined Ruthenium Carbene Complexes," *J. Am. Chem. Soc.* 118(4):784-790 (1996).

Lynn et al., "Living Ring-Opening Metathesis Polymerization in Water," *J. Am. Chem. Soc.* 120(7):1627-1628 (1998).

Ma et al., "Induced rebuilding of aspartase conformation," *Ann. NY Acad. Sci.* 672:60-65 (1992).

Macis et al., "Properties and sequence of the Coenzyme $B_{12}$-dependent glycerol dehydratase of *Clostridium pasteruianum*," *FEMS Microbiol. Lett.* 164:21-28 (1998).

Mack and Buckel, "Conversion of glutaconate CoA-transferase from *Acidaminococcus fermentans* into an acyl-CoA hydrolase by site-directed mutagenesis," *FEBS Lett.* 405(2):209-212 (1997).

Mack et al., "Location of the two genes encoding glutaconate Coenzyme A-transferase at the beginning of the hydroxyglutarate operon in *Acidaminococcus fermentans*," *Eur. J. Biochem.* 226:41-51 (1994).

Maeda et al., "Enhanced hydrogen production from glucose by metabolically engineered *Escherichia coli*," *Appl. Microbiol. Biotechnol.* 77:879-890 (2007).

Maeder et al., "The *Methanosarcina barkeri* genome: comparative analysis with *Methanosarcina acetivorans* and *Methanosarcina mazei* reveals extensive rearrangement within methanosarcinal genomes," *J. Bacteriol.* 188(22):7922-7931 (2006).

Maes et al., "Crystallization of ornithine acetyltransferase from yeast by counter-diffusion and preliminary x-ray study," *Acta. Crystallogr. Sect. F. Struct. Biol. Cryst. Commun.* 62(Pt 12):1294-1297 (2006).

Mahadevan and Schilling, "The effects of alternate optimal solutions in constraint-based genome-scale metabolic models," *Metab. Eng.* 5(4):264-276 (2003).

Mahan and Csonka, "Genetic analysis of the proBA genes of *Salmonella typhimurium*: physical and genetic analyses of the cloned proB⁺A⁺ genes of *Escherichia coli* and of a mutant allele that confers proline overproduction and enhanced osmotolerance," *J. Bacteriol.* 156:1249-1262 (1983).

Mai and Adams, "Purification and characterization of two reversible and ADP-dependent acetyl Coenzyme A synthetases from the hyperthermophilic archaeon *Pyrococcus furiosus*," *J. Bacteriol.* 178:5897-5903 (1996.).

Maicas, S. et al., "NAD(P)H regeneration is the key for heterolactic fermentation of hexoses in *Oenococcus oeni*," *Microbiology* 148:325-332 (2002).

Maitra and Sprinson, "5-Dehydro-3-deoxy-D-arabino-heptulosonic acid 7-phosphate. An intermediate in the 3-dehydroquinate synthase reaction," *J Biol. Chem.* 253:5426-5430 (1978).

Majewski and Domach, "Simple Constrained-Optimization View of Acete Overflow in *E. coli*," *Biotechnol. Bioeng.* 35(7):732-738 (1990).

Maklashina et al., "Anaerobic expression of *Escherichia coli* succinate dehydrogenase: functional replacement of fumarate reductase in the respiratory chain during anaerobic growth," *J. Bacteriol.* 180(22):5989-5996 (1998).

Manjasetty et al., "Crystallization and preliminary X-ray analysis of dmpFG-encoded 4-hydroxy-2-ketovalerate aldolase-aldehyde dehydrogenase (acylating) from *Pseudomonas* sp strain CF600," *Acta. Crystallogr. D. Biol. Crystallogr.* 57(Pt 4):582-585 (2001).

Manning and Pollitt, "Tracer studies of the interconversion of R- and S-methylmalonic semialdehydes in man," *Biochem. J.* 231(2):481-484 (1985).

Marco-Marin et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.* 334:459-476 (2003).

Marek and Henson, "Cloning and expression of the *Escherichia coli* K-12 sad gene," *J. Bacteriol.* 170:991-994 (1988).

Marks et al., "Molecular cloning and characterization of (R)-3-hydroxybutyrate dehydrogenase from human heart," *J. Biol. Chem.* 267(22):15459-15463 (1992).

Martin et al., "Engineering a mevalonate pathway in *Escherichia coli* for production of terpenoids," *Nat. Biotechnol.* 21:796-802 (2003).

Martin et al., "Nematode.net update 2008: improvements enabling more efficient data mining and comparative nematode genomics," *Nucleic Acids Res.* 37:D571-D578 (2009).

Martínez-Blanco et al., "Purification and biochemical characterization of phenylacetyl-CoA ligase from *Pseudomonas putida*. A specific enzyme for the catabolism of phenylacetic acid," *J. Biol. Chem.* 265(12):7084-7090 (1990).

Martinez-Carrion and Jenkins, "D-Alanine-D-glutamate transminase. I. Purification and characterization," *J. Biol. Chem.* 240(9):3538-3546 (1965).

Martins et al., "Crystal structure of 4-hydroxybutyryl-CoA dehydratase: radical catalysis involving a [4Fe-AS] cluster and flavin," *Proc. Natl. Acad. Sci. U.S.A.* 101(44):15645-15649 (2004).

Mason and Dufour, "Alcohol acetyltransferases and the significance of ester synthesis in yeast," *Yeast* 16(14):1287-1298 (2000).

Matiasek et al., "Volatile ketone formation in bacteria: release of 3-oxopentanoate by soil pseudomonads during growth on heptanoate," *Curr. Microbiol.* 42:276-281 (2001).

Mat-Jan et al., "Mutants of *Escherichia coli* Deficient in the Fermentative Lactate Dehydrogenase," *J. Bacteriol.* 171(1):342-348 (1989).

Matsumura et al., "Constitutive expression of catABC genes in the aniline-assimilating bacterium *Rhodococcus* species AN-22: production, purification, characterization and gene analysis of CatA, CatB and CatC," *Biochem. J.* 393:219-226 (2006).

Matsushima et al., "An enone reductase from *Nicotiana tabacum*: cDNA cloning, expression in *Escherichia coli*, and reduction of enones with the recombinant proteins," *Bioorg. Chem.* 36:23-28 (2008).

Matta et al., "Interactions of the antizyme AtoC with regulatory elements of the *Escherichia coli* atoDAEB operon," *J. Bacteriol.* 189(17):6324-6332 (2007).

Mattevi et al., "Atomic structure of the cubic core of the pyruvate dehydrogenase multienzyme complex," *Science* 255(5051):1544-1550 (1992).

Matthies and Schink, "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.* 58(5):1435-1439 (1992).

Maurus et al., "Insights into the Evolution of Allosteric Properties. The NADH Binding Site of Hexameric Type II Citrate Synthases," *Biochemistry* 42:5555-5565 (2003).

Mavrovouniotis, Estimation of standard Gibbs energy changes of biotransformations, *J. Biol. Chem.* 266:14440-14445 (1991).

Maynard et al., "Autocatalytic activation of acetyl-CoA synthase," *J. Biol. Inorg. Chem.* 9:316-322 (2004).

Mazur et al., "Cis,cis-muconate lactonizing enzyme from *Trichosporon cutaneum*: evidence for a novel class of cycloisomerases in eucaryotes," *Biochemistry* 33:1961-1970 (1994).

McAlister-Henn and Thompson, "Isolation and expression of the gene encoding yeast mitochondrial malate dehydrogenase," *J. Bacteriol.* 169:5157-5166 (1987).

McCarthy et al., "Crystal structure of methylmalonyl-Coenzyme A epimerase from *P. shermanii*: a novel enzymatic function on an ancient metal binding scaffold," *Structure* 9(7):637-646 (2001).

McCullough et al., "Enzymatic decarboxylation of the aminobenzoates," *J. Am. Chem. Soc.* 79:628-630 (1957).

McGregor et al., "argE-Encoded N-Acetyl-L-Ornithine Deacetylase from *Escherchia coli* Contains a Dinuclear Metalloactive Site," *J. Am. Chem. Soc.* 127:14100-14107 (2005).

McInerney et al., "The genome of *Syntrophus aciditrophicus*: Life at the thermodynamic limit of microbial growth," *Proc. Natl. Acad. Sci U.S.A.* 104:7600-7605 (2007).

McKinlay et al., "Prospects for a bio-based succinate industry," *Appl. Microbiol. Biotechnol.* 76(4):727-740 (2007).

McPherson and Wootton, "Complete nucleotide sequence of the *Escherichia coli* gdhA gene," *Nucleic Acids Res.* 11:5257-5266 (1983).

McPherson et al., "Multiple interactions of lysine-128 of *Escherichia coli* glutamate dehydrogenase revealed by site-directed mutagenesis studies," *Protein Eng.* 2(2):147-152 (1988).

Meagher, "Purification and partial amino acid sequence of the cyanogen bromide fragments of muconolactone isomerase from *Pseudomonas putida*," *Biochim. Biophys. Acta* 494:33-47 (1977).

Mechichi et al., "*Alicycliphilus denitrificans* gen. nov., sp. nov., a cyclohexanol-degrading, nitrate-reducing β-proteobacterium," *Int. J. Syst. Evol. Microbiol.* 53:147-152 (2003).

Megraw et al., "Formation of lactyl-Coenzyme A and pyruvyl-Coenzyme A from lactic acid by *Escherichia coli*," *J. Bacteriol.* 90(4):984-988 (1965).

Meinnel et al"Structural and Biochemical Characterization of the *Escherichia coli* argE Gene Product," *J. Bacteriol.* 174(7):2323-2331 (1992).

Melchiorsen et al., "The level of pyruvate-formate lyase controls the shift from homolactic to mixed-acid product formation in *Lactococcus lactis*," *Appl. Microbiol. Biotechnol.* 58:338-344 (2002).

Meng and Chuang, "Site-directed Mutagenesis and Functional Analysis of the Active-Site Residues of the E2 Component of Bovine Branched-Chain α-Keto Acid Dehydrogenase Complex," *Biochemistry* 33:12879-12885 (1994).

Meng and Li, "Cloning, expression and characterization of a thiolase gene from *Clostridium pasteurianum*," *Biotechnol. Lett.* 28(16):1227-1232 (2006).

Menon and Ragsdale, "Mechanism of the *Clostridium thermoaceticum* pyruvate:ferredoxin oxidoreductase: evidence for the common catalytic intermediacy of the hydroxyethylthiamine pyropyrosphate radical," *Biochemistry* 36(28):8484-8494 (1997).

Menzel et al., "Enzymatic evidence for an involvement of pyruvate dehydrogenase in the anaerobic glycerol metabolism of *Klebsiella pneumoniae*," *J. Biotech.* 56:135-142 (1997).

Menzel et al., "Kinetic, dynamic, and pathway studies of glycerol metabolism by *Klebsiella pneumoniae* in anaerobic continuous culsutre: IV. Enzymes and fluxes of pyruvate metabolism," *Botechnol. Bioeng.* 60(5):617-626 (1998).

Merkel and Nichols, "Characterization and sequence of the *Escherichia coli* panBCD gene cluster," *FEMS Microbiol. Lett.* 143(2-3):247-252 (1996).

Mermelstein et al., "Metabolic Engineering of *Clostridium acetobutylicum* ATCC 824 for Increased Solvent Production by Enhancement of Acetone Formation Enzyme Activities Using a Synthetic Acetone Operon," *Biotechnol. Bioeng.* 42(9):1053-1060 (1993).

Metz et al., "Purification of a jojoba embryo fatty acyl-Coenzyme A reductase and expression of its cDNA in high erucic acid rapeseed," *Plant Phys.* 122:635-644 (2000).

Meynial-Salles, I., et al., "A new process for the continuous production of succinic acid from glucose at high yield, titer and productivity," *Biotechnol. Bioeng.* 99(1):129-135 (2008).

Millard et al., "Enhanced production of succinic acid by overexpression of phosphoenolpyruvate carboxylase in *Escherichia coli*," *Appl. Environ. Microbiol.* 62(5):1808-1810 (1996).

Miller and Jenesel, "Enzymology of butyrate Formation by Butyrivibrio-Fibrisolvens," *J. Bacteriol.* 138:99-104 (1979).

Miller et al., "Structure of β-lactam synthetase reveals how to synthesize antibiotics instead of asparagine," *Nat. Struct. Biol.* 8(8):684-689 (2001).

Miller et al., "The catalytic cycle of β-lactam synthetase observed by x-ray crystallographic snapshots," *Proc. Natl. Acad. Sci. U.S.A.* 99(23):14752-14757 (2002).

Minard and McAlister-Henn, "Isolation, nucleotide sequence analysis, and disruption of the MDH2 gene from *Saccharomyces cerevisiae*: evidence for three isozymes of yeast malate dehydrogenase," *Mol. Cell. Biol.* 11:370-380 (1991).

Misono and Nagasaki, "Occurrence of L-Lysine ε-Dehydrogenase in *Agrobacterium tumefaciens*," *J. Bacteriol.* 150(1):398-401 (1982).

Misono et al., "Properties of L-lysine epsilon-dehydrogenase from *Agrobacterium tumefaciens*," *J. Biochem.* 105(6):1002-1008 (1989).

Miura et al., "Molecular Cloning of the nemA Gene Encoding N-Ethylmaleimide Reductase from *Escherichia coli*," *Biol. Pharm. Bull.* 20(1):110-112 (1997).

Miyazaki et al., "α-Aminoadipate aminotransferase from an extremely thermophilic bacterium, *Thermus thermophilus*," *Microbiology* 150:2327-2334 (2004).

Mizobata et al., "Purification and characterization of a thermostable class II fumarase from *Thermus thermophilus*," *Arch. Biochem. Biophys.* 355(1):49-55 (1998).

Mizugaki et al. "Studies on the metabolism of unsaturated fatty acids. IX. Stereochemical studies of the reaction catalyzed by trans-2-enoyl-Coenzyme A reductase of *Escherichia coli*," *J. Biochem.* 92(5):1649-1654 (1982).

Mizugaki et al., "Studies on the Metabolism of Unsaturated Fatty Acids. V. Isomerization of Thiol Esters of cis-2-Alkenoic Acids during Their Preparation and Alkaline Hydrolysis," *Chem. Pharm. Bull.* 30(1):206-213 (1982).

Momany et al., "Crystallization of diaminopimelate decarboxylase from *Escherichia coli*, a stereo specific D-amino-acid decarboxylase," *Acta. Crystallogr. D. Biol. Crystallogr.* 58(Pt 3):549-552 (2002).

Momany et al., "Crystallographic Structure of PLP-Dependent Ornithine Decarboxylase from *Lactobacillus* 30a to 3.0 Å Resolution," *J. Mol. Biol.* 252:643-655 (1995).

Monnet et al., "Regulation of branched-chain amino acid biosynthesis by α-acetolactate decarboxylase in *Streptococcus thermophilus*," *Lett. Appl. Microbiol.* 36(6):399-405 (2003).

Moon et al., "Metabolic engineering of *Escherichia coli* for the production of malic acid," *Biochem. Eng. J.* 40(2):312-320 (2008).

Moore et al., "Expression and Purification of Aspartate β-Semialdehyde Dehydrogenase from Infectious Microorganisms," *Protein Expr. Purif.* 25:189-194 (2002).

Moresi et al., "Fumaric acid production from hydrolysates of starch-based substrates," *J. Chem. Technol. Biotechnol.* 54(3):283-290 (1992).

Mori et al., "Characterization, Sequencing, and Expression of the Genes Encoding a Reactivating Factor for Glycerol-inactivated Adenosylcobalamin-dependent Diol Dehydratase," *J. Biol. Chem.* 272(51):32034-32041 (1997).

Morris and Jinks-Robertson, "Nucleotide sequence of the LYS2 gene of *Saccharomyces cerevisiae*: homology to *Bacillus brevis* tyrocidine synthetase 1," *Gene* 98:141-145 (1991).

Morsomme et al., "Single point mutations in various domains of a plant plasma membrane $H^+$-ATPase expressed in *Saccharomyces cerevisiae* increase $H^+$-pumping and permit yeast growth at low pH," *EMBO. J.* 15(20):5513-5526 (1996).

Morton et al., "Cloning, sequencing, and expressions of genes encoding enzymes of the autotrophic acetyl-CoA pathway in the acetogen *Clostridium thermoaceticum*," In M. Sebald (ed.), *Genetics and molecular biology of anaerobic bacteria*, Springer Verlag, New York, 389-406 (1992).

Morton et al., "The primary structure of the subunits of carbon monoxide dehydrogenase/acetyl-CoA synthase from *Clostridium thermoaceticum*," *J. Biol. Chem.* 266(35):23824-23828 (1991).

Moskowitz et al., "Metabolism of poly-β-hydroxybutyrate. II. Enzymatic synthesis of D-(-)-β-hydroxybutyryl Coenzyme A by an enoyl hydrase from *Rhodospirillum rubrum*," *Biochemistry* 8:2748-2755 (1969).

Moszer, "The complete genome of *Bacillus subtilis*: from sequence annotation to data management and analysis," *FEBS Lett.* 430:28-36 (1998).

Mouttaki et al., "Cyclohexane Carboxylate and Benzoate Formation from Crotonate in *Syntrophus aciditrophicus*," *Appl. Environl. Microbiol.* 73(3):930-938 (2007).

Müh et al., "4-Hydroxybutyryl-CoA dehydratase from *Clostridium aminobutyricum*: characterization of FAD and iron-sulfur clusters involved in an overall non-redox reaction," *Biochemistry* 35:11710-11718 (1996).

Müh et al., "Mössbauer study of 4-hydroxybutyryl-CoA dehydratase probing the role of an iron-sulfur cluster in an overall non-redox reaction," *Eur. J. Biochem.* 248:380-384 (1997).

Mukhopadhyay and Purwantini, "Pyruvate carboxylase from *Mycobacterium smegmatis*: stabilization, rapid purification, moleculare and biochemical characterization and regulation of the cellular level," *Biochim. Biophys. Acta* 1475(3):191-206 (2000).

Muller and Buckel, "Activation of (R)-2-hydroxyglutaryl-CoA dehydratase from *Acidaminococcus fermentans*," *Eur. J. Biochem.* 230(2):698-704 (1995).

Muller et al., "Nucleotide exchange and excisiion technology (NExT) DNA shuffling; a robust method for DNA fragmentation and directed evolution," *Nucleic Acids Res.* 33:e117 (2005).

Müller, "Energy Conservation in Acetogenic Bacteria," *Appl. Environ. Microbiol.* 69:6345-6353 (2003).

Murakami et al., "Purification and characterization of two muconate cycloisomerase isozymes from aniline-assimilating *Frateuria* species ANA-18," *Biosci. Biotechnol. Biochem.* 62:1129-1133 (1998).

Muratsubaki and Enomoto, "One of the fumarate reductase isoenzymes from *Saccharomyces cerevisiae* is encoded by the OSM1 gene," *Arch. Biochem. Biophys.* 352:175-181 (1998).

Musfeldt and Schönheit, "Novel type of ADP-forming acetyl Coenzyme A synthetase in hyperthermophilic archaea: heterologous expression and characterization of isoenzymes from the sulfate reducer *Archaeoglobus fulgidus* and the methanogen *Methanococcus jannaschii*," *J. Bacteriol.* 184(3):636-644 (2002).

Muyrers et al., "Rapid modification of bacterial artificial chromosomes by ET-recombination," *Nucleic Acids Res.* 27:1555-1557 (1999).

Nagasawa et al., "Cloning and Nucleotide Sequence of the Alcohol Acetyltransferase II gene (*ATF2*) from *Saccharomyces cerevisiae* Kyokai No. 7," *Biosci. Biotechnol. Biochem.* 62:1852-1857 (1998).

Nagata et al., "Gene cloning, purification, and characterization of thermostable and halophilic leucine dehydrogenase from a halophilic thermophile, *Bacillus licheniformis* TSN9," *Appl. Microbiol. Biotechnol.* 44:432-438 (1995).

Naggert et al., "Cloning, sequencing, and characterization of *Escherichia coli* thioesterase II," *J. Biol. Chem.* 266(17):11044-11050 (1991).

Nahvi et al., "Genetic Control by a Metabolite Binding mRNA," *Chem. Biol.* 9:1043-1049 (2002).

Naidu and Ragsdale, "Characterization of a three-component vanillate O-demethylase from *Moorella thermoacetica*," *J. Bacteriol.* 183(11):3276-3281 (2001).

Najafpour and Younesi, "Ethanol and acetate synthesis from waste gas using batch culture of *Clostridium ljungdahlii*," *Enzyme Microb. Technol.* 38:223-228 (2006).

Najmudin et al., "Purification, crystallization and preliminary X-ray crystallographic studies on acetolactate decarboxylase," *Acta. Crystallogr. D. Biol. Crystallogr.* 59(Pt 6):1073-1075 (2003).

Nakahigashi and Inokuchi, "Nucleotide sequence of the fadA and fadB genes from *Escherichia coli*," *Nucleic Acids Res.* 18(16):4937 (1990).

Nakano et al., "Characterization of Anaerobic Fermentative Growth of *Bacillus subtilis*: Identification of Fermentation End Products and Genes Required for Growth," *J. Bacteriol.* 179(21):6749-6755 (1997).

Nakazawa et al., "Studies on monooxygenases. V. Manifestation of amino acid oxidase activity by L-lysine monooxygenase," *J. Biol. Chem.* 247:3439-3444 (1972).

Namba et al., "Coenzyme A- and Nicotinamide Adenine Dinucleotide-dependent Branched Chain α-Keto Acid Dehydrogenase," *J. Biol. Chem.* 244(16):4437-4447 (1969).

Neidhart et al., "Mandelate racemase and muconate lactonizing enzyme are mechanistically distinct and structurally homologous," *Nature* 347:692-694 (1990).

Ness et al., "Synthetic shuffling expands functional protein diversity by allowing amino acids to recombine independently," *Nat. Biotechnol.* 20:1251-1255 (2002).

Nicolaou et al., "The Diels-Alder Reaction in Total Synthesis," *Angew Chemie Int Ed.* 41:1668-1698 (2002).

Niegemann et al., "Molecular organization of the *Escherichia coli* gab cluster: nucleotide sequence of the structural genes gabD and gabP and expression of the GABA permease gene," *Arch.Microbiol* 160:454-460 (1993).

Nimmo, "Kinetic mechanism of *Escherichia coli* isocitrate dehydrogenase and its inhibition by glyoxylate and oxaloacetate," *Biochem. J.* 234(2):317-323 (1986).

Nishimaki et al., "Studies on the Metabolism of Unsaturated Fatty Acids. XIV. Purification and Properties of NADPH-Dependent trans-2-Enoyl-CoA Reductase of *Escherichia coli* K-12," *J. Biochem.* 95(5):1315-1321 (1984).

Nishizawa et al., "Gene expression and characterization of two 2-oxoacid:ferredoxin oxidoreductases from *Aeropyrum pernix* K1," *FEBS Lett.* 579:2319-2322 (2005).

Nissen et al., "Expression of a cytoplasmic transhydrogenase in *Saccharomyces cerevisiae* results in formation of 2-oxoglutarate due to depletion of the NADPH pool," *Yeast* 18:19-32 (2001).

Nogales et al., "Characterization of the last step of the aerobic phenylacetic acid degradation pathway," *Microbiology* 153(Pt 2):357-365 (2007).

Noichinda et al., "Subcellular Localization of Alcohol Acetyltransferase in Strawberry Fruit," *Food Sci. Technol. Res.* 5(3):239-242 (1999).

Nölling et al., "Genome sequence and comparative analysis of the solvent-producing bacterium *Clostridium acetobutylicum*," *J. Bacteriol.* 183(16):4823-4838 (2001).

Norton, "The Diels-Alder Diene Synthesis," *Chem. Rev.* 31:319-523 (1942).

Nowicki et al., "Recombinant tyrosine aminotransferase from *Trypanosoma cruzi*: structural characterization and site directed mutagenesis of a broad substrate specificity enzyme," *Biochim. Bioghysica Acta* 1546:268-281 (2001).

O'Brien and Gennis, "Studies of the Thiamin Pyrophosphate Binding Site of *Escherichia coli* Pyruvate Oxidase," *J. Biol. Chem.* 255(8):3302-3307 (1980).

O'Brien et al, "Regulation by Lipids of Cofactor Binding to a Peripheral Membrane Enzyme: Binding of Thiamin Pyrophosphate to Pyruvate Oxidase," *Biochemistry* 16(14):3105-3109 (1977).

O'Brien et al., "Chemical, physical and enzymatic comparisons of formyltetrahydrofolate synthetases from thermo- and mesophilic clostridia," *Experientia. Suppl.* 26:249-262 (1976).

O'Brien et al., "Insight into the Mechanism of the $B_{12}$-Independent Glycerol Dehydratase from *Clostridium butyricum*: Preliminary Biochemical and Structural Characterization," *Biochemistry* 43:4635-4645 (2004).

Ofman et al., "2-Methyl-3-hydroxybutyryl-CoA dehydrogenase deficiency is caused by mutations in the HADH2 gene," *Am. J. Hum. Genet.* 72:1300-1307 (2003).

Ohgami et al., "Expression of acetoacetyl-CoA synthetase, a novel cytosolic ketone body-utilizing enzyme, in human brain," *Biochem. Pharmacol.* 65:989-994 (2003).

Ohsugi et al., "Metabolism of L-β-Lysine by *Pseudomonas*. Purification and Properties of a Deacetylase-Thiolestrerase Utilizing 4-Acetamidobutyryl CoA and Related Compounds," *J. Biol. Chem.* 256(14):7642-7651 (1981).

Okino et al., "An effeicient succinic acid production process in a metabolically engineered *Corynebacterium glutamicum* strain," *Appl. Microbiol. Biotechnol.* 81(3):459-464 (2008).

Oku and Kaneda, "Biosynthesis of branched-chain fatty acids in *Bacillus subtilis*. A decarboxylase is essental for branched-chain fatty acid synthetase," *J. Biol. Chem.* 263:18386-18396 (1988).

Okuno et al., "2-Aminoadipate-2-oxoglutarate aminotransferase isoenzymes in human liver: a plausible physiological role in lysine and tryptophan metabolism," *Enzyme Protein* 47:136-148 (1993).

Olivera et al., "Molecular characterization of the phenylacetic acid catabolic pathway in *Pseudomonas putida* U: the phenylacetyl-CoA catabolon," *Proc. Natl. Acad. Sci. U.S.A.* 95(11):6419-6424 (1998).

Onuffer and Kirsch, "Redesign of the substrate specificity of *Escherichia coli* aspartate aminotransferase to that of *Escherichia coli* tyrosine aminotransferase by homology modeling and site-directed mutagenesis," *Protein Sci.* 4:1750-1757 (1995).

O'Reilly and Devine, "Sequence and analysis of the citrulline biosynthetic operon argC-F from *Bacillus subtilis*," *Microbiology* 140:1023-1025 (1994).

Orencio-Trejo et al., "Metabolic reglulation analysis of an ethanologenic *Escherichia coli* strain based on RT-PCR and enzymatic activities," *Biotechnol. Biofuels* 1:8 (2008). (provided electronically by publisher as pp. 1-13).

Ostermeier et al., "A Combinatorial approach to hybrid enzymes independent of DNA homology," *Nat. Biotechnol.* 17:1205-1209 (1999).

Ostermeier et al., "Combinatorial protein engineering by incremental truncation," *Proc. Natl. Acad. Sci. U.S.A.* 96:3562-3567 (1999).

O'Sullivan et al., "Purification and characterisation of acetolactate decarboxylase from *Leuconostoc lactis* NCW1," *FEMS Microbiol. Lett* 194(2):245-249 (2001).

Otten and Quax, "Directed evolution:selecting today's biocatalysts," *Biomol. Eng.* 22:1-9 (2005).

Overkamp et al., "Functional analysis of structural genes for $NAD^+$-dependent formate dehydrogenase in *Saccharomyces cerevisiae*," *Yeast* 19:509-520 (2002).

Overkamp et al., "In vivo analysis of the mechanism for oxidation of cytosolic NADH by *Saccharomyces cerevisiae* mitochondria," *J. Bacteriol.* 182:2823-2830 (2000).

Padovani and Banerjee, "Assembly and protection of the radical enzyme, methylmalonyl-CoA mutase, by its chaperone," *Biochem.* 45(30):9300-9306 (2006).

Paik and Kim, "Enzymic syntehsis of ε-*N*-Acetyl-L-Lysine," *Arch. Biochem. Biophys.* 108:221-229 (1964).

Palosaari and Rogers, "Purification and Properties of the Inducible Coenzyme A-Linked Butyraldehyde Dehydrogenase from *Clostridium acetobutylicum*," *J. Bacteriol.* 170(7):2971-2976 (1988).

Parales and Harwood, "Characterization of the Genes Encoding β-Ketoadipate: Succinyl-Coenzyme A Transferase in *Pseudomonas putida*," J. Bacteriol. 174(14):4657-4666 (1992).

Park and Lee, "Biosynthesis of poly(3-hydroxybutyrate-co-3-hydroxyalkanoates) by metabolically engineered *Escherichia coli* strains," *Appl. Biochem. Biotechnol.* 113-116:335-346 (2004).

Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).

Park and Lee, "New FadB homologous enzymes and their use in enhanced biosynthesis of medium-chain-length polyhydroxyalkanoates in FadB mutant *Escherichia coli*," *Biotechnol. Bioeng.* 86(6):681-686 (2004).

Park et al., "Metabolic engineering of *Escherichia coli* for the production of L-valine based on transcriptome analysis and in silico gene knockout simulation," *Proc. Natl. Acad. Sci. U.S.A.* 104(19):7797-7802 (2007).

Park et al., "Regulation of succinate dehydrogenase (sdhCDAB) operon expression in *Escherichia coli* in response to carbon supply and anaerobiosis: role of ArcA and Fnr," *Mol. Microbiol.* 15(3):473-482 (1995).

Park et al., "Utilization of Electrically Reduced Neutral Red by *Actinobacillus succinogenes*: Physiological Function of Neutral Red in Membrane-Driven Fumarate Reduction and Energy Conservation," *J. Bacteriol* 181(8):2403-2410 (1999).

Parkin et al., "Rapid and efficient electrocatalytic $CO_2/CO$ interconversions by *Carboxydothermus hydrogenoformans* CO dehydrogenase I on an electrode," *J. Am. Chem. Soc.* 129(34):10328-10329 (2007).

Parsot et al., "Nucleotide sequence of *Escherichia coli* argB and argC genes: comparison of N-acetylglutamate kinase and N-acetylglutamate-γ-semialdehyde dehydrogenase with homologous and analogous enzymes," *Gene* 68:275-283 (1988).

Patel and Clark, "Acetoacetate metabolism in rat brain. Development of acetoacetyl-Coenzyme A deacylase and 3-hydroxy-3-methylglutaryl-Coenzyme A synthase," *Biochem. J.* 176(3):951-958 (1978).

Patel et al., "β-ketoadipate enol-lactone hydrolases I and II from *Acinetobacter calcoaceticus*," *J. Biol. Chem.* 250:6567-6577 (1975).

Patil et al., "Use of genome-scale microbial models for metabolic engineering," *Curr. Opin. Biotechnol.* 15(1):64-69 (2004).

Patnaik et al., "Genome shuffling of *Lactobacillus* for improved acid tolerance," *Nat. Biotechnol.* 20:707-712 (2002).

Pauli and Overath, "ato Operon: a Highly Inducible System for Acetoacetate and Butyrate Degradation in *Escherichia coli*," *Eur. J. Biochem.* 29:553-562 (1972).

Pauwels et al., "The N-acetylglutamate synthase/N-acetylgltamate kinase metabolon of *Saccharomyces cerevisiae* allows co-ordinated feedback regulation of the first two steps in arginine biosynthesis," *Eur. J. Biochem.* 270:1014-1024 (2003).

Paxton et al., "Role of branched-chain 2-oxo acid dehydrogenase and pyruvate dehydrogenase in 2-oxobutyrate metabolism," *Biochem. J.* 234:295-303 (1986).

Peisach et al., "Crystallographic study of steps along the reaction pathway of D-amino acid aminotransferase," *Biochemistry* 37(14)4958-4967 (1998).

Pelletier and Harwood, "2-Ketocyclohexanecarboxyl Coenzyme A Hydrolase, the Ring cleavage Enzyme Required for Anaerobic Benzoate Degradation of *Rhodopseudomonas palustris*," *J. Bacteriol.* 180(9):2330-2336 (1998).

Peoples and Sinskey, "Fine structural analysis of the *Zoogloea ramigera* phbA-phbB locus encoding β-ketothiolase and acetoacetyl-CoA reductase: nucleotide sequence of phbB," *Mol. Microbiol.* 3:349-357 (1989).

Pereira et al., "Active site mutants of *Escherichia coli* citrate synthase. Effects of mutations on catalytic and allosteric properties," *J. Biol. Chem.* 269:412-417 (1994).

Peretz and Burstein, "Amino acid sequence of alcohol dehydrogenase from the thermophilic bacterium *Thermoanaerobium brockii*," *Biochemistry* 28(16):6549-6555 (1989).

Peretz et al., "Molecular cloning, nucleotide sequencing, and expression of genes encoding alcohol dehydrogenases from the thermophile *Thermoanaerobacter brockii* and the mesophile *Clostridium beijerinckii*," *Anaerobe.* 3:259-270 (1997).

Perez et al., "*Escherichia coli* YqhD exhibits aldehyde reductase activity and protects from the harmful effect of lipid peroxidation-derived aldehydes," *J. Biol. Chem.* 283(12):7346-7353 (2008).

Perez-Prior et al., "Reactivity of lactones and GHB formation," *J. Org. Chem.* 70:420-426 (2005).

Petersen and Bennett, "Purification of acetoacetate decarboxylase from *Clostridium acetobutylicum* ATCC 824 and cloning of the acetoacetate decarboxylase gene in *Escherichia coli*," *Appl. Environ. Microbiol.* 56:3491-3498 (1990).

Petitdemange et al., "Regulation of the NADH and NADPH-ferredoxin oxidoreductases in clostridia of the butyric group," *Biochim. Biophys. Acta* 421(2):334-347 (1976).

Pfanner and Geissler, "Versatility of the mitochondrial protein import machinery," *Nat. Rev. Mol. Cell. Biol.* 2(5):339-349 (2001).

Pfluger et al., "Lysine-2,3-Aminomutase and β-Lysine Acetyltransferase Genes of Methanogenic Archaea Are Salt Induced and Are Essential for the Biosynthesis of $N^ε$-Acetyl-β-Lysine and Growth at High Salinity," *Appl. Environ. Microbiol.* 69(10):6047-6055 (2003).

Phalip et al., "Purification and properties of the α-acetolactate decarboxylase from *Lactococcus lactis* subsp. *Lactis* NCDO 2118," *FEBS Lett.* 351(1):95-99 (1994).

Pharkya et al., "OptiStrain: A computational Framework for redesign of microbial production systems," *Genome Res.* 14(11):2367-2376 (2004).

Pharkya et al., "Exploring the overproduction of amino acids using the bilevel optimization framework OptKnock," *Biotechnol. Bioeng.* 84(7):887-899 (2003).

Phillips et al., "High Copy Number Plasmids Compatible with Commonly Used Cloning Vectors," *Biotechniques* 28:400, 402, 404, 406, 408 (2000).

Pierce et al., "The Complete Genome Sequence of *Moorella thermoacetia* (f. *Clostridum thermoaceticum*)," *Environ. Microbiol.* 10(10):2550-2573 (2008).

Pieulle et al., "Isolation and analysis of the gene encoding the pyruvate-ferredoxin oxidoreductase of *Desulfovibrio africanus*, production of the recombinant enzyme in *Escherichia coli*, and effect of carboxy-terminal deletions on its stability," *J. Bacteriol.* 179(18):5684-5692 (1997).

Pine et al., "Titanium-Mediated Methylene-Transfer Reactions. Direct Conversion of Esters into Vinyl Ethers," *J. Am. Chem. Soc.* 102:3270-3272 (1980).

Ploux et al., "Investigation of the first step of biotin biosynthesis in *Bacillus sphericus*," *Biochem. J.* 287:685-690 (1992).

Ploux et al., "The NADPH-linked acetoacetyl-CoA reductase from *Zoogloea ramigera*, Characterization and mechanistic studies of the cloned enzyme over-produced in *Escherichia coli*," *Eur. J. Biochem.* 174:177-182 (1988).

Pohl et al., "Remarkably broad Sutstrate Tolerance of Malonyl-CoA Synthetase, an Enzyme Capable of Intracellular Synthesis of Polyketide Precursors," *J. Am. Chem. Soc.* 123:5822-5823 (2001).

Pohlmann et al., "Genome sequence of the bioplastic-producing "Knallgas" bacterium *Ralstonia eutropha* H16," *Nat. Biotechnol.* 24(10):1257-1262 (2006).

Pollard et al., "Purification, characterisation and reaction mechanisms of monofunctional 2-hydroxypentadienoic acid hydratase from *Escherichia coli*," *Eur. J. Biochem. FEBS* 251:98-106 (1998).

Pollard et al., "Substrate Selectivity and biochemical Properties of 4-Hydroxy-2-Keto-Pentanoic Acid Aldolase from *Escherichia coli*," *Appl. Environ. Microbiol.* 64(10):4093-4094 (1998).

Polovnikova et al., "Structural and kinetic analysis of catalysis by a thiamine diphosphate-deptendent enzyme, benzoylformate decarboxylase," *Biochemistry* 42:1820-1830 (2003).

Ponce, E., et al., "Cloning of the two pyruvate kinase isoenzyme structural genes from *Escherichia coli*: the relative roles of these enzymes in pyruvate biosynthesis," *J. Bacteriol.* 177(19):5719-5722 (1995).

Postma et al., "Phosphoenolpyruvate Carbohydrate Phosphotransferase Systems of Bacteria," *Microbiol Rev.* 57(3):543-594 (1993).

Poston, "Assay of leucine 2,3-aminomutase," *Methods Enzymol.* 166:130-135 (1988).

Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175(2):377-385 (1993).

Price et al., "Genome-scale microbial in silico models: the constraints-based approach," *Trends Biotechnol.* 21(4):162-169 (2003).

Price et al., "Genome-scale models of microbial cells: evaluating the consequences of constraints," *Nat. Rev. Microbiol.* 2(11):886-897 (2004).

Prieto et al., "Molecular Characterization of the 4-Hydroxyphenylacetate Catabolic Pathway of *Escherichia coli* W: Engineering a Mobile Aromatic Degradative Cluster," *J. Bacteriol.* 178(1):111-120 (1996).

Pritchard et al., "A general model of error-prone PCR," *J. Theor. Biol.* 234:497-509 (2005).

Pritchett and Metcalf, "Genetic, physiological and biochemical characterization of multiple methanol methyltransferase isozymes in *Methanosarcina acetivorans* C2A," *Mol. Microbiol.* 56(5):1183-1194 (2005).

Pronk et al., "Pyruvate metabolism in *Saccharomyces cerevisiae*," *Yeast* 12:1607-1633 (1996).

Pucci et al., "*Staphylococcus haemolyticus* contains two D-glutamic acid biosynthetic activities, a glutamate racemase and a D-amino acid transminase," *J. Bacteriol.* 177(2):336-342 (1995).

Purnell et al., "Modulation of higher-plant NAD(H)-dependent glutamate dehydrogenase activity in transgenic tobacco via alteration of β subunit levels," *Planta* 222:167-180 (2005).

Qi et al., "Functional expression of prokaryotic and eukaryotic genes in *Escherichia coli* for conversion of glucose to p-hydroxystyrene," *Metab. Eng.* 9:268-276 (2007).

Qian et al., "Metabolic engineering of *Escherichia coli* for the production of putrescine: a four carbon diamine," *Biotechnol. Bioeng.* 104(4)651-662 (2009).

Qiu et al., "Metabolic engineering of *Aeromonas hydrophila* for the enhanced production of poly(3-hydroxybutyrate-co-3-hydroxyhexanoate)," *Appl. Microbiol. Biotechnol.* 69(5):537-542 (2006).

Qu et al., "Inhibition of human ornthine decarboxylase activity by enantiomers of difluoromethylornithine," *Biochem. J.* 375:465-470 (2003).

Quail and Guest, "Purification, characterization and mode of action of pdhR, the transcriptional repressor of the PdhR-aceEF-Ipd operon of *Escherichia coli*," *Mol. Microbiol.* 15(3):519-529 (1995).

Rado and Hoch, "Phosphotransacetylase from *Bacillus subtilis*: purification and physiological studies," *Biochim. Biophys. Acta* 321:114-125 (1973).

Ragsdale et al., "Acetogenesis and the Wood-Ljungdahl pathway of $CO_2$ fixation," *Biochimica. Biophysica. Acta* 1784(12):1873-1898 (2008).

Ragsdale, "Enzymology of the wood-Ljungdahl pathway of acetogenesis," *Ann. NY Acad Sci.* 1125:129-136 (2008).

Ragsdale, "Life with carbon monoxide," *Crit. Rev. Biochem. Mol. Biol.* 39(3):165-195 (2004).

Ragsdale, "Pyruvate ferredoxin oxidoreductase and its radical intermediate," *Chem. Rev.* 103(6):2333-2346 (2003).

Rajpal et al., "A general method for greatly improving the affinity of antibodies by using combinatorial libraries," *Proc. Natl. Acad. Sci. U.S.A.* 102:8466-8471 (2005).

Ramjee et al., "*Escherichia coli* L-aspartate-α-decarboxylase: preprotein processing and observation of reaction intermediates by electrospray mass spectrometry," *Biochem. J.* 323(Pt 3):661-669 (1997).

Ramon-Maiques et al., "Structure of Acetylglutamate Kinase, a Key Enzyme for Arginine Biosynthesis and Prototype for the Amino Acid Kinase Enzyme Family, during Catalysis," *Structure* 10:329-342 (2002).

Ramos et al., "Mutations affecting the enzymes involved in the utilization of 4-aminobutyric acid as nitrogen source by the yeast *Saccharomyces cerevisiae*," *Eur.J. Biochem.* 149:401-404 (1985).

Rangarajan et al., "Structure of [NiFe] hydrogenase maturation protein HypE from *Escherichia coli* and its interaction with HypF," *J. Bacteriol.* 190(4):1447-1458 (2008).

Rasmussen, L.J., et al. "Carbon Metabolism Regulates Expression of the *pfl* (Pyruvate-Formate-Lyase) Gene in *Escherichia coli*," *J. Bacteriol.* 173(20):6390-6397 (1991).

Rathinasabapathi, "Propionate, a source of β-alanine, is an inhibitor of β-alanine methylation in Limonium latifoilium Plunbaginaces," *J. Plant Physiol.* 159:671-674 (2002).

Ratnatilleke et al., "Cloning and sequencing of the Coenzyme $B_{12}$-binding domain of isobutyryl-CoA mutase from *Streptomyces cinnamonensis*, reconstitution of mutase activity, and characterization of the recombinant enzyme produced in *Escherichia coli*," *J. Biol. Chem.* 274(44):31679-31685 (1999).

Raux et al., "The role of *Saccharomyces cerevisiae* Met1p and Met8p in sirohaem and cobalamin biosynthesis," *Biochem. J.* 338 (pt. 3):701-708 (1999).

Raux et al., "*Salmonella typhimurium* cobalamin (vitamin $B_{12}$) biosynthetic genes: functional studies in *S. typhimurium* and *Escherichia coli*," *J. Bacteriol.* 178(3):753-767 (1996).

Ravagnani et al., "Spo0A directly controls the switch from acid to solvent production in solvent-forming clostridia," *Mol. Microbiol.* 37(5):1172-1185 (2000).

Raybuck et al., "Kinetic characterization of the carbon monoxide-acetyl-CoA (carbonyl group) exchange activity of the acetyl-CoA synthesizing CO dehydrogenase from *Clostridium thermoaceticum*," *Biochemistry* 27(20):7698-7702 (1988).

Raynaud et al., "Molecular characterization of the 1,3-propanediol (1,3-PD) operon of clostridium butyricum," *Proc. Natl. Acad. Sci. U.S.A.* 100:5010-5015 (2003).

Rea et al., "Structure and Mechanism of HpcH: A Metal Ion Dependent Class II Aldolase from the Homoprotocatechuate Degradation Pathway of *Escherichia coli," J. Mol. Biol.* 373:866-876 (2007).
Recasens et al., "Cystein Sulfinate Aminotransferase and Aspartate Aminotransferase Isoenzymes of Rat Brain. Purification, Characterization, and Further Evidence of Identity," *Biochemistry* 19:4583-4589 (1980).
Reda et al., "Reversible interconversion of carbon dioxide and formate by an electroactive enzyme," *Proc. Natl. Acad. Sci. U.S.A.* 105:10654-10658 (2008).
Reetz and Carballeira, "Iterative saturation mutagenesis (ISM) for rapid directed evolution of functional enzymes," *Nat. Protoc.* 2:891-903 (2007).
Reetz et al., "Creation of Enantioselective Biocatalysts for Organic Chemistry by In Vitro Evolution," *Angew. Chem. Int. Ed. Engl.* 36:2830-2832 (1997).
Reetz et al., "Directed Evolution of an Enantioselective Enzyme through Combinatorial Multiple-Cassette Mutagenesis," *Angew. Chem. Int. Ed. Engl.* 40:3589-3591 (2001).
Reetz et al., "Expanding the Range of Substrate Acceptance Enzymes: Cominatorial Active-Site Saturation Test," *Angew. Chem. Int. Ed.* 117:4264-4268 (2005).
Reetz et al., "Iterative saturation mutagenesis on the basis of B factors as a strategy for incresing protein thermostability," *Angew. Chem. Int. Ed.* 45:7745-7751 (2006).
Regev-Rudzki et al., "Yeast Aconitase in Two Locations and Two Metabolic Pathways: Seeing Small Amounts Is Believing," *Mol. Biol. Cell* 16:4163-4171 (2005).
Reidhaar-Olson and Sauer, "Combinatorial cassette mutagenesis as a probe of the informational content of protein sequences," *Science* 241:53-57 (1988).
Reidhaar-Olson et al., "Random mutagenesis of protein sequences using oligonucleotide cassettes," *Methods Enzymmol.* 208:564-586 (1991).
Reiser and Somerville, "Isolation of mutants of Acinetobacter calcoaceticus deficient in wax ester synthesis and complementation of one mutation with a gene encoding a fatty acyl Coenzyme A reductase," *J. Bacteriol.* 179(9):2969-2975 (1997).
Reitzer et al., "Crystallization and preliminary X-ray analysis of recombinant glutamate mutase and of the isolated component S from *Clostridium cochlearium," Acta. Crystallogr. D. Biol. Crystallogr.* 54(Pt 5):1039-1042 (1998).
Repetto and Tzagoloff, "Structure and Regulation of KGD1, the Structural Gene for Yeast α-Ketoglutarate Dehydrogenase," *Mol. Cell. Biol.* 9(6):2695-2705 (1989).
Reshetnikov, et al., "Characterization of the ectoine biosynthesis genes of haloalkalotolerant obligate methanotroph '*Methylomicrobium alcaliphilum* 20Z'," *Arch. Microbiol.* 184:286-297 (2006).
Resnekov et al., "Organization and regulation of the *Bacillus subtilis* odhAB operon, which encodes two of the subenzymes of the 2-oxoglutarate dehydrogenase complex," *Mol. Gen. Genet.* 234:285-296 (1992).
Rhodes et al., "Production of fumaric acid by *Rhizopus arrhuzus," Appl. Microbiol.* 7:74-80 (1959).
Rhodes et al., "Production of Fumaric Acid in 20-Liter Fermentors," *Appl. Microbiol.* 10(1)9-15 (1962).
Rigden et al., "A cofactor-dependent phosphoglycerate mutase homolog from *Bacillus stearothermophilus* is actually a broad specificity phosphatase," *Protein Sci.* 10:1835-1846 (2001).
Ringer et al., "Monoterpene double-bond reductases of the (−)-menthol biosynthetic pathway: isolation and characterization of cDNAs encoding (−)-isopiperitenone reductase and (+)-pulegone reductase of peppermint," *Arch. Biochem. Biophys.* 418(1):80-92 (2003).
Ringquist et al., "Translation initiation in *Escherichia coli*: sequences within the ribosome-binding site," *Mol. Microbiol.* 6(9):1219-1229 (1992).
Riondet et al., "Measurement of the intracellular pH in *Escherichia coli* with the internally conjugated fluorescent probe 5- (and 6-)carboxyfluorescein succinimidyl ester." *Biotechnol. Tech.* 11:735-738 (1997).
Rioux et al., "Two outer membrane transport systems for vitamin $B_{12}$ in *Salmonella typhimurium," J. Bacteriol.* 171:2986-2993 (1989).
Rioux et al., "Vitamin $B_{12}$ transport in *Escherichia coli* K12 does not require the *btuE* gene of the *btuCED* operon," *Mol. Gen. Genet.* 217:301-308 (1989).
Riviere et al., "Acetyl:succinate CoA-transferase in procyclic *Trypanosoma brucei*. Gene identification and role in carbohydrate metabolism." *J. Biol. Chem.* 279:45337-45346 (2004).
Roa Engel et al., "Fumaric acid production by fermentation," *Appl. Microbiol. Biotechnol.* 78(3):379-389 (2008).
Roberts et al, "The Role of Enoyl-CoA Hydratase in the Metabolism of Isoleucine by *Pseudomonas putida," Arch. Microbiol.* 117:99-108 (1978).
Roberts et al., "Acetyl-Coenzyme A synthesis from methyltetrahydrofolate, CO, and Coenzyme A by enzymes purified from *Clostridium thermoaceticum*: attainment of in vivo rates and identification of rate-limiting steps," *J. Bacteriol.* 174(14):4667-4676 (1992).
Roberts et al., "Cloning and expression of the gene cluster encoding key proteins involved in acetyl-CoA synthesis in *Clostridium thermoaceticum*: CO dehydrogenase, the corrinoid/Fe-S protein, and methyltransferase," *Proc. Natl. Acad. Sci. U.S.A.* 86(1):32-36 (1989).
Robinson et al., "Studies on Rat Brain Acyl-Coenzyme A Hydrolase (Short Chain)," *Biochem. Biophys. Res. Commun.* 71(4):959-965 (1976).
Roca et al., "Metabolic engineering of ammonium assimilation in xylose-fermenting *Saccharomyces cerevisiae* improves ethanol production," *Appl. Environ. Microbiol.* 69:4732-4736 (2003).
Rodriguez et al., "Characterization of the *p*-Coumaric Acid Decarboxylase from *Lactobacillus plantarium* CECT $748^T$," *J. Agric. Food Chem.* 56:3068-3072 (2008).
Roffia et al., "Byproduct Identification in the Terepthalic Acid Production Process and Possible Mechanisms of their Formation," *Ind. Eng. Chem. Prod. Res. Dev.* 23:629-634 (1984).
Rohdich et al., "Enoate reductases of Clostridia. Cloning, sequencing, and expression," *J. Biol. Chem.* 276(8):5779-5787 (2001).
Rohwerder et al., "The alkyl tert-butyl ether intermediate 2-hydroxyisobutyrate is degraded via a novel cobalamin-dependent mutase pathway," *Appl. Environ. Microbiol.* 72(6):4128-4135 (2006).
Romero et al., "Partial purification and characterization and nitrogen regulation of the lysine ϵ-aminotransferase of *Streptomyces clavuligers," J. Ind. Microbiol. Biotechnol.* 18:241-246 (1997).
Roper et al., "Sequence of the hpcC and hpcG genes of the meta-fission homoprotocatechuic acid pathway of *Escherichia coli* C: nearly 40% amino-acid identity with the analogues enzymes of the catechol pathway," *Gene* 156:47-51 (1995).
Rose and Weaver, "The role of the allosteric B site in the fumarase reaction," *Proc. Natl. Acad. Sci. U.S.A.* 101(10):3393-3397 (2004).
Rose et al., "Enzymatic phosphorylation of acetate," *J. Biol. Chem.* 211(2):737-756 (1954).
Rosenberg, "A Comparison of Lipid Patterns in Photosynthesizing and Nonphotosynthesizing Cells of *Euglena gracilis," Biochem.* 2:1148-1154 (1963).
Roszak et al., "The Structure and Mechanism of the Type II Dehydroquinase from *Streptomyces coelicolor," Structure* 10:493-503 (2002).
Roth et al., "Characterization of the cobalamin (vitamin $B_{12}$) biosynthetic genes of *Salmonella typhimurium," J. Bacteriol.* 175:3303-3316 (1993).
Rother and Metcalf, "Anaerobic growth of *Methanosarcina acetivorans* C2A on carbon monoxide: an unusual way of life for a methanogenic archaeon," *Proc. Natl. Acad. Sci. U.S.A.* 101(48):16929-16934 (2004).
Rother et al., "Genetic and proteomic analyses of CO utilization by *Methanosarcina acetivorans," Arch. Microbiol.* 188(5):463-472 (2007).

Rous, "On the occurrence of enzymes of ketone-body metabolism in human adipose tissue," Biochem. Biophys. Res. Commun. 69(1):74-78 (1976).

Roux and Walsh, "p-aminobenzoate synthesis in Escherichia coli: kinetic and mechanistic characterization of the amidotransferase PabA," Biochemistry 31:6904-6910 (1992).

Roux and Walsh, "p-Aminobenzoate synthesis in Escherichia coli: mutational analysis of three conserved amino acid residues of the amidotransferase PabA," Biochemistry 32:3763-3768 (1993).

Roy and Dawes, "Cloning and Characterization of the gene Encoding Lipoamide Dehydrogenase in Saccharomyces cerevisiae," J. Gen. Microbiol. 133:925-933 (1987).

Roymoulik et al., "Rearrangement of L-2-hydroxyglutarate to L-threo-3-methylmalate catalyzed by adenosylcobalamin-dependent glutamate mutase," Biochem. 39(33):10340-10346 (2000).

Rozell and Benner, "Stereochemical Imperative in Enzymic Decarboxylations. Stereochemical Course of Decarboxylation Catalyzed by Acetoacetate Decarboxylase," J. Am. Chem. Soc. 106:4937-4941 (1984).

Rudman and Meister, "Transamination in Escherichia coli," J. Biol. Chem. 200(2):591-604 (1953).

Ruldeekulthamrong et al., "Molecular characterization of lysine 6-dehydrogenase from Achromobacter denitrificans," BMB Reports 790-795 (2008).

Sabo et al., "Purification and physical properties of inducible Escherichia coli lysine decarboxylase," Biochemistry 13:622-670 (1974).

Sadowski, "The Flp recombinase of the 2-μm plasmid of Saccharomyces cerevisiae," Prog. Nucleic Acid Res. Mol. Biol. 51:53-91 (1995).

Saegesser et al., "Stability of broad host range cloning vectors in the phototrophic bacterium Rhodospirillum rubrum," FEMS Microbiol. Lett. 95:7-11 (1992).

Saito and Doi, "Microbial synthesis and properties of poly(3-hydroxybutyrate-co-4-hydroxybutyrate) in Comamonas acidovorans," Int. J Biol Macromol. 16:99-104 (1994).

Sakai et al, "Acetate and Ethanol Production from $H_2$ and $CO_2$ by Morrella sp. Using a Repeated Batch Culture," J. Biosci. Bioeng. 99:252-258 (2005).

Sakanyan et al., "A re-examination of the pathway for ornithine biosynthesis in a thermophilic and two mesophilic Bacillus species," J. Gen. Microbiol. 138:125-130 (1992).

Sakurada et al., "Acetylpolyamine Amidohydrolase from Mycoplana ramosa: Gene Cloning and Characterization of the Metal-Substituted Enzyme," J. Bacteriol. 178(19):5781-5786 (1996).

Salmon et al., "Global gene expression profiling in Escherichia coli K12. Effects of oxygen availability and ArcA," J. Biol. Chem. 280(15):15084-15096 (2005).

Saltzgaber-Muller et al., "Nuclear genes coding the yeast mitochondrial adenosine triphosphatase complex. Isolation of ATP2 coding the $F_1$-ATPase β subunit," J. Bio. Chem. 258(19):11465-11470 (1983).

Samanta and Harwood, "Use of Rhodopseudomonas palustris genome sequence to identify a single amino acid that contributes to the activity of Coenzyme A ligase with chlorinated substrates," Mol. Microbiol. 55(4):1151-1159 (2005).

Samsonova et al., "Molecular cloning and characterization of Escherichia coli K12 ygjG gene," BMC Microbiol. 3:2 (2003).

Samuelov et al., "Whey fermentation by Anaerobiospirillum succiniciproducens for production of a succinate-based animal feed additive," Appl. Environ. Microbiol. 65(5):2260-2263 (1999).

San et al., "Metabolic Engineering through Cofactor Manipulation and its Effects on Metabolic Flux Redistribution in Escherichia coli," Metab Eng. 4(2):182-192 (2002).

Sanchez et al., "Efficient succinic acid production from glucose through overexpression of pyruvate carboxylase in an Escherichia coli alcohol dehydrogenase and lactate dehydrogenase mutant," Biotechnol. Prog. 21(2):358-365 (2005).

Sanchez et al., "Novel pathway engineering design of the anaerobic central metabolic pathway in Escherichia coli to increase succinate yield and productivity," Metab. Eng. 7(3): 229-239 (2005).

Sanchez et al., "Batch culture characterization and metabolic flux analysis of succinate-producing Escherichia coli strains," Metab Eng. 8(3):209-226 (2006).

Sanchez et al., "Effect of different levels of NADH availability on metabolic fluxes of Escherichia coli chemostat cultures in defined medium," J. Biotechnol. 117(4):395-405 (2005).

Sankaranarayanan et al., "Preliminary x-ray crystallographic analysis of ornithine acetyltransferase (Rv1653) from Mycobacterium tuberculosis," Acta. Crystallogr. Sect. F. Struct. Biol. Cryst. Commun. 65(Pt 2):173-176 (2009).

Sanyal et al., "Biosyntehsis of pimeloyl-CoA, a biotin precursor in Escherichia coli, follows a modified fatty acid synthesis pathway: $^{13}$C-labeling studies," J. Am. Chem. Soc. 116:2637-2638 (1994).

Sariaslani, "Development of a Combined biological and Chemical Process for Production of Industrial aromatics from Renewable Resources," Annu. Rev. Microbiol. 61:51-69 (2007).

Sass et al., "Folding of fumarase during mitochondrial import determines its dual targeting in yeast," J. Biol. Chem. 278(46):45109-45116 (2003).

Sato et al., "Poly[(R)-3-hydroxybutyrate] formation in Escherichia coli from glucose through an enoyl-CoA hydratase-mediated pathway," J. Biosci. Bioeng. 103(1):38-44 (2007).

Sauer and Thauer, "Methanol:Coenzyme M methyltransferase from Methanosarcina barkeri. Identification of the active-site histidine in the corrinoid-harboring subunit MtaC by site-directed mutagenesis," Eur. J. Biochem. 253(3):698-705 (1998).

Sauer et al., "Methanol:Coenzyme M methyltransferase from Methanosarcina barkeri. Purification, properties and encoding genes of the corrinoid protein MT1," Eur. J. Biochem. 243(3):670-677 (1997).

Sauer, "Diels-Alder Reactions II: The Reaction Mechanism," Angew. Chem. Int. Ed. 6:16-33 (1967).

Sauvageot et al., "Characterisation of the diol dehydratase pdu operon of Lactobacillus collinoides," FEMS Microbiol. Lett. 209:69-74 (2002).

Sawers and Boxer, "Purification and properties of membrane-bound hydrogenase isoenzyme 1 from anaerobically grown Escherichia coli K12," Eur. J. Biochem. 156(2):265-275 (1986).

Sawers et al., "Characterization and physiological roles of membrane-bound hydrogenase isoenzymes from Salmonella typhimurium," J. Bacteriol. 168(1):398-404 (1986).

Sawers et al., "Differential expression of hydrogenase isoenzymes in Escherichia coli K-12: evidence for a third isoenzyme," J. Bacteriol. 164(3):1324-1331 (1985).

Sawers, "The hydrogenases and formate dehydrogenases of Escherichia coli," Antonie Van Leeuwenhoek 66(1-3):57-88 (1994).

Saz and Weil, "The mechanism of the formation of α-methylbutyrate from carbohydrate by Ascaris lumbricoides muscle," J. Biol. Chem. 235:914-918 (1960).

Schadt et al., "2-Amino-2-deoxyisochorismate is a key intermediate in Bacillus subtilis p-aminobenzoic acid biosynthesis," J. Am. Chem. Soc. 131:3481-3483 (2009).

Scher and Jakoby, "Maleate isomerase," J. Biol. Chem. 244:1878-1882 (1969).

Scherf and Buckel, "Purification and properties of 4-hydroxybutyrate Coenzyme A transferase from Clostridium aminobutyricum," Appl. Environ. Microbiol. 57(9):2699-2702 (1991).

Scherf and Buckel, "Purification and properties of an iron-sulfur and FAD-containing 4-hydroxybutyryl-CoA dehadratase/vinylacetyl-CoA $\Delta^3$-$\Delta^2$-isomerase from Clostridium aminobutricum," Eur. J. Biochem. 215:421-429 (1993).

Scherf et al, "Succinate-ethanol fermentation in Clostridium kluyveri: purification and characterisation of 4-hydroxybutyryl-CoA dehydratase/vinylacetyl-CoA $\Delta^3$-$\Delta^2$-isomerase," Arch. Microbiol. 161(3):239-245 (1994).

Schilling et al., "Genome-Scale Metabolic Model of Helicobacter pylori 26695," J. Bacteriol. 184:4582-4593 (2002).

Schilling et al., "Combining Pathway Analysis with Flux Balance Analysis for the Comprehensive Study of Metabolic Systems," Biotechnol. Bioeng. 71(4):286-306 (2000/2001).

Schilling et al., "Theory for the Systematic Definition of Metabolic Pathways and Their Use in Interpreting Metabolic Function from a Pathway-Oriented Perspective," *J. Theor. Biol.* 203(3):229-248 (2000).

Schilling et al., "Toward Metabolic Phenomics: Analysis of Genomic Data Using Flux Balances," *Biotechnol. Prog.* 15(3):288-295 (1999).

Schmid et al., "Plasmid-mediated uptake and metabolism of sucrose by *Escherichia coli* K-12," *J. Bacteriol.* 151(1):68-76 (1982).

Schmitzberger et al., "Structural constraints on protein self-processing in L-aspartate-α-decarboxylase," *EMBO J.* 22:6193-6204 (2003).

Schneider and Betz, "Waxmonoester Fermentation in *Euglena gracilis* T Factors Favoring the Synthesis of Odd-Numbered Fatty-Acids and Alcohols," *Planta.* 166:67-73 (1985).

Schneider et al., "The *Escherichia coli* gabDTPC operon: specific γ-aminobutyrate catabolism and nonspecific induction," *J. Bacteriol.* 184:6976-6986 (2002).

Schnell et al., "Anaerobic degradation of aniline and dihydroxybenzenes by newly isolated sulfate-reducing bacteria and description of *Desulfobacterium anilini*," *Arch. Microbiol.* 152:556-563 (1989).

Schousboe et al., "Purification and Characterization of the 4-Aminobutyrate-2-Ketoglurate Transaminase from Mouse Brain," *Biochem.* 2(15):2868-2873 (1973).

Schrock et al., "Preparation and Reactivity of Several Alkylidene Complexes of the Type $W(CHR')(N-2, 6-C_6H_3-i-Pr_2)(OR)_2$ and Related Tungstacyclobutane complexes. Controlling Metathesis Activity through the Choice of Alkoxide Ligand," *J. Am. Chem. Soc.* 110:1423-1435 (1988).

Schulz et al., "Stereospecific production of the herbicide phosphinothricin (glufosinate) by transamination: isolation and characterization of a phosphinothricin-specific transaminase from *Escherichia coli*," *Appl. Environ. Microbiol.* 56(1):1-6 (1990).

Schurmann and Sprenger, "Fructose-6-phosphate aldolase is a novel class I aldolase from *Escherichia coli* and is related to a novel group of bacterial transaldolases," *J. Biol. Chem.* 276(14): p. 11055-11061 (2001).

Schwarzer et al., "Nonribosomal peptides: from genes to products," *Nat. Prod. Rep.* 20:275-287 (2003).

Schweiger and Buckel, "On the dehydration of (R)-lactate in the fermentation of alanine to propionat by *Clostridium propionicum*," *FEBS Lett.* 171:79-84 (1984).

Schweiger et al., "Purification of 2-hydroxyglutaryl-CoA dehydratase from *Acidaminococcus fermentans*. An iron-sulfur protein," *Eur. J. Biochem.* 169(2):441-448 (1987).

Scott and Jakoby, "Soluble γ-Aminobutyric-Glutamic Transaminase from *Pseudomonas fluorescens*," *J. Biol. Chem.* 234:932-936 (1959).

Scott, A.I., "Discovering nature's diverse pathways to vitamin $B_{12}$: a 35-year odyssey," *J. Org. Chem.* 68:2529-2539 (2003).

Seedorf et al., "The genome of *Clostridium kluyveri*, a strict anaerobe with unique metabolic features," *Proc. Natl. Acad. Sci. U.S.A.* 105(6):2128-2133 (2008).

Seffernick et al., "Melamine deaminase and Atrazine chlorohydrolase: 98 percent identical but functionally different," *J. Bacteriol.* 183 (8):2405-2410 (2001).

Segre et al., "Analysis of optimality in natural and perturbed metabolic networks," *Proc. Natl. Acad. Sci. U.S.A.* 99:15112-15117 (2002).

Seibert et al., "Characterization of a gene cluster encoding the maleylacetate reductase from *Ralstonia eutropha* 335T, and enzyme recruited for growth with 4-fluorobenzoate," *Microbiology* 150:463-472 (2004).

Seibert et al., "Characterization of the maleylacteate reductase MacA of *Rhodococcus opacus* 1CP and evidence for the presence of an isofunctional enzyme," *J. Bacteriol.* 180:3503-3508 (1998).

Seibert et al., "Purification and characterization of maleylacetate reductase from *Alcaligenes eutrophys* JMP134(pJP4)," *J. Bacteriol.* 175:6745-6754 (1993).

Selifonova et al., "Rapid evolution of novel traits in microorganisms," *Appl Environ Microbiol.* 67:3645-3649 (2001).

Selmer et al., "Propionate CoA-transferase from *Clostridium propionicum*. Cloning of gene identification of glutamate 324 at the active site," *Eur. J. Biochem.* 269:372-380 (2002).

Seltzer, "Purification and properties of maleylacetone cis-trans isomerase from Vibrio 01," *J. Biol. Chem.* 248:215-222 (1973).

Sen et al., "Developments in directed evolution for improving enzyme functions," *Appl. Biochem. Biotechnol.* 143:212-223 (2007).

Sennett et al., "Transmembrane transport of cobalamin in prokaryotic and eukaryotic cells," *Ann. Rev. Biochem.* 50:1053-1086 (1981).

Seravalli et al., "Evidence that NiNi acetyl-CoA synthase is active and that the CuNi enzyme is not," *Biochemistry* 43(13):3944-3955 (2004).

Seravalli et al., "Mechanism of transfer of the methyl group from (6S)-methyltetrahydrofolate to the corrinoid/iron-sulfur protein catalyzed by the methyltransferase from *Clostridium thermoaceticum*: a key step in the Wood-Ljungdahl pathway of acetyl-CoA synthesis," *Biochemistry* 38(18):5728-5735 (1999).

Seyfried et al., "Cloning, Sequencing, and Overexpression of the Genes Encoding Coenzyme $B_{12}$-Dependent Glycerol Dehydratase of *Citrobacter freundii*," *J. Bacteriol.* 178(19):5793-5796 (1996).

Shafiani et al., "Cloning and characterization of aspartate-β-semialdehyde dehydrogenase from *Mycobacterium tuberculosis* H37 Rv," *J. Appl. Microbiol.* 98:832-838 (2005).

Shalel-Levanon et al., "Effect of ArcA and FNR on the expression of genes related to the oxygen regulation and the glycolysis pathway in *Eschericiha coli* under microaerobic growth conditions," *Biotechnol. Bioeng.* 92(2):147-159 (2005).

Shames et al., "Interaction of Aspartate and Aspartate-derived Antimetabolites with the Enzymes of the Threonine Biosynthetic Pathway of *Escherichia coli*," *J. Biol. Chem.* 258(24):15331-15339 (1984).

Shanley et al., "Cloning and expression of *Acinetobacter calcoaceticus* catBCDE genes in *Pseudomonas putida* and *Escherichia coli*," *J. Bacteriol.* 165:557-563 (1986).

Shao et al., "Random-priming in vitro recombination: an effective tool for directed evolution," *Nucleic Acids Res.* 26:681-683 (1998).

Sharma et al., "Menaquinone (Vitamin $K_2$) Biosynthesis: Nucleotide Sequence and Expression of themenB Gene from *Escherichia coli*," *J. Bacteriol.* 174(15): 5057-5062 (1992).

Sheppard et al., "Purification and Properties of NADH-Dependent 5,10-Methylenetetrahydrofolate Reductase (MetF) from *Escherichia coli*," *J. Bacteriol.* 181(3):718-725 (1999).

Shi et al., "The Structure of I-Aspartate Ammonia-Lyase from *Escherichia coli*," *Biochemistry* 36:9136-9144 (1997).

Shiba et al., "Engineering of the pyruate dehydrogenase bypass in *Saccharomyces cerevisiae* for high-level production of isoprenoids," *Metab. Eng.* 9:160-168 (2007).

Shibata et al., "Purification, characterization, and immunological properties of fumarase from *Euglena gracilis* var. bacillaris," *J. Bacteriol.* 164(2):762-768 (1985).

Shigeoka and Nakano, "Characterization and molecular properties of 2-oxoglutarate decarboxylase from *Euglena gracilis*," *Arch. Biochem. Biophys.* 288:22-28 (1991).

Shigeoka and Nakano, "The effect of thiamin on the activation of thiamin pyrophosphate-dependent 2-oxoglutarate decarboxylase in *Euglena gracilis*," *Biochem. J.* 292 (Pt 2):463-467 (1993).

Shigeoka et al., "Effect of L-glutamate on 2-oxoglutarate decarboxylase in *Euglena gracilis*," *Biochem. J.* 282 ( Pt 2):319-323 (1992).

Shimaoka et al, "Effects of edd and pgi Disruptions on Inosine Accumulation in *Escherichia coli*," *Biosci. Boitechnol. Biochem.* 69(7):1248-1255 (2005).

Shimoda et al., "Asymmetric Transformation of Enones with *Synechococcus* sp. PCC 7943," *Bulletin of the Chemical Society of Japan* 77(12):2269-2272 (2004).

Shimomura et al., "3-hydroxyisobutyryl-CoA hydrolase," *Methods Enzymol.* 324:229-240 (2000).

Shimomura et al., "Purification and partial characterization of 3-hydroxyisobutyryl-Coenzyme A hydrolase of rat liver," *J. Biol. Chem.* 269(19):14248-14253 (1994).

Shimoyama et al., "MmcBC in *Pelotomaculum thermopropionicum* represents a novel group of prokaryotic fumarases," *FEMS Microbiol Lett.* 270(2):207-213 (2007).

Shingler et al., "Nucleotide sequence and functional analysis of the complete phenol/3,4-dimethylphenol catabolic pathway of *Pseudomonas* sp. strain CF600," *J. Bacteriol.* 174(3):711-724 (1992).

Shlomi et al., "Regulatory on/off minimization of metabolic flux changes after genetic perturbations," *Proc. Natl. Acad. Sci. U.S.A.* 102:7695-7700 (2005).

Shukla et al., "Production of D(−)-lactate from sucrose and molasses," *Biotechnol. Lett.* 26(9):689-693 (2004).

Shuler and Kargi, Operating Considerations for Bioreactors for Suspension and Immobilized Cultures, in *Bioprocess Engineering: Basic Concepts*, Prentice Hall, Inc., Upper Saddle River, NJ., p. 245-247 (2002).

Sibilli et al., "Two regions of the bifunctional protein aspartokinase I-homoserine dehydrogenase I are connected by a short hinge," *J. Biol. Chem.* 256 (20):10228-10230 (1981).

Sieber et al., "Libraries of hybrid proteins from distantly related sequences," *Nat. Biotechnol.* 19:456-460 (2001).

Siegert et al., "Exchanging the substrate specificities of pyruvate decarboxylase from *Zymomonas mobilis* and benzoylformate decarboxylase from *Pseudomonas putida*," *Protein. Eng. Des. Set.* 18:345-357 (2005).

Siew et al., "Localization and characteristics of rat liver mitochondrial aldehyde dehydrogenases," *Arch. Biochem. Biophys.* 176(2):638-649 (1976).

Sikorski and Heiter, "A system of shuttle vectors and yeast host strains designed for efficient manipulation of DNA in *Saccharomyces cerevisiae*," *Genetics* 122(1):19-27 (1989).

Simanshu et al., "Structure and function of enzymes involved in the anaerobic degradation of L-threonine to propionate," *J. Biosci.* 32(6):1195-1206 (2007).

Siminov et al., "Application of Gas Chromatography and Gas Chromatography-Mass Spectrometry to the Detection of γ-Hydroxybutyric Acid and Its Precursors in Various Materials," *J. Anal. Chem.* 59:965-971 (2004).

Simon et al., "Chiral Compounds Synthesized by Biocatalytic Reductions," *Angew. Chem. Int. Ed. Engl.* 24:539-553 (1985).

Sinclair et al., "Purification and characterization of the branched chain α-ketoacid dehydrogenase complex from *Saccharomyces cerevisiae*," *Biochem. Mol. Biol. Int.* 31(5):911-922 (1993).

Sipma et al., "Microbial CO conversions with applications in synthesis gas purification and bio-desulfurization," *Crit. Rev. Biotechnol.* 26:41-65 (2006).

Sivaraman et al., "Codon choice in genes depends on flanking sequence information—implications for theoretical reverse translation," *Nucleic Acids Res.* 36(3):e16 (2008).

Sjöström et al., "Purification and characterisation of a plasminogen-binding protein from *Haemophilus influenzae*. Sequence determination reveals identity with aspartase," *Biochim. Biophys. Acta* 1324(2):182-190 (1997).

Skarstedt and Silverstein, "*Escherichia coli* acetate kinase mechanism studied by net initial rate, equilibrium, and independent isotopic exchange kinetics," *J. Biol. Chem.* 251:6775-6783 (1976).

Slater et al., "Multiple β-ketothiolases mediate poly(β-hydroxyalkanoate) copolymer synthesis in *Ralstonia eutropha*," *J. Bacteriol.* 180(8):1979-1987 (1998).

Sloane et al., "Studies on the metabolism of p-aminobenzoic acid by *Mycobacterium smegmatis*," *J Biol. Chem.* 193:453-458 (1951).

Slock et al., "An apparent *Bacillus subtilis* folic acid biosynthetic operon containing pab, an amphibolic *trpG* gene, a third gene required for synthesis of para-aminobenzoic acid, and the dihydropteroate synthase gene," *J. Bacteriol.* 172:7211-7226 (1990).

Smit et al., "Identification, cloning and characterization of *Lactococcus lactis* branched-chain α-keto acid decarboxylase involved in flavor formation," *Appl. Environ. Microbiol.* 71:303-311 (2005).

Smith and Gray, "Catalysis of the oxidation of 1,4-cyclohexadiene to benzene by electroactive binuclear rhodium complexes," *Catalysis Lett.* 6:195-199 (1990).

Smith and Kaplan, "Purification, properties and kinetic mechanism of Coenzyme A-linked aldehyde dehydrogenase from *Clostridium kluyveri*," *Arch. Biochem. Biophys.* 203:663-675 (1980).

Smith et al., "Purification and characteristics of a γ-glutamyl kinase involved in *Escherichia coli* proline biosynthesis," *J. Bacteriol.* 157:545-551 (1984).

Smith et al., "Fumarate metabolism and the microaerophily of *Campylobacter* species," *Int. J. Biochem. Cell Biol.* 31(9):961-975 (1999).

Smith et al., "Structural and functional organization of the animal fatty acid synthase," *Prog. Lipid. Res.* 42(4):289-317 (2003).

Sobue et al., "Actin polymerization induced by calspectin, a calmodulin-binding spectrin-like protein," *FEBS Lett* 148(2):221-225 (1982).

Soda and Misono, "L-Lysine:α-ketoglutarate aminotransferase. II. Purification, crystallization, and properties," *J. Bacteriol.* 7:4110-4119 (1968).

Söhling and Gottschalk, "Molecular analysis of the anaerobic succinate degradation pathway in *Clostridium kluyveri*," *J. Bacteriol.* 178:871-880 (1996).

Söhling and Gottschalk, "Purification and characterization of a Coenzyme-A-dependent succinate-semialdehyde dehydrogenase from *Clostridium kluyveri*," *Eur. J. Biochem.* 212:121-127 (1993).

Soini et al., "High cell density media for *Escherichia coli* are generally designed for aerobic cultivations—consequences for large-scale bioprocesses and shake flask cultures," *Microb. Cell. Fact.* 7:26 (2008).

Sokatch et al., "Purification of a Branched-Chain Keto Acid Dehydrogenase from *Pseudomonas putida*," *J. Bacteriol.* 148(2):647-652 (1981).

Somerville, "The Billion-Ton Biofuels Vision," *Science* 312(5778):1277 (2006).

Sone et al., "Nucleotide sequence and expression of the Enterobacter aerogenes α-acetolactate decarboxylase gene in brewer's yeast," *Appl. Environ. Microbiol.* 54:38-42 (1988).

Song et al, "Effects of dissolved $CO_2$ levels on the growth of *Mannheimia succiniciproducens* and succinic acid production," *Biotechnol. Bioeng.* 98(6):1296-1304 (2007).

Song et al., "Construction of recombinant *Escherichia coli* strains producing poly (4-hydroxybutyric acid) homopolyester from glucose," *Wei Sheng Wu Xue.Bao.* 45:382-386 (2005).

Song et al., "Ultrasound-mediated DNA transfer for bacteria," *Nucl. Acids Res.* 35:e129 (2007).

Song et al., "Recovery of succinic acid produced by fermentation of a metabolically engineered *Mannheimia succiniciproducens* strain," *J. Biotechnol.* 132:445-452 (2007).

Song et al., "Structure, function, and mechanism of the phenylacetate pathway hot dog-fold thioesterase Paal," *J. Biol. Chem.* 281(16):11028-11038 (2006).

Soucaille et al., "Butanol tolerance and autobacteriocin production by *Clostridium acetobutylicum*," *Curr. Microbiol.* 14:295-299 (1987).

Sovik, "Mitochondrial 2-methylacetoacetyl-CoA thiolase deficiency: an inborn error of isoleucine and ketone body metabolism," *J. Inherit. Metab. Dis.* 16:46-54 (1993).

Sramek and Frerman, "Purification and properties of *Escherichia coli* Coenzyme A-transferase," *Arch. Biochem. Biophys.* 171(1):14-26 (1975).

St. Maurice et al., "Flavodoxin:quinone reductase (FqrB): a redox partner of pyruvate:ferredoxin oxidoreductase that reversibly couples pyruvate oxidation to NADPH production in *Helicobacter pylori* and *Campylobacter jejuni*," *J. Bacteriol.* 189:4764-4773 (2007).

Stadtman, "The enzyme synthesis of β-alanyl Coenzyme A," *J. Plant Chem. Soc.* 77:5765-5766 (1955).

Stanley et al., "Expression and stereochemical and isotope effect studies of active 4-oxalocrotonate decarboxylase," *Biochemistry* 39:718-726 (2000).

Starai et al., "Acetate excretion during growth of *Salmonella enerica* on ethanolamine requires phosphotransacetylase (EutD) activity, and acetate recapture requires acetyl-CoA synthetase (Acs) and phosphotransacetylase (Pta) activities," *Microbiology* 151:3793-3801 (2005).

Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005).

Starnes et al., "Threonine-sensitive aspartokinase-homoserine dehydrogenase complex, amino acid composition, molecular weight, and subunit composition of the complex," *Biochemistry* 11:677-687 (1973).

Steen et al., "Metabolic engineering of *Saccharomyces cerevisiae* for the production of n-butanol," *Microb. Cell Fact.* 7:36 (provided electronically by publisher as pp. 1-8) (2008).

Steffan and McAlister-Henn, "Isolation and characterization of the yeast gene encoding the MDH3 isozyme of malate dehydrogenase," *J. Biol. Chem.* 267:24708-24715 (1992).

Steinbacher et al., "Enoate reductase family," in Flavins and Flavoproteins, Proceedings of the Fourteenth International Symposium, St. John's College, University of Cambridge, UK, Jul. 14-18, 2002, Chapman et al., pp. 941-949, Rudolf Weber, Agency for Scientific Publications Berlin.

Steinbüchel and Schlegel, "NAD-linked L(+)-lactate dehydrogenase from the strict aerobe *Alcaligenes eutrophus*. 2. Kinetic properties and inhibition by oxaloacetate," *Eur. J. Biochem.* 130(2):329-334 (1983).

Steinbuchel and Schlegel, "A multifunctional fermentative alcohol dehydrogenase from the strict aerobe *Alcaligenes eutrophus*: purification and properties," *Eur. J. Biochem.* 141:555-564 (1984).

Steiner and Sauer, "Long-term continuous evolution of acetate resistant *Acetobacter aceti*," *Biotechnol. Bioeng.* 84:40-44 (2003).

Stemmer, "DNA shuffling by random fragmentation and reassembly: in vitro recombination for molecular evolution," *Proc. Natl. Acad. Sci. U.S.A.* 91:10747-10751 (1994).

Stemmer, "Rapid evolution of a protein in vitro by DNA shuffling," *Nature* 370:389-391 (1994).

Stim-Herndon et al., "Characterization of an acetyl-CoA C-acetyltransferase (thiolase) gene from *Clostridium acetobutylicum* ATCC 824," *Gene* 154(1):81-85 (1995).

Stirling and Perry, "Purification and Properties of a Nicotinamide Adenine Dinucleotide-Linked Cyclohexanol Dehydrogenase from a *cocardia* Species," *Curr. Microbiol.* 4:37-40 (1980).

Stokell et al., "Probing the roles of key residues in the unique regulatory NADH binding site of type II citrate synthase of *Escherichia coli*," *J. Biol. Chem.* 278:35435-35443 (2003).

Stols and Donnelly, "Production of succinic acid through overexpression of $NAD^+$-dependent malic enzyme in an *Escherichia coli* mutant," *Appl. Environ. Microbiol.* 63(7):2695-2701 (1997).

Stols et al., "Expression of *Ascaris suum* malic enzyme in a mutant *Escherichia coli* allows production of succinic acid from glucose," *Appl. Biochem. Biotechnol.* 63-65:153-158 (1997).

Stols et al., "New vectors for co-expression of proteins: Structure of *Bacillus subtilis* ScoAB obtained by High-throughput protocols," *Protein Expr. Purif.* 53:396-403 (2007).

Stoyan et al., "Cloning, sequencing and overexpression of the leucine dehydrogenase gene from *Bacillus cereus*," *J. Biotechnol.* 54:77-80 (1997).

Straathof et al., "Feasibility of acrylic acid production by fermentation," *Appl. Microbiol. Biotechnol.* 67:727-734 (2005).

Strauss and Fuchs, "Enzymes of a novel autotrophic $CO_2$ fixation pathway in the phototrophic bacterium *Chloroflexus aurantiacus*, the 3-hydroxypropionate cycle," *Eur. J. Biochem.* 215:633-643 (1993).

Streit and Entcheva, "Biotin in microbes, the genes involved in its biosynthesis, its biochemical role and perspectives for biotechnological production," *Appl. Microbiol. Biotechnol.* 61:21-31 (2003).

Stringfellow et al., "Sequence of the *Escherichia coli* C homoprotocatechuic acid degradative operon completed with that of the 2,4-dihydroxyhept-2-ene-1,7-dioicic acide aldolase-encoding gene (hpdH)," *Gene* 166:73-76 (1995).

Stryer, *Biochemistry*. 3rd Ed. New York: W.H. Freeman and Company, pp. 374-376 (1988).

Suarez de Mata et al., "Propionyl-CoA condensing enzyme from Ascaris muscle mitochondria. I. Isolation and characterization of multiple forms," *Arch. Biochem. Biophys.* 285(1):158-165 (1991).

Suarez de Mata et al., "Propionyl-CoA condensing enzyme from Ascaris muscle mitochondria. II. Coenzyme A modulation," *Arch. Biochem. Biophys.* 285:166-171 (1991).

Suda et al., "Purification and properties of α-ketoadipate reductase, a newly discovered enzyme from human placenta," *Arch. Biochem. Biophys.* 176(2):610-620 (1976).

Suda et al., "Subcellular localization and tissue distribution of α-ketoadipate reduction and oxidation in the rat," *Biochem. Biophys. Res. Commun.* 77(2):586-591 (1977).

Suematsu et al., "Molecular cloning and functional expression of rat liver cytosolic acetyl-CoA hydrolase," *Eur. J. Biochem.* 268(9):2700-2709 (2001).

Sulzenbacher et al., "Crystal structure of *E. coli* alcohol dehydrogenase YqhD: evidence of a covalently modified NADP Coenzyme," *J. Mol. Biol.* 342(2):489-502 (2004).

Suthers et al., "Metabolic flux elucidation for large-scale models using $^{13}C$ labeled isotopes," *Metab. Eng.* 9:387-405 (2007).

Suzuki et al., "Acetylputrescine deacetylase from *Micrococcus luteus* K-11," *Biochim. Biophys. Acta* 882:140-142 (1986).

Suzuki et al., "GriC and GriD Constitute a carboxylic acid reductase involved in grixazone biosynthesis in *Streptomyces griseus*," *J. Antibiot.* 60(6):380-387 (2007).

Suzuki et al., "Properties and metabolic role of mesaconate hydratase of an aerobic bacterium," *J. Biochem.* 81:1917-1925 (1977).

Suzuki, "Phospotransacetylase of *Escherichia coli* B., activation by pyruvate and inhibition by NADH and certain nucleotides," *Biochem. Biophys. Acta* 191:559-569 (1969).

Svensson et al., "Characterization and isolation of enzymes that hydrolyze short-chain acyl-CoA in rat-liver mitochondria," *Eur. J. Biochem.* 238(2):526-531 (1996).

Svetlitchnyi et al., "A functional Ni-Ni-[4Fe-4S] cluster in the monomeric acetyl-CoA synthase from *Carboxydothermus hydrogenoformans*," *Proc. Natl. Acad. Sci. U.S.A.* 101(2):446-451 (2004).

Svetlitchnyi et al., "Two membrane-associated NiFeS-carbon monoxide dehydrogenases from the anaerobic carbon-monoxide-utilizing eubacterium *Carboxydothermus hydrogenoformans*," *J. Bacteriol.* 183(17):5134-5144 (2001).

Switzer, "Glutamate mutase," In Dolphin, D. ed., *Vitamin $B_{12}$* (vol. 2: Biochemistry and Medicine), Wiley-Interscience: New York, p. 289-305 (1982).

Tae-Kang et al., "Purification and characterization of a cyclohexanol dehydrogenase from *Rhodococcus* sp. TK6," *J. Microbiol. Biotechnol.* 12:39-45 (2002).

Tahlan et al., "Two sets of paralogous genes encode the enzymes involved in the early stages of clavulanic acid and clavam metabolite biosynthesis in *Streptomyces clavuligerus*," *Antimicrob. Agents Chemother.* 48(3):930-939 (2004).

Takacs et al., "Formate hydrogenlyase in the hyperthermophilic archaeon, *Thermococcus litoralis*," *BMC Microbiol.* 8:88 (2008).

Takagi et al, "Purification, crystallization, and molecular properties of aspartase from *Pseudomonas fluorescens*," *J. Biochem.* 96(2):545-552 (1984).

Takagi et al., "Isolation of a versatile *Serratia marcescens* mutant as a host and molecular cloning of the aspartase gene," *J. Bacteriol.* 161:1-6 (1985).

Takagi et al., "Cloning and nucleotide sequence of the aspartase gene of *Pseudomonas fluorescens*," *J. Biochem.* 100(3):697-705 (1986).

Takahashi and Yamada, "Metabolic pathways for cytoxic and end product formation from glutamate- and aspartate-containing peptides by *Porphyromonas gingivalis*," *J. Bacteriol.* 182:4704-4710 (2000).

Takahashi-Abbe et al., "Biochemical and functional properties of a pyruvate formate-lyase (PFL)-activating system in *Streptococcus mutans*," *Oral Microbiol. Immunol.* 18:293-297 (2003).

Takanashi et al., "Characterization of a novel 3-hydroxybutyrate dehydrogenase from *Ralstonia pickettii* T1," *Antonie van Leeuwnhoek* 95(3):249-262 (2009).

Takatsuka et al., "Gene cloning and molecular characterization of lysine decarboxylase from *Selenomonas ruminantium* delineate its evolutionary relationship to ornithine decarboxylases from eukaryotes," *J. Bacteriol.* 182:6732-6741 (2000).

Takatsuka et al., "Identification of the amino acid residues conferring substrate specificity upon *Selenomonas ruminantium* lysine decarboxylase," *Bioxci. Biotechnol. Biochem.* 63:1843-1846 (1999).

Takeo, "Existence and Properties of Two Malic Enzymes in *Escherichia coli* Especially of NAD-linked Enzyme," *J. Biochem.* 66:379-387 (1969).

Takigawa et al., "Probabilistic path ranking based on adjacent pairwise coexpression for metabolic transcripts analysis," *Bioinform.* 24(2):250-257 (2008).

Tallant and Krzycki, "Coenzyme M methylase activity of the 480-kilodalton corrinoid protein from *Methanosarcina barkeri*," *J. Bacteriol.* 178(5):1295-1301 (1996).

Tallant and Krzycki, "Methylthiol:Coenzyme M Methyltransferase from *Methanosarcina barkeri*, an enzyme of methanogenesis from dimethylsulfide and methylmercaptopropionate," *J. Bacteriol.* 179(22):6902-6911 (1997).

Tallant et al., "The MtsA subunit of the methylthiol:Coenzyme M methyltransferase of *Methanosarcina barkeri* catalyses both half-reactions of corrinoid-dependent dimethylsulfide: Coenzyme M methyl transfer," *J. Biol. Chem.* 276(6):4485-4493 (2001).

Tamaki et al., "Purification, properties, and sequencing of aminoisobutyrate aminotransferases from rat liver," *Methods Enzymol.* 324:376-389 (2000).

Tanaka et al., "Cloning and characterization of a human orthologue of testis-specific succinyl CoA: 3-oxo acid CoA transferase (Scot-t) cDNA," *Mol. Hum. Reprod.* 8:16-23 (2002).

Tanaka et al., "Lysine decarboxylase of Vibrio parahaemolyticus: kinetics of transcription and role in acid resistance," *J. Appl. Microbiol.* 104:1283-1293 (2008).

Tang et al., "Identification of a novel pyridoxal 5'-phosphaste binding site in adenosylcobalamin-dependent lysine 5,6-aminomutase from *Porphyromonas gingivalis*," *Biochemistry* 41(27):8767-8776 (2002).

Tani et al., "Thermostable NADP+-dependent medium-chain alcohol dehydrogenase from *Acinetobacter* sp. strain M-1: purification and characterization and gene expression in *Escherichia coli*," *Appl. Environ. Microbiol.* 66(12):5231-5235 (2000).

Tanizawa et al., "The primary structure of thermostable D-amino acid aminotransferase from a thermophilic *Bacillus* species and its correlation with L-amino acid aminotransferases," *J. Biol. Chem.* 264(5):2450-2454 (1989).

Tanous et al., "Glutamate dehydrogenase activity can be transmitted naturally to *Lactococcus lactis* strains to stimulate amino acid conversion to aroma compounds," *Appl. Environ. Microbiol.* 72(2):1402-1409 (2006).

Tardif et al., "Electrotransformation studies in *Clostridium cellulolyticum*," *J. Ind. Microbiol. Biotechnol.* 27(5):271-274 (2001).

Taylor and Fotheringham, "Nucleotide sequence of the *Bacillus licheniformis* ATCC 10716 dat gene and comparison of the predicted amino acid sequence with those of other bacterial species," *Biochim. Biophys. Acta* 1350(1):38-40 (1997).

Tebbe et al., "Titanium-Catalyzed Olefin Metathesis," *J. Am. Chem. Soc.* 101(17):5074-5075 (1979).

Teipel et al., "The substrate specificity of fumarase," *J. Biol. Chem.* 243:5684-5694 (1968).

ter Schure et al., "Pyruvate decarboxylase catalyzes decarboxylation of branched-chain 2-oxo acids but is not essential for fusel alcohol production by *Saccharomyces cerevisiae*," *Appl. Environ. Microbiol.* 64:1303-1307 (1998).

Teufel et al., "3-hydroxypropionyl-Coenzyme A dehydratase and acryloyl-Coenzyme A reductase, enzymes of the autotrophic 3-hydroxypropionate/4-hydroxybutyrate cycle in the Sulfolbales," *J. Bacteriol.* 191:4572-4581 (2009).

Thanos and Simon, "Electro-enzymic viologen-mediated stereospecific reduction of 2-enoates with free and immobilized enoate reductase on cellulose filters or modified carbon electrodes," *J. Biotechnol.* 6:13-29 (1987).

Thauer, "Microbiology. A Fifth Pathway of Carbon Fixation," *Science* 318:1732-1733 (2007).

Thomas et al., "Bimetallic nanocatalysts for the conversion of muconic acid to adipic acid," *Chem. Commun.* 21:1126-1127 (2003).

Thornton et al., "Primary structure of the monomer of the 12S subunit of transcarboxylase as deduced from DNA and characterizatio nof the product expressed in *Escherichia coli*," *J. Bacteriol.* 175:5301-5308 (1993).

Thykaer et al., "Metabolic network analysis of an adipoyl-7-ADCA-producing strain of *Penicillium chrysogenum*: elucidation of adipate degradation," *Metab. Eng.* 4(2):151-158 (2002).

Tian et al., "Variant tricarboxylic acid cycle in Mycobacterium tuberculosis: identification of α-ketoglutarate decarboxylase," *Proc. Natl. Acad. Sci. U.S.A.* 102:10670-10675 (2005).

Tischer et al., "Purification and Some Properties of a Hitherto-Unknown Enzyme Reducing the Carbon-Carbon Double Bond of α,β-Unsaturated Carboxylate Anions," *Eur. J. Biochem.* 97(1):103-112 (1979).

Tobimatsu et al., "Molecular cloning, Sequencing and Characterization of the Genes for Adenosylcobalamin-deptendent Diol Dehydratase of *Klebsiella pneumoniae*," *Biosci. Biotechnol. Biochem.* 62(9):1744-1777 (1998).

Tobimatsu et al., "Molecular cloning, Sequencing and Expression of the Genes Encoding Adenosylcobalamin-dependent Diol Dehydrase of *Klebsiella oxytoca*," *J. Biol. Chem.* 270(13):7142-7148 (1995).

Tobin et al., "Localization of the Lysine ε-Aminotransferase (lat) and δ-Aminoadipyl)-L-Cysteinyl-D-Valine Synthetase (pcbAB) Genes from *Streptomyces clavuligerus* and Production of Lysine ε-Aminotransferase Activity in *Escherichia coli*," *J. Bacteriol.* 173(19):6223-6229 (1991).

Tolentino et al., "A pH-regulated promoter for the expression of recombinant proteins in *Escherichia coli*," *Biotechnol. Lett.* 14:157-162. (1992).

Tomas et al., "Overexpression of groESL in *Clostridium acetobutylicum* Results in Increased Solvent Production and Tolerance, Prolonged Metabolism, and Changes in the Cell's Transcriptional Program," *Appl. Environ. Microbiol.* 69:4951-4965 (2003).

Toraya et al., "Substrate Specificity of Coenzyme $B_{12}$-Dependent Diol Dehydrase: Glycerol as Both a Good Substrate and a Potent Inactivator," *Biochem. Biophys. Res. Commun.* 69:475-480 (1976).

Toth et al., "The ald Gene, Encoding a Coenzyme A-Acylating Aldehyde Dehydrogenase, Distinguishes *Clostridium beijerinckii* and Two Other Solvent-Producing Clostridia from *Clostridium acetobutylicum*," *App. Environ. Microbiol.* 65(11):4973-4980 (1999).

Tretter and Adam-Vizi, "Alpha-ketoglutarate dehydrogenase: a target and generator of oxidative stress," *Philos. Trans. R. Soc. B* 360:2335-2345 (2006).

Trower et al., "Isolation and Characterization of a Cyclohexane-Metabolizing *Xanthobacter* sp.," *Appl. Environ. Microbiol.* 49(5):1282-1289 (1985).

Truscott et al., "Mechanisms of protein import into mitochondria," *Curr. Biol.* 13(8):R326-R337 (2003).

Tsao et al., "Production of multifunctional organic acids from renewable resources," *Adv. Biochem. Eng. Biotechnol.* 65:243-280 (1999).

Tseng et al., "Metabolic Engineering of *Escherichia coli* for Enhanced Production of (R)- and (S)-3-Hydroxybutyrate," *App. Environ. Microbiol.* 75(10):3137-3145 (2009).

Tseng et al., "Oxygen- and growth rate-dependent regulation of *Escherichia coli* fumarase (FumA, FumB, and BumC) activity," *J. Bacteriol.* 183(2):461-467 (2001).

Tsujimoto et al., "L-Lysine biosynthetic pathway of *Methylophilus methylotrophus* and construction of an L-Lysine producer," *J. Biotechnol.* 124:327-337 (2006).

Tucci and Martin, "A novel prokaryotic trans-2-enoyl-CoA reductase from the spirochete *Treponema denticola*," *FEBS Lett.* 581(8):1561-1566 (2007).

Tutino et al., "Expression of *Sulfolobus solfataricus trpE* and *trpG* genes in *E. coli*," *Biochem. Biophys. Res. Commun.* 230:306-310 (1997).

Twarog and Wolfe, "Role of butyryl phosphate in the energy metabolism of *Clostridium tetanomorphum*," *J. Bacteriol.* 86:112-117 (1963).

Tyurin et al., "Electrotransformation of *Clostridum acetobutylicum* ATCC 824 using high-voltage radio frequency modulated square pulses," *J. Appl. Microbiol.* 88(2):220-227 (2000).

Tyurin et al., "Electrotransformation of *Clostridium thermocellum*," *Appl. Environ. Microbiol.* 70(2):883-890 (2004).

Tzagoloff and Dieckmann, "PET genes of *Saccharomyces cerevisiae*," *Microbiol. Rev.* 54(3):211-225 (1990).

Uchiyama et al., "Identification of the 4-Hydroxycinnamate Decarboxylase (PAD) Gene of *Klebsiella oxytoca*," *Biosci. Biotechnol. Biochem.* 72: 116-123 (2008).

Ulaganathan et al., "Structure of *Staphylococcus aureus* 1,4-dihydroxy-2-naphthoyl-CoA synthase (MenB) in complex with acetoacetyl-CoA," *Acta. Crystallogr. Sect. F. Struct. Biol. Cryst. Commun.* 63(Pt 11):908-913 (2007).

Umbarger and Brown, "Threonine deamination in *Escherichia coli*. II. Evidence fro two L-threonine deaminases," *J. Bacteriol.* 73(1):105-112 (1957).

Underwood et al., "Genetic Changes to Optimize Carbon Partitioning between Ethanol and Biosynthesis in Ethanologenic *Escherichia coli*," *App. Environ. Microbiol.* 68(12):6263-6272 (2002).

Urbance et al., "Evaluation of succinic acid continuous and repeat-batch biofilm fermentation by *Actinobacillus succinogenes* using plastic composite support bioreactors," *Appl. Microbiol. Biotechnol.* 65(6):664-670 (2004).

Uttaro and Opperdoes, "Purification and characterisation of a novel isopropanol dehydrogenase from *Phytomonas* sp.," *Mol. Biochem. Parasitol.* 85:213-219 (1997).

Vadali et al., "Enhanced Isoamyl Acetate Production upon Manipulation of the Acetyl-CoA node in *Escherichia coli*," *Biotech. Prog.* 20:692-697 (2004).

Vadali et al., "Production of isoamyl acetate in ackA-pta and/or *ldh* mutants of *E. coli* with overexpression of yeast ATF2," *Appl. Microbiol. Biotechnol.* 63:698-704 (2004).

Vadali et al., "Cofactor engineering of intercellular CoA/acetyl-CoA and its effect on metabolic flux redistribution in *Escherichia coli*," *Metab Eng.* 6(2): 133-139 (2004).

Valdes-Hevia and Gancedo, "Isolation and characterization of the gene encoding phosphoenolpyruvate carboxykinase from *Saccharomyces cerevisiae*," *FEBS Lett.* 258:313-316 (1989).

Valentin et al., "Metabolic pathway for biosynthesis of poly(3-hydroxybutyrate-co-4-hydroxybutyrate) from 4-hydroxybutyrate by *Alcaligenes eutrophus*," *Eur. J. Biochem.* 227(1-2):43-60 (1995).

Valentine and Wolfe, "Purification and role of phosphotransbutyrylase," *J. Biol. Chem.* 235:1948-1952 (1960).

Vamecq et al., "The microsomal dicarboxylyl-CoA synthetase," *Biochem. J.* 230(3):683-693 (1985).

Van Beilen et al., "Cloning of Baeyer-Villiger monooxygenases from comamonas, Xantherobacter and Rhodococcus using polymerase chain reaction with highly degenerate primers," *Environ. Microbiol.* 5(3):174-182 (2003).

van der Voorhorst et al., "Genetic and biochemcial characterization of a short-chain alcohol dehydrogenase from the hyperthermophilic archaeon *Pyrococcus furiosus*," *Eur. J. Biochem.* 268:3062-3068 (2001).

Van Der Westhuizen, et al., "Autolytic Activity and Butanol tolerance of *Clostridium acetobutylicum*," *Appl. Environ. Microbiol.* 44:1277-1281 (1982).

van Grinsven et al., "Acetate:succinate CoA-transferase in the hydrogenosomes of *Trichomonas vaginalis*: identification and characterization," *J. Biol. Chem.* 283:1411-1418 (2008).

van Loon and Young, "Intracellular sorting of alcohol dehydregenase isoenzymes in yeast: a cytosolic location oreflects absence of an amino-terminal targeting sequence for the mitochondrion," *EMBO J.* 5:161-165 (1986).

van Maris et al., "Directed evolution of pyruvate decarboxylase-negative *Saccharomyces cerevisiae*, yielding a $C_2$-independent, glucose-tolerant, and pyruvate-hyperproducing yeast," *Appl. Environ. Microbiol.* 7:159-166 (2004).

Van Mullem et al., "Construction of a set of *Saccharomyces cerevisiae* vectors designed for recombinational cloning," *Yeast* 20(8):739-746 (2003).

Vanderwinkel et al., "Growth of *Escherichia coli* on fatty acids: requirement for Coenzyme A transferase activity," *Biochem. Biophys. Res. Commun.* 33(6):902-908 (1968).

Vanrolleghem et al., "Validation of a Metabolic Network for *Saccharomyces cerevisiae* Using Mixed Substrate Studies," *Biotechnol. Prog.* 12(4):434-448 (1996).

Varadarajan and Miller, "Catalytic Upgrading of Fermentation-Derived Organic Acids," *Biotechnol. Prog.* 15:845-854 (1999).

Vardar-Schara et al., "Metabolically engineered bacteria for producing hydrogen via fermentation," *Microbio. Biotechnol.* 1:107-125 (2008).

Varma and Palsson, "Stoichiometric Flux Balance Models Quantitatively Predice Growth and Metabolic By-Product Secretion in Wild-Type *Escherichia coli* W3110," *Appl Env. Microbiol.* 60(10):3724-3731 (1994).

Varma and Palsson, "Metabolic Flux Balancing: Basic Concepts, Scientific and Practical Use," *Biotechnology* 12:994-998 (1994).

Varma et al., "Biochemical Production Capabilities of *Escherichia coli*," *Biotechnol. Bioeng.* 42:59-73 (1993).

Varma et al., "Stoichiometric Interpretation of *Escherichia coli* Glucose Catabolism under Various Oxygenation Rates," *Appl. Environ. Microbiol.* 59:2465-2473 (1993).

Vazquez et al., "Phosphtransbutyrylase expression in *Bacillus megaterium*," *Curr. Microbiol.* 42:345-349 (2001).

Vega et al., "The Biological Production of Ethanol from Synthesis Gas," *Appl. Biochem. Biotechnol.* 20/21:781-797 (1989).

Vellanki et al., "Expression of hepatitis B surface antigen in *Saccharomyces cerevisiae* utilizing glyceraldehyde-3-phosphate dehydrogenase promoter of *Pichia pastoris*," *Biotechnol. Lett.* 29(2):313-318 (2007).

Vemuri et al. "Succinate production in dual-phase *Escherichia coli* fermentations depends on the time of transition from aerobic to anaerobic conditions," *J. Ind. Microbiol. Biotechnol.* 28:325-332 (2002).

Vemuri et al., "Effects of growth mode and pyruvate carboxylase on succinic acid production by metabolically engineered strains of *Escherichia coli*," *Appl. Environ. Microbiol.* 68(4):1715-1727 (2002).

Venkitasubramanian et al. *Biocatalysis in the Pharmaceutical and Biotechnology Industires*, ed. R.N. Patel, Chapter 15, pp. 425-440, CRC Press LLC, Boca Raton, FL. 2007.

Venkitasubramanian et al., "Reduction of Carboxylic Acids by Nocardia Aldehyde Oxidoreductase Requires a Phosphopantetheinylated Enzyme," *J. Biol. Chem.* 282(1):478-485 (2007).

Verhaert et al., "Enzyme kinetics in reversed micelles. 2. Behaviour of enoate reductase," *Eur. J. Biochem.* 187:73-79 (1990).

Vernal et al., "Cloning and heterologous expression of a broad specificity aminotransferase of Leishmania mexicana promastigotes," *FEMS Microbiol. Lett.* 229:217-222 (2003).

Vernal et al., "Isolation partial characterization of a broad specificity aminotransferase from leishmania mexicana promastigotes," *Mol. Biochem. Parasitol.* 96:83-92 (1998).

Vey et al., "Structural basis for glycyl radical formation by pyruvate formate-lyase activating enzyme," *Proc. Natl. Acad. Sci. U.S.A.* 105:16137-16141 (2008).

Vijay et al., "Diels-Alder reactions between cyclic five-membered dienes and acetylene," *J. Mol. Struc.* 589-590:291-299 (2002).

Viola, "L-Aspartase: New Tricks From an Old Enzyme," *Adv. Enzymol. Relat. Areas. Mol. Biol.* 74:295-341 (2000).

Voellmy and Leisinger, "Role of 4-Aminobutyrate Aminotransferase in the Arginine Metabolism of *Pseudomonas aeruginosa*," *J. Bacteriol.* 128(3):722-729 (1976).

Voets et al., "Reduced intracellular ionic strength as the initial trigger for activation of endothelial volume-regulated anion channels," *Proc. Natl. Acad. Sci. U.S.A.* 96:5298-5303 (1999).

Volkert, et al., "The Δ(*argF-lacZ*)205(U169) Deletion Greatly Enhances Resistance to Hydrogen Peroxide in Stationary-Phase *Escherichia coli*," *J. Bact.* 176(3):1297-1302 (1994).

Volkov et al., "Random chimeragenesis by heteroduplex recombination," *Methods.Enzymol.* 328:456-463 (2000).

Volkov et al., "Recombination and chimeragenesis by in vitro heteroduplex formation and in vivo repair," *Nucleic Acids Res.* 27:e18 (1999).

Vrijbloed et al., "Insertional inactivation of methylmalonyl Coenzyme A (CoA) mutase and isobutyryl-CoA mutase genes in Streptomyces cinnamonensis: influence on polyketide antibiotic biosynthesis," *J. Bacteriol.* 181(18):5600-5605 (1999).
Wakil et al., "Studies on the fatty acid oxidizing system of animal tissues. VI. β-Hydroxyacyl Coenzyme A dehydrogenase," *J. Biol. Chem.* 207(2):631-638 (1954).
Walker et al., "Yeast pyruvate carboxylase: identification of two genes encoding isoenzymes," *Biochem. Biophys. Res. Commun.* 176:1210-1217 (2007).
Walter et al., "Molecular characterization of two *Clostridium acetobutylicum* ATCC 824 butanol dehydrogenase isozyme genes," *J. Bacteriol.* 174(22):7149-7158 (1992).
Walter et al., "Sequence and arrangement of two genes of the butyrate-synthesis pathway of *Clostridium acetobutylicum* ATCC 824," *Gene* 134(1):107-111 (1993).
Wang and Barker, "Purification and Properties of L-citramalate hydrolase," *J. Biol. Chem.* 244(10):2516-2526 (1969).
Wang and Seah, "Determination of the metal ion dependence and substrate specificty of a hydratase involve din the degradation pathway of biphenyl/chlorobiphenyl," *FEBS J.* 272: 966-974 (2005).
Wang et al, "Molecular cloning and functional identification of a novel phenylacetyl-CoA ligase gene from *Penicillium chrysogenum*," *Biochem. Biopyhs. Res. Commun.* 360(2):453-458 (2007).
Wang et al., "The primary structure of branched-chain α-oxo acid dehydrogenase from *Bacillus subtilis* and its similarity to other α-oxo acid dehydrogenases," *Eur. J. Biochem.* 213:1091-1099 (1993).
Wang et al., "Bioconversion of fumaric acid to succinic acid by recombinant *E. coli*," *App. Biochem. Biotechnol.* 70-72: 919-928 (1998).
Wang et al., "Cloning, Sequencing, and Expression of the Pyruvate Carboxylase Gene in *Lactococcus lactis* subsp. *lactis* C2," *App. Environ. Microbiol.* 66(3):1223-1227 (2000).
Wang et al., "Expression of galactose permease and pyruvate carboxylase in *Escherichia coli* ptsG mutant increases the growth rate and succinate yield under anaerobic conditions," *Biotechnol. Lett.* 28(2):89-93 (2006).
Wang et al., "Genome-scale in silico aided metabolic analysis and flux comparisons of *Escherichia coli* to improve succinate production," *Appl. Microbiol. Biotechnol.* 73(4):887-894 (2006).
Wang et al., "Screening microorganisms for utilization of furfural and possible intermediates in its degradative pathway," *Biotechnol. Lett.* 16(9):977-982 (1994).
Wang et al., "Site-directed mutagenesis of the phosphorylatable serine (Ser$^8$) in C$_4$ phosphoenolpyruvate carboxylase from sorghum. The effect of negative charge at position 8," *J. Biol. Chem.* 267:16759-16762. (1992).
Wanner and Tressl, "Purification and characterization of two enone reductases from *Saccharomyces cerevisia*," *Eur. J. Biochem.* 255(1):271-278 (1998).
Ward et al., "Molecular analysis of the rele of two aromatic aminotransferases and a broad-specificity aminotransferase in the aromatic amino acid metabolism of *Pyococcus furiosus*," *Archaea* 1:133-141 (2002).
Weaver, "Structure of free fumarase C from *Escherichia coli*," *Acta. Crystallogr. D. Biol. Crystallogr.* 61(Pt 10):1395-1401 (2005).
Weber and Falbe, "Oxo Synthesis Technology," *Ind. Eng. Chem. Res.* 62:33-37 (1970).
Weidner and Sawers, "Molecular characterization of the Genes Encoding Pyruvate Formate-Lyase and Its Activating enzyme of *Clostridium pasteruianum*," *J. Bacteriol.* 178(8):2440-2444 (1996).
Welch et al., "Purification and Characterization of the NADH-Dependent Butanol Dehydrogenase from *Clostridium acetobutylicum* (ATCC 824)," *Arch. Biochem. Biophys.* 273(2):309-318 (1989).
Wengrovius et al., "Tungsten-Oxo Alkylidene Complexes as Olefin Metathesis Catalysts and the Crystal Structure of W(O)(CHCMe$_3$)(PEt$_3$)Cl$_2$$^1$," *J. Am. Chem. Soc.* 102:4515-4516 (1980).
Westin et al., "The identification of a succinyl-CoA thioesterase suggests a novel pathway for succinate production in peroxisomes," *J. Biol. Chem.* 280(46):38125-38132 (2005).
Wexler et al., "A wide host-range metagenomic library from a waste water treatment plant yields a novel alcohol/aldehyde dehydrogenase," *Environ. Microbiol.* 7:1917-1926 (2006).

Whalen and Berg, "Analysis of an avtA::Mu d1(Ap lac) Mutant: Metabolic Role of Transaminase C," *J. Bacteriol.* 150(2):739-746 (1982).
Whalen and Berg, "Gratuitous repression of avtA in *Escherichia coli* and *Salmonella typhimurium*," *J. Bacteriol.* 158(2):571-574 (1984).
Whelan et al., "Nylon 6 (PA6)," *Kunststof en Rubber*, Wyt en Zonen Uitgevers. Rotterdam, NL. 39(3):38-39 (1986).
Whisstock et al., "Prediction of protein function from protein sequence and structure," *Q. Rev. Biophysics.* 36(3):307-340 (2003).
White et al., "Long-chain alcohol production by yeasts," *7th Int. Symp. Yeasts* S465-S470 (1989).
White et al., "The structural biology of type II fatty acid biosynthesis," *Ann. Rev. Biochem.* 74:791-831 (2005).
Whitehead and Rabinowitz, "Cloning and expression in *Escherichia coli* of the gene for 10-formyltetrahydrofolate synthetase from *Clostridium acidiurici* ("*Clostridium acidi-urici*")," *J. Bacteriol.* 167:205-209 (1986).
Whitehead and Rabinowitz, "Nucleotide Sequence of the *Clostridium acidiurici* ("*Clostridium acidi-urici*") Gene for 10-Formyltetrahydrofolate Synthetase Shows Extensive Amino Acid Homology with the Trifunctional Enzyme C$_1$-Tetrahydrofolate Synthase from *Saccharomyces cerevisiae*," *J. Bacteriol.* 170(7):3255-3261 (1988).
Wiesenborn et al., "Coenzyme A Transferase from *Clostridium acetobutylicum* ATCC 824 and Its Role in the Uptake of Acids," *Appl. Environ. Microbiol.* 55(2):323-329 (1989).
Wiesenborn et al., "Phosphotransbutyrylase from *Clostridium acetobutylicum* ATCC 824 and its role in acidogenesis," *Appl. Environ. Microbiol.* 55:317-322 (1989).
Wilkie and Warren, "Recombinant expression, purification, and characterization of three isoenzymes of aspartate aminotransferase from *Arabidopsis thaliana*," *Protein Expr. Purif.* 12:381-389 (1998).
Wilks et al., "A specific, Highly Active Malate Dehydrogenase by Redesign of a Lactate Dehydrogenase Framework," *Science* 242:1541-1544 (1988).
Wilks et al., "Design of a Specific Phenyllactate Dehydrogenase by Peptide Loop Exchange on the *Bacillus stearothermophilus* Lactate Dehydrogenase Framework," *Biochemistry* 31:7802-7806 (1992).
Wilks et al., "Designs for a Broad Substrate Specificity Keto Acid Dehydrogenase," *Biochemistry* 29:8587-8591 (1990).
Willke and Vorlop, "Biotechnological production of itaconic acid," *Appl. Microbiol. Biotechnol.* 56(3-4):289-295 (2001).
Willke and Vorlop, "Industrial bioconversion of renewable resources as an alternative to conventional chemistry," *Appl. Microbiol. Biotechnol.* 66(2):131-142 (2004).
Winkler et al., "A new type of a multifunctional β-oxidation enzyme in euglena," *Plant. Physiol.* 131(2):753-762 (2003).
Winzeler et al., "Functional Characterization of *S. cerevisiae* Genome by Gene Deletion and Parallel Analysis," *Science* 285:901-906 (1999).
Winzer et al., "Differential regulation of two thiolase genes from *Clostridium acetobutylicum* DSM 792," *J. Mol. Microbiol. Biotechnol.* 2(4):531-541 (2000).
Witkowski et al., "Conversion of β-ketoacyl synthase to a Malonyl Decarboxylase by replacement of the active cysteine with glutamine," *Biochemistry* 38:11643-11650 (1999).
Wittich and Walter, "Putrescine *N*-acetyltransferase in *Onchocerca volvulus* and *Ascaris suum*, an enzyme which is involved in polyamine degradation and release of *N*-acetylputrescine," *Mol. Biochem. Parasitol.* 38:13-17 (1990).
Wolff and Kenealy, "Purification and characterization of the oxygen-sensitive 4-hydroxybutanoate dehydrogenase from *Clostridium kluyveri*," *Protein Expr. Purif.* 6:206-212 (1995).
Wong et al., "Molecular Properties of Pyruvate Formate-Lyase Activating Enzyme," *Biochemistry* 32:14102-14110 (1993).
Wong et al., "Sequence saturation mutagenesis (SeSaM): a novel method for directed evolution," *Nucleic Acids Res* 32:e26 (2004).
Wong et al., "Sequence saturation mutagenesis with tunable mutation frequencies," *Anal. Biochem.* 341:187-189 (2005).
Wong et al., "Transversion-enriched sequence saturation mutagenesis (SeSaM-Tv$^+$): a random mutagenesis method with consecutive nucleotide exchanges that complements the bias of error-prone PCR," *Biotechnol. J.* 3:74-82 (2008).

Wood, "Life with CO or $CO_2$ and $H_2$ as a source of carbon and energy," *Fed. Amer. Societies Experi. Biol. J.* 5:156-163 (1991).
Woods, "Two biochemically distinct classes of fumarase in *Escherichia coli*," *Biochim. Biophys. Acta* 954(1):14-26 (1988).
Wu and Woodard, "New insights into the evolutionary links relating to the 3-deoxy-D-arabino-heptulosonate 7-phosphate synthase subfamilies," *J. Biol. Chem.* 281:4042-4048 (2006).
Wu et al., "Microbial synthesis of cis-cis-muconic acid by *Sphingobacterium* sp. GcG generated from effluent of a styrene monomer (SM) production plant," *Enzyme Microbial Tech.* 35:598-604 (2004).
Wu et al., "Thermotoga maritima 3-deoxy-D-arabino-heptulosonate 7-phosphate (DAHP) synthase: the ancestral eubacterial DAHP synthase?" *J. Biol. Chem.* 278:27525-27531 (2003).
Wu et al., "Life in hot carbon monoxide: the complete genome sequence of *Carboxydothermus hydrogenoformans* Z-2901," *PLoS Genet.* 1(5):e65 (2005).
Wylie et al., "Nematode.net: a tool for navigating sequences from parasitic and free-living nematodes," *Nucleic Acids Res.* 32:D423-D426 (2004).
Wynn et al., "Chaperonins GroEL and GroES promote assembly of heterotetramers ($\alpha_2\beta_2$) of mammalian mitochondrial branched-chain $\alpha$-keto acid decarboxylase in *Escherichia coli*," *J. Biol. Chem.* 267:12400-12403 (1992).
Wynn et al., "Cloning and expression in *Escherichia coli* of mature E1 $\beta$ subunit of bovine mitochondrial branched-chain $\alpha$-keto acid dehydrogenase complex. Mapping of the E1 $\beta$-binding region on E2," *J. Biol. Chem.* 267:1881-1887 (1992).
Yabutani et al., "Analysis of $\beta$-ketothiolase and acetoacetyl-CoA reductase genes of a methylotrophic bacterium, *Paracoccus denitrificans*, and their expression in *Escherichia coli*," *FEMS Microbiol. Lett.* 133:85-90 (1995).
Yagi et al., "Aspartate: 2-oxoglutarate aminotransferase from bakers' yeast: crystallization and characterization," *J. Biochem.* 92(1):35-43 (1982).
Yagi et al., "Crystallization and properties of aspartate aminotransferase from *Escherichia coli* B," *FEBS Lett.* 100(1):81-84 (1979).
Yagi et al., "Glutamate-aspartate transaminase from microorganisms," *Methods Enzymol.* 113:83-89 (1985).
Yamamoto et al., "Carboxylation reaction catalyzed by 2-oxoglutarate:ferredoxin oxidoreductases from *Hydrogenobacter thermophilus*," *Extremophiles* 14:79-85 (2010).
Yamamoto et al., "Purification and Properties of NADP-dependent Formate Dehydrogenase from *Clostridium thermoaceticum*, a tungsten-Selenium-Iron Protein," *J. Biol. Chem.* 258(3):1826-1832 (1983).
Yamano et al., "Construction of a brewer's yeast having $\alpha$-acetolactate decarboxylase gene from *acetobacter aceti* ssp. xylinum integrated in the genome," *J. Biotechnol.* 32:173-178 (1994).
Yan and Chen, "Coenzyme A-acylating aldehyde dehydrogenase from *Clostridium beijerinckii* NRRL B592," *Appl. Environ. Microbiol.* 56:2591-2599 (1990).
Yang et al., "Aspartate Dehydrogenase, a Novel Enzyme Identified from Structural and Functional Studies of TM1643," *J. Biol. Chem.* 278(10):8804-8808 (2003).
Yang et al., "Effect of inactivation of *nuo* and *ackA-pta* on redistribution of metabolic fluxes in *Escherichia coli*," *Biotechnol Bioeng.* 65(3):291-297 (1999).
Yang et al., "Effect of Variation of *Klebsiella pneumoniae* Acetolactate Synthase Expression on Metabolic Flux Redistribution in *Escherichia coli*," *Biotechnol. Bioeng.* 69(2)150-159 (2000).
Yang et al., "Metabolic Flux Analysis of *Escherichia coli* Deficient in the Acetate Production Pathway and Expressing the *Bacillus subtilis* Acetolactate Synthase," *Metab. Eng.* 1(1):26-34 (1999).
Yang et al., "Nucleotide sequence of the fadA gene. Primary structure of 3-ketoacyl-Coenzyme A thiolase from *Escherichia coli* and the structural organization of the fadAB operon," *J. Biol. Chem.* 265(18):10424-10429 (1990).
Yang et al., "Nucleotide sequence of the fadA gene. Primary structure of 3-ketoacyl-Coenzyme A thiolase from *Escherichia coli* and the structural organization of the fadAB operon," *J. Biol. Chem.* 266(24):16255 (1991).
Yang et al., "Nucleotide sequence of the promoter and fadB gene of the fadBA operon and primary structure of the multifunctional fatty acid oxidation protein from *Escherichia coli*," *Biochem.* 30(27):6788-6795 (1991).
Yang et al., "Redistribution of Metabolic Fluxes in *Escherichia coli* with Fermentative Lactate Dehydrogenase Overexpression and Deletion," *Metab. Eng.* 1:141-152 (1999).
Yang et al., "The effects of feed and intracellular pyruvate levels on the redistribution of metabolic fluxes in *Escherichia coli*," *Metab Eng.* 3(2):115-123 (2001).
Yang, "Location of the fadBA operon on the physical map of *Escherichia coli*," *J. Bacteriol.* 173(23):7405-7406 (1991).
Yanisch-Perron et al., "Improved M13 phage cloning vectors and host strains: nucleotide sequences of the M13mp18 and pUC19 vectors," *Gene* 33:103-119 (1985).
Yano et al., "Directed evolution of an aspartate aminotransferase with new substrate specificities," *Proc. Natl. Acad. Sci U.S.A.* 95:5511-5515 (1998).
Yarlett et al., "*Trichomonas vaginalis*: characterization of ornithine decarboxylase," *Biochem. J.* 293(Pt2):487-493 (1993).
Yeh and Ornston, Evolutionarily Homologous $\alpha_2\beta_2$ Oligomeric Structures in $\beta$-Ketoadipate Succinyl-CoA Transferases from *Acinetobacter calcoaceticus* and *Pseudomonas putida*, *J. Biol. Chem.* 256(4):1565-1569 (1981).
Ylianttila et al., "Crystal Structure of Yeast Peroxisomal Multifunctional Enzyme: Structural Basis for Substrate Specificity of (3R)-hydroxyacyl-CoA Dehydrogenase Units," *J. Mol. Biol.* 258:1286-1295 (2006).
Ylianttila et al., "Site-directed mutagenesis to enable and improve crystallizability of *Candida tropicalis* (3R)-hydroxyacyl-CoA dehydrogenase," *Biochem. Biophys. Res. Commun.* 324:25-30 (2004).
Yoshida et al., "The Structures of L-Rhamnose Isomerase from *Pseudomonas stutzeri* in Complexes with L-Rhamnose and D-Allose Provide Insights into Broad Substrate Specificity," *J. Mol. Biol.* 365:1505-1516 (2007).
Yoshimoto, et al., "Isolation and Characterization of the *ATF2* Gene Encoding Alcohol Acetyltransferase II in the Bottom Fermenting Yeast *Saccharomyces* pastorianus," *Yeast* 15:409-417 (1999).
Yoshioka and Hashimoto, "Ester formation by Alcohol Acetyltransferase from Brewers' Yeast," *Agric. Biol. Chem.* 45: 2183-2190 (1981).
Youngleson et al., "Homology between hydroxybutyryl and hydroxyacyl Coenzyme A dehydrogenase enzymes from *Clostridium acetobutylicum* fermentation and vertebrate fatty acid $\beta$-oxidation pathways," *J. Bacteriol.* 171(12):6800-6807 (1989).
Yun et al., "The genes for anabolic 2-oxoglutarate: ferredoxin oxidoreductse from hydrogenobacter thermophilus TK-6," *Biochem. Biophys. Res. Commun.* 282(2):589-594 (2001).
Yun et al., "$\omega$-Amino acid:pyruvate transaminase from *Alcaligenes denitrificans* Y2k-2: a new catalyst for kinetic resolution of $\beta$-amino acids and amines," *Appl. Environ. Microbiol.* 70(4):2529-2534 (2004).
Yun et al., "Enhancement of lactate and succinate formation in adhE or pta-ackA mutants of NADH dehydrogenase-deficient *Escherichia coli*," *J. Appl. Microbiol.* 99(6):1404-1412 (2005).
Zeiher and Randall, "Identification and characterization of Mitochondrial Acetyl-Coenzyme A Hydrolase from *Pisum sativum* L. Seedlings," *Plant. Physiol.* 94:20-27 (1990).
Zeikus et al., "Biotechnology of succinic acid production and markets for derived industrial products," *Appl. Microbiol. Biotechnol.* 51: 545-552 (1999).
Zelle et al., "Malic acid production by *Saccharomyces cerevisiae*: engineering of pyruvate carboxylation, oxaloacetate reduction, and malate export," *Appl. Environ. Microbiol.* 74(9):2766-2777 (2008).
Zerbe-Burkhardt et al., "Cloning, sequencing, expression, and insertional inactivation of the gene for the large subunit of the Coenzyme $B_{12}$-dependent isobutyryl-CoA mutase from *Streptomyces cinnamonensis*," *J. Biol. Chem.* 273(11):6508-6517 (1998).

Zhang et al., "2-Oxoacid:Ferredoxin Oxidoreductase from the thermoacidophilic Archaeon, sulfolobus sp. Strain 7," *J. Biochem.* 120:587-599 (1996).

Zhang et al., "A new logic for DNA engineering using recombination in *Escherichia coli*," *Nat. Genet.* 20:123-128 (1998).

Zhang et al., "Directed evolution of a fucosidase from a galactosidase by DNA shuffling and screening," *Proc. Natl. Acad. Sci. U.S.A.* 94(9):4504-4509 (1997).

Zhang et al., "Functional characterization of the first two actinomycete 4-amino-4-deoxychorismate lyase genes," *Microbiology* 155:2450-2459 (2009).

Zhang et al., "Genes encoding acyl-CoA dehydrogenase (AcdH) homologues from *Streptomyces coelicolor* and *Streptomyces avermitilis* provide insights into the metabolism of small branched-chain fayy acids and marcrolide antibiotic production," *Microbiol.* 145 (Pt 9):2323-2334 (1999).

Zhang et al., "Isolation and properties of a levo-lactonase from *Fusarium proliferatum* ECU2002: a robust biocatalyst for production of chiral lactones," *Appl. Microbiol. Biotechnol.* 75:1087-1094 (2007).

Zhang et al., "Molecular basis for the inhibition of the carboxyltransferase domain of acetyl-Coenzyme-A carboxylase by haloxfop and dicofop," *Proc. Natl. Acad. Sci. U.S.A.* 101:5910-5915 (2004).

Zhao and Winkler, "A novel α-ketoglutarate reductase activity of the serA-encoded 3-phosphoglycerate dehydrogenase of *Escherichia coli* K-12 and its possible implications for human 2-hydroxyglutaric aciduria," *J. Bacteriol.* 178(1):232-239 (1996).

Zhao et al., "Molecular evolution by staggered extension process (StEP) in vitro recombination," *Nat. Biotechnol.* 16:258-261 (1998).

Zhou et al., "Comparison of fumaric acid production by Rhizopus oryzae using different neutralizing agents," *Bioproc. Biosyst. Eng.* 25(3):179-181 (2002).

Zhou et al., "Engineering a native homoethanol pathway in *Escherichia coli* B for ethanol production," *Biotechnol. Lett.* 30:335-342 (2008).

Zhou et al., "Mycelial pellet formation by *Rhizopus oryzae* ATCC 20344," *Appl. Biochem. Biotechnol.* 84-86:779-789 (2000).

Zhou et al., "The remarkable structural and functional organization of the eukaryotic pyruvate dehydrogenase complexes," *Proc. Natl. Acad. Sci. U.S.A.* 98:14802-14807 (2001).

Zhou et al., "Isolation, crystallization and preliminary X-ray analysis of a methanol-induced corrinoid protein from *Moorella thermoacetica*," *Acta. Crystallogr. Sect. F. Struct. Biol. Cryst. Commun.* 61(Pt 5):537-540 (2005).

Zhu and Sadowski, "Cleavage-dependent ligation by the FLP recombinase. Characterization of a mutant FLP protein with an alteration in a catalytic amino acid," *J. Biol. Chem.* 270(39):23044-23054 (1995).

Zhuang et al., "The YbgC protein encoded by the ybgC gene of the tol-pal gene cluster of *Haemophilus influenzae* catalyzes acyl-Coenzyme A thioester hydrolysis," *FEBS Lett.* 516(1-3):161-163 (2002).

Zou et al., "Metabolic engineering for microbial production and applications of copolyesters consisting of 3-hydroxybutyrate and medium-chain-length 3-hydroxyalkanoates," *Macromol. Biosci.* 7:174-182 (2007).

One page from URL: 1.eee.energy.gov/biomass/information_resources.html (printed Apr. 19, 2010).

One page from URL: expressys.de/ (Printed Dec. 21, 2009).

Two pages from URL: toxnet.nlm.nih.gov/cgi-bin/sis/search/f?./temp/~FwAsma:1:BASIC (printed Feb. 17, 2010).

Two pages from URL: web.archive.org/web/20080302001450/http://www.verenium.com/Pages/Technology/EnzymeTech/TechEnzyTGR.html (printed Apr. 12, 2010).

Gene Bridges, "Quick & Easy BAC Modification Kit by Red®/ET® Recombination," Technical Protocol, Cat. No. K001, Version 2.6 (2007).

Ferreira-Torres et al., "Microscale process evaluation of recombinant biocatalyst libraries: application to Baeyer-Villiger monooxygenase catalysed lactone synthesis," *Bioprocess Biosyst. Eng.* 28(2):83-93 (2005).

Locher et al., "Crystal structure of the *Acidaminococcus fermentans* 2-hydroxyglutaryl-CoA dehydratase component A," *J. Mol. Biol.* 307(1):297-308 (2001).

Niu et al., "Benzene-free synthesis of adipic acid," *Biotechnol. Prog.* 18:201-211 (2002).

Reed et al., "An expanded genome-scale model of *Escherichia coli* K-12 (iJR904 GSM/GPR)," *Genome. Biol.* 4(9):R54 (2003).

Database REAXYS [Online] Elsevier Properties SA; RX-ID Nos. 715357 and 5957085; Volmar: Comptes Rendus Hebdomadaires Des Seances De L'Academie Des Sciences, vol. 181; (1925); p. 467 (document printed Apr. 11, 2011).

Tsuji et al., "Purification and Properties of 4-Aminobenzoate Hydroxylase, a New Monooxygenase from *Agaricus bisporus*," *J. Biol. Chem.* 261(28):13203-13209 (1986).

Nichols et al., "*para*-Aminobenzoate Synthesis from Chorismate Occurs in Two Steps," *J. Biol. Chem.* 264(15):8597-8601 (1989).

Dosselaere et al., "A Metabolic Node in Action: Chorismate-Utilizing Enzymes in Microorganisms," *Crit. Rev. Microbiol.* 27(2):75-131 (2001).

Nicolaou et al., "Total Synthesis of Abyssomicin C, Atrop-abyssomicin C, and Abyssomicin D: Implications for Natural Origins of Atrop-abyssomicin C," *J. Am. Chem. Soc.* 129(2):429-440 (2007).

Bister et al., "Abyssomicin C—A polycyclic antibiotic from a marine Verrucosispora strain as an inhibitor of the p-aminobenzoic acid/tetrahydrofolate biosynthesis pathway," *Angew Chem. Int. Ed. Engl.* 43(19):2574-2576 (2004).

Feist et al., "Modeling methanogenesis with a genome-scale metabolic reconstruction of *Methanosarcina barkeri*," *Mol. Syst. Biol.* 2:2006.0004 (2006).

One page from URL: <www.dtu.dk/English/Service/Phonebook.aspx?Ig=showcommon&id=193466> Containing 182 page document: Patil, Ph.D. Thesis, "Systems Biology of Metabolic Networks: Uncovering Regulatory and stoichiometric Principles," 2006. (Printed from the Internet Jun. 8, 2011).

Tweedy et al., "Metabolism of 3-(p-bromophenyl)-1-methoxy-1-methylurea (metobromuron) by selected soil microorganisms," *J. Agric. Food Chem.* 18(5):851-853 (1970).

Peres et al., "Biodegradation of nitrobenzene by its simultaneous reduction into aniline and mineralization of the aniline formed," *Appl. Microbiol. Biotechnol.* 49(3):343-349 (1998).

Victory et al., "A Non-Obvious Reaction Pathway in the Formation of 2-Aminobenzene-1,3-dicarbonitriles from α,β-Unsaturated Ketones or Aldehydes," *TETRAHEDRON* 51(1):235-242 (1995).

White, "Biosynthesis of methanopterin," *Biochemistry* 35(11):3447-3456 (1996).

Kizer et al., "Application of Functional Genomics to Pathway Optimization for Increased Isoprenoid Production," *Appl. Environ. Microbiol.* 74(10):3229-3241 (2008).

Two pages from URL: scientificamerican.com/article.cfm?id=turning-bacteria-into-plastic-factories-replacing-fossil-fuels (Printed Feb. 17, 2011).

Monastiri et al., "β-Ketothiolase (2-methylacetoacetyl-CoA thiolase) deficiency: A frequent disease in Tunisia?" *J. Inher. Metab. Dis.* 22:932-933 (1999).

Ichiyama et al., "Oxalate synthesis in mammals: properties and subcellular distribution of serine:pyruvate/alanine:glyoxylate aminotransferase in the liver," *Mol. Urol.* 4(4):333-340 (2000).

Oda et al., "Purification and characterization of the active serine:pyruvate aminotransferase of rat liver mitochondria expressed in *Escherichia coli*," *J. Biochem.* 106(3):460-467 (1989).

Oda et al., "In vitro association with peroxisomes and conformational change of peroxisomal serine:pyruvate/alanine:glyoxylate aminotransferase in rat and human livers," *Biochem. Biophys. Res. Commun.* 228(2):341-346 (1996).

Nagata et al., "Assay of alanine:glyoxylate aminotransferase in human liver by its serine: glyoxylate aminotransferase activity," *Biomed. Res.* 30(5):295-301 (2009).

Han et al., "Comparative characterization of Aedes 3-hydroxykynurenine transaminase/alanine glyoxylate transaminase and *Drosophila* serine pyruvate aminotransferase," *FEBS Lett.* 527(1-3):199-204 (2002).

Liepman et al., "Peroxisomal alanine : glyoxylate aminotransferase (AGT1) is a photorespiratory enzyme with multiple substrates in *Arabidopsis thaliana*," *Plant J.* 25(5):487-498 (2001).

Hagishita et al., "Cloning and expression of the gene for serine-glyoxylate aminotransferase from an obligate methylotroph *Hyphomicrobium methylovorum* GM2," *Eur. J. Biochem.* 241(1):1-5 (1996).

Chumakov et al., "Genetic and physiological data implicating the new human gene G72 and the gene for D-amino acid oxidase in schizophrenia," *Proc. Natl. Acad. Sci. U. S. A.* 99(21):13675-13680 (2002).

Dixon and Kleppe, "D-Amino Acid Oxidase. II. Specificity, Competitive Inhibition and Reaction Sequence," *Biochim. Biophys. Acta.* 96: 368-382 (1965).

De Miranda et al., "Human serine racemase: moleular cloning, genomic organization and functional analysis," *Gene* 256(1-2):183-188 (2000).

Kretovich et al., "The enzyme catalyzing the reductive amination of oxypyruvate," *Izy. Akad. Nauk. SSSR Biol.* 2:295-301 (1966). (Includes English Translation of Abstract).

Mohammadi et al., "Preliminary report of NAD+-dependent amino acid dehydrogenase producing bacteria isolated from soil," *Iran Biomed. J.* 11(2):131-135 (2007).

Hendrick et al., "The Nonoxidative Decarboxylation of Hydroxypyruvate in Mammalian Systems," *Arch. Biochem. Biophys.* 105:261-269 (1964).

Rofe et al., "Hepatic oxalate production: the role of hydroxypyruvate," *Biochem. Med. Metab. Biol.* 36(2):141-150 (1986).

de la Plaza et al., "Biochemical and molecular characterization of alpha-ketoisovalerate decarboxylase, an enzyme involved in the formation of aldehydes from amino acids by *Lactococcus lactis*," *FEMS Microbiol. Lett.* 238(2):367-374 (2004).

Cusa et al., "Genetic analysis of a chromosomal region containing genes required for assimilation of allantoin nitrogen and linked glyoxylate metabolism in *Escherichia coli*," *J. Bacteriol.* 181(24):7479-7484 (1999).

Obradors et al., "Site-directed mutagenesis studies of the metal-binding center of the iron-dependent propanediol oxidoreductase from *Escherichia coli*," *Eur. J. Biochem.* 258(1):207-213 (1998).

Boronat et al., "Experimental evolution of a metabolic pathway for ethylene glycol utilization by *Escherichia coli*," *J. Bacteriol.* 153(1):134-139 (1983).

Rontein et al., "Plants synthesize ethanolamine by direct decarboxylation of serine using a pyridoxal phosphate enzyme," *J. Biol. Chem.* 276(38):35523-35529 (2001).

Summers et al., "Choline Synthesis in Spinach in Relation to Salt Stress," *Plant.Physiol.* 103(4):1269-1276 (1993).

Schomburg et al., "Ethanolamine Oxidase," in Springer handbook of enzymes: Class 1 : Oxidoreductases VII EC 1.4, vol. 22, 2nd ed., p. 320-323, New York (2005).

Nuñez et al., "Biochemical characterization of the 2-ketoacid reductases encoded by *ycdW* and *yiaE* genes in *Escherichia coli*," *Biochem. J.* 354(Pt 3):707-715 (2001).

Chistoserdova et al., "Methylotrophy in *Methylobacterium extorquens* AM1 from a genomic point of view," *J. Bacteriol.* 185(10):2980-2987 (2003).

Yoshida et al., "Cloning and expression of the gene for hydroxypyruvate reductase (d-glycerate dehydrogenase from an obligate methylotroph *Hyphomicrobium methylovorum* GM2," *Eur. J. Biochem.* 223(3):727-732 (1994).

Chistoserdova et al., "Purification and characterization of hydroxypyruvate reductase from the facultative methylotroph *Methylobacterium extorquens* AM1," *J. Bacteriol.* 173(22):7228-7232 (1991).

Booth et al., "Structural basis of substrate specificity in human glyoxylate reductase/hydroxypyruvate reductase," *J. Mol. Biol.* 360(1):178-189 (2006).

Furuyoshi et al., "Purification and characterization of a new NAD(+)-dependent enzyme, L-tartrate decarboxylase, from *Pseudomonas* sp. group Ve-2," *J. Biochem.* 110(4):520-525 (1991).

Randall et al., "3-Phosphoglycerate Phosphatase in Plants: III. Activity Associated with Starch Particles," *Plant Physiol.* 48(4):488-492 (1971).

Randall et al., "3-Phosphoglycerate phosphatase in plants. I. Isolation and characterization from sugarcane leaves," *J. Biol. Chem.* 246(17):5510-5517 (1971).

Fallon et al., "2-phosphoglyceric acid phosphatase: identification and properties of the beef-liver enzyme," *Biochim. Biophys. Acta.* 105(1):43-53 (1965).

Coleman, "Structure and mechanism of alkaline phosphatase," *Annu. Rev. Biophys. Biomol. Struct.* 21:441-483 (1992).

van Mourik et al., "Functional analysis of a *Campylobacter jejuni* alkaline phosphatase secreted via the Tat export machinery," *Microbiology* 154(Pt 2):584-592 (2008).

Oshima et al., "Regulation of phosphatase synthesis in *Saccharomyces cerevisiae*—a review," *Gene* 179(1):171-177 (1996).

Shah and Blobel, "Repressible alkaline phosphatase of *Staphylococcus aureus*," *J. Bacteriol.* 94(3):780-781 (1967).

Bartsch et al., "Only plant-type (GLYK) glycerate kinases produce d-glycerate 3-phosphate," *FEBS Lett.* 582(20):3025-3028 (2008).

Doughty et al., "Purification and properties of d-glycerate 3-kinase from *Escherichia coli*," *J. Biol. Chem.* 241(3):568-572 (1966).

Chang et al., "Molecular cloning, DNA sequencing, and biochemical analyses of *Escherichia coli* glyoxylate carboligase. An enzyme of the acetohydroxy acid synthase-pyruvate oxidase family," *J. Biol. Chem.* 268(6):3911-3919 (1993).

Eschmann and Kaltwasser, "Inhibition of Purine Utilization by Adenine in *Alcaligenes eutrophus* H16," *Arch. Microbiol.* 125:29-34 (1980).

Ashiuchi and Misono, "Biochemical evidence that *Escherichia coli* hyi (orf b0508, gip) gene encodes hydroxypyruvate isomerase," *Biochim. Biophys. Acta.* 1435(1-2):153-159 (1999).

De Windt and Van Der Drift, "Purification and some properties of hydroxypyruvate isomerase of *Bacillus fastidiosus*," *Biochim. Biophys. Acta.* 613(2):556-562 (1980).

Rintala et al., "The ORF YNL274c (GOR1) codes for glyoxylate reductase in *Saccharomyces cerevisiae*," *Yeast* 24(2):129-136 (2007).

Hoover et al., "Kinetic mechanism of a recombinant Arabidopsis glyoxylate reductase: studies of initial velocity, dead-end inhibition and product inhibition," *Can. J. Bot.* 85:896-902 (2007).

Allan et al., "γ-hydroxybutyrate accumulation in Arabidopsis and tobacco plants is a general response to abiotic stress: putative regulation by redox balance and glyoxylate reductase isoforms," *J. Exp. Bot.* 59(9):2555-2564 (2008).

Hansen et al., "De novo biosynthesis of vanillin in fission yeast (*Schizosaccharomyces pombe*) and baker's yeast (*Saccharomyces cerevisiae*)," *Appl. Environ. Microbiol.* 75(9):2765-2774 (2009).

Pestka et al., "2-phosphoglycerate phosphatase and serine biosynthesis in *Veillonella alcalescens*," *Can. J. Microbiol.* 27(8):808-814 (1981).

Yoneyama et al., "Characterization of a novel acid phosphatase from embryonic axes of kidney bean exhibiting vanadate-dependent chloroperoxidase active," *J. Biol. Chem.* 279(36):37477-37484 (2004).

Olczak et al., "Purification and characterization of acid phosphatase from yellow lupin (*Lupinus luteus*) seeds," *Biochim. Biophys. Acta.* 1341(1):14-25 (1997).

Duff et al., "Purification, characterization, and subcellular localization of an acid phosphatase from black mustard cell-suspension cultures: comparison with phosphoenolpyruvate phosphatase," *Arch. Biochem. Biophys.* 286(1):226-232 (1991).

Liu et al., "A MOFRL family glycerate kinase from the thermophilic crenarchaeon, *Sulfolobus tokodaii*, with unique enzymatic properties," *Biotechnol. Lett.* 31(12):1937-1941 (2009).

Kehrer et al., "Glycerate kinase of the hyperthermophilic archaeon Thermoproteus tenax: new insights into the phylogenetic distribution and physiological role of members of the three different glycerate kinase classes," *BMC Genomics* 8:301 (2007).

Reher et al., "Characterization of glycerate kinase (2-phosphoglycerate forming), a key enzyme of the nonphosphorylative Entner-Doudoroff pathway, from the thermoacidophilic euryarchaeon *Picrophilus torridus*," *FEMS Microbiol. Lett.* 259(1):113-119 (2006).

Gruez et al., "Crystal structure and kinetics identify *Escherichia coli* YdcW gene product as a medium-chain aldehyde dehydrogenase," *J. Mol. Biol.* 343(1):29-41 (2004).

Watanabe et al., "A novel α-ketoglutaric semialdehyde dehydrogenase: evolutionary insight into an alternative pathway of bacterial I-arabinose metabolism," *J. Biol. Chem.* 281(39):28876-28888 (2006).

Grochowski et al., "Identification of lactaldehyde dehydrogenase in *Methanocaldococcus jannaschii* and its involvement in production of lactate for $F_{420}$ biosynthesis," *J. Bacteriol.* 188(8):2836-2844 (2006).

Chang et al., "Glutarate semialdehyde dehydrogenase of *Pseudomonas*. Purification, properties, and relation to I-lysine catabolism," *J. Biol. Chem.* 252(22):7979-7986 (1977).

Vandecasteele et al., "Aldehyde dehydrogenases from *Pseudomonas aeruginosa*," *Methods Enzymol.* 89 Pt D:484-490 (1982).

Tamaki et al., "Purification and properties of aldehyde dehydrogenase from *Saccharomyces cerevisiae*," *J. Biochem.* 82(1):73-79 (1977).

Koshiba et al., "Purification and Properties of Flavin- and Molybdenum-Containing Aldehyde Oxidase from Coleoptiles of Maize," *Plant Physiol.* 110(3):781-789 (1996).

Sekimoto et al., "Cloning and molecular characterization of plant aldehyde oxidase," *J. Biol. Chem.* 272(24):15280-15285 (1997).

Monterrubio et al., "A common regulator for the operons encoding the enzymes involved in d-galactarate, d-glucarate, and d-glycerate utilization in *Escherichia coli*," *J. Bacteriol.* 182(9):2672-2674 (2000).

Njau et al., "Novel p-hydroxyacid dehydrogenases in *Escherichia coli* and *Haemophilus influenza*," *J. Biol. Chem.* 275(49):38780-38786 (2000).

Osipiuk et al., "X-ray crystal structure of GarR-tartronate semialdehyde reductase from *Salmonella typhimurium*," *J. Struct. Funct. Genomics* 10(3):249-253 (2009).

Parke et al., "Cloning and Genetic Characterization of *dca* Genes Required for β-Oxidation of Straight-Chain Dicarboxylic Acids in *Acinetobacter* sp. Strain ADP1," *Appl. Environ. Microbiol.* 67(10):4817-4827 (2001).

Matsuyama et al., "Industrial production of (*R*)-1,3-butanediol by new biocatalysts," *J. Mol. Catal. B: Enzym.* 11:513-521 (2001).

One page from home page URL: http://toxnet.nlm.nih.gov/cgi-bin/sis/search/r?dbs+hsdb:@term+@rn+@rel+79-10-7;and Fifty-four pages of text document downloaded from website Sep. 2, 2011.

\* cited by examiner

Syngas to Chemicals - Pathways 1

CO + H$_2$ + CO$_2$ (Syngas) ⟶ Chemicals, Fuels

2 Branches of Pathway

1.) Methyl Branch: Syngas ⟶ Methyl-tetrahydrofolate (Me-THF)

2.) Carbonyl Branch: Me-THF + Syngas ⟶ Acetyl-CoA

Methyl Branch- CO and CO$_2$ reduction

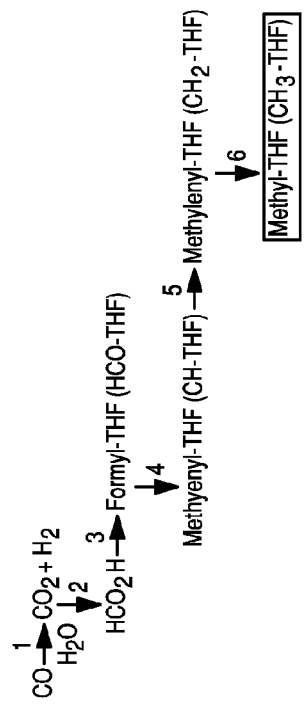

Methyl Branch
Enzymes Implicated

1. Ferredoxin oxidoreductase
2. Formate dehydrogenase
3. Formyltetrahydrofolate synthetase
4. Methenyltetrahydrofolate cyclodehydratase
5. Methylenetetrahydrofolate dehydrogenase
6. Methylenetetrahydrofolate reductase

FIG. 1

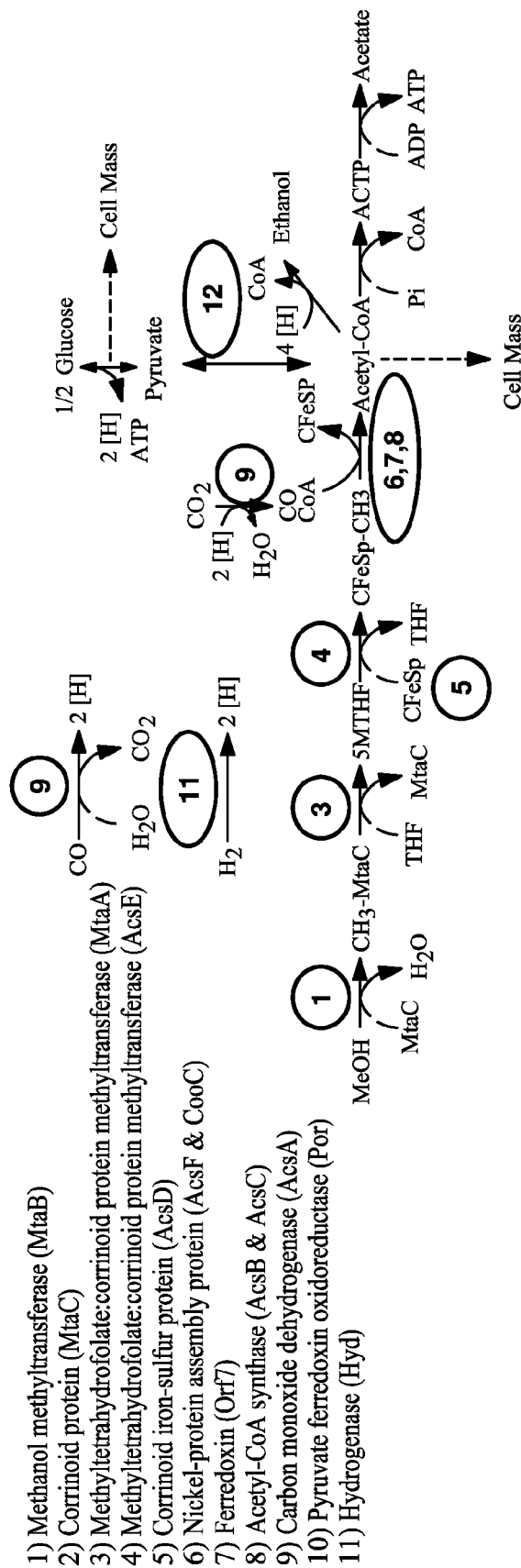

FIG. 7

1) Methanol methyltransferase (MtaB)
2) Corrinoid protein (MtaC)
3) Methyltetrahydrofolate:corrinoid protein methyltransferase (MtaA)
4) Methyltetrahydrofolate:corrinoid protein methyltransferase (AcsE)
5) Corrinoid iron-sulfur protein (AcsD)
6) Nickel-protein assembly protein (AcsF & CooC)
7) Ferredoxin (Orf7)
8) Acetyl-CoA synthase (AcsB & AcsC)
9) Carbon monoxide dehydrogenase (AcsA)
10) Pyruvate ferredoxin oxidoreductase (Por)
11) Hydrogenase (Hyd)

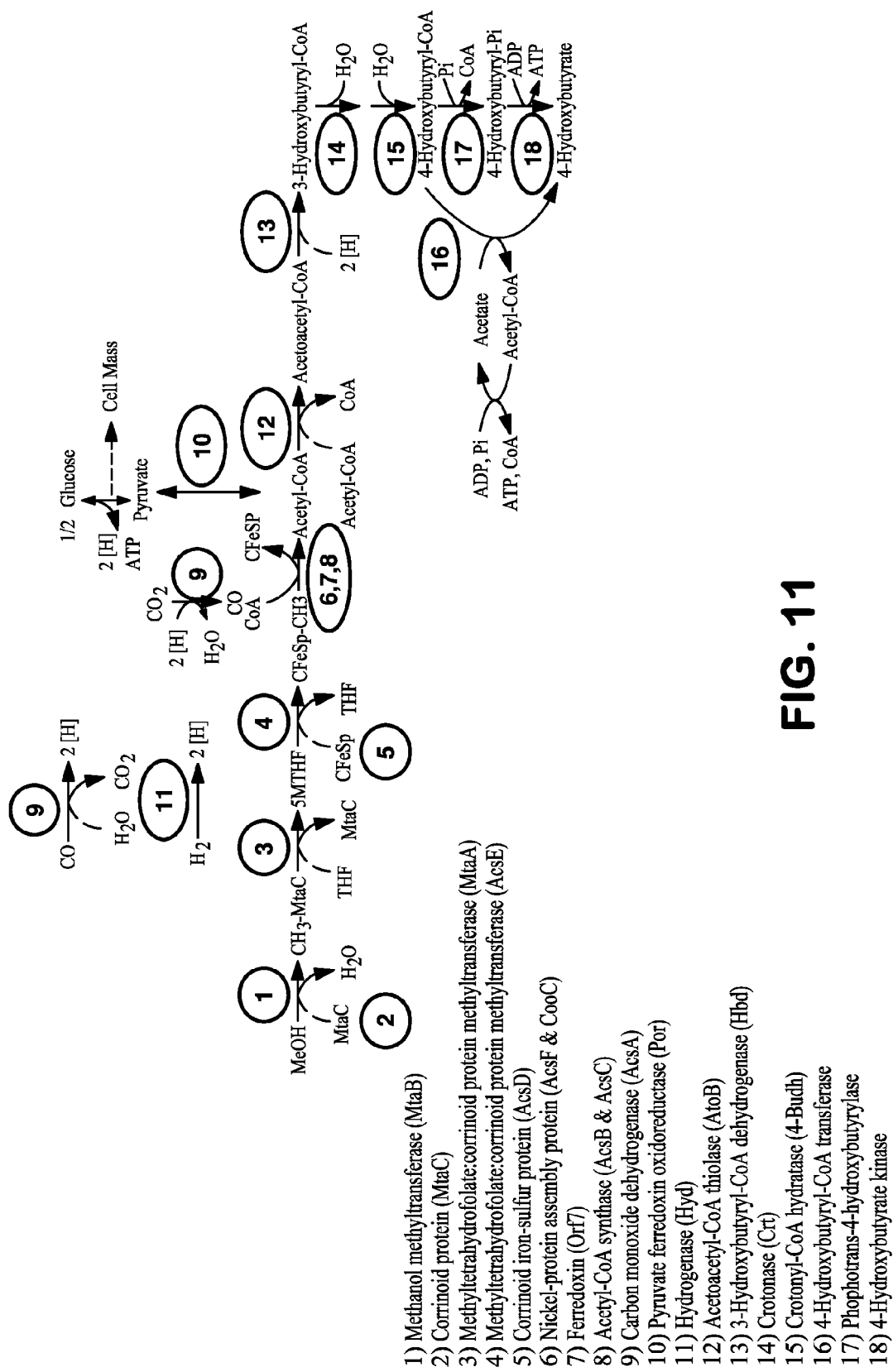

FIG. 11

1) Methanol methyltransferase (MtaB)
2) Corrinoid protein (MtaC)
3) Methyltetrahydrofolate:corrinoid protein methyltransferase (MtaA)
4) Methyltetrahydrofolate:corrinoid protein methyltransferase (AcsE)
5) Corrinoid iron-sulfur protein (AcsD)
6) Nickel-protein assembly protein (AcsF & CooC)
7) Ferredoxin (Orf7)
8) Acetyl-CoA synthase (AcsB & AcsC)
9) Carbon monoxide dehydrogenase (AcsA)
10) Pyruvate ferredoxin oxidoreductase (Por)
11) Hydrogenase (Hyd)
12) Acetoacetyl-CoA thiolase (AtoB)
13) 3-Hydroxybutyryl-CoA dehydrogenase (Hbd)
14) Crotonase (Crt)
15) Crotonyl-CoA hydratase (4-Budh)
16) 4-Hydroxybutyryl-CoA transferase
17) Phophotrans-4-hydroxybutyrylase
18) 4-Hydroxybutyrate kinase

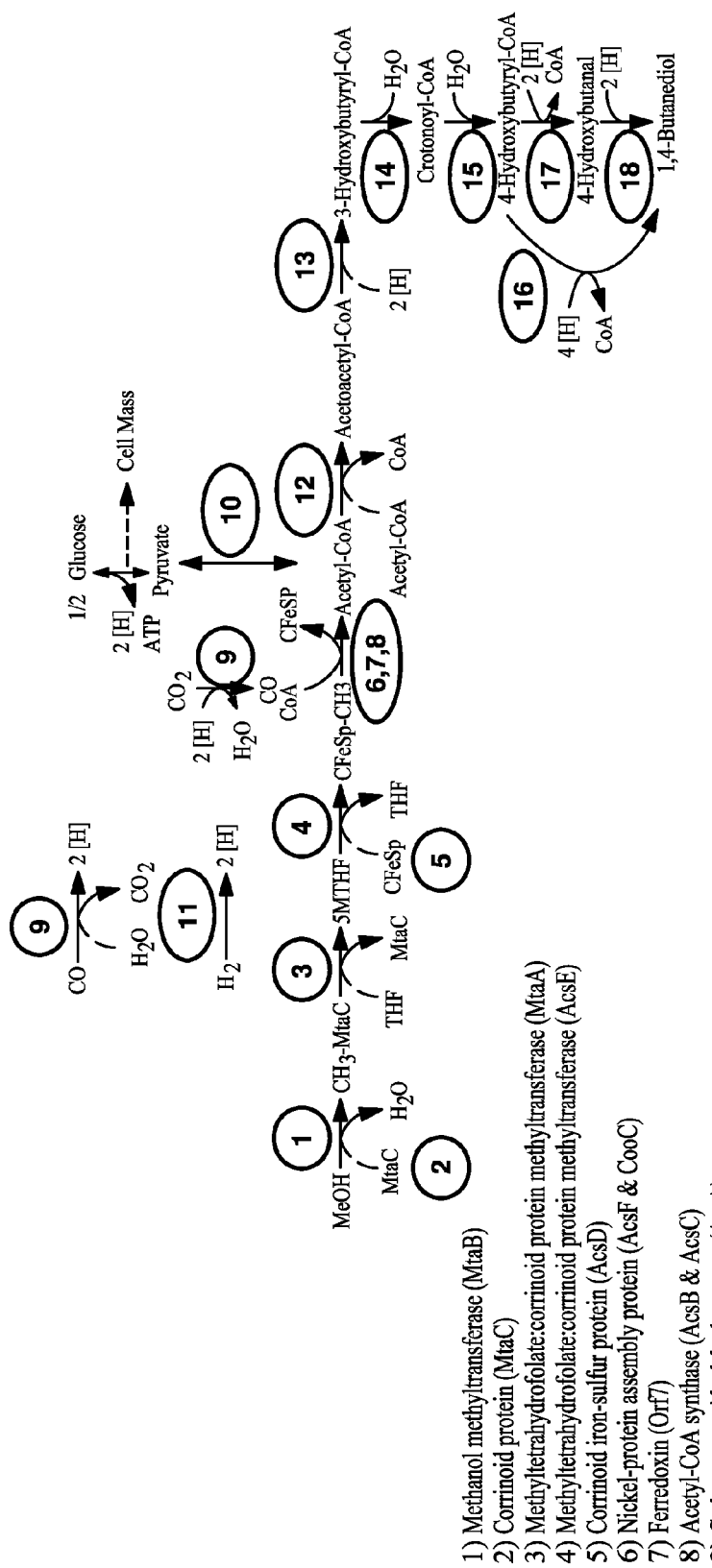

FIG. 12

1) Methanol methyltransferase (MtaB)
2) Corrinoid protein (MtaC)
3) Methyltetrahydrofolate:corrinoid protein methyltransferase (MtaA)
4) Methyltetrahydrofolate:corrinoid protein methyltransferase (AcsE)
5) Corrinoid iron-sulfur protein (AcsD)
6) Nickel-protein assembly protein (AcsF & CooC)
7) Ferredoxin (Orf7)
8) Acetyl-CoA synthase (AcsB & AcsC)
9) Carbon monoxide dehydrogenase (AcsA)
10) Pyruvate ferredoxin oxidoreductase (Por)
11) Hydrogenase (Hyd)
12) Acetoacetyl-CoA thiolase (AtoB)
13) 3-Hydroxybutyryl-CoA dehydrogenase (Hbd)
14) Crotonase (Crt)
15) Crotonyl-CoA hydratase (4-Budh)
16) 4-Hydroxybutyryl-CoA reductase (alcohol forming)
17) 4-Hydroxybutyryl-CoA reductase (aldehyde forming)
18) 1,4-Butanediol dehydrogenase

METHODS AND ORGANISMS FOR UTILIZING SYNTHESIS GAS OR OTHER GASEOUS CARBON SOURCES AND METHANOL

This application is a continuation of application Ser. No. 12/863,978, filed as a U.S. national stage application on Jul. 21, 2010, and which is a 371 of PCT US09/31737, having an international filing date of Jan. 22, 2009, which claims the benefit of priority of U.S. Provisional Ser. No. 61/022,804, filed Jan. 22, 2008, and U.S. Provisional Ser. No. 61/059,256, filed Jun. 5, 2008, each of which the entire contents are incorporated herein by reference.

BACKGROUND OF THE INVENTION

The present invention relates generally to biosynthetic processes and more specifically to organisms capable of using synthesis gas or other gaseous carbon sources and methanol.

Synthesis gas (syngas) is a mixture of primarily $H_2$ and CO that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1 $H_2$/CO mixture. Steam is sometimes added to increase the hydrogen content, typically with increased $CO_2$ production through the water gas shift reaction.

Today, coal is the main substrate used for industrial production of syngas, which is traditionally used for heating and power and as a feedstock for Fischer-Tropsch synthesis of methanol and liquid hydrocarbons. Many large chemical and energy companies employ coal gasification processes on large scale and there is experience in the industry using this technology.

In addition to coal, many types of biomass have been used for syngas production. Gaseous substrates such as syngas and $CO_2$ represent the most inexpensive and most flexible feedstocks available for the biological production of renewable chemicals and fuels. During World War II, there were over 1 million small scale biomass gasification units in operation, mainly in Europe, for running cars, trucks, boats, and buses. Currently, there are at least three major biomass gasification technologies that have been or are in the process of being validated on a commercial scale (>20 million lb biomass/yr). Biomass gasification technologies are being practiced commercially, particularly for heat and energy generation. Integration with fuels or chemicals production is being developed and has not yet been demonstrated widely at a commercial scale.

Overall, technology now exists for cost-effective production of syngas from a plethora of materials, including coal, biomass, wastes, polymers, and the like, at virtually any location in the world. The benefits of using syngas include flexibility, since syngas can be produced from most organic substances, including biomass. Another benefit is that syngas is inexpensive, costing ≦$6 per million Btu, representing raw material costs of ≦$0.10/lb product. In addition, there are known pathways, as in organisms such as *Clostridium* spp., that utilize syngas effectively.

Despite the availability of organisms that utilize syngas, in general the known organisms are poorly characterized and are not well suited for commercial development. For example, *Clostridium* and related bacteria are strict anaerobes that are intolerant to high concentrations of certain products such as butanol, thus limiting titers and commercialization potential. The *Clostridia* also produce multiple products, which presents separations issues in obtaining a desired product. Finally development of facile genetic tools to manipulate *Clostridial* genes is in its infancy; therefore, they are not readily amenable to genetic engineering to improve yield or production characteristics of a desired product.

Thus, there exists a need to develop microorganisms and methods of their use to utilize syngas or other gaseous carbon sources for the production of desired chemicals and fuels. More specifically, there exists a need to develop microorganisms for synthesis gas utilization that also have existing and efficient genetic tools to enable their rapid engineering to produce valuable products at useful rates and quantities. The present invention satisfies this need and provides related advantages as well.

SUMMARY OF INVENTION

The invention provides a non-naturally occurring microbial organism having an acetyl-CoA pathway and the capability of utilizing syngas or syngas and methanol. In one embodiment, the invention provides a non-naturally occurring microorganism, comprising one or more exogenous proteins conferring to the microorganism a pathway to convert CO, $CO_2$ and/or $H_2$ to acetyl-coenzyme A (acetyl-CoA), methyl tetrahydrofolate (methyl-THF) or other desired products, wherein the microorganism lacks the ability to convert CO or $CO_2$ and $H_2$ to acetyl-CoA or methyl-THF in the absence of the one or more exogenous proteins. For example, the microbial organism can contain at least one exogenous nucleic acid encoding an enzyme or protein in an acetyl-CoA pathway. The microbial organism is capable of utilizing synthesis gases comprising CO, $CO_2$ and/or $H_2$, alone or in combination with methanol, to produce acetyl-CoA. The invention additionally provides a method for producing acetyl-CoA, for example, by culturing an acetyl-CoA producing microbial organism, where the microbial organism expresses at least one exogenous nucleic acid encoding an acetyl-CoA pathway enzyme or protein in a sufficient amount to produce acetyl-CoA, under conditions and for a sufficient period of time to produce acetyl-CoA.

BRIEF DESCRIPTION OF THE DRAWINGS

FIG. 1 shows an exemplary Wood-Ljungdahl pathway utilizing syngas as a carbon source. A methyl branch is depicted showing utilization of syngas to produce methyl-tetrahydrofolate (Me-THF).

FIG. 4 shows a diagram depicting a process for utilizing syngas to produce butanol.

FIG. 7 shows a synthetic metabolic pathway that allows the conversion of gases comprising CO, $CO_2$, and/or $H_2$ and methanol to acetyl-CoA. The specific enzymatic transformations that can be engineered into a production host are numbered. Additional abbreviation: MeOH: methanol.

FIG. 11 shows a synthetic metabolic pathway for the conversion of gases including CO, $CO_2$, and/or $H_2$, and methanol to acetyl-CoA and further to 4-hydroxybutyrate.

FIG. 12 shows a synthetic metabolic pathway for the conversion of gases including CO, $CO_2$, and/or $H_2$, and methanol to acetyl-CoA and further to 1,4-butanediol.

DETAILED DESCRIPTION OF THE INVENTION

Figure 2:
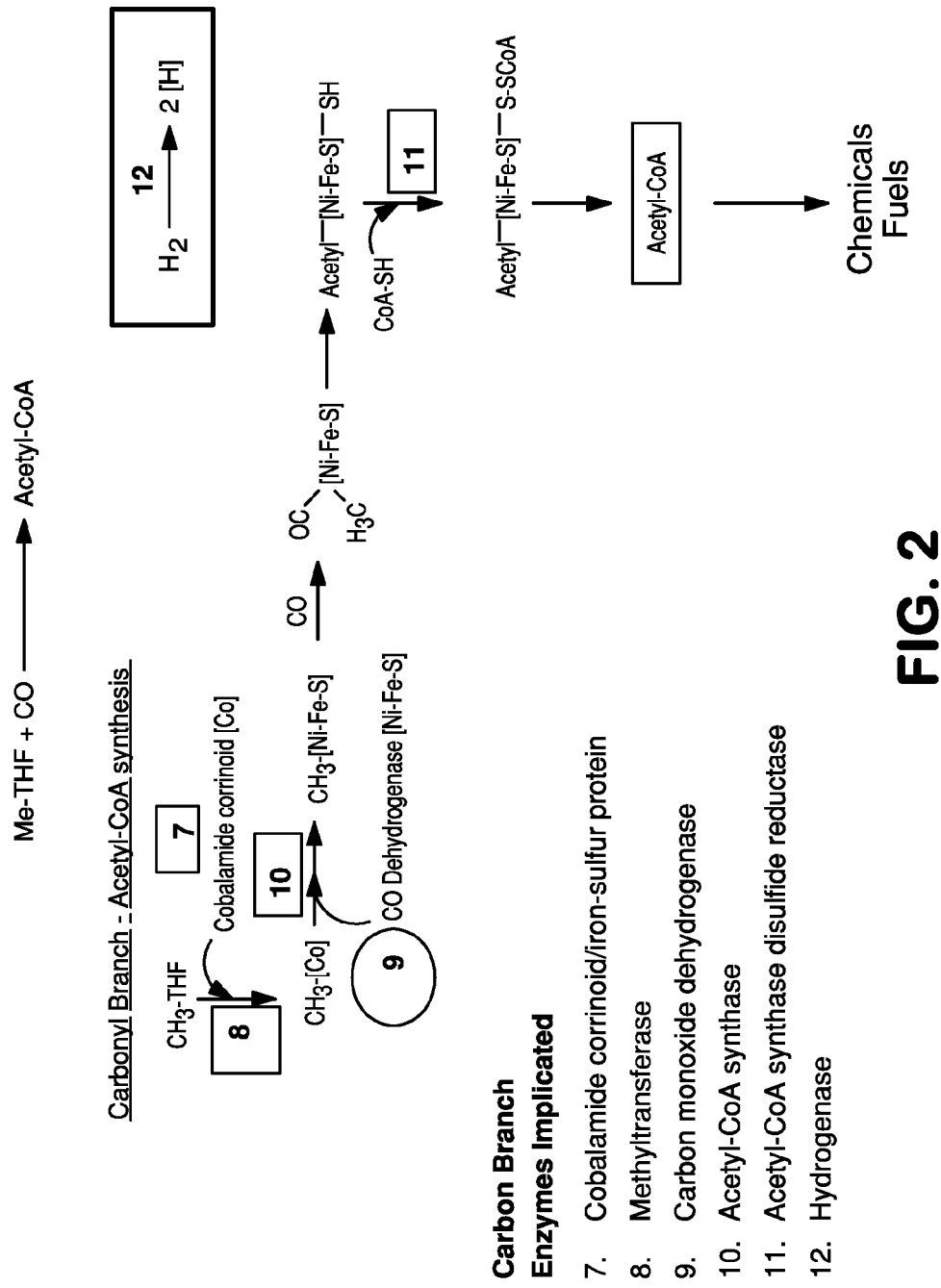
FIG. 2 shows an exemplary Wood-Ljungdahl pathway using syngas as a carbon source. A carbonyl branch is depicted showing utilization of syngas to produce acetyl-coenzyme A (acetyl-CoA). Hydrogenase (12) is required to convert hydrogen from syngas into reducing equivalents that are needed in many of the reactions depicted.

The present invention relates to developing and using microorganisms capable of utilizing syngas or other gaseous carbon sources to produce a desired product. The invention further relates to expanding the product range of syngas-utilizing microorganisms and generating recombinant organisms capable of utilizing syngas to produce a desired product and optimizing their yields, titers, and productivities. Development of a recombinant organism, for example, *Escherichia coli* or other organisms suitable for commercial scale up, that can efficiently utilize syngas as a substrate for growth and for chemical production provides cost-advantaged processes for renewable chemical and fuel manufacturing. The organisms can be optimized and tested rapidly and at reasonable costs.

The great potential of syngas as a feedstock resides in its ability to be efficiently and cost-effectively converted into chemicals and fuels of interest. Two main technologies for syngas conversion are Fischer-Tropsch processes and fermentative processes. The Fischer-Tropsch (F-T) technology has been developed since World War II and involves inorganic and metal-based catalysts that allow efficient production of methanol or mixed hydrocarbons as fuels. The drawbacks of F-T processes are: 1) a lack of product selectivity, which results in difficulties separating desired products; 2) catalyst sensitivity to poisoning; 3) high energy costs due to high temperatures and pressures required; and 4) the limited range of products available at commercially competitive costs.

For fermentative processes, syngas has been shown to serve as a carbon and energy source for many anaerobic microorganisms that can convert this material into products such as ethanol, acetate and hydrogen (see below and Table 1). The main benefits of fermentative conversion of syngas are the selectivity of organisms for production of single products, greater tolerance to syngas impurities, lower operating temperatures and pressures, and potential for a large portfolio of products from syngas. The main drawbacks of fermentative processes are that organisms known to convert syngas tend to generate only a limited range of chemicals, such as ethanol and acetate, and are not efficient producers of other chemicals, the organisms lack established tools for genetic manipulation, and the organisms are sensitive to end products at high concentrations.

The present invention relates to the generation of microorganisms that are effective at producing desired products, including chemicals and fuels, from syngas or other gaseous carbon sources. The organisms and methods of the present invention allow production of chemicals and fuels at costs that are significantly advantaged over both traditional petroleum-based products and products derived directly from glucose, sucrose or lignocellulosic sugars. In one embodiment, the invention provides a non-naturally occurring microorganism capable of utilizing syngas or other gaseous carbon sources to produce desired products in which the parent microorganism lacks the natural ability to utilize syngas (see Example VIII). In such microorganisms, one or more proteins or enzymes are expressed in the microorganism, thereby conferring a pathway to utilize syngas or other gaseous carbon source to produce a desired product. In other embodiments, the invention provides a non-naturally occurring microorganism that has been genetically modified, for example, by expressing one or more exogenous proteins or enzymes that confer an increased efficiency of production of a desired product, where the parent microorganism has the ability to utilize syngas or other gaseous carbon source to produce a desired product. Thus, the invention relates to generating a microorganism with a new metabolic pathway capable of utilizing syngas as well as generating a microorganism with improved efficiency of utilizing syngas or other gaseous carbon source to produce a desired product.

The present invention additionally provides a non-naturally occurring microorganism expressing genes encoding enzymes that catalyze and proteins associated with the carbonyl-branch of the Wood-Ljungdahl pathway in conjunction with a MtaABC-type methyltransferase system. Such an organism is capable of converting methanol, a relatively inexpensive organic feedstock that can be derived from synthesis gas, and gases comprising CO, $CO_2$, and/or $H_2$ into acetyl-CoA, cell mass, and products.

*Escherichia coli* is an industrial workhorse organism with an unrivaled suite of genetic tools. Engineering the capability to convert synthesis gas into acetyl-CoA, the central metabolite from which all cell mass components and many valuable products can be derived, into a foreign host such as *E. coli* can be accomplished following the expression of exogenous genes that encode various proteins of the Wood-Ljungdahl pathway. This pathway is highly active in acetogenic organisms such as *Moorella thermoacetica* (formerly, *Clostridium thermoaceticum*), which has been the model organism for elucidating the Wood-Ljungdahl pathway since its isolation in 1942 (Fontaine et al., *J. Bacteriol.* 43:701-715 (1942)). The Wood-Ljungdahl pathway comprises two branches: the Eastern, or methyl, branch that allows the conversion of $CO_2$ to methyltetrahydrofolate (Me-THF) and the Western, or carbonyl, branch that allows the conversion of methyl-THF, CO, and Coenzyme-A into acetyl-CoA (see FIGS. 1 and 2). As disclosed herein, the invention provides a non-naturally occurring microorganism expressing genes that catalyze both branches of the Wood-Ljungdahl pathway. Such an organism is capable of converting gasses comprising CO, CO2, and/or H2 into acetyl-CoA, cell mass, and products. The invention additionally provides a non-naturally occurring microorganism expressing genes encoding enzymes that catalyze the carbonyl-branch of the Wood-Ljungdahl pathway in conjunction with a MtaABC-type methyltransferase system. Such an organism is capable of converting methanol, a relatively inexpensive organic feedstock that can be derived from synthesis gas, and gases comprising CO, $CO_2$, and/or $H_2$ into acetyl-CoA, cell mass, and products.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

As disclosed herein, gaseous carbon sources such as syngas comprising CO and/or $CO_2$ can be utilized by non-naturally occurring microorganisms of the invention to produce a desired product. Although generally exemplified herein as syngas, it is understood that any source of gaseous carbon comprising CO and/or $CO_2$ can be utilized by the non-naturally occurring microorganisms of the invention. Thus, the invention relates to non-naturally occurring microorganisms that are capable of utilizing CO and/or $CO_2$ as a carbon source.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

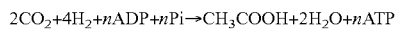

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a acetyl-CoA pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains one branch or the complete Wood-Ljungdahl pathway will confer syngas utilization ability.

Thus, the non-naturally occurring microorganisms of the invention can use syngas or other gaseous carbon sources providing CO and/or $CO_2$ to produce a desired product. In the case of $CO_2$, additional sources include, but are not limited to, production of $CO_2$ as a byproduct in ammonia and hydrogen plants, where methane is converted to $CO_2$; combustion of wood and fossil fuels; production of $CO_2$ as a byproduct of fermentation of sugar in the brewing of beer, whisky and other alcoholic beverages, or other fermentative processes; thermal decomposition of limestone, $CaCO_3$, in the manufacture of lime, CaO; production of $CO_2$ as byproduct of sodium phosphate manufacture; and directly from natural carbon dioxide springs, where it is produced by the action of acidified water on limestone or dolomite.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within an acetyl-CoA biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism or microogranism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having acetyl-CoA biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionally related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In one embodiment, the invention provides a non-naturally occurring microorganism comprising one or more exogenous proteins conferring to the microorganism a pathway to convert CO and/or $CO_2$ and $H_2$ to acetyl-coenzyme A (acetyl-CoA), wherein the microorganism lacks the ability to convert CO and/or $CO_2$ and $H_2$ to acetyl-CoA in the absence of the one or more exogenous proteins. For example, the one or more exogenous proteins or enzymes can be selected from cobalamide corrinoid/iron-sulfur protein, methyltransferase, carbon monoxide dehydrogenase, acetyl-CoA synthase, acetyl-CoA synthase disulfide reductase and hydrogenase (see FIG. 1 and Examples VII and VIII). The microorganism can also express two or more, three or more, and the like, including up to all the proteins and enzymes that confer a pathway to convert CO and/or $CO_2$ and $H_2$ to acetyl-CoA, for example, cobalamide corrinoid/iron-sulfur protein, methyltransferase, carbon monoxide dehydrogenase, acetyl-CoA synthase, acetyl-CoA synthase disulfide reductase and hydrogenase.

As disclosed herein, an embodiment of the invention relates to generating a non-naturally occurring microorganism that can utilize CO and/or $CO_2$ as a carbon source to produce a desired product. For example, the proteins and enzymes of the carbonyl and/or methyl branch of the Wood-Ljungdahl pathway (FIGS. 1 and 2) are introduced into a microorganism that does not naturally contain the Wood-Ljungdahl enzymes. A particularly useful organism for genetically engineering a Wood-Ljungdahl pathway is *E. coli*, which is well characterized in terms of available genetic manipulation tools as well as fermentation conditions (see Example VIII).

In another embodiment, the invention provides a non-naturally occurring microorganism comprising one or more exogenous proteins conferring to the microorganism a pathway to convert synthesis gas, also known as syngas, or other gaseous carbon source, comprising CO and $H_2$ to acetyl-coenzyme A (acetyl-CoA), wherein the microorganism lacks the ability to convert CO and $H_2$ to acetyl-CoA in the absence of the one or more exogenous proteins. Such a synthesis gas or other gas can further comprise $CO_2$. Thus, a non-naturally occurring microorganism of the invention can comprise a pathway that increases the efficiency of converting $CO_2$, CO and/or $H_2$ to acetyl-CoA. In addition, the invention provides a non-naturally occurring microorganism comprising one or more exogenous proteins conferring to the microorganism a pathway to convert a gaseous carbon source comprising $CO_2$ and $H_2$ to acetyl-CoA, wherein the microorganism lacks the ability to convert $CO_2$ and $H_2$ to acetyl-CoA in the absence of the one or more exogenous proteins. The gas can further comprise CO. As discussed herein, the exogenous proteins can be selected from cobalamide corrinoid/iron-sulfur protein, methyltransferase, carbon monoxide dehydrogenase, acetyl-CoA synthase, acetyl-CoA synthase disulfide reductase and hydrogenase.

In yet another embodiment, the invention provides a non-naturally occurring microorganism comprising one or more exogenous proteins conferring to the microorganism a pathway to convert CO and/or $CO_2$ and $H_2$ to methyl-tetrahydrofolate (methyl-THF), wherein the microorganism lacks the ability to convert CO and/or $CO_2$ and $H_2$ to methyl-THF in the absence of the one or more exogenous proteins. As disclosed herein, the one or more exogenous proteins can be selected from ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase (see FIG. 1 and Example VIII). The microorganism can also express two or more, three or more, and the like, including up to all the proteins and enzymes that confer a pathway to convert CO and/or $CO_2$ and $H_2$ to methyl-THF, including up to all of ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase.

The invention additionally provides a non-naturally occurring microorganism comprising one or more exogenous proteins conferring to the microorganism a pathway to convert synthesis gas or other gaseous carbon source comprising CO and $H_2$ to methyl-THF, wherein the microorganism lacks the ability to convert CO and $H_2$ to methyl-THF in the absence of the one or more exogenous proteins. The synthesis gas can further comprise $CO_2$. In addition, the invention provides a non-naturally occurring microorganism comprising one or more exogenous proteins conferring to the microorganism a pathway to convert a gaseous carbon source comprising $CO_2$ and $H_2$ to methyl-THF, wherein the microorganism lacks the ability to convert $CO_2$ and $H_2$ to methyl-THF in the absence of the one or more exogenous proteins. The gaseous carbon source can further comprise CO. As discussed above, the exogenous proteins can be selected from ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase.

Figure 6:
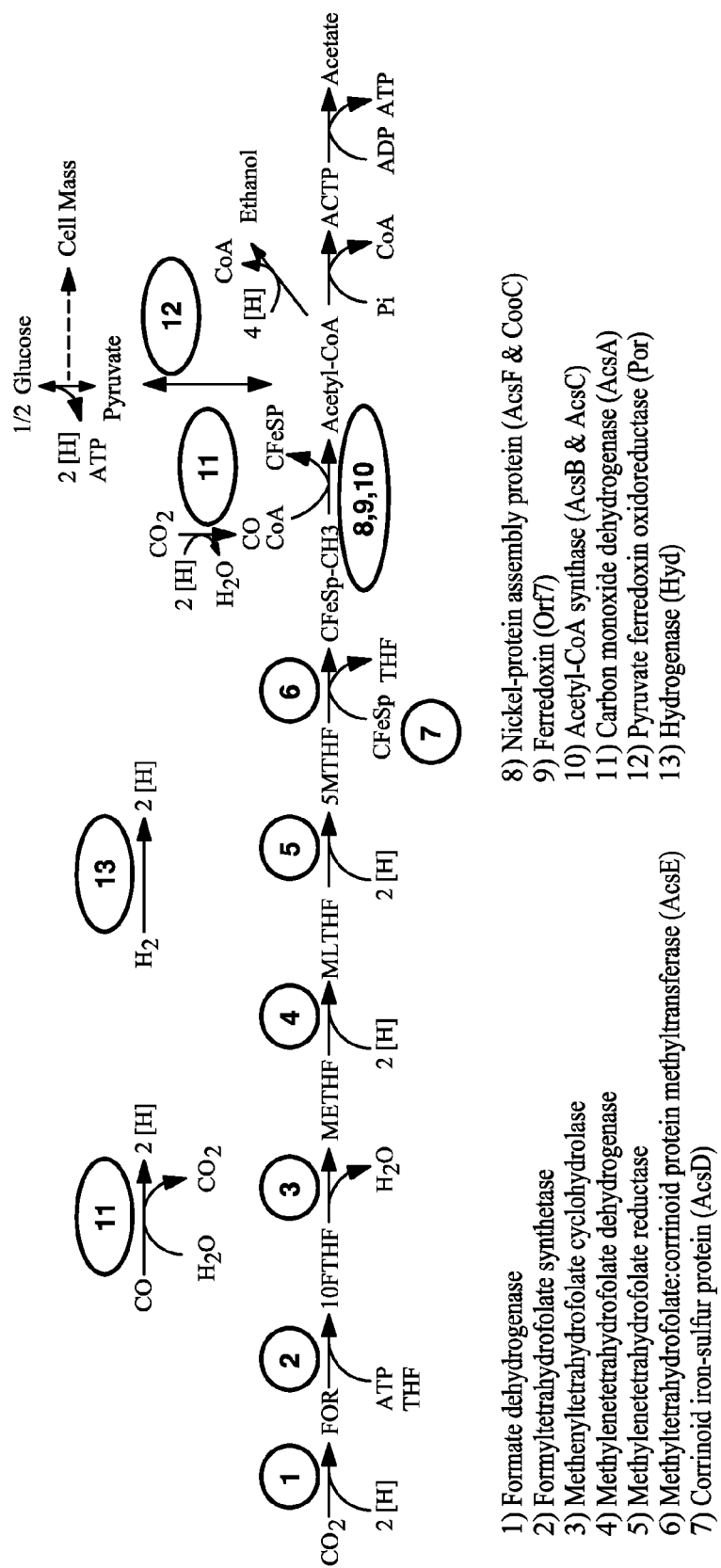
FIG. 6 shows a complete Wood-Ljungdahl pathway that allows the conversion of gases comprising CO, $CO_2$, and/or $H_2$ to acetyl-CoA, which can subsequently be converted to cell mass and products such as ethanol or acetate. Exemplary specific enzymatic transformations that can be engineered into a production host are numbered. Abbreviations: 10FTHF: 10-formyltetrahydrofolate, 5MTHF: 5-methyltetrahydrofolate, ACTP: acetyl phosphate, FOR: formate, METHF: methylene-tetrahydrofolate, MLTHF: methenyltetrahydrofolate, THF: tetrahydrofolate.

Thus, the invention relates to non-naturally occurring microorganisms and methods of utilizing such microorganisms to produce a desired product such as acetyl-CoA or methyl-THF from a synthesis gas or other gas comprising CO and/or $CO_2$ and particularly generating microorganisms capable of utilizing syngas or other gas comprising CO and/or $CO_2$ that were not previously capable of utilizing syngas or another gas comprising CO and/or $CO_2$ as a carbon source (see Example VIII). Further, a microorganism can be engineered to contain both the methyl and carbonyl branches of the Wood-Ljungdahl pathway (FIGS. 1, 2 and 6). In addition, other desired products can also be produced by engineering the microorganisms to produce a desired product by expressing proteins or enzymes capable of producing a desired product, for example, producing a product having acetyl-CoA or methyl-THF as a precursor (see FIG. 3). As disclosed herein, such microorganisms can be generated by expressing proteins or genes that confer a desired metabolic pathway or by determining deletions that can drive metabolism towards a desired product.

In addition, the invention provides a non-naturally occurring microorganism comprising a genetic modification conferring to the microorganism an increased efficiency of producing acetyl-CoA from CO and/or $CO_2$ and $H_2$ relative to the microorganism in the absence of the genetic modification, wherein the microorganism comprises a pathway to convert CO and/or $CO_2$ and $H_2$ to acetyl-CoA. In such a microorganism, the genetic modification can comprise expression of one or more nucleic acid molecules encoding one or more exogenous proteins, whereby expression of the one or more exogenous proteins increases the efficiency of producing acetyl-CoA from CO and/or $CO_2$ and $H_2$. The one or more exogenous proteins can be selected from cobalamide corrinoid/iron-sulfur protein, methyltransferase, carbon monoxide dehydrogenase, acetyl-CoA synthase, acetyl-CoA synthase disulfide reductase and hydrogenase, including up to all such proteins, as disclosed herein. Such a non-naturally occurring microorganism can alternatively or additionally have a genetic modification comprising one or more gene disruptions, whereby the one or more gene disruptions increases the efficiency of producing acetyl-CoA from CO and/or $CO_2$ and $H_2$. In addition, the invention provides a non-naturally occurring microorganism comprising a genetic modification conferring an increased efficiency of producing methyl-THF or other desired products using the methods disclosed herein. Thus, the invention additionally relates to improving the efficiency of production of a desired product in a microorganism already having the ability to produce the desired product from syngas or other gases comprising CO and/or $CO_2$.

The invention also relates to a non-naturally occurring microorganism comprising one or more proteins conferring utilization of syngas or other gas comprising CO and/or $CO_2$ as a carbon source to the microorganism, wherein the microorganism lacks the ability to utilize the carbon source in the absence of the one or more proteins conferring utilization of CO and/or $CO_2$. Further, the invention provides a non-naturally occurring microorganism comprising one or more proteins conferring utilization of carbon monoxide and/or carbon dioxide as a carbon source to the microorganism, wherein the microorganism lacks the ability to utilize the carbon source in the absence of the one or more proteins. In yet another embodiment, the invention provides a non-naturally occurring microorganism, comprising one or more proteins conferring utilization of CO and/or $CO_2$, in combination with $H_2$, as a carbon source to the microorganism, wherein the microorganism lacks the ability to utilize the carbon source in the absence of the one or more proteins. The invention additionally provides a non-naturally occurring microorganism comprising one or more proteins conferring utilization of CO, in combination with $H_2$ and $CO_2$, as a carbon source to the microorganism, wherein the microorganism lacks the ability to utilize the carbon source in the absence of the one or more proteins. Such a microorganism can be used to produce a desired product from the carbon source, for example, methyl-tetrahydrofolate or acetyl-coenzyme A (acetyl-CoA) or other desired products, as disclosed herein, including products synthesized from acetyl-CoA or methyl-THF. Such a non-naturally occurring microorganism can express one or more exogenous proteins that increase production of the product, as disclosed herein (see FIGS. 1 and 2).

The invention further provides a non-naturally occurring microorganism comprising one or more exogenous proteins conferring utilization of syngas or other gaseous carbon source to the microorganism, wherein the microorganism has the ability to utilize the carbon source in the absence of the one or more exogenous proteins, whereby expression of the one or more exogenous proteins increases the efficiency of utilization of the carbon source. Additionally the invention provides a non-naturally occurring microorganism comprising one or more exogenous proteins conferring utilization of carbon monoxide as a carbon source to the microorganism, wherein the microorganism has the ability to utilize the carbon source in the absence of the one or more exogenous proteins, whereby expression of the one or more exogenous proteins increases the efficiency of utilization of the carbon source.

In yet another embodiment, the invention provides a non-naturally occurring microorganism comprising one or more exogenous proteins conferring utilization of CO and/or $CO_2$, in combination with $H_2$, as a carbon source to the microorganism, wherein the microorganism has the ability to utilize the carbon source in the absence of the one or more exogenous proteins, whereby expression of the one or more exogenous proteins increases the efficiency of utilization of the carbon source. Additionally provided is a non-naturally occurring microorganism comprising one or more exogenous proteins conferring utilization of CO, in combination with $H_2$ and $CO_2$, as a carbon source to the microorganism, wherein the microorganism has the ability to utilize the carbon source in the absence of the one or more exogenous proteins, whereby expression of the one or more exogenous proteins increases the efficiency of utilization of the carbon source. Such a microorganism can be used to produce a desired product such as acetyl-CoA, methyl-THF or other desired products from the carbon source, as disclosed herein.

The invention also provides a non-naturally occurring microbial organism capable of producing acetyl-CoA utilizing methanol and syngas. Thus, the microbial organism is capable of utilizing methanol and CO, $CO_2$ and/or $H_2$, for example, $CO_2$, $CO_2$ and $H_2$, CO, CO and $H_2$, $CO_2$ and CO, or $CO_2$, CO and $H_2$, to produce acetyl-CoA. Since acetyl-CoA is produced in most microbial organisms, it is understood that a non-naturally occurring microbial organism of the invention that is capable of producing acetyl-CoA is one that has been engineered to include a desired pathway. Furthermore, the microbial organism is engineered to utilize methanol and syngas to produce acetyl-CoA (see Examples). In one embodiment, the invention provides a non-naturally occurring microbial organism having an acetyl-coenzyme A (acetyl-CoA) pathway comprising at least one exogenous nucleic acid encoding an acetyl-CoA pathway enzyme or protein expressed in a sufficient amount to produce acetyl-CoA, the acetyl-CoA pathway comprising methanol-methyltransferase and acetyl-CoA synthase/carbon monoxide dehydrogenase. In such a non-naturally occurring microbial organism, the acetyl-CoA pathway can confer the ability to convert $CO_2$, CO and/or $H_2$, that is, a combination thereof, to acetyl CoA. The methanol-methyltransferase activity of such an acetyl-CoA pathway can comprise, for example, an enzyme or protein selected from methanol methyltransferase, corrinoid protein (such as MtaC) and methyltetrahydrofolate: corrinoid protein methyltransferase (such as MtaA)(see Examples II and III). The acetyl-CoA synthase/carbon monoxide dehydrogenase activity of such an acetyl-CoA pathway can comprise, for example, an enzyme or protein selected from methyltetrahydrofolate:corrinoid protein methyltransferase (such as AcsE), corrinoid iron-sulfur protein (such as AcsD), nickel-protein assembly protein (such as AcsF), ferredoxin, acetyl-CoA synthase, carbon monoxide dehydrogenase and nickel-protein assembly protein (such as CooC)(see Examples II and III). As disclosed herein, two or more, three or more, four or more, five or more, six or more, seven or more, eight or more, nine or more, and so forth, nucleic acids encoding an acetyl-CoA pathway can be expressed in a non-naturally occurring microbial organism of the invention. In a particular embodiment, the non-naturally occurring microbial organism can comprise ten exogenous nucleic acids that encode a methanol-methyltransferase comprising methanol methyltransferase, corrinoid protein (such as MtaC) and methyltetrahydrofolate:corrinoid protein methyltransferase (such as MtaA) and an acetyl-CoA synthase/carbon monoxide dehydrogenase comprising methyltetrahydrofolate:corrinoid protein methyltransferase (such as AcsE), corrinoid iron-sulfur protein (such as AcsD), nickel-protein assembly protein (such as CooC), ferredoxin, acetyl-CoA synthase, carbon monoxide dehydrogenase and nickel-protein assembly protein (such as AcsF).

In yet another embodiment, the non-naturally occurring microbial organism can further comprise pyruvate ferredoxin oxidoreductase. For example, the pyruvate ferredoxin oxidoreductase can be encoded by an exogenous nucleic acid. In still another embodiment, the non-naturally occurring microbial organism can further comprise hydrogenase, which can be encoded by an endogenous or exogenous nucleic acid, as disclosed herein (see Examples II and III).

As disclosed herein, a non-naturally occurring microbial organism can contain, for example, at least one exogenous nucleic acid that is a heterologous nucleic acid. As further disclosed herein, the non-naturally occurring microbial organism can be grown, for example, in a substantially anaerobic culture medium.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms of the invention can be produced by introducing expressible nucleic acids encoding one or more of the enzymes or proteins participating in one or more acetyl-CoA biosynthetic pathways. Depending on the host microbial organism chosen for biosynthesis, nucleic acids for some or all of a particular acetyl-CoA biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve acetyl-CoA biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as acetyl-CoA.

Depending on the acetyl-CoA biosynthetic pathway constituents of a selected host microbial organism, the non-naturally occurring microbial organisms of the invention will include at least one exogenously expressed acetyl-CoA pathway-encoding nucleic acid and up to all encoding nucleic acids for one or more acetyl-CoA biosynthetic pathways. For example, acetyl-CoA biosynthesis can be established in a host deficient in a pathway enzyme or protein through exogenous expression of the corresponding encoding nucleic acid. In a host deficient in all enzymes or proteins of a acetyl-CoA pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of acetyl-CoA can be included, such as the methanol-methyltransferase, which can include methanol methyltransferase, corrinoid protein (such as MtaC) and methyltetrahydrofolate:corrinoid protein methyltransferase (such as MtaA), and the acetyl-CoA synthase/carbon monoxide dehydrogenase, which can include methyltetrahydrofolate:corrinoid protein methyltransferase (such as AcsE), corrinoid iron-sulfur protein (such as AcsD), nickel-protein assembly protein (such as AcsF), ferredoxin, acetyl-CoA synthase, carbon monoxide dehydrogenase and nickel-protein assembly protein (such as CooC).

In another embodiment, in a pathway for producing acetyl-CoA from syngas or other gaseous carbon source, one or more proteins in the biosynthetic pathway can be selected from cobalamide corrinoid/iron-sulfur protein, methyltransferase, carbon monoxide dehydrogenase, acetyl-CoA synthase, acetyl-CoA synthase disulfide reductase and hydrogenase (see FIG. 2 and Examples VII and VIII). In a pathway for producing methyl-THF, one or more proteins in the biosynthetic pathway can be selected from ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase (see FIG. 1 and Example VIII). In addition, genes that encode the enzymes required to produce both acetyl-CoA and methyl-THF can be introduced into a microorganism (see FIG. 3 and Example VIII). Metabolic pathways for production of additional desired products, including succinate, 4-hydroxybutyrate and 1,4-butanediol are described, for example, in U.S. application Ser. No. 11/891,602, filed Aug. 10, 2007, and WO/2008/115840 (see Example VIII).

Given the teachings and guidance provided herein, those skilled in the art will understand that the number of encoding nucleic acids to introduce in an expressible form will, at least, parallel the acetyl-CoA pathway deficiencies of the selected host microbial organism. Therefore, a non-naturally occurring microbial organism of the invention can have one, two, three, four, five, six, seven, eight, nine or up to all nucleic acids encoding the enzymes or proteins constituting a acetyl-CoA biosynthetic pathway disclosed herein. In some embodiments, the non-naturally occurring microbial organisms also can include other genetic modifications that facilitate or optimize acetyl-CoA biosynthesis or that confer other useful functions onto the host microbial organism. One such other functionality can include, for example, augmentation of the synthesis of one or more of the acetyl-CoA pathway precursors such as methanol.

Generally, a host microbial organism is selected such that it produces the precursor of an acetyl-CoA pathway, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism and further engineered to express enzymes or proteins of an acetyl-CoA pathway.

In some embodiments, a non-naturally occurring microbial organism of the invention is generated from a host that contains the enzymatic capability to synthesize acetyl-CoA. In this specific embodiment it can be useful to increase the synthesis or accumulation of an acetyl-CoA pathway product to, for example, drive acetyl-CoA pathway reactions toward acetyl-CoA production. Increased synthesis or accumulation can be accomplished by, for example, overexpression of nucleic acids encoding one or more of the above-described acetyl-CoA pathway enzymes or proteins. Over expression the enzyme or enzymes and/or protein or proteins of the acetyl-CoA pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing acetyl-CoA, through overexpression of one, two, three, four, five, six, seven, eight, nine, or ten, that is, up to all nucleic acids encoding acetyl-CoA biosynthetic pathway enzymes or proteins. In addition, a non-naturally occurring organism can be generated by mutagenesis of an endogenous gene that results in an increase in activity of an enzyme in the acetyl-CoA biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, an acetyl-CoA biosynthetic pathway onto the microbial organism. Alternatively, encoding nucleic acids can be introduced to produce an intermediate microbial organism having the biosynthetic capability to catalyze some of the required reactions to confer acetyl-CoA biosynthetic capability. For example, a non-naturally occurring microbial organism having a acetyl-CoA biosynthetic pathway can comprise at least two exogenous nucleic acids encoding desired enzymes or proteins, such as the combination of methanol methyltransferase and corrinoid protein; methanol methyltransferase and methyltetrahydrofolate:corrinoid protein methyltransferase; corrinoid protein and corrinoid iron-sulfur protein; nickel-protein assembly protein and ferredoxin, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, methanol methyltransferase, corrinoid iron-sulfur protein (such as AcsD) and acetyl-CoA synthase; corrinoid protein (such as MtaC), carbon monoxide dehydrogenase and nickel-protein assembly protein (such as CooC or AcsF); methyltetrahydrofolate:corrinoid protein methyltransferase (such as AcsE), ferredoxin and acetyl-CoA synthase, and so forth, as desired, so long as the combination of enzymes and/or proteins of the desired biosynthetic pathway results in production of the corresponding desired product. Similarly, any combination of four, five, six, seven, eight, nine or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of acetyl-CoA as described herein, the non-naturally occurring microbial organisms and methods of the invention also can be utilized in various combinations with each other and with other microbial organisms and methods well known in the art to achieve product biosynthesis by other routes. For example, one alternative to produce acetyl-CoA other than use of the acetyl-CoA producers is through addition of another microbial organism capable of converting an acetyl-CoA pathway intermediate to acetyl-CoA. One such procedure includes, for example, the fermentation of a microbial organism that produces an acetyl-CoA pathway intermediate. The acetyl-CoA pathway intermediate can then be used as a substrate for a second microbial organism that converts the acetyl-CoA pathway intermediate to acetyl-CoA. The acetyl-CoA pathway intermediate can be added directly to another culture of the second organism or the original culture of the acetyl-CoA pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, acetyl-CoA. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of acetyl-CoA can be accomplished by constructing a microbial organism that contains biosynthetic pathways for conversion of one pathway intermediate to another pathway intermediate or the product. Alternatively, acetyl-CoA also can be biosynthetically produced from microbial organisms through co-culture or co-fermentation using two organisms in the same vessel, where the first microbial organism produces an acetyl-CoA intermediate and the second microbial organism converts the intermediate to acetyl-CoA.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce acetyl-CoA. In addition, since acetyl-CoA is a precursor of other desirable products, a non-naturally occurring microbial organism of the invention can be used as a host organism into which other desired pathways utilizing acetyl-CoA as a precursor or intermediate can be conferred, as desired.

Sources of encoding nucleic acids for an acetyl-CoA pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Methanosarcina barkeri, Methanosarcina acetivorans, Moorella thermoacetica, Carboxydothermus hydrogenoformans, Rhodospirillum rubrum, Acetobacterium woodii, Butyribacterium methylotrophicum, Clostridium autoethanogenum, Clostridium carboxidivorans, Clostridium ljungdahlii, Eubacterium limosum, Oxobacter pfennigii, Peptostreptococcus productus, Rhodopseudomonas palustris* P4, *Rubrivivax gelatinosus, Citrobacter* sp Y19, *Methanosarcina acetivorans* C2A, *Methanosarcina barkeri, Desulfosporosinus orientis, Desulfovibrio desulfuricans, Desulfovibrio vulgaris, Moorella thermoautotrophica, Carboxydibrachium pacificus, Carboxydocella thermoautotrophica, Thermincola carboxydiphila, Thermolithobacter carboxydivorans, Thermosinus carboxydivorans, Methanothermobacter thermoautotrophicus, Desulfotomaculum carboxydivorans, Desulfotomaculum kuznetsovii, Desulfotomaculum nigrificans, Desulfotomaculum thermobenzoicum* subsp. *thermosyntrophicum, Syntrophobacter fumaroxidans, Clostridium acidurici, Desulfovibrio africanus*, and the like, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite acetyl-CoA biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of acetyl-CoA described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative acetyl-CoA biosynthetic pathway exists in an unrelated species, acetyl-CoA biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize acetyl-CoA.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris. E. coli* is a particularly useful host organisms since it is a well characterized microbial organism suitable for genetic engineering. Other particularly useful host organisms include yeast such as *Saccharomyces cerevisiae*. Exemplary acetogens suitable as host organisms include, but are not limited to, *Rhodospirillum rubrum, Moorella thermoacetica* and *Desulfitobacterium hafniense* (see Examples).

Methods for constructing and testing the expression levels of a non-naturally occurring acetyl-CoA-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of acetyl-CoA can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280: 4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more acetyl-CoA biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The invention additionally provides a method for producing acetyl-CoA by culturing a non-naturally occurring microbial organism of the invention having an acetyl-CoA pathway. The acetyl-CoA pathway can comprise, for example, at least one exogenous nucleic acid encoding an acetyl-CoA pathway enzyme or protein expressed in a sufficient amount to produce acetyl-CoA, under conditions and for a sufficient period of time to produce acetyl-CoA, the acetyl-CoA pathway comprising methanol-methyltransferase and acetyl-CoA synthase/carbon monoxide dehydrogenase. In such an acetyl-CoA pathway, the methanol-methyltransferase can comprise an enzyme or protein selected from methanol methyltransferase, corrinoid protein (such as MtaC) and methyltetrahydrofolate:corrinoid protein methyltransferase (MtaA). Further, in such an acetyl-CoA pathway, the acetyl-CoA synthase/carbon monoxide dehydrogenase can comprise an enzyme or protein selected from methyltetrahydrofolate:corrinoid protein methyltransferase (such as AcsE), corrinoid iron-sulfur protein (such as AcsD), nickel-protein assembly protein (such as AcsF), ferredoxin, acetyl-CoA synthase, carbon monoxide dehydrogenase and nickel-protein assembly protein (such as CooC). A non-naturally occurring microbial organism can be in a substantially anaerobic culture medium. In a particular embodiment, the non-naturally occurring microbial organism can be cultured in the presence of $CO_2$, CO and/or $H_2$, that is, a combination thereof, and methanol. The non-naturally occurring microbial organism can further comprise pyruvate ferredoxin oxidoreductase, which can be expressed by an exogenous nucleic acid. The non-naturally occurring microbial organism can also further comprise hydrogenase, for example, encoded by an endogenous or exogenous nucleic acid.

In another embodiment, the non-naturally occurring microbial organism can be cultured in the presence of an electron acceptor, for example, nitrate, in particular under substantially anaerobic conditions (see Example III). It is understood that an appropriate amount of nitrate can be added to a microbial culture to achieve a desired increase in biomass, for example, 1 mM to 100 mM nitrate, or lower or higher concentrations, as desired, so long as the amount added provides a sufficient amount of electron acceptor for the desired increase in biomass. Such amounts include, but are not limited to, 5 mM, 10 mM, 15 mM, 20 mM, 25 mM, 30 mM, 40 mM, 50 mM, as appropriate to achieve a desired increase in biomass.

Suitable purification and/or assays to test for the production of acetyl-CoA can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art (see Example III).

The acetyl-CoA, or products derived from acetyl-CoA, can be separated from other components in the culture using a variety of methods well known in the art. Products derived from acetyl-CoA include, but are not limited to, ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the acetyl-CoA producers can be cultured for the biosynthetic production of acetyl-CoA, or products derived from acetyl-CoA.

For the production of acetyl-CoA, the recombinant strains are cultured in a medium with a carbon and energy source of methanol and gases comprising CO, $CO_2$ and/or $H_2$ and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. patent application Ser. No. 11/891,602, filed Aug. 10, 2007, and WO/2008/115840. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of acetyl-CoA.

Accordingly, given the teachings and guidance provided herein, those skilled in the art will understand that a non-naturally occurring microbial organism can be produced that expresses intracellular or secretes the biosynthesized compounds of the invention when grown on a carbon source such as a carbohydrate, methanol, and gases comprising CO, $CO_2$, and/or $H_2$. Such compounds include, for example, acetyl-CoA and any of the intermediate metabolites in the acetyl-CoA pathway, and products derived from acetyl-CoA including ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid. All that is required is to engineer in one or more of the required enzyme or protein activities to achieve biosynthesis of the desired compound or intermediate including, for example, inclusion of some or all of the acetyl-CoA biosynthetic pathways. Accordingly, the invention provides a non-naturally occurring microbial organism that produces acetyl-CoA when grown on a carbohydrate or other carbon source and produces and/or secretes any of the intermediate metabolites shown in the acetyl-CoA pathway or produces and/or secretes a product derived from acetyl-CoA when grown on a carbohydrate or other carbon source. The acetyl-CoA producing microbial organisms of the invention can initiate synthesis from an intermediate, for example, 5-methyl-tetrahydrofolate (Me-THF).

The non-naturally occurring microbial organisms of the invention are constructed using methods well known in the art as exemplified herein to exogenously express at least one nucleic acid encoding an acetyl-CoA pathway enzyme or protein in sufficient amounts to produce acetyl-CoA. It is understood that the microbial organisms of the invention are cultured under conditions sufficient to produce acetyl-CoA. Following the teachings and guidance provided herein, the non-naturally occurring microbial organisms of the invention can achieve biosynthesis of acetyl-CoA resulting in intracellular concentrations between about 0.001-200 mM or more. Generally, the intracellular concentration of acetyl-CoA is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application Ser. No. 11/891,602, filed Aug. 10, 2007, and WO/2008/115840. Any of these conditions can be employed with the non-naturally occurring microbial organisms as well as other anaerobic conditions well known in the art. Under such anaerobic conditions, the acetyl-CoA producers can synthesize acetyl-CoA at intracellular concentrations of 5-10 mM or more as well as all other concentrations exemplified herein. It is understood that the above description refers to intracellular concentrations, and acetyl-CoA producing microbial organisms can produce acetyl-CoA intracellularly. In addition, a product derived from acetyl-CoA can be produced intracellularly and/or secreted. Such products include, but are not limited to, ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of acetyl-CoA includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of acetyl-CoA. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of acetyl-CoA. Generally, and as with non-continuous culture procedures, the continuous and/or near-continuous production of acetyl-CoA will include culturing a non-naturally occurring acetyl-CoA producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of acetyl-CoA can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the acetyl-CoA producers of the invention for continuous production of substantial quantities of acetyl-CoA, the acetyl-CoA producers also can be, for example, simultaneously subjected to chemical synthesis procedures to convert the product to other compounds or the product can be separated from the fermentation culture and sequentially subjected to chemical conversion to convert the product to other compounds, if desired.

At least thirty different wild-type organisms have been isolated through the years and shown to grow on syngas or components of syngas, including microorganisms capable of converting syngas to ethanol (Vega et al., *Appl. Biochem. Biotechnol.* 20/21:781-797 (1989))(see Table 1). Candidate organisms for improved syngas fermentation include acetogens, phototrophs, sulfate reducing bacteria, and methanogens, which can utilize CO and/or $CO_2/H_2$ as the sole carbon and energy source (Sipma et al., *Crit. Rev. Biotechnol.* 26:41-65. (2006)). The mesophilic acetogen *Clostridium carboxidivorans* represents one of the most promising organisms for a syngas-to-chemicals platform as it has fast doubling times and have been shown to naturally produce ethanol and small quantities of butanol during growth on syngas (Henstra et al., *Curr. Opin. Biotechnol.* 18:200-206 (2007)). Genetic tools can be developed for this organism. The hydrogenic purple nonsulfur bacteria, *Rhodospirillum rubrum*, for which genetic tools exist for targeted gene deletions or insertions, is another good candidate organism for development of syngas utilization to produce desired products, although it naturally produces hydrogen from syngas and so metabolic changes can be engineered, as required.

Figure 3:
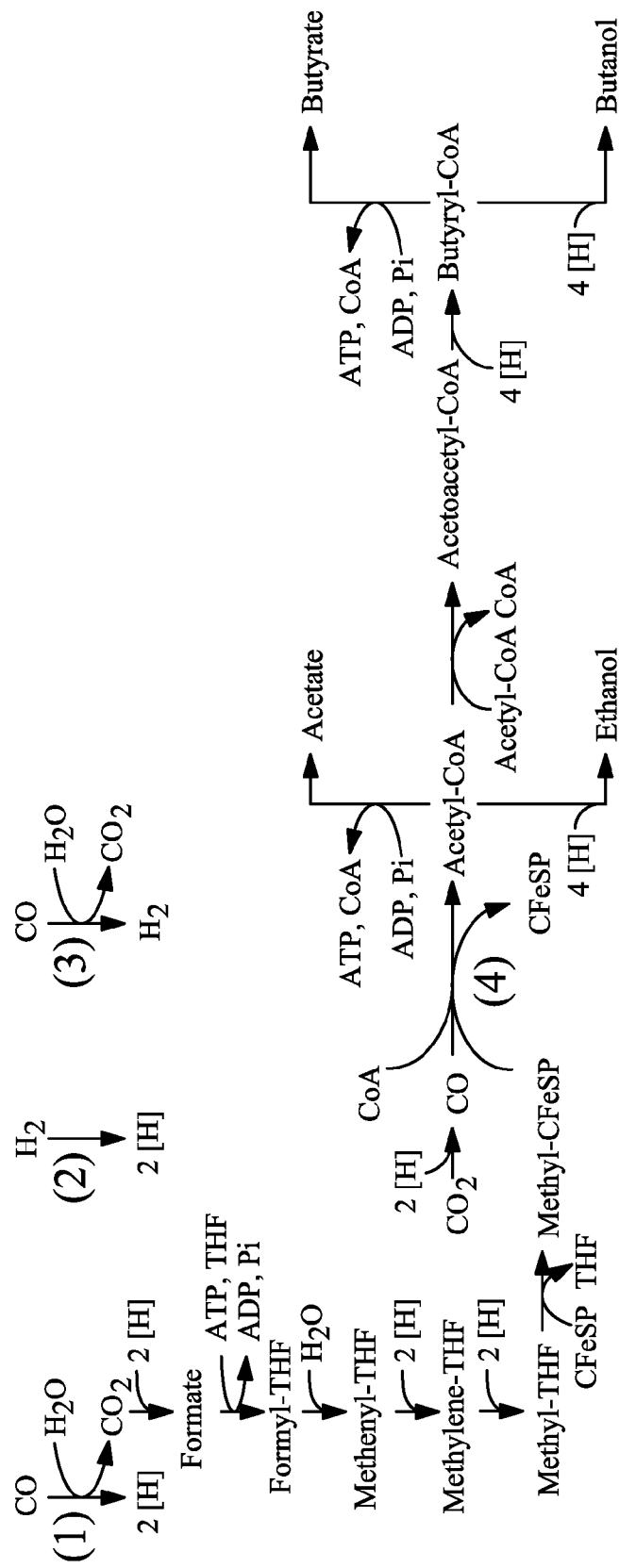
FIG. 3 shows a metabolic pathway diagram depicting the integration of the Wood-Ljungdahl and butanol production pathways. The transformations that are typically unique to organisms capable of growth on synthesis gas are: 1) CO dehydrogenase, 2) hydrogenase, 3) energy-conserving hydrogenase (ECH), and 4) bi-functional CO dehydrogenase/acetyl-CoA synthase.

The metabolism of some syngas utilizing organisms is known. For example, acetogens such as *C. carboxidivorans* can grow in the presence of CO or $CO_2$ by utilizing the Wood-Ljungdahl pathway, even in the absence of glucose, as long as hydrogen is present to supply the necessary reducing equivalents. The Wood-Ljungdahl pathway is illustrated in FIG. 3 (see also FIGS. 1 and 2) and shows the capacity of acetogens to utilize CO as the sole carbon and energy source through the production of the key metabolic intermediate acetyl-CoA. Specifically, CO can be oxidized to produce reducing equivalents and $CO_2$, or can be directly assimilated into acetyl-CoA, which is subsequently converted to either biomass or metabolites. Importantly, acetyl-CoA is a key metabolic intermediate that can serve as a precursor to a wide range of metabolites and other chemical entities. Hence, the ability of a microorganism to produce acetyl-CoA from syngas or other gaseous carbon source allows engineering of syngas-utilizing organisms, or organisms capable of utilizing other gaseous carbon sources, for production of a wide range of chemicals and fuels as desired products.

In order to characterize the use of syngas or other gaseous carbon sources as a viable feedstock for the commercial production of chemicals and fuels through fermentation, feasibility studies are performed to address key questions and challenges associated with current systems. Preliminary metabolic modeling efforts have indicated that conversion of syngas to chemicals can be thermodynamically very favorable, and that specific chemicals can be made as the exclusive product. Not only does this reduce downstream processing needs, but also maximizes product yield. Furthermore, production of a desired product can be growth-associated, so that the fermentation can be done continuously, if desired. Because continuous processes are maintained at high cell concentration, and avoid batch turnaround time, they are more economically favorable.

As disclosed herein, the present invention relates to the development of microorganisms capable of utilizing syngas or other gaseous carbon sources, allowing the efficient conversion of CO and/or $CO_2$ to chemical products in high yield, titer, and productivity. One exemplary useful commercial embodiment relates to the development of an organism that can achieve production of a specific chemical with yields $\geq 80\%$ of theoretical maximum, product tolerance $\geq 50$ g/L, titers $\geq 50$ g/L and productivity of at least 2 g/L/h. Although these criteria are particularly useful commercially, it is understood that an organism capable of achieving less than any or all of these criteria is also useful in the invention. For example, an organism can achieve production of a specific chemical with yields greater than or equal to any of 75%, 70%, 65%, 60%, 55%, 50%, 45%, 40%, 35%, 30%, 25%, 20%, and so forth so long as sufficient yields are achieved for a desired application. Similarly, an organism can achieve product tolerance greater than or equal to any of 45 g/L, 40 g/L, 35 g/L, 30 g/L, 25 g/L, 20 g/L, 15 g/L, 10 g/L, and so forth so long as sufficient yields are achieved for a desired application. Moreover, an organism can achieve titers greater than or equal to any of 200 g/L, 190 g/L, 180 g/L, 170 g/L, 160 g/L, 150 g/L, 140 g/L, 130 g/L, 120 g/L, 110 g/L, 100 g/L, 90 g/L, 80 g/L, 70 g/L, 60 gL, 50 g/l, 45 g/L, 40 g/L, 35 g/L, 30 g/L, 25 g/L, 20 g/L, 15 g/L, 10 g/L, and so forth so long as sufficient yields are achieved for a desired application. In addition, an organism can achieve productivity of at least any of 1.5 g/L/h, 1 g/L/h, 0.5 g/L/h, and so forth so long as sufficient yields are achieved for a desired application.

As disclosed herein, the hypothetical analysis of butanol as a product from syngas utilization indicates that the ability to efficiently utilize cheap and readily available syngas as a feedstock and can lead to processes that potentially are $\geq 50\%$ cost-advantaged over current petrochemical processes, especially in view of the low cost of syngas as a feedstock. In addition to low cost, syngas is an abundant and flexible substrate that can be produced from coal and many types of biomass, including energy crops such as switchgrass, as well as waste products such as wood waste, agricultural waste, dairy waste, and municipal solid waste. Thus, the ability to generate organisms capable of utilizing syngas or other gaseous carbon sources to produce a desired product allows production from almost any biomass source. This feature obviates the need to develop different processes specific for each type of biomass used for biofuel or chemical production. The use of waste products for the production of syngas can also be utilized to decrease environmental pollutants and alleviate serious disposal problems of biowaste materials. In addition, syngas as a feedstock does not suffer from a feed versus fuel controversy associated with, for example, corn-based ethanol production. Given the broad range of substrates available for syngas production, the supply and cost structure of this feedstock is expected to remain relatively stable from year to year. Finally, syngas is used extensively for heating and energy and can therefore be used as a source of biomass-derived energy that can supplement or eliminate the need for petroleum-based energy for production, providing additional cost savings.

Although exemplified in various embodiments herein with butanol as a desired product, it is understood that any product capable of being produced by a microorganism of the invention can be generated and utilized to produce the product, as desired. Generally, desired products include but are not limited to hydrocarbons useful in chemical synthesis or as a fuel. Exemplary desired products include but are not limited to methanol, ethanol, butanol, acetate, butyrate, lactate, succinate, 4-hydroxybutyrate, 1,4-butanediol, and the like.

In other aspects, the present invention provides a non-naturally occurring microbial organism having a 4-hydroxybutryate pathway that can include at least one exogenous nucleic acid encoding an 4-hydroxybutryate pathway enzyme expressed in a sufficient amount to produce 4-hydroxybutryate. The 4-hydroxybutryate pathway enzyme can include an acetoacetyl-CoA thiolase, a 3-hydroxybutyryl-CoA dehydrogenase, a crotonase, a crotonyl-CoA hydratase, a 4-hydroxybutyryl-CoA transferase, a phosphotrans-4-hydroxybutyrylase, and a 4-hydroxybutyrate kinase.

In still other aspects, the present invention provides a non-naturally occurring microbial organism having a 1,4-butanediol pathway that can include at least one exogenous nucleic acid encoding a 1,4-butanediol pathway enzyme expressed in a sufficient amount to produce 1,4-butanediol. The 1,4-butanediol pathway enzyme can include an acetoacetyl-CoA thiolase, a 3-Hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), and a 1,4-butanediol dehydrogenase. Such an organism also can include an acetyl-CoA pathway having at least one exogenous nucleic acid encoding an acetyl-CoA pathway enzyme expressed in a sufficient amount to produce acetyl-CoA. The acetyl-CoA pathway enzyme can include a corrinoid protein, a methyltetrahydrofolate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In yet other aspects, the present invention provides a non-naturally occurring microbial organism having a 1,4-butanediol pathway that can include at least one exogenous nucleic acid encoding a 1,4-butanediol pathway enzyme expressed in a sufficient amount to produce 1,4-butanediol. The 1,4-butanediol pathway enzyme can include an acetoacetyl-CoA thiolase, a 3-Hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), and a 1,4-butanediol dehydrogenase. Such an organism also can include an acetyl-CoA pathway having at least one exogenous nucleic acid encoding an acetyl-CoA pathway enzyme expressed in a sufficient amount to produce acetyl-CoA. The acetyl-CoA pathway enzyme can include an acetyl-CoA synthase, a formate dehydrogenase, a formyltetrahydrofolate synthetase, a methenyltetrahydrofolate cyclohydrolase, a methylenetetrahydrofolate dehydrogenase, and a methylenetetrahydrofolate reductase.

In yet still further aspects, the present invention provides a method for producing 4-hydroxybutyrate that can include culturing a non-naturally occurring microbial organism having an 4-hydroxybutyrate pathway. The pathway can include at least one exogenous nucleic acid encoding an 4-hydroxybutyrate pathway enzyme expressed in a sufficient amount to produce 4-hydroxybutyrate under conditions and for a sufficient period of time to produce 4-hydroxybutyrate. The 4-hydroxybutyrate pathway can include an acetoacetyl-CoA thiolase, a 3-hydroxybutyryl-CoA dehydrogenase, a crotonase, a crotonyl-CoA hydratase, a 4-hydroxybutyryl-CoA transferase, a phosphotrans-4-hydroxybutyrylase, and a 4-hydroxybutyrate kinase.

In still other aspects, the present invention provides a method for producing 1,4-butanediol that can include culturing a non-naturally occurring microbial organism having an 1,4-butanediol pathway. The pathway can include at least one exogenous nucleic acid encoding an 1,4-butanediol pathway enzyme expressed in a sufficient amount to produce 1,4-butanediol under conditions and for a sufficient period of time to produce 1,4-butanediol. The 1,4-butanediol pathway can include an acetoacetyl-CoA thiolase, a 3-hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), a 1,4-butanediol dehydrogenase. Such an organism also can include an acetyl-CoA pathway comprising at least one exogenous nucleic acid encoding an acetyl-CoA pathway enzyme expressed in a sufficient amount to produce acetyl-CoA. The acetyl-CoA pathway enzyme can include a corrinoid protein, a methyltetrahydro-folate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

Finally, in some aspects, the present invention provides a method for producing 1,4-butanediol that can include culturing a non-naturally occurring microbial organism having an 1,4-butanediol pathway. The pathway can include at least one exogenous nucleic acid encoding an 1,4-butanediol pathway enzyme expressed in a sufficient amount to produce 1,4-butanediol under conditions and for a sufficient period of time to produce 1,4-butanediol. The 1,4-butanediol pathway can include an acetoacetyl-CoA thiolase, a 3-hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), and a 1,4-butanediol dehydrogenase. Such an organism also can include an acetyl-CoA pathway having at least one exogenous nucleic acid encoding an acetyl-CoA pathway enzyme expressed in a sufficient amount to produce acetyl-CoA. The acetyl-CoA pathway enzyme can include an acetyl-CoA synthase, a formate dehydrogenase, a formyltetrahydrofolate synthetase, a methenyltetrahydrofolate cyclohydrolase, a methylenetetrahydrofolate dehydrogenase, and a methylenetetrahydrofolate reductase.

In other embodiments, organisms of the present invention have a functional methyltransferase system, the ability to synthesize acetyl-CoA, and the ability to synthesize 4-HB from acetyl-CoA as depicted in FIG. 11. Still other organisms described herein have a functional methyltransferase system, the ability to synthesize acetyl-CoA, and the ability to synthesize BDO from acetyl-CoA depicted in FIG. 12.

The invention also provides a non-naturally occurring microbial organism having a 4-hydroxybutryate pathway that can include at least one exogenous nucleic acid encoding an 4-hydroxybutryate pathway enzyme expressed in a sufficient amount to produce 4-hydroxybutryate. The 4-hydroxybutryate pathway enzyme can include an acetoacetyl-CoA thiolase, a 3-hydroxybutyryl-CoA dehydrogenase, a crotonase, a crotonyl-CoA hydratase, a 4-hydroxybutyryl-CoA transferase, a phosphotrans-4-hydroxybutyrylase, and a 4-hydroxybutyrate kinase.

Such organisms can also include at least one enzyme or polypeptide such as a corrinoid protein, a methyltetrahydrofolate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In some embodiments, organisms that have a 4-hydroxybutyrate pathway can include a methanol methyltransferase. Such organisms utilize a feedstock such as 1) methanol and CO, 2) methanol, $CO_2$, and $H_2$, 3) methanol, CO, $CO_2$, and $H_2$, 4) methanol and synthesis gas comprising CO and $H_2$, and 5) methanol and synthesis gas comprising CO, $CO_2$, and $H_2$.

Other organisms that have a 4-hydroxybutyrate pathway can have a formate dehydrogenase, a formyltetrahydrofolate synthetase, a methenyltetrahydrofolate cyclohydrolase, a methylenetetrahydrofolate dehydrogenase, and a methylenetetrahydrofolate reductase. Such organisms utilize a feedstock such as 1) CO, 2) $CO_2$ and $H_2$, 3) CO and $CO_2$, 4) synthesis gas comprising CO and $H_2$, and 5) synthesis gas comprising CO, $CO_2$, and $H_2$.

The present invention also provides a non-naturally occurring microbial organism having a 1,4-butanediol pathway that can include at least one exogenous nucleic acid encoding a 1,4-butanediol pathway enzyme expressed in a sufficient amount to produce 1,4-butanediol. The 1,4-butanediol pathway enzyme include, for example, an acetoacetyl-CoA thiolase, a 3-Hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), and a 1,4-butanediol dehydrogenase.

Such organisms can also include at least one enzyme or polypeptide such as a corrinoid protein, a methyltetrahydrofolate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In some embodiments, an organism having a 1,4-butanediol pathway can include a methanol methyltransferase. Such organisms utilize a feedstock such as 1) methanol and CO, 2) methanol, $CO_2$, and $H_2$, 3) methanol, CO, $CO_2$, and $H_2$, 4) methanol and synthesis gas comprising CO and $H_2$, and 5) methanol and synthesis gas comprising CO, $CO_2$, and $H_2$.

In other embodiments, an organism having a 1,4-butanediol pathway can include a formate dehydrogenase, a formyltetrahydrofolate synthetase, a methenyltetrahydrofolate cyclohydrolase, a methylenetetrahydrofolate dehydrogenase, and a methylenetetrahydrofolate reductase. Such organisms utilize a feedstock selected from the group consisting of: 1) CO, 2) $CO_2$ and $H_2$, 3) CO and $CO_2$, 4) synthesis gas comprising CO and $H_2$, and 5) synthesis gas comprising CO, $CO_2$, and $H_2$.

Figure 13:
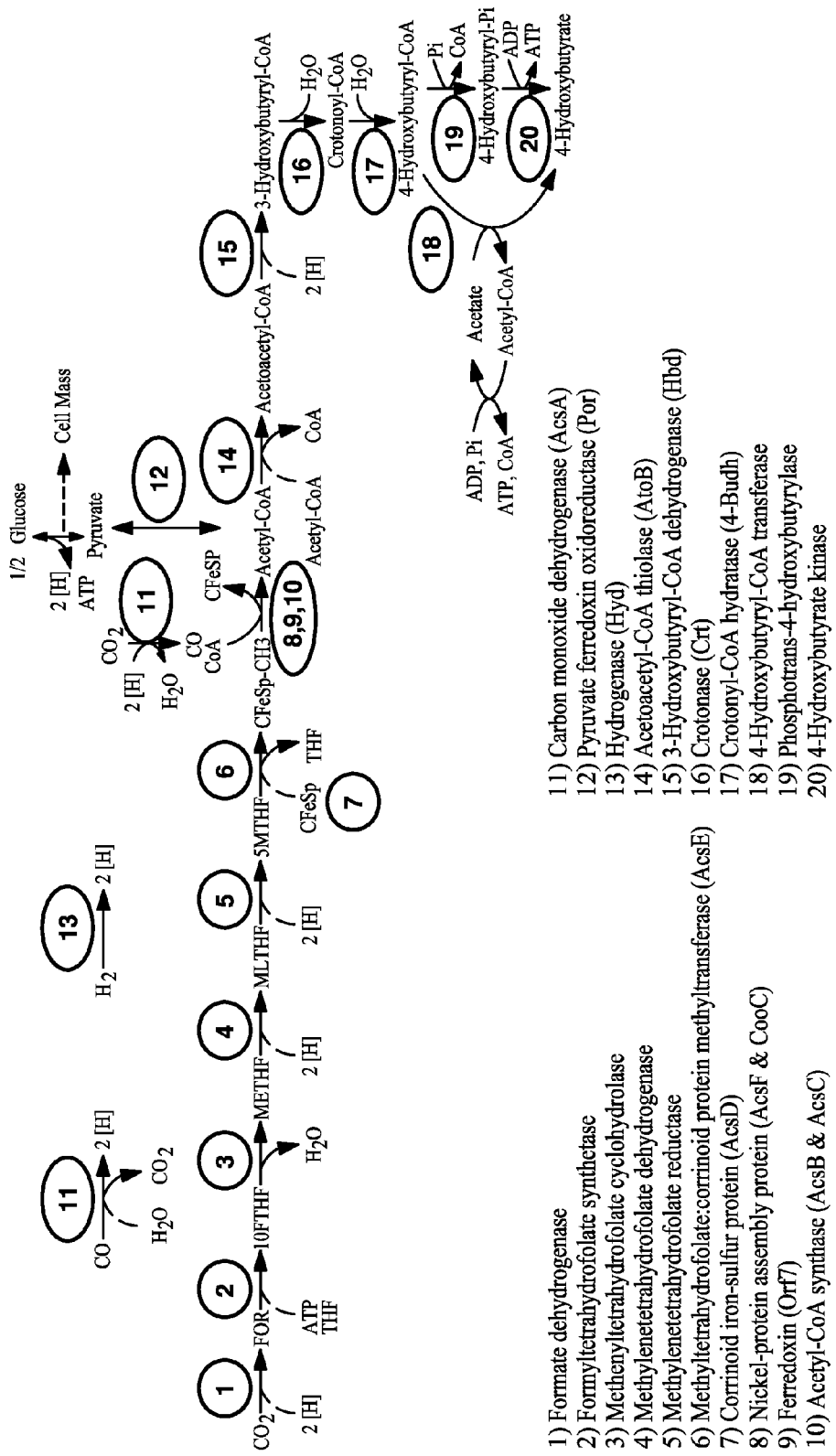
FIG. 13 shows a synthetic metabolic pathway for the conversion of gases including CO, $CO_2$, and/or $H_2$ to acetyl-CoA, and further to 4-hydroxybutyrate.
Figure 14:
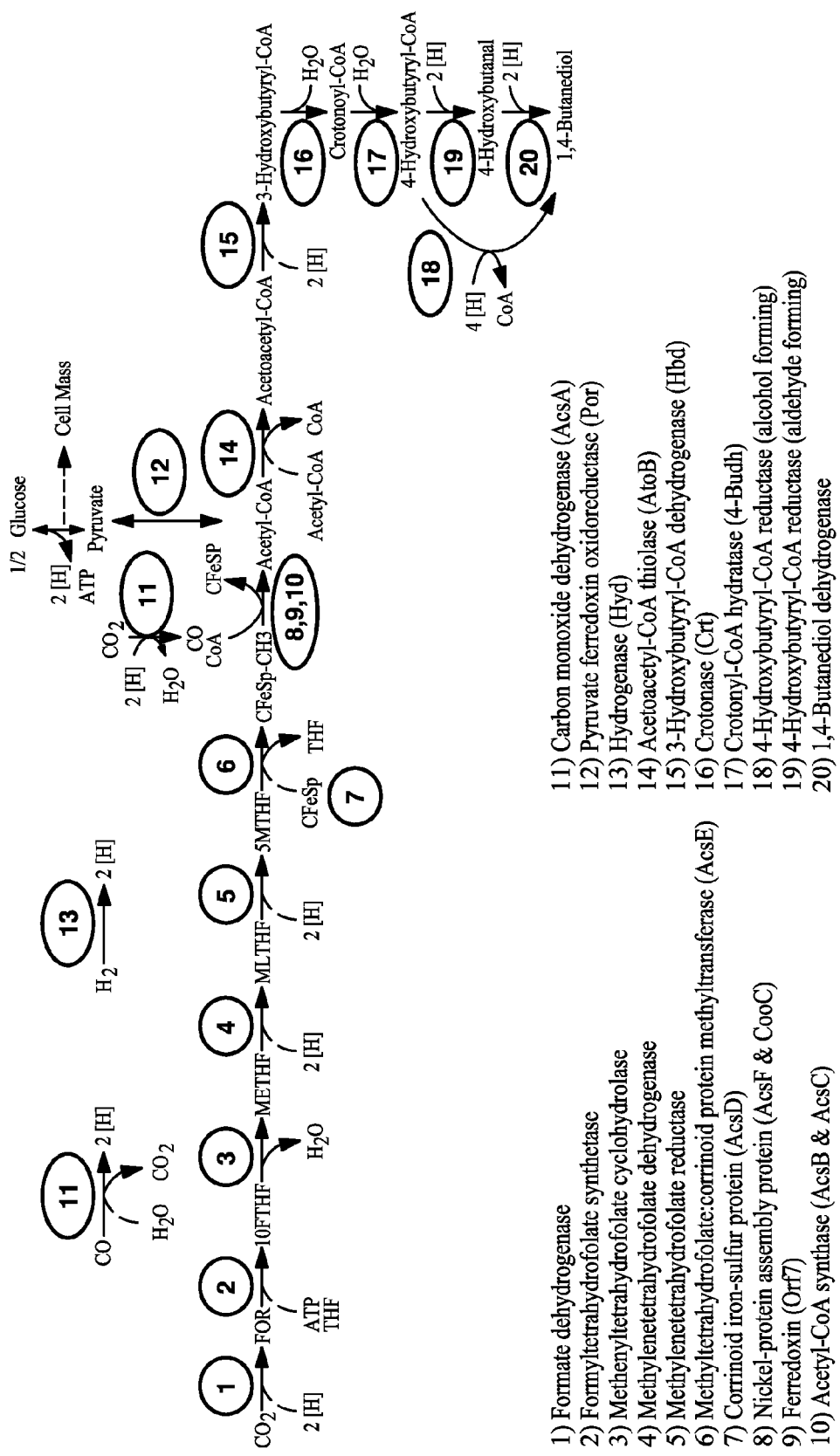
FIG. 14 shows a synthetic metabolic pathway for the conversion of gases including CO, $CO_2$, and/or $H_2$ to acetyl-CoA, and further to 1,4-butanediol.

An exemplary microbial organisms of the invention can contain a pathway as depicted in FIG. 13. Such an organism can contain a functional methyl branch of the Wood-Ljungdahl pathway, the ability to synthesize acetyl-CoA, and the ability to synthesize 4-hydroxybutyrate from acetyl-CoA. Another exemplary microbial organism of the invention can contain a pathway as depicted in FIG. 14. Such an microbial organism can contain a functional methyl branch of the Wood-Ljungdahl pathway, the ability to synthesize acetyl-CoA, and the ability to synthesize 1,4-butanediol from acetyl-CoA.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of acetyl-CoA or products derived from acetyl-CoA.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. patent application Ser. No. 11/891,602, filed Aug. 10, 2007, and WO/2008/115840.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

It is understood that modifications which do not substantially affect the activity of the various embodiments of this invention are also provided within the definition of the invention provided herein. Accordingly, the following examples are intended to illustrate but not limit the present invention.

Example I

Organisms and Pathways for Syngas Fermentation

This example describes organisms capable of utilizing syngas and exemplary pathways.

At least thirty different organisms have been isolated through the years and shown to grow on syngas or components of syngas such as CO, $CO_2$, and $H_2$ (Henstra et al., *Curr. Opin. Biotechnol.* 18:200-206 (2007); Sipma et al., *Crit. Rev. Biotechnol.* 26:41-65 (2006)). Table 1 provides examples of such organisms as well as a number of their properties such as their optimal temperature for growth, optimal pH for growth, doubling time, product profile, and physiological group.

TABLE 1

Examples of CO utilizing species and their physiological characteristics.

|  | Species | Physiological Characterization | T (° C.) | pH | $t_d$ (h) | Products |
|---|---|---|---|---|---|---|
| Mesophillic Bacteria | Acetobacterium woodii | Acetogenic | 30 | 6.8 | 13 | Acetate |
|  | Butyribacterium metholytrophicum | Acetogenic | 37 | 6 | 12-20 | Acetate, ethanol, butyrate, butanol |
|  | Clostridium autoethanogenum | Acetogenic | 37 | 5.8-6.0 | nr | Acetate, ethanol |
|  | Clostridium carboxidivorans | Aceteogenic | 38 | 6.2 | 6.25 | Acetate, ethanol, butyrate, butanol |
|  | Clostridium ljungdahlii | Acetogenic | 37 | 6 | 3.8 | Acetate, ethanol |
|  | Eubacterium limosum | Acetogenic | 38-39 | 7.0-7.2 | 7 | Acetate |
|  | Oxobacter pfennigii | Acetogenic | 36-38 | 7.3 | 13.9 | Acetate, n-butyrate |

TABLE 1-continued

Examples of CO utilizing species and their physiological characteristics.

|  | Species | Physiological Characterization | T (° C.) | pH | $t_d$ (h) | Products |
|---|---|---|---|---|---|---|
|  | *Peptostrepococcus productus* | Acetogenic | 37 | 7 | 1.5 | Acetate |
|  | *Rhodopseudomonas palustris* P4 | Hydrogenogenic, Phototroph | 30 | nr | 23 | $H_2$ |
|  | *Rhodospirillum rubrum* | Hydrogenogenic, Phototroph | 30 | 6.8 | 8.4 | $H_2$ |
|  | *Rubrivivax gelatinosus* | Hydrogenogenic, Phototroph | 34 | 6.7-6.9 | 6.7 | $H_2$ |
|  | *Citrobacter* sp Y19 | Hydrogenogenic, Facultative Anaerobe | 30-40 | 5.5-7.5 | 8.3 | $H_2$ |
|  | *Methanosarcina acetivorans* C2A | Methanogenic | 37 | 7 | 24 | Acetate, formate, $CH_4$ |
|  | *Methanosarcina barkeri* | Methanogenic | 37 | 7.4 | 65 | $CH_4$, $CO_2$ |
|  | *Desulfosporosinus orientis* | Sulfate reducing bacteria | 35 | 7 | nr | $H_2S$, $CO_2$ |
|  | *Desulfovibrio desulfuricans* | Sulfate reducing bacteria | 37 | nr | nr | $H_2$, $CO_2$, $H_2S$ |
|  | *Desulfovibrio vulgaris* | Sulfate reducing bacteria | 37 | nr | nr | $H_2$, $CO_2$, $H_2S$ |
| Thermophillic Bacteria | *Moorella thermoacetica* | Acetogenic | 55 | 6.5-6.8 | 10 | Acetate |
|  | *Moorella thermoautotrophica* | Acetogenic | 58 | 6.1 | 7 | Acetate |
|  | *Carboxydibrachium pacificus* | Hydrogenogenic, Obligate Anearobe | 70 | 6.8-7.1 | 7.1 | $H_2$ |
|  | *Carboxydocella thermoautotrophica* | Hydrogenogenic, Obligate Anearobe | 58 | 7 | 1.1 | $H_2$ |
|  | *Carboxydothermus hydrogenoformans* | Hydrogenogenic, Obligate Anearobe | 70-72 | 6.8-7.0 | 2 | $H_2$ |
|  | *Thermincola carboxydiphila* | Hydrogenogenic, Obligate Anearobe | 55 | 8 | 1.3 | $H_2$ |
|  | *Thermolithobacter carboxydivorans* | Hydrogenogenic, Obligate Anearobe | 70 | 7 | 8.3 | $H_2$ |
|  | *Thermosinus carboxydivorans* | Hydrogenogenic, Obligate Anearobe | 60 | 6.8-7.0 | 1.2 | $H_2$ |
|  | *Methanothermobacter thermoautotrophicus* | Methanogenic | 65 | 7.4 | 140 | $CH_4$, $CO_2$ |
|  | *Desulfotomaculum carboxydivorans* | Sulfate reducing bacteria | 55 | 7 | 1.7 | $H_2$, $H_2S$ |
|  | *Desulfotomaculum kuznetsovii* | Sulfate reducing bacteria | 60 | 7 | nr | Acetate, $H_2S$ |
|  | *Desulfotomaculum nigrificans* | Sulfate reducing bacteria | 55 | 7 | nr | $H_2S$, $CO_2$ |
|  | *Desulfotomaculum thermobenzoicum* subsp. *thermosyntrophicum* | Sulfate reducing bacteria | 55 | 7 | nr | Acetate, $H_2S$ |

Adapted from Henstra et al., *Curr. Opin. Biotechnol.* 18:200-206 (2007); Sipma et al., *Crit. Rev. Biotechnol.* 26:41-65 (2006)).

One type of organism for consideration of utilizing syngas is thermophilic acetogens due to their ability to tolerate temperatures as high as 72° C., which would reduce contamination issues and lower the heating cost associated with separating a product such as butanol via distillation. However, alcohol production from synthesis gas has yet to be demonstrated in thermophiles and their primary products are hydrogen, acetate, and/or $H_2S$. The doubling times of the acetogenic thermophiles were also longer than for mesophilic acetogens. Thus, initial studies were focused on mesophilic acetogenes for the production of a desired product such as butanol as these organisms have the fastest doubling times and have been shown to produce alcohols from syngas. Initial characterizations are performed on *Clostridium ljungdahlii* and *Clostridium carboxidivorans*. Of all syngas-utilizing organisms, *C. ljungdahlii* has a substantial body of knowledge relating to its metabolic capabilities and optimum fermentation conditions. *C. carboxidivorans* has been shown to naturally produce small quantities of butanol during growth on syngas (Henstra et al., *Curr. Opin. Biotechnol.* 18:200-206 (2007)).

The metabolic pathways of some exemplary syngas utilizing organisms are known. Two exemplary pathways utilizing syngas are shown in FIGS. 1 and 2.

Acetogens, such as *C. ljungdahlii* and *C. carboxidivorans*, can grow on a number of carbon sources ranging from hexose sugars to carbon monoxide. Hexoses, such as glucose, are metabolized first via Embden-Meyerhof-Parnas (EMP) glycolysis to pyruvate, which is then converted to acetyl-CoA via pyruvate:ferredoxin oxidoreductase. Acetyl-CoA can be used to build biomass precursors or can be converted to acetate, which produces energy via acetate kinase and phosphotransacetylase. The overall conversion of glucose to acetate, energy, and reducing equivalents is:

$$C_6H_{12}O_6 + 4ADP + 4Pi \rightarrow 2CH_3COOH + 2CO_2 + 4ATP + 8[H]$$

Acetogens extract even more energy out of the glucose to acetate conversion while also maintaining redox balance by further converting the $CO_2$ to acetate via the Wood-Ljungdahl pathway $$2CO_2 + 8[H] + nADP + nPi \rightarrow CH_3COOH + nATP$$

The coefficient n in the above equation signify that this conversion is an energy generating endeavor, as many acetogens can grow in the presence of $CO_2$ via the Wood-Ljungdahl pathway even in the absence of glucose as long as hydrogen is present to supply the necessary reducing equivalents.

$$2CO_2 + 4H_2 + nADP + nP \rightarrow CH_3COOH + 2H_2O + nATP$$

The Wood-Ljungdahl pathway, illustrated in FIG. 3, is coupled to the creation of $Na^+$ or $H^+$ ion gradients that can generate ATP via an $Na^+$- or $H^+$-dependant ATP synthase, respectively (Muller, *Appl. Environ. Microbiol.* 69:6345-6353 (2003)). Based on these known transformations, acetogens also have the capacity to utilize CO as the sole carbon and energy source. Specifically, CO can be oxidized to produce reducing equivalents and $CO_2$, or directly assimilated into acetyl-CoA which is subsequently converted to either biomass or acetate.

$$4CO + 2H_2O \rightarrow CH_3COOH + 2CO_2$$

Even higher acetate yields, however, can be attained when enough hydrogen is present to satisfy the requirement for reducing equivalents.

$$2CO + 2H_2 \rightarrow CH_3COOH$$

Following from FIG. 3, the production of acetate via acetyl-CoA generates one ATP molecule, whereas the production of ethanol from acetyl-CoA does not and requires two reducing equivalents. Thus ethanol production from syngas is not expected to generate sufficient energy for cell growth in the absence of acetate production. However, under certain conditions, *Clostridium ljungdahlii* produces mostly ethanol from synthesis gas (Klasson et al., *Fuel* 72:1673-1678 (1993)), indicating that some combination of the following pathways $$2CO_2 + 6H_2 \rightarrow CH_3CH_2OH + 3H_2O$$

$$6CO + 3H_2O \rightarrow CH_3CH_2OH + 4CO_2$$

$$2CO + 4H_2 \rightarrow CH_3CH_2OH + H_2O$$

does indeed generate enough energy to support cell growth. Hydrogenic bacteria such as *R. rubrum* can also generate energy from the conversion of CO and water to hydrogen (see FIG. 3) (Sipma et al., *Crit. Rev. Biotechnol.* 26:41-65 (2006)). The key mechanism is the coordinated action of an energy converting hydrogenase (ECH) and CO dehydrogenase. The CO dehydrogenase supplies electrons from CO which are then used to reduce protons to $H_2$ by ECH, whose activity is coupled to energy-generating proton translocation. The net result is the generation of energy via the water-gas shift reaction.

The product profile from syngas fermentations is determined by the choice of organism and experimental conditions. For example, *Clostridium ljungdahlii* produces a mixture of ethanol and acetate (Klasson et al., *Fuel* 72:1673-1678 (1993); Gaddy and Clausen, U.S. Pat. No. 5,173,429) while *Clostridium carboxidivorans* produces a mixture of ethanol, acetate, butanol, and butyrate (Liou et al., *Int. J. Syst. Evol. Microbiol.* 55(Pt 5):2085-2091 (2005)). Acetate and biomass concentrations as high as 26.8 g/L and 12.4 g/L, respectively, together with ethanol concentrations below 1 g/L have been reported with *C. ljungdahlii* (Gaddy, U.S. Pat. Nos. 5,807,722, 6,136,577 and 6,340,581). This product profile can be shifted, however, towards increased ethanol formation by traditional means of increasing solvent formation over acid production in *Clostridia*, for example, using nutrient limitation, media alteration, lower pH, reducing agent addition, and the like. Product profile sensitivity to a number of conditions, for example, calcium pantothenate limitation, cobalt limitation, H2 oversupply, CO oversupply, acetate conditioning, and the like, has been described (Gaddy et al., U.S. Pat. No. 7,285,402). Ethanol, acetate, and cell concentrations of 33.0 g/L, 4.0 g/L, and 2.7 g/L, respectively, were demonstrated with *C. ljungdahlii* strain C-01 without cell recycle under conditions optimized for ethanol production. Maximum ethanol productivities ranged from 21 g/L/day without cell recycle to 39 g/L/day with cell recycle.

Sensitivity of syngas fermentations to inhibitors can also be determined. Fewer efforts to optimize the fermentation conditions of *C. carboxidivorans* (Liou et al., *Int. J. Syst. Evol. Microbiol.* 55(Pt 5):2085-2091 (2005)) for the generation of a particular product have been reported. However, a number of recent studies have been aimed at the inhibition of *C. carboxidivorans* growth by syngas inhibitors. Specifically, inhibitors present in the biomass-generated producer gas stopped *C. carboxidivorans* growth and $H_2$ utilization, although growth could be recovered when "clean" bottled gasses consisting of only CO, $CO_2$, $N_2$, and $H_2$ were introduced (Datar et al., *Biotechnol. Bioeng.* 86:587-594 (2004)). Passing the gas through a 0.025 μm filter cleaned it well enough to allow cell growth, although $H_2$ utilization was still blocked (Ahmed et al., *Biomass Bioenergy* 30:665-672 (2006)). A scanning electron microscope analysis of the filter indicated that tar particulates, and not ash, was the likely culprit leading to cell dormancy. Potential tar species were identified as benzene, toluene, ethylbenzene, p-xylene, o-xylene, and napthalene. Cells were able to adapt to the tars present following the 0.2 μm filter within 10-15 days. The fact that $H_2$ utilization ceased regardless of filter size indicated that a non-filtered component was inhibiting the hydrogenase enzyme. This compound was later identified as nitric oxide. NO inhibits hydrogenase at ≧60 ppm levels (Ahmed and Lewis, *Biotechnol. Bioeng.* 97:1080-1086 (2007)). Similar studies can be performed to determine appropriate conditions for the utilization of syngas in a particular organism to produce a desired product.

In an exemplary experiment, it is assumed that synthesis gas exiting the gasifier is passed though a cyclone, a condensation tower, a scrubber, and a 0.2 μm filter, similar to the system described previously for switchgrass gasification (Datar et al., *Biotechnol. Bioeng.* 86:587-594 (2004); Ahmed et al., *Biomass Bioenergy* 30:665-672 (2006))). Oxygen blown gasification, as opposed to air blown, is used so that NO levels under 40 ppm can be achieved, as suggested previously (Ahmed and Lewis, *Biotechnol. Bioeng.* 97:1080-1086 (2007)). Furthermore, studies with *C. ljungdahlii* revealed that $H_2S$ levels under 2.7% are not inhibitory (Klasson et al., *Fuel* 72:1673-1678 (1993)), even when the cells are not acclimated beforehand, and levels are expected to be below that level with syngas obtained from biomass or even coal gasification. In addition, tolerance to tar particulates can be achieved through evolution or adaptation (Ahmed et al., *Biomass Bioenergy* 30:665-67. (2006)).

Example II

Design and Modeling of Microbial Strains for Utilization of Syngas

This example describes the design of exemplary microbial strains for the production of a desired product from syngas.

Initial studies utilize genome-scale models of *C. ljungdahlii*, *C. carboxidivorans*, and *R. rubrum* for the design of microbial strains capable of utilizing syngas as a carbon source. Metabolic models and simulation algorithms are used to develop strains that utilize syngas. Genomic sequences of desired microorganisms are utilized, along with sequences from closely related species, to construct genome-scale metabolic models of the target organisms. To facilitate this process, Genomatica has developed a comprehensive methodology to automatically build a first draft of a metabolic network based on an exhaustive sequence comparison with our existing high quality manually built metabolic models. Next, the automatically generated gene-protein-reaction (GPR) assignments, see FIG. 2, are checked manually and detailed notes are catalogued within SimPheny™, Genomatica's proprietary model construction and simulation platform, to ensure that they are as transparent as possible. For the production of butanol as an exemplary product, enzymes in the butanol pathway are expressed in those organisms that do not produce butanol naturally, for example, *C. ljungdahlii* and *R. rubrum*.

The metabolic models are interrogated using a constraint-based modeling approach (Schilling et al., *Biotechnol. Prog.* 15:288-295 (1999); Edwards et al., *Environ. Microbiol.* 4:133-40 (2002); Varma and Palsson, *Biotechnol.* 12:994-998 (1994); Patil et al., *Curr. Opin. Biotechnol.* 15:64-69 (2004)). Briefly, rather than attempting to calculate and predict exactly what an organism does, the constraint-based approach narrows the range of possible phenotypes that an organism can display based on the successive imposition of governing physico-chemical constraints, for example, stoichiometric, thermodynamic, capacity, and regulatory (Price et al., *Trends Biotechnol.* 21:162-169 (2003); Price et al., *Nat. Rev. Microbiol.* 2:886-897 (2004)). Thus, instead of calculating an exact phenotypic "solution," that is exactly how an organism will behave under given genetic and environmental conditions, it can determine the feasible set of phenotypic solutions in which the organism can operate. In general, genome-scale constraint-based models have been shown to be useful in predicting several physiological properties such as growth and by-product secretion patterns (Edwards and Palsson, *Proc. Natl. Acad. Sci. USA* 97:5528-5533 (2000); Varma et al., *Appl. Environ. Microbiol.* 59:2465-2473 (1993); Varma and Palsson, Appl Environ Microbiol, 60:3724-3731 (1994); Edwards et al., *Nat. Biotechnol.* 19:125-130 (2001)), determining the range of substrate utilization (Edwards and Palsson, supra, 2000), determining the minimal media for growth (Schilling et al., *J. Bacteriol.* 184:4582-4593 (2002), predicting the outcome of adaptive evolution (Ibarra et al., *Nature* 420:186-189 (2002)), calculating theoretical product yields (Varma et al., *Biotechnol. Bioengineer.* 42:59-73 (1993)), predicting knockout phenotypes (Edwards and Palsson, *BMC Bioinformatics* 1:1 (2000); Segre et al., *Proc. Natl. Acad. Sci. USA* 99:15112-15117 (2002); Shlomi et al., *Proc. Natl. Acad. Sci. USA* 102:7695-7700 (2005)) and comparing metabolic capabilities of different organisms (Forster et al., *Genome Res.* 13:244-253 (2003)). Based on these predictive capabilities, the models are used to characterize the metabolic behavior of industrial microbes under laboratory and production scale fermentation conditions. Constraint-based approaches have matured to the point where they are commonly applied to pinpoint successful genetic manipulations aimed at improving strain performance (Bro et al., *Metab. Eng.* 8:102-111 (2006); Alper et al., *Nat. Biotechnol.* 23:612-616 (2005); Alper et al., *Metab. Eng.* 7:155-164 (2005); Fong et al., *Biotechnol. Bioeng.* 91:643-648 (2005); Park et al., *Proc. Natl. Acad. Sci. USA* 104:7797-7802 (2007)). Characteristics are continued to be monitored in order to implement further optimization of conditions.

Additional optimization of organisms can be performed by determining gene knockouts to enhance for production of a desired product, including growth-coupled production of a desired product such as butanol (see Example V). *C. ljundahlii* currently can convert mixtures of CO, $CO_2$, and $H_2$ to acetate and ethanol, while *C. carboxidivorans* produces a mixture of acetate, ethanol, butyrate, and butanol. *R. rubrum* does not produce alcohols naturally, but has been shown to accumulate high levels of poly-β-hydroxyalkanoates (PHAs). Modeling analysis allows predictions of the effects on cell growth of shifting the metabolism of a biocatalyst organism towards more efficient production of a desired product such as butanol. The modeling also points at metabolic manipulations aimed at driving the metabolic flux through a desired production pathway, for example, the production of butanol. One modeling method is the bilevel optimization approach, OptKnock (Burgard et al., *Biotechnol. Bioengineer.* 84:647-657 (2003)), which is applied to select gene knockouts that collectively result in the growth-coupled production of a desired product such as butanol. Strains designed with a gene knockout strategy are forced, due to network stoichiometry, to produce high levels of a desired product such as butanol for efficient growth, because all other growth options have been removed. Such strains are self-optimizing and stable. Accordingly, they typically maintain or improve upon production levels even in the face of strong growth selective pressures, making them amenable to batch or continuous bioprocessing and also evolutionary engineering.

Several candidate strain are designed and optimization of production conditions are performed. Fermentation conditions are tested in triplicate, alongside control fermentations using the original process parameters. Using data from test fermentations, simulations can be performed to assess changes in metabolism that result from process changes and compared to predictions. If productivity significantly falls short of that anticipated, further simulations are performed using this new knowledge for a second iteration of the design process in order to optimize strains.

Example III

Development of Genetic Tools for Target Organisms

This example describes the development of tools for genetic manipulation and engineering of target organisms.

Genetic systems are developed in candidate strains for utilization of syngas. In particular, genetic systems are developed for *C. ljungdahlii* and *C. carboxidivorans*. Genetic transformations are also tested in *Rhodospirillum rubrum*. Antibiotic resistance is tested to determine potential markers for selection of desired genetic elements. For example, many *Clostridia* are sensitive to erythromycin and chloramphenicol. DNA transfer methods are developed using well known methods, including but not limited to electroporation, conjugation or ultrasound transformation. Additional testing is performed on several expression vectors of gram positive bacteria, particularly the vectors used in *C. acetobutylicum*, to determine their effectiveness for expression of desired genetic elements in *C. ljungdahlii* and/or *C. carboxidivorans*. Additional vectors can be developed by replacing the promoter of the vectors with a native *C. ljungdahlii* or *C. carboxidivorans* promoter. In addition, several suicide plasmids, including those of *C. acetobutylicum* and *C. cellulolyticum*, are tested for genetic manipulation. The knockdown technique of antisense RNA inhibition developed for other *Clostridia* are also tested.

The transformation, expression and antisense RNA inhibition tools are available for mesophilic species *Clostridium cellulolyticum* and *Clostridium acetobutylicum*. *C. cellulolyticum* is a model system for cellulose degradation (Desvaux, *FEMS Microbiol Rev.* 741-764 (2005)), whereas *C. acetobutylicum* has been intensively characterized for its ability to produce solvents such as butanol (Dune, *Biotechnol. J.* 2:1525-1534 (2007)). Notably, both species are capable of producing ethanol and hydrogen as an end product. Therefore, knowledge from these two strains is instructive for other ethanol- and/or hydrogen-producing *Clostridia* species. Studies of targeted mutagenesis in *C. cellulolyticum* have been initiated and can be similarly used on other candidate organisms.

The results of these studies allow for phenotypic characterization of the mutants generated as well as allow genetic engineering of *C. ljungdahlii* and/or *C. carboxidivorans*. Additional optimization is performed, as needed, to develop genetic systems by varying methods, plasmids and conditions to achieve an optimized result (Lynd et al., *Microbiol. Mol. Biol. Rev.* 66:506-577 (2002)).

In more detail, profiling the antibiotic resistance capacities of *C. ljungdahlii* and *C. carboxidivorans* is performed. An important step in developing genetic systems is to determine the native antibiotic resistance characteristics of the target strains. Erythromycin and chloramphenicol are two antibiotics with resistance markers that have been shown to be functional on plasmids in *C. acetobutylicum* and *C. cellulolyticum* (Kashket and Cao, *Appl. Environ. Microbiol.* 59:4198-4202 (1993); Green and Bennett, *Biotechnol. Bioeng.* 58:215-221 (1998)). However, they are usually not available for common suicide plasmids, which instead often contain antibiotic markers of ampicillin, gentamycin, rifampicin, kanamycin and tetracycline. In order to determine antibiotic sensitivity, *C. ljungdahlii* and *C. carboxidivorans* are grown in defined medium in an anaerobic chamber (Ahmed and Lewis, *Biotechnol. Bioeng.* 97:1080-1086 (2007); Younesi et al., *Bioresour. Technol.* Jun. 18, 2007). Common antibiotics as indicated above are added at gradient concentrations from 1 μg/ml to 500 μg/ml. An instrument such as a Type FP-1100-C Bioscreen C machine (Thermo Labsystems; Waltham Mass.) is used to control the growth temperature at 37° C. and automatically measure the optical density of cell growth at different intervals. All of the physiological studies are performed in replicate, for example, triplicates, so that the average and standard deviation can be calculated. This growth data indicates the sensitivity of *C. ljungdahlii* and *C. carboxidivorans* to the antibiotics being tested. The antibiotics that inhibit growth of the strain are used in further studies.

In more detail, DNA transfer methods and gene expression systems are developed to provide simple and efficient DNA delivery methods for genetic engineering. Methods for bacterial DNA transfer include conjugation, electroporation, chemical transformation, transduction and ultrasound transformation. Among them, electroporation and conjugation have been previously established in several *Clostridial* species (Jennert et al., *Microbiol.* 146:3071-3080 (2000); Tardif et al., *J. Ind. Microbiol. Biotechnol.* 27:271-274 (2001); Tyurin et al., *J. Appl. Microbiol.* 88:220-227 (2000); Tyurin et al., *Appl. Environ. Microbiol.* 70:883-890 (2004)). Ultrasound transformation is a convenient and efficient method that provides high transformation efficiency ($>10^6$ CFU/μg DNA) for gram negative bacteria (Song et al., *Nucl. Acids Res.* 35:e129 (2007)) and can be tested in gram positive bacteria.

Electroporation, ultrasound transformation, and conjugation are tested for *C. ljungdahlii* and *C. carboxidivorans* transformation efficiencies. A variety of plasmids from gram positive bacteria with different replicons, for example, pIP404, pAMβ1 and pIM13, are tested. If needed, subcloning is employed to replace the antibiotic resistance cassettes of existing plasmids with the suitable ones based on antibiotic resistance testing. Standard molecular subcloning techniques, including restriction enzyme digestion, ligation by T4 ligase and *E. coli* transformation, are used for engineering of the plasmids (Sambrook et al., *Molecular Cloning: A Laboratory Manual* Cold Spring Harbor Laboratory Press (1989)). As required for many other *Clostridial* species, these plasmids are methylated prior to DNA delivery to protect them from degradation by the host bacteria. For electroporation and conjugation, existing protocols of *C. cellulolyticum* and *C. acetobutylicum* are tested first. Parameters such as electroporation setup, recovery time, and concentration of $Ca^{2+}$ and $Mg^{2+}$ in the electroporation buffer are varied to optimize the transformation efficiency. For ultrasound transformation, experiments are conducted under conditions of low frequency ultrasound, for example, 40 kHz, and extended recovery time as previously described (Song et al., supra, 2007)).

Once an efficient DNA transfer protocol is established for certain plasmids, the plasmids are engineered to incorporate a native *C. ljungdahlii* or *C. carboxidivorans* promoter followed by a multiple cloning site to generate expression vectors. It is expected that the existing expression vectors of *C. acetobutylicum*, such as pSOS95 and pIMP1, can likely work in *C. ljungdahlii* or *C. carboxidivorans* without changes of the promoter, so these plasmids are used for initial testing.

To develop gene disruption methods, several suicide plasmids such as pKNOCK, pDS3.0, pSPUC and pBluescript SKII are screened for suitability as suicide plasmids for *C. ljungdahlii* and/or *C. carboxidivorans*. As discussed above, if the results either existing antibiotic resistance cassettes are used or are replaced with suitable antibiotic resistance cassettes. A DNA fragment of a selected target gene is subcloned into appropriate suicide plasmids. The genes selected as the initial targets are those encoding the alcohol dehydrogenases responsible for ethanol production. These genes were selected because they lead to byproduct formation, are likely to be identified as targets for disruption for butanol-producing strains, and provide for an easy screen by analyzing ethanol in the fermentation broth. If deletion of an alcohol dehydrogenase in *C. carboxidivorans* lowers butanol production in addition to lowering ethanol production due to the broad substrate specificity of these enzymes, an alcohol dehydrogenase which favors butanol formation over ethanol formation, such as the adhE2 from *C. acetobutylicum* (Atsumi et al., *Metab. Eng.* Sep. 14, 2007), can be cloned along with the other butanol pathway genes to construct a butanol pathway.

The engineered suicide plasmids are methylated and transferred into *C. ljungdahlii* and *C. carboxidivorans*. Colonies are selected on solid medium containing the appropriate antibiotics. PCR amplification and subsequent sequencing of the disrupted genomic region, southern blot, and physiological studies are employed to verify the correct disruption of the targeted gene(s) in the genome. The expression systems can also be used as an alternative to gene disruption to express the antisense RNA of the target gene, which will inhibit but not completely abolish its gene expression. Therefore, the antisense RNA system serves as a convenient approach of gene knock-down of a desired gene.

Example IV

Genetic Assessment of *Rhodospirillum rubrum*

This example describes development of genetic tools for *Rhodospirillum rubrum* as an organism for utilization of syngas.

Figure 5:
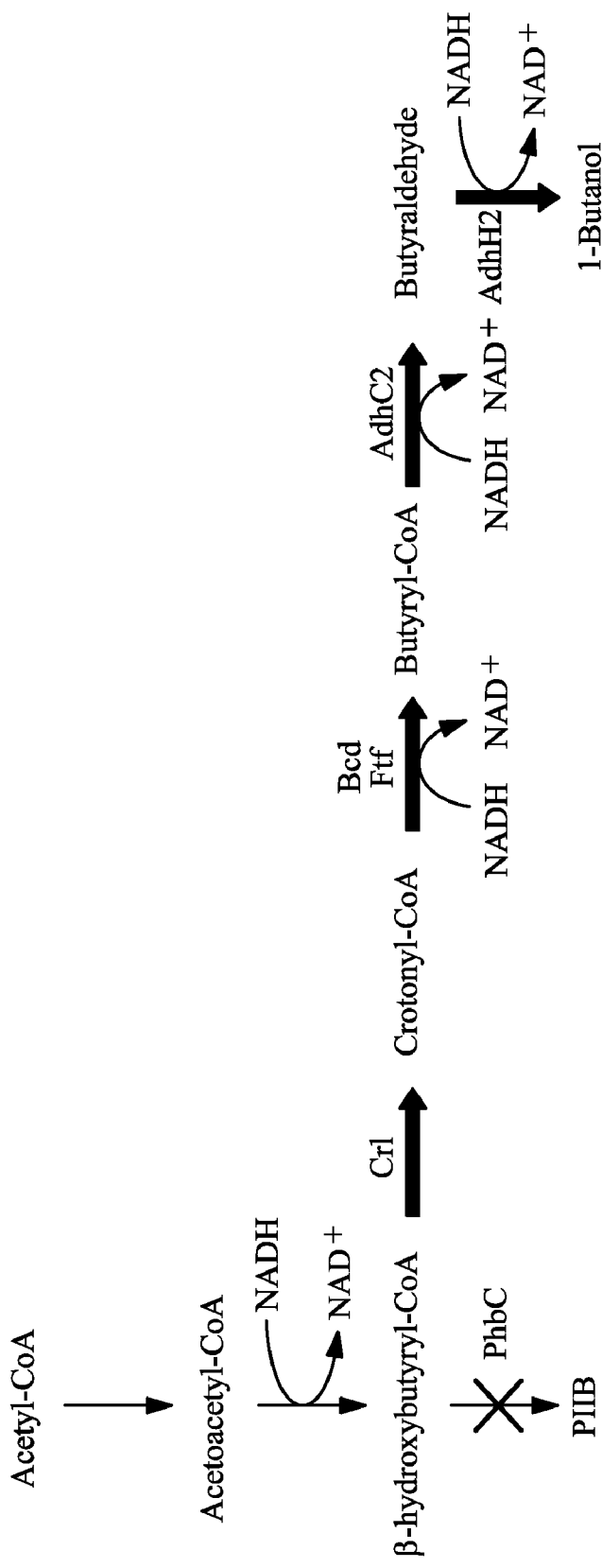
FIG. 5 shows a proposed polyhydroxybutyrate (PHB) pathway modification in *R. rubrum* to form 1-butanol. Bold arrows indicate reaction steps that are introduced via heterologous expression of a 4-gene operon forming the 1-butanol pathway from *C. acetobutylicum*. Abbreviations used are PHB, poly-β-hydroxybutyrate; PhbC, PHB synthase; Crt, crotonase; Bcd, butyryl-CoA dehydrogenase; Etf, electron transfer flavoprotein; AdhE2, aldehyde/alcohol dehydrogenase.

*Rhodospirillum rubrum* is a Gram negative, purple nonsulfur bacterium which oxidizes CO under anaerobic conditions (Kerby et al., *J. Bacteriol.* 177:2241-2244 (1995); Kerby et al., *J. Bacteriol.* 174:5284-5294 (1992)). *R. rubrum* possess a Ni—Fe—S CO dehydrogenase (CODH) that catalyzes the oxidation of CO, which is coupled to the formation of hydrogen (Ensign and Ludden, *J. Biol. Chem.* 1991. 266: 18395-18403 (1991)). Given its CO oxidation capacity and ability to fix $CO_2$, *R. rubrum* is capable of efficient growth on syngas in the dark (Do et al., *Biotechnol. Bioeng.* 97:279-286 (2007)). In addition, it has been shown that during growth on syngas, up to 34% of the total cellular carbon is stored in the form of poly-β-hydroxyalkanoates (PHA) that consist primarily of β-hydroxybutyrate (PHB). The ability of *R. rubrum* to efficiently direct cellular carbon to form reduced 4-carbon compounds make it an attractive platform for engineering production of a desired product such as 1-butanol. In addition, a genetic system has been established for *R. rubrum*, and a wide range of cloning vectors including the broad-host range RK2 derivatives are available (Saegesser et al., *FEMS Microbiol. Lett.* 95:7-12 (1992)). Another attractive aspect of utilizing *R. rubrum* is that there is considerable overlap in the pathways leading to PHB and 1-butanol synthesis (FIG. 5). Since PHB synthesis has been studied for its use as a biodegradable plastic, considerable information is available regarding PHB pathway regulation and over expression (Anderson and Dawes, *Microbiol. Rev.* 54:450-472 (1990)). In parallel to establishing the genetic tools necessary for manipulating the *Clostridial* strains as discussed above, a synthetic operon consisting of several genes from *Clostridium acetobutylicum* that form the 1-butanol synthesis pathway is developed as well.

Since *R. rubrum* has been sequenced and has a tractable genetic system (Saegesser et al., *FEMS Microbiol. Lett.* 95:7-12 (1992)), it is expected that targeted deletions can be made in selected loci. Broad-host range, site-specific gene excision systems are available which allow markerless deletions to be generated (Hoang et al., *Gene* 212:77-86 (1998)). Therefore, it will be possible to generate multiple knockouts in a single strain without relying on multiple antibiotic selections. This method can be tested by deleting the PHB synthase gene, which is the terminal step in PHB synthesis (Hustede et al., *FEMS Microbiol. Lett.* 72:285-290 (1992)). This is chosen because PHB synthesis will likely compete with the proposed butanol pathway for 4-carbon precursors and reducing equivalents (FIG. 5). Successful deletion of the equivalent gene in *Methylobacterium extorquens*, a gram negative bacterium also known to accumulate over 30% by weight PHB, has been reported with no deleterious effect on growth (Korotkova and Lidstrom, *J. Bacteriol.* 183:1038-1046 (2001)).

Example V

Engineering Microorganisms for Production of Butanol from Syngas

This example describes engineering microorganisms for production of butanol formation from syngas.

In initial studies, *Clostridial* strains, in particular, *C. carboxidivorans*, are used to engineer utilization of syngas for production of and tolerance to butanol. *C. carboxidivorans* has been shown to produce butanol from synthesis gas (Liou et al., *Int. J. Syst. Evol. Microbiol.* 55(Pt 5):2085-2091 (2005)). *C. carboxidivorans* is engineered to increase syngas utilization efficiency, increase the efficiency of butanol production from syngas as an exemplary desired product, and to increase product tolerance so that higher yields of a desired product can be obtained.

Preliminary metabolic network analysis has revealed that the theoretical conversion of lignocellulosic-derived syngas to butanol compares favorably to sugar fermentation.

Syngas to Butanol:

$$12CO+5H_2O \rightarrow 8ATP+8CO_2+1C_4H_{10}O$$

$$4CO+8H_2 \rightarrow 4ATP+3H_2O+1C_4H_{10}O$$

$$4CO_2+12H_2 \rightarrow 2ATP+7H_2O+1C_4H_{10}O$$

Sugar to Butanol:

$$1C_6H_{12}O_6 \rightarrow 2ATP+2CO_2+1H_2O+C_4H_{10}O$$

$$1.2C_5H_{10}O_5 \rightarrow 1.7ATP+2CO_2+1H_2O+C_4H_{10}O$$

Given that biomass gasification can optimally provide a 1:1 ratio of CO to $H_2$, the production of one mole of butanol will require 12 moles of $CO+H_2$. Importantly, the fermentative conversion of syngas to butanol is an energy-generating endeavor, therefore supporting cell growth at high product yields. Furthermore, initial calculations reveal the substrate cost to be cheaper than the equivalent amount of sugar that would be required.

As discussed above, models and genetic tools are utilized to design strains that facilitate the production of butanol or other desired products as an obligatory product of cell growth. In other words, the cell is engineered so that butanol is a necessary electron sink during growth on CO. The strains are constructed, which may have a combination of gene knockouts and overexpression of appropriate enzymes, and can be evolved for improved production and tolerance of growth conditions.

For construction of *Clostridial* strains producing butanol, genome analysis as discussed above is used to identify biological pathways necessary for establishing and/or improving butanol production in *C. ljungdahlii* and *C. carboxidivorans*. Additional improvement in butanol production can be achieved by increasing expression of syngas utilization pathway and/or butanol production pathway proteins and enzymes. To express the gene(s) in the targeted biological pathway, gene expression vectors developed as discussed above are used. If there is more than one gene, the genes are PCR amplified and cloned into an expression vector as a synthetic operon. The resulting expression plasmid is transferred into *C. ljungdahlii* and *C. carboxidivorans*. Northern blot and/or real time PCR, or other suitable techniques, are used to examine gene expression at the transcriptional level.

To improve butanol production, it is likely that endogenous gene(s) of *C. ljungdahlii* and *C. carboxidivorans* will be inactivated to reroute the redox potential toward butanol production. To this end, an internal DNA fragment of a targeted gene will be PCR amplified and cloned into a suicide plasmid. Then the plasmid is transferred into *C. ljungdahlii* and *C. carboxidivorans*, resulting in disruption of the target gene by single crossover recombination. The correct disruption is confirmed by sequencing of the PCR product amplified from the disrupted genomic locus and/or Southern blot, or using other suitable analytical techniques. If there is more than one targeted gene, the suicide plasmids are engineered to change antibiotic marker so that multiple gene knockouts can be generated in a single strain. It is expected that up to 3 to 6 gene deletions may be beneficial in optimizing butanol production.

For genetic engineering of *Rhodospirillum rubrum* for butanol production, a synthetic operon is developed consisting of several genes that form the butanol synthesis pathway in *Clostridium acetobutylicum*. A similar approach for allowing butanol production in *E. coli* was recently reported, proving that heterologous expression of the pathway in Gram negative organisms is possible (Atsumi et al., *Metab. Eng.* Sep. 14, 2007). The necessary genes for butanol production in *R. rubrum* can be expressed on a broad-host-range expression vector. Expression can be controlled using an inducible promoter such as the tac promoter. The synthetic, 4-gene operon is constructed using a fusion PCR technique and will include genes for crotonase, butyryl-CoA dehydrogenase, electron transfer flavoprotein, and aldehyde/alcohol dehydrogenase activities. Fusion/assembly PCR techniques have been used to construct synthetic operons for expression in heterologous hosts (Craney et al., *Nucl. Acids Res.* 35:e46 (2007); Hill et al., *Mol. Gen. Genet.* 226:41-48 (1991)). The butanol operon is transformed into both the wild-type and PHB synthesis deficient *R. rubrum* strains, and tested as described below. It is also possible that more than one gene is desirable to be targeted for removal based on modeling studies. These deletions can be implemented using the markerless method, as discussed above.

As intermediate strains are being constructed, they are tested physiologically to evaluate progress towards butanol production, as well as the ability to sustain robust growth and reduced byproduct formation. Initial screening for growth and butanol production is performed initially in 1 mL microreactors (such as MicroReactor Technologies, Inc.; Mountain View, Calif.). Configurations such as 24-well plates can be controlled for pH, temperature, and gas composition. As a next step, serum bottles are vigorously shaken in temperature and gas composition controlled incubators. This allows sampling and analysis of the gas headspace as well as the liquid phase. Products such as butanol, ethanol, and organic acids can be analyzed by gas chromatography (GC/MS) or HPLC using routine procedures. $H_2$, CO, and $CO_2$ in the headspace will be analyzed by GC with Thermal Conductivity Detector (TCD) detection using 15% Ar as an internal standard, as described previously (Najafpour and Younesi, *Enzyme Microb. Technol.* 38:223-228 (2006)). In these experiments, synthetic syngas with 1/1 ratio of $H_2$ in CO is used. The effect of gas composition is explored during the fermentation optimization.

Initially, strains with one or more deletions is analyzed to compare growth and fermentation profiles relative to wild-type cells. It is possible that growth in multiple deletion strains will be poor without enhanced expression of the butanol pathway. Strains expressing one or more butanol pathway genes, or other targets identified by metabolic modeling, are tested in the wild-type host to assess the ability to enhance flux through the butanol pathway and provide a preliminary assessment of which steps are likely bottlenecks. Different gene orders, and if possible alternate promoters and ribosome binding sites, are tested to optimize the synthetic operon construct. The construct(s) yielding the most positive results are transformed into the host containing the prescribed gene deletions, and tested as described above. Results are compared to model predictions to assess where unforeseen limitations and metabolic bottlenecks may exist.

After genetic engineering manipulations are made, adaptive evolution can be utilized to optimize production in a desired strain. Based on strain design that couples the production of butanol to growth applies selection pressure that favors cells with improved growth rate and/or yield and will lead to higher butanol yield. Adaptive evolution is therefore performed to improve both growth and production characteristics (Fong and Palsson, *Nat. Genet.* 36:1056-1058 (2004); Alper et al., *Science* 314:1565-1568 (2006)). Based on the results, subsequent rounds of modeling and genetic engineering can be utilized to further optimize production. The evolutionary engineering step can be carried out in a device that automatically maintains cells in prolonged exponential growth by the serial passage of batch cultures into fresh medium before the stationary phase is attained. Specifically, when a certain cell density is reached, a fraction of the media with exponentially growing cells is passed from one region to an adjacent region while fresh media is added for the dilution. By automating optical density measurement and liquid handling, serial transfer can be performed at high rates, thus approaching the efficiency of a chemostat for evolution of cell fitness (Dykhuizen, *Methods Enzymol.* 224:613-631 (1993)). However, in contrast to a chemostat, which maintains cells in a single vessel, this procedure eliminates the possibility of detrimental selection for cells adapted for wall-growth (Chao and Ramsdell, *J. Gen. Microbiol.* 131:1229-1236 (1985); Lynch et al., *Nat. Methods* 4:87-93 (2007)). In addition, this method allows the cells to be maintained in a closed system that ensures strict anaerobic conditions, a requirement for growing the *Clostridia*.

An additional role that adaptive evolution can play is to develop strains that are more tolerant to butanol and impurities such as NOx and tars. Butanol tolerance levels have not been published for *C. ljungdahlii* and *C. carboxidivorans*, and this is measured for wild-type cells to determine tolerated levels. Wild-type *C. acetobutylicum* has been reported to have a tolerance of approximately 180 mM (1.2% w/v) (Tomas et al., *Appl. Environ. Microbiol.* 69:4951-4965 (2003)) and have been engineered to achieve a tolerance levels as high as 2.1% (Ezeji et al., *Chem. Rec.* 4:305-314 (2004)). Two approaches are currently prevalent to improve the butanol tolerance capacity of *Clostridia*. One involves changing the lipid composition and the fluidity of the membrane via rational genetic modification of lipid content, or by evolution methods such as serial enrichment (Soucaille et al., *Curr. Microbiol.* 14:295-299 (1987)) or random mutagenesis (Jain et al., U.S. Pat. No. 5,192,673 1993). However, tolerance is a complex function of multiple factors and is difficult to achieve with directed modification alone. Further, the cells are reported to lyse at high concentrations of butanol (Van Der Westhuizen et al., *Appl. Environ. Microbiol.* 44:1277-1281 (1982)). Therefore, optimization of strains is based on a combination of genetics, evolution, and metabolic modeling. The wild type strains can be evolved adaptively in the presence of successively increasing concentrations of butanol to demonstrate that butanol tolerance in *Clostridium* can be improved through this process. One goal is to optimize cells by evolving the cells to obtain a tolerance of butanol, for example, a concentration as high as 25 g/L. A similar procedure can be performed a similar procedure can be used to evaluate the tolerance of strains to syngas impurities using, for example, NO and aromatic compounds prevalent in tars. Adaptive evolutions for optimization of production and/or tolerance of impurities can be performed sequentially or concurrently. This approach can also be integrated with directed mutation of genes associated with butanol tolerance and membrane fluidity, to optimize tolerance levels suitable for commercial scale production.

Figure 4A:
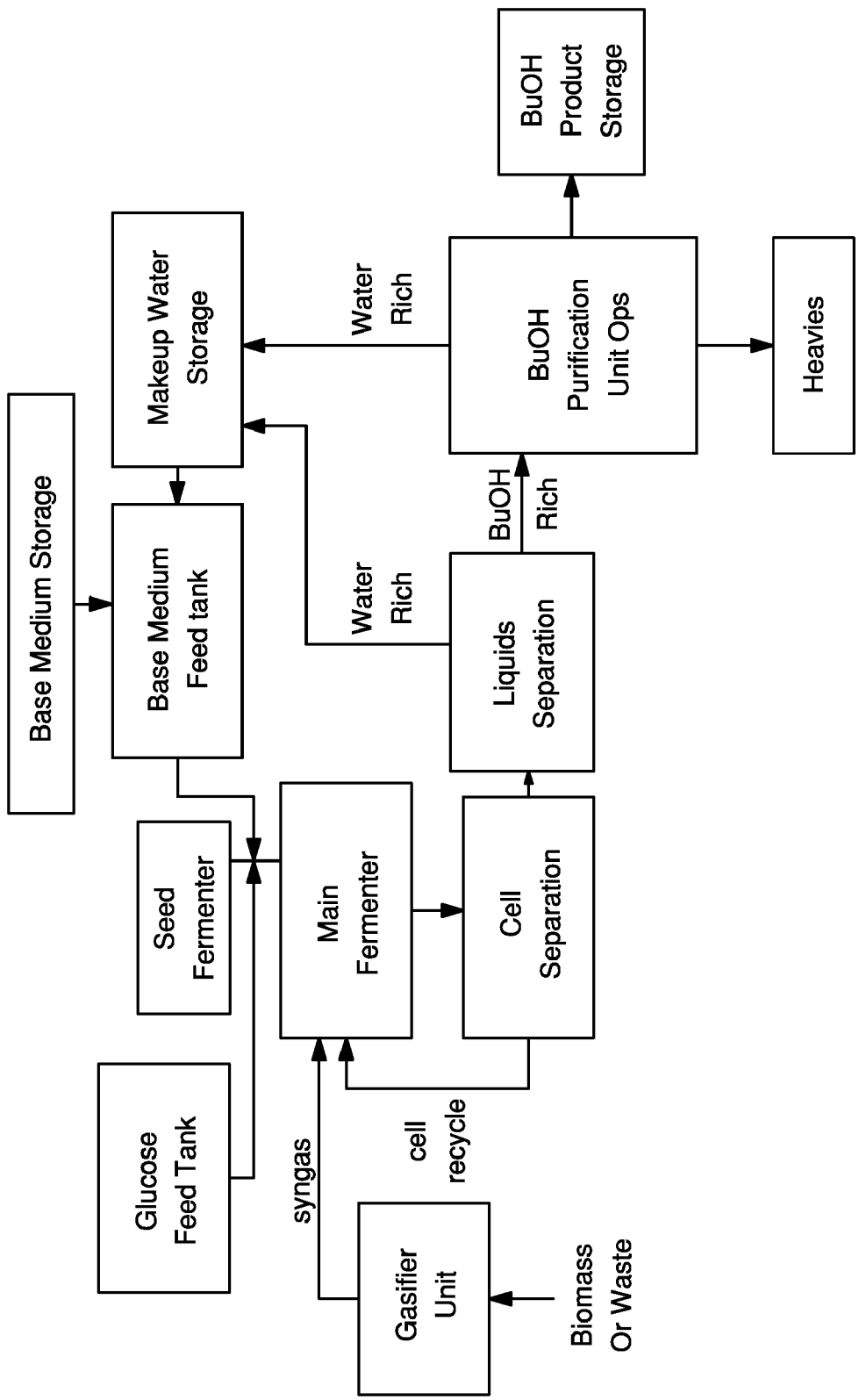
FIG. 4A shows a block flow diagram for a syngas to butanol process.
Figure 4B:
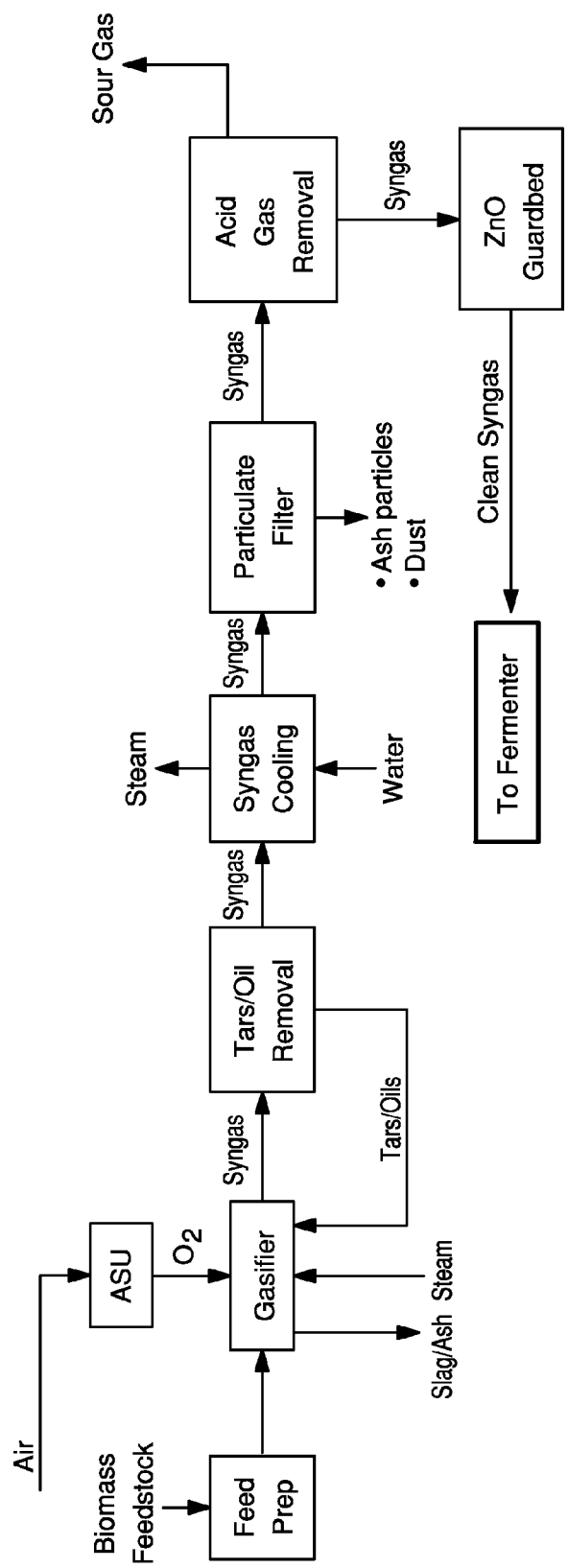
FIG. 4B shows details of the gasifier. ASU represents air separation unit.

An exemplary syngas to butanol process is illustrated in FIG. 4. FIG. 4 illustrates a block flow diagram for a process of utilizing syngas to produce butanol.

Example VI

Development and Optimization of Syngas Fermentation Processes

This example describes the development and optimization of syngas fermentation processes. A laboratory-scale syngas fermentation using authentic syngas is performed to demonstrate and optimize target yields for commercial scale production.

Important process considerations for a syngas fermentation are high biomass concentration and good gas-liquid mass transfer (Bredwell et al., *Biotechnol. Prog.* 15:834-844 (1999)). The solubility of CO in water is somewhat less than that of oxygen. Continuously gas-sparged fermentations can be performed in controlled fermenters with constant off-gas analysis by mass spectrometry and periodic liquid sampling and analysis by GC and HPLC. The liquid phase can function in batch mode. Butanol and byproduct formation is measured as a function of time. Although the final industrial process will likely have continuous liquid flow, batch operation can be utilized to study physiology in the early stages of characterization and optimization. All piping in these systems are glass or metal to maintain anaerobic conditions. The gas sparging is performed with glass fits to decrease bubble size and improve mass transfer. Various sparging rates are tested, ranging from about 0.1 to 1 vvm (vapor volumes per minute). To obtain accurate measurements of gas uptake rates, periodic challenges are performed in which the gas flow is temporarily stopped, and the gas phase composition is monitored as a function of time.

Fermentation systems specific for syngas utilization are also developed. Although designs are tested with engineered organisms, testing of fermentation systems can be done in parallel to strain development, using wild-type organisms at first. In order to achieve the overall target productivity, methods of cell retention or recycle are employed. A usual concern about such systems operated continuously is that cells could evolve to non-producing phenotypes. Because the organisms are designed for growth-coupled production of a desired product, the organisms are genetically stable. One method to increase the microbial concentration is to recycle cells via a tangential flow membrane from a sidestream. Repeated batch culture can also be used, as previously described for production of acetate by *Moorella* (Sakai S., Y. Nakashimada, K. Inokuma, M. Kita, H. Okada, and N. Nishio, Acetate and ethanol production from H2 and CO2 by *Moorella* sp. using a repeated batch culture. *J. Biosci. Bioeng.* 99:252-258 (2005)). Various other methods can also be used (Bredwell et al., *Biotechnol. Prog.* 15:834-844 (1999); Datar et al., *Biotechnol. Bioeng.* 86:587-594 (2004)). Additional optimization can be tested such as overpressure at 1.5 atm to improve mass transfer (Najafpour and Younesi, *Enzyme Microb. Technol.* 38:223-228 (2006)).

Once satisfactory performance is achieved using pure $H_2$/CO as the feed, synthetic gas mixtures are generated containing inhibitors likely to be present in commercial syngas. For example, a typical impurity profile is 4.5% $CH_4$, 0.1% $C_2H_2$, 0.35% $C_2H_6$, 1.4% $C_2H_4$, and 150 ppm nitric oxide (Datar et al., *Biotechnol. Bioeng.* 86:587-594 (2004)). Tars, represented by compounds such as benzene, toluene, ethylbenzene, p-xylene, o-xylene, and naphthalene, are added at ppm levels to test for any effect on production. For example, it has been shown that 40 ppm NO is inhibitory to *C. carboxidivorans* (Ahmed and Lewis, *Biotechnol. Bioeng.* 97:1080-1086 (2007)). Cultures are tested in shake-flask cultures before moving to a fermenter. Also, different levels of these potential inhibitory compounds are tested to quantify the effect they have on cell growth. This knowledge is used to develop specifications for syngas purity, which is utilized for scale up studies and production. If any particular component is found to be difficult to decrease or remove from syngas used for scale up, adaptive evolution procedure can be utilized, as discussed above, to adapt cells to tolerate one or more impurities.

Example VII

Minimal Gene Sets for Generating Syngas Utilizing Microorganisms

This example describes determination of a minimal gene/protein sets for generation of syngas utilizing microorganisms, particularly in an microorganism that does not naturally utilize syngas to produce a desired product.

In general, microorganisms have the ability to generate tetrahydrofolate, and methyl-tetrahydrofolate (Me-THF) is a common intermediate in biosynthesis, for example, in methionine production. Hence, the Methyl Branch outlined above and shown in FIG. 1 is not a unique feature of organisms that utilize syngas. However, the enzymes required for generating Me-THF have been found to be much more active in syngas-utilizing organisms relative to organisms that do not use syngas. In fact, tetrahydrofolate-dependent enzymes from acetogens have 50 to 100× higher specific activities than those from other sources such as *E. coli* and eukaryotes (Morton et al., *Genetics and Molecular Biology of Anaerobic Bacteria*, M. Sebald, ed., Chapter 28, pp 389-406, Springer-Verlage, New York, N.Y. (1993)). A more appropriate and unique way to define a set of genes/proteins for designing an organism that can utilize syngas is to use the Carbonyl Branch of the pathway (see FIG. 2). This branch includes genes for the following six (6) proteins: cobalamide corrinoid/iron-sulfur protein, methyltransferase, carbon monoxide dehydrogenase (CODH), acetyl-CoA synthase (ACS), acetyl-CoA synthase disulfide reductase, and a CO-tolerant hydrogenase. Therefore, these six genes/proteins represent a set of one or more proteins for conferring a syngas utilization pathway capable of producing acetyl-CoA.

Example VIII

Gene Sets for Generating Syngas Utilizing Microorganisms

This example describes exemplary gene sets for generating syngas utilizing microorganisms.

Formate Dehydrogenase. Formate dehydrogenase is a two subunit selenocysteine-containing protein that catalyzes the incorporation of $CO_2$ into formate in *Moorella thermoacetica* (Andreesen and Ljungdahl, *J. Bacteriol.* 116:867-873 (1973); Li et al., *J. Bacteriol.* 92:405-412 (1966); Yamamoto et al., *J. Biol. Chem.* 258:1826-1832 (1983). The loci, Moth__2312 and Moth__2313, are actually one gene that is responsible for encoding the alpha subunit of formate dehydrogenase while the beta subunit is encoded by Moth_2314 (Pierce et al., *Environ. Microbiol.* (2008)). Another set of genes encoding formate dehydrogenase activity with a propensity for $CO_2$ reduction is encoded by Sfum_2703 through Sfum_2706 in *Syntrophobacter fumaroxidans* (de Bok et al., *Eur. J. Biochem.* 270:2476-2485 (2003)); Reda et al., *Proc. Natl. Acad. Sci. U.S.A.* 105:10654-10658 (2008)). Similar to their *M. thermoacetica* counterparts, Sfum_2705 and Sfum_2706 are actually one gene. A similar set of genes presumed to carry out the same function are encoded by CHY_0731, CHY_0732, and CHY_0733 in *C. hydrogenoformans* (Wu et al., *PLoS Genet.* 1:e65 (2005)).

| Protein | GenBank ID | Organism |
|---|---|---|
| Moth_2312 | YP_431142 | *Moorella thermoacetica* |
| Moth_2313 | YP_431143 | *Moorella thermoacetica* |
| Moth_2314 | YP_431144 | *Moorella thermoacetica* |
| Sfum_2703 | YP_846816.1 | *Syntrophobacter fumaroxidans* |
| Sfum_2704 | YP_846817.1 | *Syntrophobacter fumaroxidans* |
| Sfum_2705 | YP_846818.1 | *Syntrophobacter fumaroxidans* |
| Sfum_2706 | YP_846819.1 | *Syntrophobacter fumaroxidans* |
| CHY_0731 | YP_359585.1 | *Carboxydothermus hydrogenoformans* |
| CHY_0732 | YP_359586.1 | *Carboxydothermus hydrogenoformans* |
| CHY_0733 | YP_359587.1 | *Carboxydothermus hydrogenoformans* |

Formyltetrahydrofolate synthetase. Formyltetrahydrofolate synthetase ligates formate to tetrahydrofolate at the expense of one ATP. This reaction is catalyzed by the gene product of Moth_0109 in *M. thermoacetica* (Lovell et al., *Arch. Microbiol* 149:280-285 (1988); Lovell et al., *Biochemistry* 29:5687-5694 (1990); O'brien et al., *Experientia. Suppl.* 26:249-262 (1976), FHS in *Clostridium acidurici* (Whitehead and Rabinowitz, *J. Bacteriol.* 167:205-209(1986); Whitehead and Rabinowitz, *J. Bacteriol.* 170:3255-3261 (1988)), and CHY_2385 in *C. hydrogenoformans* (Wu et al., *PLoS Genet.* 1:e65 (2005)).

| Protein | GenBank ID | Organism |
|---|---|---|
| Moth_0109 | YP_428991.1 | *Moorella thermoacetica* |
| CHY_2385 | YP_361182.1 | *Carboxydothermus hydrogenoformans* |
| FHS | P13419.1 | *Clostridium acidurici* |

Methenyltetrahydrofolate cyclohydrolase and methylenetetrahydrofolate dehydrogenase. In *M. thermoacetica, E. coli,* and *C. hydrogenoformans,* methenyltetrahydrofolate cyclohydrolase and methylenetetrahydrofolate dehydrogenase are carried out by the bi-functional gene products of Moth_1516, folD, and CHY_1878, respectively (D'Ari and Rabinowitz, *J. Biol. Chem.* 266:23953-23958 (1991); Pierce et al., *Environ. Microbiol* (2008); Wu et al., *PLoS Genet.* 1:e65 (2005)).

| Protein | GenBank ID | Organism |
|---|---|---|
| Moth_1516 | YP_430368.1 | *Moorella thermoacetica* |
| folD | NP_415062.1 | *Escherichia coli* |
| CHY_1878 | YP_360698.1 | *Carboxydothermus hydrogenoformans* |

Methylenetetrahydrofolate reductase. The final step of the methyl branch of the Wood-Ljungdahl pathway is catalyzed by methylenetetrahydrofolate reductase. In *M. thermoacetica*, this enzyme is oxygen-sensitive and contains an iron-sulfur cluster (Clark and Ljungdahl, *J Biol Chem.* 259:10845-10849 (1984)). This enzyme is encoded by metF in *E. coli* (Sheppard et al., *J. Bacteriol.* 181:718-725 (1999)) and CHY_1233 in *C. hydrogenoformans* (Wu et al., *PLoS Genet.* 1:e65 (2005)). The *M. thermoacetica* genes, and its *C. hydrogenoformans* counterpart, are located near the CODH/ACS gene cluster, separated by putative hydrogenase and heterodisulfide reductase genes.

| Protein | GenBank ID | Organism |
|---|---|---|
| metF | NP_418376.1 | *Escherichia coli* |
| CHY_1233 | YP_360071.1 | *Carboxydothermus hydrogenoformans* |

Acetyl-CoA synthase/Carbon monoxide dehydroenase (ACS/CODH) and related proteins. ACS/CODH is the central enzyme of the carbonyl branch of the Wood-Ljungdahl pathway. It catalyzes the reversible reduction of carbon dioxide to carbon monoxide and also the synthesis of acetyl-CoA from carbon monoxide, Coenzyme A, and the methyl group from a methylated corrinoid-iron-sulfur protein. The corrinoide-iron-sulfur-protein is methylated by methyltetrahydrofolate via a methyltransferase. Expression of ACS/CODH in a foreign host involves introducing many, if not all, of the following proteins and their corresponding activities.

Methyltetrahydrofolate:corrinoid protein methyltransferase (AcsE)
Corrinoid iron-sulfur protein (AcsD)
Nickel-protein assembly protein (AcsF)
Ferredoxin (Orf7)
Acetyl-CoA synthase (AcsB and AcsC)
Carbon monoxide dehydrogenase (AcsA)
Nickel-protein assembly protein (CooC)

The genes required for carbon-monoxide dehydrogenase/acetyl-CoA synthase activity typically reside in a limited region of the native genome that may be an extended operon (Morton et al., *J. Biol. Chem.* 266:23824-23828 (1991); Ragsdale, *Crit. Rev. Biochem. Mol. Biol.* 39:165-195 (2004); Roberts et al., *Proc. Natl. Acad. Sci. USA* 86:32-36 (1989)). Each of the genes in this operon from the acetogen, *M. thermoacetica,* has already been cloned and expressed actively in *E. coli* (Lu et al., *J. Biol. Chem.* 268:5605-5614 (1993); Morton et al., supra, 1991; Roberts et al., supra, 1989)). The protein sequences of these genes can be identified by the following GenBank accession numbers.

| Protein | GenBank ID | Organism |
|---|---|---|
| AcsE | YP_430054 | *Moorella thermoacetica* |
| AcsD | YP_430055 | *Moorella thermoacetica* |
| AcsF | YP_430056 | *Moorella thermoacetica* |
| Orf7 | YP_430057 | *Moorella thermoacetica* |
| AcsC | YP_430058 | *Moorella thermoacetica* |
| AcsB | YP_430059 | *Moorella thermoacetica* |
| AcsA | YP_430060 | *Moorella thermoacetica* |
| CooC | YP_430061 | *Moorella thermoacetica* |

The hydrogenogenic bacterium, *Carboxydothermus hydrogenoformans,* can utilize carbon monoxide as a growth substrate by means of acetyl-CoA synthase (Wu et al., *PLoS Genet.* 1:e65. (2005)). In strain Z-2901, the acetyl-CoA synthase enzyme complex lacks carbon monoxide dehydrogenase due to a frameshift mutation (We et al., supra, 2005), whereas in strain DSM 6008, a functional unframeshifted full-length version of this protein has been purified (Svetlitchnyi et al., *Proc. Natl. Acad. Sci. USA* 101:446-451 (2004)). The protein sequences of the *C. hydrogenoformans* genes from strain Z-2901 can be identified by the following GenBank accession numbers. Sequences for *Carboxydothermus hydrogenoformans* DSM 6008 are not currently accessible in publicly available databases but can be readily determined as the sequences become available.

| Protein | GenBank ID | Organism |
|---|---|---|
| AcsE | YP_360065 | *Carboxydothermus hydrogenoformans* |
| AcsD | YP_360064 | *Carboxydothermus hydrogenoformans* |
| AcsF | YP_360063 | *Carboxydothermus hydrogenoformans* |
| Orf7 | YP_360062 | *Carboxydothermus hydrogenoformans* |
| AcsC | YP_360061 | *Carboxydothermus hydrogenoformans* |
| AcsB | YP_360060 | *Carboxydothermus hydrogenoformans* |
| CooC | YP_360059 | *Carboxydothermus hydrogenoformans* |

The methanogenic archaeon, *Methanosarcina acetivorans*, can also grow on carbon monoxide, exhibits acetyl-CoA synthase/carbon monoxide dehydrogenase activity, and produces both acetate and formate (Lessner et al., *Proc. Natl. Acad. Sci. USA* 103:17921-17926 (2006)). This organism contains two sets of genes that encode ACS/CODH activity (Rother and Metcalf, *Proc. Natl. Acad. Sci. USA* 101:16929-16934 (2004)). The protein sequences of both sets of *M. acetivorans* genes can be identified by the following GenBank accession numbers.

| Protein | GenBank ID | Organism |
|---|---|---|
| AcsC | NP_618736 | *Methanosarcina acetivorans* |
| AcsD | NP_618735 | *Methanosarcina acetivorans* |
| AcsF, CooC | NP_618734 | *Methanosarcina acetivorans* |
| AcsB | NP_618733 | *Methanosarcina acetivorans* |
| AcsEps | NP_618732 | *Methanosarcina acetivorans* |
| AcsA | NP_618731 | *Methanosarcina acetivorans* |
| AcsC | NP_615961 | *Methanosarcina acetivorans* |
| AcsD | NP_615962 | *Methanosarcina acetivorans* |
| AcsF, CooC | NP_615963 | *Methanosarcina acetivorans* |
| AcsB | NP_615964 | *Methanosarcina acetivorans* |
| AcsEps | NP_615965 | *Methanosarcina acetivorans* |
| AcsA | NP_615966 | *Methanosarcina acetivorans* |

The AcsC, AcsD, AcsB, AcsEps, and AcsA proteins are commonly referred to as the gamma, delta, beta, epsilon, and alpha subunits of the methanogenic CODH/ACS. Homologs to the epsilon encoding genes are not present in acetogens such as *M. thermoacetica* or hydrogenogenic bacteria such as *C. hydrogenoformans*. Hypotheses for the existence of two active CODH/ACS operons in *M. acetivorans* include catalytic properties (that is, $K_m$, $V_{max}$, $k_{cat}$) that favor carboxidotrophic or aceticlastic growth or differential gene regulation enabling various stimuli to induce CODH/ACS expression (Rother et al., *Arch. Microbiol.* 188:463-472 (2007)).

In both *M. thermoacetica* and *C. hydrogenoformans*, additional CODH encoding genes are located outside of the ACS/CODH operons. These enzymes provide the ability to extract electrons, or reducing equivalents, from the conversion of carbon monoxide to carbon dioxide. The reducing equivalents are then passed to accepters such as oxidized ferredoxin, NADP+, water, or hydrogen peroxide to form reduced ferredoxin, NADPH, $H_2$, or water, respectively. In some cases, hydrogenase encoding genes are located adjacent to a CODH. In *Rhodospirillum rubrum*, the encoded CODH/hydrogenase proteins form a membrane-bound enzyme complex that is proposed to be a site where energy, in the form of a proton gradient, is generated from the conversion of CO to $CO_2$ and $H_2$ (Fox et al., *J. Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J. Am. Chem. Soc.* 129:10328-10329 (2007)). The genes encoding the *C. hydrogenoformans* CODH-II and CooF, a neighboring protein, were cloned and sequenced (Gonzalez and Robb, *FEMS Microbiol. Lett.* 191: 243-247 (2000)). The resulting complex was membrane-bound, although cytoplasmic fractions of CODH-II were shown to catalyze the formation of NADPH suggesting an anabolic role (Svetlitchnyi et al., *J. Bacteriol.* 183:5134-5144 (2001)). The crystal structure of the CODH-II is also available (Dobbek et al., *Science* 293:1281-1285 (2001)). The protein sequences of exemplary CODH and hydrogenase genes can be identified by the following GenBank accession numbers.

| Protein | GenBank ID | Organism |
|---|---|---|
| CODH (putative) | YP_430813 | *Moorella thermoacetica* |
| CODH-I (CooS-I) | YP_360644 | *Carboxydothermus hydrogenoformans* |
| CooF | YP_360645 | *Carboxydothermus hydrogenoformans* |
| HypA | YP_360646 | *Carboxydothermus hydrogenoformans* |
| CooH | YP_360647 | *Carboxydothermus hydrogenoformans* |
| CooU | YP_360648 | *Carboxydothermus hydrogenoformans* |
| CooX | YP_360649 | *Carboxydothermus hydrogenoformans* |
| CooL | YP_360650 | *Carboxydothermus hydrogenoformans* |
| CooK | YP_360651 | *Carboxydothermus hydrogenoformans* |
| CooM | YP_360652 | *Carboxydothermus hydrogenoformans* |
| CooM | AAC45116 | *Rhodospirillum rubrum* |
| CooK | AAC45117 | *Rhodospirillum rubrum* |
| CooL | AAC45118 | *Rhodospirillum rubrum* |
| CooX | AAC45119 | *Rhodospirillum rubrum* |
| CooU | AAC45120 | *Rhodospirillum rubrum* |
| CooH | AAC45121 | *Rhodospirillum rubrum* |
| CooF | AAC45122 | *Rhodospirillum rubrum* |
| CODH (CooS) | AAC45123 | *Rhodospirillum rubrum* |
| CooC | AAC45124 | *Rhodospirillum rubrum* |
| CooT | AAC45125 | *Rhodospirillum rubrum* |
| CooJ | AAC45126 | *Rhodospirillum rubrum* |
| CODH-II (CooS-II) | YP_358957 | *Carboxydothermus hydrogenoformans* |
| CooF | YP_358958 | *Carboxydothermus hydrogenoformans* |

Acetyl-CoA synthase disulfide reductase. In *Moorella thermoacetica*, a set of genes encoding a heterodisulfide reductase (Moth_1194 to Moth_1196) is located directly downstream of the acs gene cluster discussed above. In addition, like *M. thermoacetica*, *C. hydrogenoformans* contains a set of genes encoding heterodisulfide reductase directly following acsE.

| Protein | GenBank ID | Organism |
|---|---|---|
| HdrC | YP_430053 | *Moorella thermoacetica* |
| HdrB | YP_430052 | *Moorella thermoacetica* |
| HdrA | YP_430052 | *Moorella thermoacetica* |
| HdrC | YP_360066 | *Carboxydothermus hydrogenoformans* |
| HdrB | YP_360067 | *Carboxydothermus hydrogenoformans* |
| HdrA | YP_360068 | *Carboxydothermus hydrogenoformans* |

Hydrogenase (Hvd). Unlike the redox neutral conversion of CO and methanol to acetyl-CoA or acetate, the production of more highly reduced products such as ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid at the highest possible yield requires the extraction of additional reducing equivalents from both CO and $H_2$ (for example, see ethanol formation in FIG. 7). Specifically, reducing equivalents (for example, 2 [H] in FIG. 6) are obtained by the conversion of CO and water to $CO_2$ via carbon monoxide dehydrogenase as described in Example II or directly from the activity of a hydrogen-utilizing hydrogenase which transfers electrons from $H_2$ to an acceptor such as ferredoxin, flavodoxin, FAD+, NAD+, or NADP+.

Native to *E. coli* and other enteric bacteria are multiple genes encoding up to four hydrogenases (Sawers, *Antonie Van Leeuwenhoek* 66:57-88 (1994); Sawers et al., *J. Bacteriol.* 164:1324-1331 (1985); Sawers and Boxer, *Eur. J. Biochem.* 156:265-275 (1986); Sawers et al., *J. Bacteriol.* 168:398-404 (1986)). Given the multiplicity of enzyme activities, it is possible that *E. coli* or another host organism can provide sufficient hydrogenase activity to split incoming molecular hydrogen and reduce the corresponding acceptor. Among the endogenous hydrogen-lyase enzymes of *E. coli* are hydrogenase 3, a membrane-bound enzyme complex using ferredoxin as an acceptor, and hydrogenase 4, which also uses a ferredoxin acceptor. Hydrogenase 3 and 4 are encoded by the hyc and hyf gene clusters, respectively. Hydrogenase activity in *E. coli* is also dependent upon the expression of the hyp genes whose corresponding proteins are involved in the assembly of the hydrogenase complexes (Jacobi et al., *Arch. Microbiol.* 158:444-451 (1992); Rangarajan et al., *J. Bacteriol.* 190:1447-1458 (2008)). The *M. thermoacetica* hydrogenases are suitable candidates should the production host lack sufficient endogenous hydrogenase activity. *M. thermoacetica* can grow with $CO_2$ as the exclusive carbon source, indicating that reducing equivalents are extracted from $H_2$ to allow acetyl-CoA synthesis via the Wood-Ljungdahl pathway (Drake, *J. Bacteriol.* 150:702-709 (1982); Drake and Daniel, *Res. Microbiol.* 155:869-883 (2004); Kellum and Drake, *J. Bacteriol.* 160:466-469 (1984)) (see FIG. 6). *M. thermoacetica* has homologs to several hyp, hyc, and hyf genes from *E. coli*. These protein sequences encoded for by these genes can be identified by the following GenBank accession numbers. In addition, several gene clusters encoding hydrogenase and/or heterodisulfide reductase functionality are present in *M. thermoacetica* and their corresponding protein sequences are also provided below.

Hyp assembly proteins.

| Protein | GenBank ID | Organism |
| --- | --- | --- |
| HypA | NP_417206 | *Escherichia coli* |
| HypB | NP_417207 | *Escherichia coli* |
| HypC | NP_417208 | *Escherichia coli* |
| HypD | NP_417209 | *Escherichia coli* |
| HypE | NP_417210 | *Escherichia coli* |
| HypF | NP_417192 | *Escherichia coli* |

Proteins in *M. thermoacetica* whose genes are homologous to the *E. coli* hyp genes.

| Protein | GenBank ID | Organism |
| --- | --- | --- |
| Moth_2175 | YP_431007 | *Moorella thermoacetica* |
| Moth_2176 | YP_431008 | *Moorella thermoacetica* |
| Moth_2177 | YP_431009 | *Moorella thermoacetica* |
| Moth_2178 | YP_431010 | *Moorella thermoacetica* |
| Moth_2179 | YP_431011 | *Moorella thermoacetica* |
| Moth_2180 | YP_431012 | *Moorella thermoacetica* |
| Moth_2181 | YP_431013 | *Moorella thermoacetica* |

Hydrogenase 3.

| Protein | GenBank ID | Organism |
| --- | --- | --- |
| HycA | NP_417205 | *Escherichia coli* |
| HycB | NP_417204 | *Escherichia coli* |
| HycC | NP_417203 | *Escherichia coli* |
| HycD | NP_417202 | *Escherichia coli* |
| HycE | NP_417201 | *Escherichia coli* |
| HycF | NP_417200 | *Escherichia coli* |
| HycG | NP_417199 | *Escherichia coli* |
| HycH | NP_417198 | *Escherichia coli* |
| HycI | NP_417197 | *Escherichia coli* |

Hydrogenase 4.

| Protein | GenBank ID | Organism |
| --- | --- | --- |
| HyfA | NP_416976 | *Escherichia coli* |
| HyfB | NP_416977 | *Escherichia coli* |
| HyfC | NP_416978 | *Escherichia coli* |
| HyfD | NP_416979 | *Escherichia coli* |
| HyfE | NP_416980 | *Escherichia coli* |
| HyfF | NP_416981 | *Escherichia coli* |
| HyfG | NP_416982 | *Escherichia coli* |
| HyfH | NP_416983 | *Escherichia coli* |
| HyfI | NP_416984 | *Escherichia coli* |
| HyfJ | NP_416985 | *Escherichia coli* |
| HyfR | NP_416986 | *Escherichia coli* |

Proteins in *M. thermoacetica* whose genes are homologous to the *E. coli* hyc and/or hyf genes.

| Protein | GenBank ID | Organism |
| --- | --- | --- |
| Moth_2182 | YP_431014 | *Moorella thermoacetica* |
| Moth_2183 | YP_431015 | *Moorella thermoacetica* |
| Moth_2184 | YP_431016 | *Moorella thermoacetica* |
| Moth_2185 | YP_431017 | *Moorella thermoacetica* |
| Moth_2186 | YP_431018 | *Moorella thermoacetica* |
| Moth_2187 | YP_431019 | *Moorella thermoacetica* |
| Moth_2188 | YP_431020 | *Moorella thermoacetica* |
| Moth_2189 | YP_431021 | *Moorella thermoacetica* |
| Moth_2190 | YP_431022 | *Moorella thermoacetica* |
| Moth_2191 | YP_431023 | *Moorella thermoacetica* |
| Moth_2192 | YP_431024 | *Moorella thermoacetica* |

Additional hydrogenase-encoding gene clusters in *M. thermoacetica*.

| Protein | GenBank ID | Organism |
| --- | --- | --- |
| Moth_0439 | YP_429313 | *Moorella thermoacetica* |
| Moth_0440 | YP_429314 | *Moorella thermoacetica* |
| Moth_0441 | YP_429315 | *Moorella thermoacetica* |
| Moth_0442 | YP_429316 | *Moorella thermoacetica* |
| Moth_0809 | YP_429670 | *Moorella thermoacetica* |

| Protein | GenBank ID | Organism |
| --- | --- | --- |
| Moth_0810 | YP_429671 | Moorella thermoacetica |
| Moth_0811 | YP_429672 | Moorella thermoacetica |
| Moth_0812 | YP_429673 | Moorella thermoacetica |
| Moth_0813 | (possible psuedogene, GenBank ID unavailable) | Moorella thermoacetica |
| Moth_0814 | YP_429674 | Moorella thermoacetica |
| Moth_0815 | YP_429675 | Moorella thermoacetica |
| Moth_0816 | YP_429676 | Moorella thermoacetica |
| Moth_1193 | YP_430050 | Moorella thermoacetica |
| Moth_1194 | YP_430051 | Moorella thermoacetica |
| Moth_1195 | YP_430052 | Moorella thermoacetica |
| Moth_1196 | YP_430053 | Moorella thermoacetica |
| Moth_1717 | YP_430562 | Moorella thermoacetica |
| Moth_1718 | YP_430563 | Moorella thermoacetica |
| Moth_1719 | YP_430564 | Moorella thermoacetica |
| Moth_1883 | YP_430726 | Moorella thermoacetica |
| Moth_1884 | YP_430727 | Moorella thermoacetica |
| Moth_1885 | YP_430728 | Moorella thermoacetica |
| Moth_1886 | YP_430729 | Moorella thermoacetica |
| Moth_1887 | YP_430730 | Moorella thermoacetica |
| Moth_1888 | YP_430731 | Moorella thermoacetica |
| Moth_1452 | YP_430305 | Moorella thermoacetica |
| Moth_1453 | YP_430306 | Moorella thermoacetica |
| Moth_1454 | YP_430307 | Moorella thermoacetica |

A host organism engineered with these capabilities that also naturally possesses the capability for anapleurosis (for example, E. coli) can potentially grow more efficiently on the syngas-generated acetyl-CoA in the presence of a suitable external electron acceptor such as nitrate. This electron acceptor is required to accept electrons from the reduced quinone formed via succinate dehydrogenase. A further advantage of adding an external electron acceptor is that additional energy for cell growth, maintenance, and product formation can be generated from respiration of acetyl-CoA. An alternative strategy involves engineering a pyruvate ferredoxin oxidoreductase (PFOR) enzyme into the strain to allow synthesis of biomass precursors in the absence of an external electron acceptor.

Pyruvate ferredoxin oxidoreductase (PFOR). Anaerobic growth on synthesis gas and methanol in the absence of an external electron acceptor is conferred upon the host organism with ACS/CODH activity by allowing pyruvate synthesis via pyruvate ferredoxin oxidoreductase (PFOR). The PFOR from *Desulfovibrio africanus* has been cloned and expressed in *E. coli*, resulting in an active recombinant enzyme that was stable for several days in the presence of oxygen (Pieulle et al., *J. Bacteriol.* 179:5684-5692 (1997)). Oxygen stability is relatively uncommon in PFORs and is believed to be conferred by a 60 residue extension in the polypeptide chain of the *D. africanus* enzyme. The *M. thermoacetica* PFOR is also well characterized (Menon and Ragsdale, *Biochemistry* 36:8484-8494 (1997)) and was shown to have high activity in the direction of pyruvate synthesis during autotrophic growth (Furdui and Ragsdale, *J. Biol. Chem.* 275:28494-28499 (2000)). Further, *E. coli* possesses an uncharacterized open reading frame, ydbK, that encodes a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). The protein sequences of these exemplary PFOR enzymes can be identified by the following GenBank accession numbers. Several additional PFOR enzymes have been described (Ragsdale, *Chem. Rev.* 103:2333-2346 (2003)).

| Protein | GenBank ID | Organism |
| --- | --- | --- |
| Por | CAA70873.1 | Desulfovibrio africanus |
| Por | YP_428946.1 | Moorella thermoacetica |
| YdbK | NP_415896.1 | Escherichia coli |

This example describes exemplary gene sets for engineering an organism to produce acetyl-CoA from gasses comprising at least one of CO, $CO_2$, and $H_2$.

Example IX

Engineering a Syngas Utilization Pathway into a Microorganism

This example describes engineering a microorganism to contain a syngas utilization pathway.

In addition to improving the efficiency of microorganisms such as *Clostridial* species that have the natural ability to utilize CO and/or $CO_2$ as a carbon source (Examples II, III and V), microorganisms that do not have the natural ability to utilize CO and/or $CO_2$ are engineered to express one or more proteins or enzymes that confer a CO and/or $CO_2$ utilization pathway. One exemplary pathway is the Wood-Ljungdahl pathway, which allows the utilization of CO and/or $CO_2$ as a carbon source, thereby allowing the microorganism to utilize syngas or other gaseous carbon source (see Examples I and VII).

In initial studies, *Escherichia coli*, which does not utilize syngas naturally, is used as a target organism to introduce a CO and/or $CO_2$ utilization pathway such as the Wood-Ljungdahl pathway. The Wood-Ljungdahl pathway involves oxygen sensitive and membrane bound proteins as well as specific co-factors that are not native in *E. coli*. While several Wood-Ljungdahl pathway genes have been cloned into *E. coli*, only one enzyme, methyltransferase, was found be expressed in active form (Roberts et al., *Proc. Natl. Acad. Sci. USA* 86:32-36 (1989)). Purification of the carbonyl branch (see FIG. 2) pathway genes from *Clostridium thermoaceticum* revealed the minimum set of enzymes required for in vitro conversion of methyl-THF to acetyl-CoA studies (Roberts et al., *J. Bacteriol.* 174:4667-4676 (1992)).

Initial studies are directed to engineering a Wood-Ljungdahl pathway, in particular the carbonyl branch (FIG. 2), into *E. coli* and testing growth and acetate production from both methyl-THF and syngas. *E. coli* provides a good model for developing a non-naturally occurring microorganism capable of utilizing syngas or other gaseous carbon sources since it is amenable to genetic manipulation and is known to be capable of producing various products like ethanol, acetate, and succinate effectively under anaerobic conditions from glucose.

To generate an *E. coli* strain engineered to contain a Wood-Ljungdahl pathway, nucleic acids encoding proteins and enzymes required for the carbonyl branch of the pathway (see FIG. 2 and Example VII) are expressed in *E. coli* using well known molecular biology techniques (see, for example, Sambrook, supra, 2001; Ausubel supra, 1999; Roberts et al., supra, 1989). As described previously, the gene cluster encoding key proteins in acetyl-CoA synthesis in *Clostridium thermoaceticum* has been cloned and expressed in *E. coli* (Roberts et al., supra, 1989). Specific variation of conditions, such as metal composition of the medium, is required to ensure production of active proteins. Genes encoding cobalamide corrinoid/iron-sulfur protein, methyltransferase, carbon monoxide dehydrogenase (CODH), acetyl-CoA synthase (ACS), acetyl-CoA synthase disulfide reductase, and a CO-tolerant hydrogenase are cloned and expressed in E. coli to introduce carbonyl branch enzymes of the Wood-Ljungdahl pathway (for Wood-Ljungdahl pathway genes, see also Ragsdale, Critical Rev. Biochem. Mol. Biol. 39:165-195 (2004)). Since E. coli does not normally synthesize cobalamin or cobalamin-like cofactors, which is required for the cobalamide-corrinoid/iron sulfur protein activity, the cofactors or genes encoding proteins and enzymes for synthesis of the required cofactors can also be introduced. The cobalamin or cobalamin-like cofactors can be provided to the medium, although cost would possibly prohibit this approach for scale up and commercial manufacture. A better alternative is to clone and express the requisite genes in the E. coli strain expressing the cobalamin-requiring proteins. This has been demonstrated by transfer and functional expression of a cobalamin operon containing 20 genes from *Salmonella typhimurium* into E. coli (Raux et al., J. Bacteriol. 178:753-767 (1996)).

The expression of Wood-Ljungdahl pathway genes is tested using routine assays for determining the expression of introduced genes, for example, Northern blots, PCR amplification of mRNA, immunoblotting, or other well known assays to confirm nucleic acid and protein expression of introduced genes. Enzymatic activity of the expressed enzymes can be tested individually or for production of a product such as acetyl-CoA (see, for example, Roberts et al., supra, 1989). The ability of the engineered E. coli strain to utilize CO and/or $CO_2$ as a carbon source to produce acetyl-CoA can be analyzed directly using gas chromatography-mass spectrometry (GCMS) or liquid chromatography-mass spectrometry (LCMS), or through the use of metabolic radioactive or isotopic labeling, for example, with radioactive CO or $CO_2$ and analysis of incorporation of radioactive label into the acetyl-CoA product or incorporation of an isotopically labeled CO or $CO_2$ precursor and analysis by techniques such as mass spectrometry (GCMS or LCMS) or nuclear magnetic resonance spectroscopy (NMR). Growth of E. coli using only CO and/or $CO_2$ as a sole carbon source, with or without the presence of $H_2$, is another useful test for a fully functional pathway.

Once a functional Wood-Ljungdahl pathway has been engineered into an E. coli strain, the strain is optimized for efficient utilization of the pathway. The engineered strain can be tested to determine if any of the introduced genes are expressed at a level that is rate limiting. As needed, increased expression of one or more proteins or enzymes that may limit the flux through the pathway can be used to optimize utilization of the pathway and production of acetyl-CoA.

Metabolic modeling can be utilized to optimize growth conditions (see Example II). Modeling can also be used to design gene knockouts that additionally optimize utilization of the pathway (see Examples II, IV and V and, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows predictions of the effects on cell growth of shifting the metabolism towards more efficient production of acetyl-CoA or other desired product. One modeling method is the bilevel optimization approach, OptKnock (Burgard et al., Biotechnol. Bioengineer. 84:647-657 (2003)), which is applied to select gene knockouts that collectively result in the growth-coupled production of acetyl-CoA or other desired products, as discussed below. Strains designed with a gene knockout strategy are forced, due to network stoichiometry, to produce high levels of a desired product for efficient growth, because all other growth options have been removed. Such strains are self-optimizing and stable. Accordingly, they typically maintain or improve upon production levels even in the face of strong growth selective pressures, making them amenable to batch or continuous bioprocessing and also evolutionary engineering. Adaptive evolution can be used to further optimize the production of acetyl-CoA (see Example V). Adaptive evolution is therefore performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be utilized to further optimize production and tolerance of enzymes to syngas or impurities in syngas.

Once an engineered microbial strain has been optimized for utilization of the Wood-Ljungdahl pathway, optimization of the fermentation process can be performed to increase yields using well known methods and as described, for example, in Example VI). For example, a productivity level of 20 g/L acetate at 0.5 g/L/h from syngas would represent a desirable production range towards which further optimization of the strain for efficient utilization of the pathway as well as optimization of fermentation conditions can be employed to achieve a desired production level.

Although exemplified with introduction of the carbonyl branch to confer the ability to utilize CO and/or $CO_2$ to an engineered microbial strain, a similar approach is applied to introduce enzymes for production of methyl-THF to E. coli. As discussed above in Example VII, E. coli has the ability to produce methyl-THF, but THF-dependent enzymes from acetogens have higher specific activities (Morton et al., supra, 1993). Using methods as described above to introduce the carbonyl branch of the Wood-Ljungdahl pathway, methyl branch enzymes are introduced into E. coli using similar techniques. Genes encoding one or more of the enzymes ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase are introduced (see FIG. 1). In this case, the genes are introduced to increase an endogenous enzyme activity and/or to increase the efficiency of utilization of CO and/or $CO_2$ to produce methyl-THF. Optimization of the pathway and fermentation conditions is carried out as described above. In addition, both the carbonyl and methyl branches of the Wood-Ljungdahl pathway can be introduced into the same microorganism. In such an engineered organism, the increased production of methyl-THF from CO and/or $CO_2$ can be utilized to further increase the production of acetyl-CoA in an organism engineered to utilize CO and/or $CO_2$ using the carbonyl branch of the Wood-Ljungdahl pathway (see FIGS. 3 and 6).

Acetyl-CoA can function as a precursor for other desired products. Once the acetyl-CoA-producing microorganism has been generated, additional genes can be introduced into the microorganism to utilize acetyl-CoA as a precursor to produce other desired products from CO and/or $CO_2$ as carbon source. For example, enzymes for butanol production can be introduced (see FIG. 3 and Example V). Representative genes for butanol pathway from acetyl-CoA are: AtoB, acetyl-CoA acetyltransferase; Thl, acetyl-CoA thiolase; Hbd, 3-hydroxybutyrl-CoA dehydrogenase; Crt, crotonase; Bcd, butyryl-CoA dehydrogenase; Etf, electron transfer flavoprotein; AdhE2, aldehyde/alcohol dehydroenase (see Atsumi et al., Metabolic Engineering Sep. 14, 2007).

Metabolic pathways for production of additional desired products, including succinate, 4-hydroxybutyrate and 1,4- butanediol are described, for example, in U.S. application Ser. No. 11/891,602, filed Aug. 10, 2007, and WO/2008/115840, and enzymes for such pathways can similarly be introduced, for example, succinyl-CoA ligase, succinyl-CoA:CoA transferase, succinate semialdehyde dehydrogenase, 4-hydroxybutyric acid dehydrogenase, glutamate:succinic semialdehyde transaminase, 4-hydroxybutyryl-CoA transferase, a CoA-dependent aldehyde dehydrogenase, alcohol dehydrogenase, and the like. Acetyl-CoA feeds directly into the TCA cycle of all cells and succinate is a TCA cycle intermediate. Thus, additional enzymes conferring pathways capable of utilizing acetyl-CoA produced from CO and/or $CO_2$ can be engineered and optimized, as described above, to produce a desired product from the engineered microorganism.

Example X

Pathways for the Production of Acetyl-CoA from Synthesis Gas and Methanol

This example describes exemplary pathways for utilization of synthesis gas (syngas) and methanol to produce acetyl-CoA.

An organism capable of producing acetyl-CoA from syngas and methanol contains two key capabilities, which are depicted in FIG. 7. One capability is a functional methyltransferase system that allows the production of 5-methyl-tetrahydrofolate (Me-THF) from methanol and THF. A second capability is the ability to combine CO, Coenzyme A, and the methyl group of Me-THF to form acetyl-CoA. The organism is able to 'fix' carbon from exogenous CO and/or $CO_2$ and methanol to synthesize acetyl-CoA, cell mass, and products. This pathway to form acetyl-CoA from methanol and syngas is energetically advantageous compared to utilizing the full Wood-Ljungdahl pathway. For example, the direct conversion of synthesis gas to acetate is an energetically neutral process (see FIG. 6). Specifically, one ATP molecule is consumed during the formation of formyl-THF by formyl-THF synthase, and one ATP molecule is produced during the production of acetate via acetate kinase. This new strategy involving methanol circumvents the ATP consumption requirement by ensuring that the methyl group on the methyl branch product, methyl-THF, is obtained from methanol rather than $CO_2$. This thereby ensures that acetate formation has a positive ATP yield that can help support cell growth and maintenance. A host organism engineered with these capabilities that also naturally possesses the capability for anapleurosis (for example, E. coli) can grow on the methanol and syngas-generated acetyl-CoA in the presence of a suitable external electron acceptor such as nitrate. This electron acceptor is required to accept electrons from the reduced quinone formed via succinate dehydrogenase. A further advantage of adding an external electron acceptor is that additional energy for cell growth, maintenance, and product formation can be generated from respiration of acetyl-CoA.

An alternative strategy involves engineering a pyruvate ferredoxin oxidoreductase (PFOR) enzyme into the strain to allow synthesis of biomass precursors in the absence of an external electron acceptor. A further characteristic of the engineered organism is the capability for extracting reducing equivalents from molecular hydrogen. This allows a high yield of reduced products such as ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid.

The organisms can produce acetyl-CoA, cell mass, and targeted chemicals from the following sources: 1) methanol and CO, 2) methanol, $CO_2$, and $H_2$, 3) methanol, CO, $CO_2$, and $H_2$, 4) methanol and synthesis gas comprising CO and $H_2$, and 5) methanol and synthesis gas comprising CO, $CO_2$, and $H_2$.

Successfully engineering this pathway into an organism involves identifying an appropriate set of enzymes, cloning their corresponding genes into a production host, optimizing the stability and expression of these genes, optimizing fermentation conditions, and assaying for product formation following fermentation (see Examples II-IV). Described below are a number of enzymes that catalyze each step of the pathway required for the conversion of synthesis gas and methanol to acetyl-CoA. To engineer a production host for the utilization of syngas and methanol, one or more exogenous DNA sequence(s) encoding the requisite enzymes are expressed in the microorganism.

This example describes exemplary pathways for acetyl-CoA production from syngas and methanol.

Example XI

Gene Sets for Generating Methanol and Syngas Utilizing Microorganisms

This example describes exemplary gene sets for generating methanol and syngas utilizing microorganisms.

Methanol-methyltransferase (MTR). Expression of the modified Wood-Ljungdahl pathway in a foreign host (see FIG. 7) requires introducing a set of methyltransferases to utilize the carbon and hydrogen provided by methanol and the carbon provided by CO and/or $CO_2$. A complex of 3 methyltransferase proteins, denoted MtaA, MtaB, and MtaC, perform the desired methanol methyltransferase activity (Naidu and Ragsdale, *J. Bacteriol.* 183:3276-3281 (2001); Ragsdale, *Crit. Rev. Biochem. Mol. Biol.* 39:165-195 (2004); Sauer et al., *Eur. J. Biochem.* 243:670-677 (1997); Tallant and Krzycki, *J. Bacteriol.* 178:1295-1301 (1996); Tallant and Krzycki, *J. Bacteriol.* 179:6902-6911 (1997); Tallant et al., *J. Biol. Chem.* 276:4485-4493 (2001)).

Methanol methyltransferase (MtaB) and Corrinoid protein (MtaC). MtaB is a zinc protein that catalyzes the transfer of a methyl group from methanol to MtaC, a corrinoid protein. Exemplary genes encoding MtaB and MtaC can be found in methanogenic archaea such as *Methanosarcina barkeri* (Maeder et al., *J. Bacteriol.* 188:7922-7931 (2006)) and *Methanosarcina acetivorans* (Galagan et al., *Genome Res.* 12:532-542 (2002)), as well as the acetogen, *Moorella thermoacetica* (Das et al., *Proteins* 67:167-176 (2007)). In general, the MtaB and MtaC genes are adjacent to one another on the chromosome as their activities are tightly interdependent. The protein sequences of various MtaB and MtaC encoding genes in *M. barkeri, M. acetivorans*, and *M. thermoaceticum* can be identified by their following GenBank accession numbers.

| Protein | GenBank ID | Organism |
|---|---|---|
| MtaB1 | YP_304299 | *Methanosarcina barkeri* |
| MtaC1 | YP_304298 | *Methanosarcina barkeri* |
| MtaB2 | YP_307082 | *Methanosarcina barkeri* |
| MtaC2 | YP_307081 | *Methanosarcina barkeri* |
| MtaB3 | YP_304612 | *Methanosarcina barkeri* |
| MtaC3 | YP_304611 | *Methanosarcina barkeri* |
| MtaB1 | NP_615421 | *Methanosarcina acetivorans* |

| Protein | GenBank ID | Organism |
| --- | --- | --- |
| MtaB1 | NP_615422 | Methanosarcina acetivorans |
| MtaB2 | NP_619254 | Methanosarcina acetivorans |
| MtaC2 | NP_619253 | Methanosarcina acetivorans |
| MtaB3 | NP_616549 | Methanosarcina acetivorans |
| MtaC3 | NP_616550 | Methanosarcina acetivorans |
| MtaB | YP_430066 | Moorella thermoacetica |
| MtaC | YP_430065 | Moorella thermoacetica |

The MtaB1 and MtaC1 genes, YP_304299 and YP_304298, from *M. barkeri* were cloned into *E. coli* and sequenced (Sauer et al., *Eur. J. Biochem.* 243:670-677 (1997)). The crystal structure of this methanol-cobalamin methyltransferase complex is also available (Hagemeier et al., *Proc. Natl. Acad. Sci. USA* 103:18917-18922 (2006)). The MtaB genes, YP_307082 and YP_304612, in *M. barkeri* were identified by sequence homology to YP_304299. In general, homology searches are an effective means of identifying methanol methyltransferases because MtaB encoding genes show little or no similarity to methyltransferases that act on alternative substrates such as trimethylamine, dimethylamine, monomethylamine, or dimethylsulfide. The MtaC genes, YP_307081 and YP_304611, were identified based on their proximity to the MtaB genes and also their homology to YP_304298. The three sets of MtaB and MtaC genes from *M. acetivorans* have been genetically, physiologically, and biochemically characterized (Pritchett and Metcalf, *Mol. Microbiol.* 56:1183-1194 (2005)). Mutant strains lacking two of the sets were able to grow on methanol, whereas a strain lacking all three sets of MtaB and MtaC genes sets could not grow on methanol. This suggests that each set of genes plays a role in methanol utilization. The *M. thermoacetica* MtaB gene was identified based on homology to the methanogenic MtaB genes and also by its adjacent chromosomal proximity to the methanol-induced corrinoid protein, MtaC, which has been crystallized (Zhou et al., *Acta Crystallogr. Sect. F Struct. Biol. Cryst. Commun.* 61:537-540 (2005)) and further characterized by Northern hybridization and Western blotting (Das et al., *Proteins* 67:167-176 (2007)).

Methenyltetrahydrofolate:corrinoid protein methyltransferase (MtaA). MtaA is zinc protein that catalyzes the transfer of the methyl group from MtaC either to Coenzyme M in methanogens or to tetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931 (2006)) and *Methanosarcina acetivorans* (Galagan et al., *Genome Res.* 12:532-542 (2002)), as well as the acetogen, *Moorella thermoacetica* (Das et al., *Proteins* 67:167-176 (2007)). In general, MtaA proteins that catalyze the transfer of the methyl group from $CH_3$-MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

| Protein | GenBank ID | Organism |
| --- | --- | --- |
| MtaA | YP_304602 | Methanosarcina barkeri |
| MtaA1 | NP_619241 | Methanosarcina acetivorans |
| MtaA2 | NP_616548 | Methanosarcina acetivorans |

The MtaA gene, YP_304602, from *M. barkeri* was cloned, sequenced, and functionally overexpressed in *E. coli* (Harms and Thauer, *Eur. J. Biochem.* 235:653-659 (1996)). In *M. acetivorans*, MtaA1 is required for growth on methanol, whereas MtaA2 is dispensable even though methane production from methanol is reduced in MtaA2 mutants (Bose et al., *J. Bacteriol.* 190:4017-4026 (2008)). It is also important to note that there are multiple additional MtaA homologs in *M. barkeri* and *M. acetivorans* that are as yet uncharacterized, but may also catalyze corrinoid protein methyltransferase activity.

Putative MtaA encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. Unlike methanogenic MtaA proteins that naturally catalyze the transfer of the methyl group from $CH_3$-MtaC to Coenzyme M, an *M. thermoacetica* MtaA is likely to transfer the methyl group to tetrahydrofolate given the similar roles of tetrahydrofolate and Coenzyme M in methanogens and acetogens, respectively. The protein sequences of putative MtaA encoding genes from *M. thermoacetica* can be identified by the following GenBank accession numbers.

| Protein | GenBank ID | Organism |
| --- | --- | --- |
| MtaA | YP_430937 | Moorella thermoacetica |
| MtaA | YP_431175 | Moorella thermoacetica |
| MtaA | YP_430935 | Moorella thermoacetica |

Acetyl-CoA synthase/Carbon monoxide dehydroenase (ACS/CODH). ACS/CODH is the central enzyme of the carbonyl branch of the Wood-Ljungdahl pathway. It catalyzes the reversible reduction of carbon dioxide to carbon monoxide and also the synthesis of acetyl-CoA from carbon monoxide, Coenzyme A, and the methyl group from a methylated corrinoid-iron-sulfur protein. The corrinoide-iron-sulfur-protein is methylated by methyltetrahydrofolate via a methyltransferase. Expression of ACS/CODH in a foreign host involves introducing many, if not all, of the following proteins and their corresponding activities.

Methyltetrahydrofolate:corrinoid protein methyltransferase (AcsE)

Corrinoid iron-sulfur protein (AcsD)

Nickel-protein assembly protein (AcsF)

Ferredoxin (Orf7)

Acetyl-CoA synthase (AcsB and AcsC)

Carbon monoxide dehydrogenase (AcsA)

Nickel-protein assembly protein (CooC)

The genes required for carbon-monoxide dehydrogenase/acetyl-CoA synthase activity typically reside in a limited region of the native genome that may be an extended operon (Morton et al., *J. Biol. Chem.* 266:23824-23828 (1991); Ragsdale, *Crit. Rev. Biochem. Mol. Biol.* 39:165-195 (2004); Roberts et al., *Proc. Natl. Acad. Sci. USA* 86:32-36 (1989)). Each of the genes in this operon from the acetogen, *M. thermoacetica*, has already been cloned and expressed actively in *E. coli* (Lu et al., *J. Biol. Chem.* 268:5605-5614 (1993); Morton et al., supra, 1991; Roberts et al., supra, 1989)). The protein sequences of these genes can be identified by the following GenBank accession numbers.

| Protein | GenBank ID | Organism |
| --- | --- | --- |
| AcsE | YP_430054 | Moorella thermoacetica |
| AcsD | YP_430055 | Moorella thermoacetica |
| AcsF | YP_430056 | Moorella thermoacetica |
| Orf7 | YP_430057 | Moorella thermoacetica |
| AcsC | YP_430058 | Moorella thermoacetica |
| AcsB | YP_430059 | Moorella thermoacetica |
| AcsA | YP_430060 | Moorella thermoacetica |
| CooC | YP_430061 | Moorella thermoacetica |

The hydrogenogenic bacterium, *Carboxydothermus hydrogenoformans*, can utilize carbon monoxide as a growth substrate by means of acetyl-CoA synthase (Wu et al., *PLoS Genet.* 1:e65. (2005)). In strain Z-2901, the acetyl-CoA synthase enzyme complex lacks carbon monoxide dehydrogenase due to a frameshift mutation (We et al., supra, 2005), whereas in strain DSM 6008, a functional unframeshifted full-length version of this protein has been purified (Svetlitchnyi et al., *Proc. Natl. Acad. Sci. USA* 101:446-451 (2004)). The protein sequences of the *C. hydrogenoformans* genes from strain Z-2901 can be identified by the following GenBank accession numbers. Sequences for *Carboxydothermus hydrogenoformans* DSM 6008 are not currently accessible in publicly available databases but can be readily determined as the sequences become available.

| Protein | GenBank ID | Organism |
| --- | --- | --- |
| AcsE | YP_360065 | Carboxydothermus hydrogenoformans |
| AcsD | YP_360064 | Carboxydothermus hydrogenoformans |
| AcsF | YP_360063 | Carboxydothermus hydrogenoformans |
| Orf7 | YP_360062 | Carboxydothermus hydrogenoformans |
| AcsC | YP_360061 | Carboxydothermus hydrogenoformans |
| AcsB | YP_360060 | Carboxydothermus hydrogenoformans |
| CooC | YP_360059 | Carboxydothermus hydrogenoformans |

The methanogenic archaeon, *Methanosarcina acetivorans*, can also grow on carbon monoxide, exhibits acetyl-CoA synthase/carbon monoxide dehydrogenase activity, and produces both acetate and formate (Lessner et al., *Proc. Natl. Acad. Sci. USA* 103:17921-17926 (2006)). This organism contains two sets of genes that encode ACS/CODH activity (Rother and Metcalf, *Proc. Natl. Acad. Sci. USA* 101:16929-16934 (2004)). The protein sequences of both sets of *M. acetivorans* genes can be identified by the following GenBank accession numbers.

| Protein | GenBank ID | Organism |
| --- | --- | --- |
| AcsC | NP_618736 | Methanosarcina acetivorans |
| AcsD | NP_618735 | Methanosarcina acetivorans |
| AcsF, CooC | NP_618734 | Methanosarcina acetivorans |
| AcsB | NP_618733 | Methanosarcina acetivorans |
| AcsEps | NP_618732 | Methanosarcina acetivorans |
| AcsA | NP_618731 | Methanosarcina acetivorans |
| AcsC | NP_615961 | Methanosarcina acetivorans |
| AcsD | NP_615962 | Methanosarcina acetivorans |
| AcsF, CooC | NP_615963 | Methanosarcina acetivorans |
| AcsB | NP_615964 | Methanosarcina acetivorans |
| AcsEps | NP_615965 | Methanosarcina acetivorans |
| AcsA | NP_615966 | Methanosarcina acetivorans |

The AcsC, AcsD, AcsB, AcsEps, and AcsA proteins are commonly referred to as the gamma, delta, beta, epsilon, and alpha subunits of the methanogenic CODH/ACS. Homologs to the epsilon encoding genes are not present in acetogens such as *M. thermoacetica* or hydrogenogenic bacteria such as *C. hydrogenoformans*. Hypotheses for the existence of two active CODH/ACS operons in *M. acetivorans* include catalytic properties (that is, $K_m$, $V_{max}$, $k_{cat}$) that favor carboxidotrophic or aceticlastic growth or differential gene regulation enabling various stimuli to induce CODH/ACS expression (Rother et al., *Arch. Microbiol.* 188:463-472 (2007)).

In both *M. thermoacetica* and *C. hydrogenoformans*, additional CODH encoding genes are located outside of the ACS/CODH operons. These enzymes provide a means for extracting electrons (or reducing equivalents) from the conversion of carbon monoxide to carbon dioxide. The reducing equivalents are then passed to accepters such as oxidized ferredoxin, NADP+, water, or hydrogen peroxide to form reduced ferredoxin, NADPH, $H_2$, or water, respectively. In some cases, hydrogenase encoding genes are located adjacent to a CODH. In *Rhodospirillum rubrum*, the encoded CODH/hydrogenase proteins form a membrane-bound enzyme complex that is proposed to be a site where energy, in the form of a proton gradient, is generated from the conversion of CO to $CO_2$ and $H_2$ (Fox et al., *J. Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J. Am. Chem. Soc.* 129:10328-10329 (2007)). The genes encoding the *C. hydrogenoformans* CODH-II and CooF, a neighboring protein, were cloned and sequenced (Gonzalez and Robb, *FEMS Microbiol. Lett.* 191: 243-247 (2000)). The resulting complex was membrane-bound, although cytoplasmic fractions of CODH-II were shown to catalyze the formation of NADPH suggesting an anabolic role (Svetlitchnyi et al., *J. Bacteriol.* 183:5134-5144 (2001)). The crystal structure of the CODH-II is also available (Dobbek et al., *Science* 293:1281-1285 (2001)). The protein sequences of exemplary CODH and hydrogenase genes can be identified by the following GenBank accession numbers.

| Protein | GenBank ID | Organism |
| --- | --- | --- |
| CODH (putative) | YP_430813 | Moorella thermoacetica |
| CODH-I (CooS-I) | YP_360644 | Carboxydothermus hydrogenoformans |
| CooF | YP_360645 | Carboxydothermus hydrogenoformans |
| HypA | YP_360646 | Carboxydothermus hydrogenoformans |
| CooH | YP_360647 | Carboxydothermus hydrogenoformans |
| CooU | YP_360648 | Carboxydothermus hydrogenoformans |
| CooX | YP_360649 | Carboxydothermus hydrogenoformans |
| CooL | YP_360650 | Carboxydothermus hydrogenoformans |
| CooK | YP_360651 | Carboxydothermus hydrogenoformans |
| CooM | YP_360652 | Carboxydothermus hydrogenoformans |
| CooM | AAC45116 | Rhodospirillum rubrum |
| CooK | AAC45117 | Rhodospirillum rubrum |
| CooL | AAC45118 | Rhodospirillum rubrum |
| CooX | AAC45119 | Rhodospirillum rubrum |
| CooU | AAC45120 | Rhodospirillum rubrum |
| CooH | AAC45121 | Rhodospirillum rubrum |
| CooF | AAC45122 | Rhodospirillum rubrum |
| CODH (CooS) | AAC45123 | Rhodospirillum rubrum |
| CooC | AAC45124 | Rhodospirillum rubrum |
| CooT | AAC45125 | Rhodospirillum rubrum |
| CooJ | AAC45126 | Rhodospirillum rubrum |
| CODH-II (CooS-II) | YP_358957 | Carboxydothermus hydrogenoformans |
| CooF | YP_358958 | Carboxydothermus hydrogenoformans |

Pyruvate ferredoxin oxidoreductase (PFOR). Anaerobic growth on synthesis gas and methanol in the absence of an external electron acceptor is conferred upon the host organism with MTR and ACS/CODH activity by allowing pyruvate synthesis via pyruvate ferredoxin oxidoreductase (PFOR). The PFOR from *Desulfovibrio africanus* has been cloned and expressed in *E. coli*, resulting in an active recombinant enzyme that was stable for several days in the presence of oxygen (Pieulle et al., *J. Bacteriol.* 179:5684-5692 (1997)). Oxygen stability is relatively uncommon in PFORs and is believed to be conferred by a 60 residue extension in the polypeptide chain of the *D. africanus* enzyme. The *M. thermoacetica* PFOR is also well characterized (Menon and Ragsdale, *Biochemistry* 36:8484-8494 (1997)) and was shown to have high activity in the direction of pyruvate synthesis during autotrophic growth (Furdui and Ragsdale, *J. Biol. Chem.* 275:28494-28499 (2000)). Further, *E. coli* possesses an uncharacterized open reading frame, ydbK, that encodes a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). The protein sequences of these exemplary PFOR enzymes can be identified by the following GenBank accession numbers. Several additional PFOR enzymes have been described (Ragsdale, *Chem. Rev.* 103: 2333-2346 (2003)).

| Protein | GenBank ID | Organism |
| --- | --- | --- |
| Por | CAA70873.1 | *Desulfovibrio africanus* |
| Por | YP_428946.1 | *Moorella thermoacetica* |
| YdbK | NP_415896.1 | *Escherichia coli* |

Hydrogenase (Hyd). Unlike the redox neutral conversion of CO and methanol to acetyl-CoA or acetate, the production of more highly reduced products such as ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid at the highest possible yield requires the extraction of additional reducing equivalents from both CO and $H_2$ (for example, see ethanol formation in FIG. 7). Specifically, reducing equivalents (for example, 2 [H] in FIG. 6) are obtained by the conversion of CO and water to $CO_2$ via carbon monoxide dehydrogenase as described in Example II or directly from the activity of a hydrogen-utilizing hydrogenase which transfers electrons from $H_2$ to an acceptor such as ferredoxin, flavodoxin, FAD+, NAD+, or NADP+.

Native to *E. coli* and other enteric bacteria are multiple genes encoding up to four hydrogenases (Sawers, *Antonie Van Leeuwenhoek* 66:57-88 (1994); Sawers et al., *J. Bacteriol.* 164:1324-1331 (1985); Sawers and Boxer, *Eur. J. Biochem.* 156:265-275 (1986); Sawers et al., *J. Bacteriol.* 168: 398-404 (1986)). Given the multiplicity of enzyme activities, it is possible that *E. coli* or another host organism can provide sufficient hydrogenase activity to split incoming molecular hydrogen and reduce the corresponding acceptor. Among the endogenous hydrogen-lyase enzymes of *E. coli* are hydrogenase 3, a membrane-bound enzyme complex using ferredoxin as an acceptor, and hydrogenase 4, which also uses a ferredoxin acceptor. Hydrogenase 3 and 4 are encoded by the hyc and hyf gene clusters, respectively. Hydrogenase activity in *E. coli* is also dependent upon the expression of the hyp genes whose corresponding proteins are involved in the assembly of the hydrogenase complexes (Jacobi et al., *Arch. Microbiol.* 158:444-451 (1992); Rangarajan et al., *J. Bacteriol.* 190: 1447-1458 (2008)). The *M. thermoacetica* hydrogenases are suitable candidates should the production host lack sufficient endogenous hydrogenase activity. *M. thermoacetica* can grow with $CO_2$ as the exclusive carbon source, indicating that reducing equivalents are extracted from $H_2$ to allow acetyl-CoA synthesis via the Wood-Ljungdahl pathway (Drake, *J. Bacteriol.* 150:702-709 (1982); Drake and Daniel, *Res. Microbiol.* 155:869-883 (2004); Kellum and Drake, *J. Bacteriol.* 160:466-469 (1984)) (see FIG. 6). *M. thermoacetica* has homologs to several hyp, hyc, and hyf genes from *E. coli*. These protein sequences encoded for by these genes can be identified by the following GenBank accession numbers. In addition, several gene clusters encoding hydrogenase and/or heterodisulfide reductase functionality are present in *M. thermoacetica* and their corresponding protein sequences are also provided below.

Hyp assembly proteins.

| Protein | GenBank ID | Organism |
| --- | --- | --- |
| HypA | NP_417206 | *Escherichia coli* |
| HypB | NP_417207 | *Escherichia coli* |
| HypC | NP_417208 | *Escherichia coli* |
| HypD | NP_417209 | *Escherichia coli* |
| HypE | NP_417210 | *Escherichia coli* |
| HypF | NP_417192 | *Escherichia coli* |

Proteins in *M. thermoacetica* whose genes are homologous to the *E. coli* hyp genes.

| Protein | GenBank ID | Organism |
| --- | --- | --- |
| Moth_2175 | YP_431007 | *Moorella thermoacetica* |
| Moth_2176 | YP_431008 | *Moorella thermoacetica* |
| Moth_2177 | YP_431009 | *Moorella thermoacetica* |
| Moth_2178 | YP_431010 | *Moorella thermoacetica* |
| Moth_2179 | YP_431011 | *Moorella thermoacetica* |
| Moth_2180 | YP_431012 | *Moorella thermoacetica* |
| Moth_2181 | YP_431013 | *Moorella thermoacetica* |

Hydrogenase 3.

| Protein | GenBank ID | Organism |
| --- | --- | --- |
| HycA | NP_417205 | *Escherichia coli* |
| HycB | NP_417204 | *Escherichia coli* |
| HycC | NP_417203 | *Escherichia coli* |
| HycD | NP_417202 | *Escherichia coli* |
| HycE | NP_417201 | *Escherichia coli* |
| HycF | NP_417200 | *Escherichia coli* |
| HycG | NP_417199 | *Escherichia coli* |
| HycH | NP_417198 | *Escherichia coli* |
| HycI | NP_417197 | *Escherichia coli* |

Hydrogenase 4.

| Protein | GenBank ID | Organism |
| --- | --- | --- |
| HyfA | NP_416976 | *Escherichia coli* |
| HyfB | NP_416977 | *Escherichia coli* |
| HyfC | NP_416978 | *Escherichia coli* |
| HyfD | NP_416979 | *Escherichia coli* |
| HyfE | NP_416980 | *Escherichia coli* |

-continued

| Protein | GenBank ID | Organism |
| --- | --- | --- |
| HyfF | NP_416981 | Escherichia coli |
| HyfG | NP_416982 | Escherichia coli |
| HyfH | NP_416983 | Escherichia coli |
| HyfI | NP_416984 | Escherichia coli |
| HyfJ | NP_416985 | Escherichia coli |
| HyfR | NP_416986 | Escherichia coli |

Proteins in *M. thermoacetica* whose genes are homologous to the *E. coli* hyc and/or hyf genes.

| Protein | GenBank ID | Organism |
| --- | --- | --- |
| Moth_2182 | YP_431014 | Moorella thermoacetica |
| Moth_2183 | YP_431015 | Moorella thermoacetica |
| Moth_2184 | YP_431016 | Moorella thermoacetica |
| Moth_2185 | YP_431017 | Moorella thermoacetica |
| Moth_2186 | YP_431018 | Moorella thermoacetica |
| Moth_2187 | YP_431019 | Moorella thermoacetica |
| Moth_2188 | YP_431020 | Moorella thermoacetica |
| Moth_2189 | YP_431021 | Moorella thermoacetica |
| Moth_2190 | YP_431022 | Moorella thermoacetica |
| Moth_2191 | YP_431023 | Moorella thermoacetica |
| Moth_2192 | YP_431024 | Moorella thermoacetica |

Additional hydrogenase-encoding gene clusters in *M. thermoacetica*.

| Protein | GenBank ID | Organism |
| --- | --- | --- |
| Moth_0439 | YP_429313 | Moorella thermoacetica |
| Moth_0440 | YP_429314 | Moorella thermoacetica |
| Moth_0441 | YP_429315 | Moorella thermoacetica |
| Moth_0442 | YP_429316 | Moorella thermoacetica |
| Moth_0809 | YP_429670 | Moorella thermoacetica |
| Moth_0810 | YP_429671 | Moorella thermoacetica |
| Moth_0811 | YP_429672 | Moorella thermoacetica |
| Moth_0812 | YP_429673 | Moorella thermoacetica |
| Moth_0813 | (possible psuedogene, GenBank ID unavailable) | Moorella thermoacetica |
| Moth_0814 | YP_429674 | Moorella thermoacetica |
| Moth_0815 | YP_429675 | Moorella thermoacetica |
| Moth_0816 | YP_429676 | Moorella thermoacetica |
| Moth_1193 | YP_430050 | Moorella thermoacetica |
| Moth_1194 | YP_430051 | Moorella thermoacetica |
| Moth_1195 | YP_430052 | Moorella thermoacetica |
| Moth_1196 | YP_430053 | Moorella thermoacetica |
| Moth_1717 | YP_430562 | Moorella thermoacetica |
| Moth_1718 | YP_430563 | Moorella thermoacetica |
| Moth_1719 | YP_430564 | Moorella thermoacetica |
| Moth_1883 | YP_430726 | Moorella thermoacetica |
| Moth_1884 | YP_430727 | Moorella thermoacetica |
| Moth_1885 | YP_430728 | Moorella thermoacetica |
| Moth_1886 | YP_430729 | Moorella thermoacetica |
| Moth_1887 | YP_430730 | Moorella thermoacetica |
| Moth_1888 | YP_430731 | Moorella thermoacetica |
| Moth_1452 | YP_430305 | Moorella thermoacetica |
| Moth_1453 | YP_430306 | Moorella thermoacetica |
| Moth_1454 | YP_430307 | Moorella thermoacetica |

This example describes exemplary gene sets for engineering an organism to produce acetyl-CoA from syngas and methanol.

Example XII

Cloning, Expression and Activity Assays for Genes and Encoded Enzymes for Engineering an Organism to Produce Acetyl-CoA from Synthesis Gas and Methanol This example describes the cloning and expression of genes encoding enzymes that provide a syngas and methanol utilizing organism.

Methanol-methyltransferase (MTR). At least the minimal set of genes, for example, MtaA, MtaB, and MtaC, for producing Me-THF from methanol are cloned and expressed in *E. coli*. These genes are cloned via proof-reading PCR and linked together for expression in a high-copy number vector such as pZE22-S under control of the repressible PA1-lacO1 promoter (Lutz and Bujard, *Nucleic Acids Res.* 25:1203-1210 (1997)). Coenzyme B12 is added to the growth medium as these methyltransferase activities require cobalamin as a cofactor. Cloned genes are verified by PCR and/or restriction enzyme mapping to demonstrate construction and insertion of the 3-gene set into the expression vector. DNA sequencing of the presumptive clones is carried out to confirm the expected sequences of each gene. Once confirmed, the final construct is expressed in *E. coli* K-12 (MG1655) cells by addition of isopropyl β-D-1-thiogalactopyranoside (IPTG) inducer between 0.05 and 1 mM final concentration. Expression of the cloned genes is monitored using SDS-PAGE of whole cell extracts. To determine if expression of the MtaABC proteins confers upon *E. coli* the ability to transfer methyl groups from methanol to tetrahydrofolate (THF), methanol is fed to the recombinant strain at varying concentrations and its uptake is monitored along with methyl-THF synthesis. Activity of the methyltransferase system is assayed anaerobically as described for vanillate as a methyl source in *M. thermoacetica* (Naidu and Ragsdale, *J. Bacteriol.* 183: 3276-3281 (2001)) or for the *Methanosarcina barkeri* methanol methyltransferase (Sauer et al., *Eur. J. Biochem.* 243:670-677 (1997); Tallant and Krzycki. *J. Bacteriol.* 178:1295-1301 (1996); Tallant and Krzycki. *J. Bacteriol.* 179:6902-6911 (1997); Tallant et al., *J. Biol. Chem.* 276:4485-4493 (2001)). For a positive control, *E. coli* cells are cultured in parallel, and endogenous methyltransferase activity is monitored. Demonstration that activity depends on exogenously added coenzyme B12 confirms expression of methanol:corrinoid methyltransferase activity in *E. coli*.

Acetyl-CoA synthase/Carbon monoxide dehydrogenase (ACS/CODH). Using standard PCR methods, the entire operons encoding the genes essential for ACS/CODH activity from *M. thermoacetica, C. hydrogenoformans*, and *M. acetivorans* are assembled into a low or medium copy number vector such as pZA33-S (P15A-based) or pZS13-S (pSC101-based). As described for the methyltransferase genes, the structure and sequence of the cloned genes are confirmed. Expression is monitored via protein gel electrophoresis of whole-cell lysates grown under strictly anaerobic conditions with the requisite metals (Ni, Zn, Fe) and coenzyme B12 provided. As necessary, the gene cluster is modified for *E. coli* expression by identification and removal of any apparent terminators and introduction of consensus ribosomal binding sites chosen from sites known to be effective in *E. coli* (Barrick et al., *Nucleic Acids Res.* 22:1287-1295 (1994); Ringquist et al., *Mol. Microbiol.* 6:1219-1229 (1992)). However, each gene cluster is cloned and expressed in a manner parallel to its native structure and expression. This helps ensure the desired stoichiometry between the various gene products, most of which interact with each other. Once satisfactory expression of the CODH/ACS gene cluster under anaerobic conditions is achieved, the ability of cells expressing these genes to fix CO and/or $CO_2$ into cellular carbon is assayed. Initial conditions employ strictly anaerobically grown cells provided with exogenous glucose as a carbon and energy source via substrate-level phosphorylation or anaerobic respiration with nitrate as an electron acceptor. Additionally, exogenously provided $CH_3$-THF is added to the medium.

Assaying activity of the combined MTR and ACS/CODH pathway. The ACS/CODH genes as described in Example II are cloned and expressed in cells also expressing the methanol-methyltransferase system also as described in Example II. This is achieved by introduction of compatible plasmids expressing ACS/CODH into MTR-expressing cells. For added long-term stability, the ACS/CODH and MTR genes can also be integrated into the chromosome. After strains of *E. coli* capable of utilizing methanol to produce Me-THF and of expressing active CODH/ACS gene are made, they are assayed for the ability to utilize both methanol and syngas for incorporation into cell mass and acetate. Initial conditions employ strictly anaerobically grown cells provided with exogenous glucose as a carbon and energy source. Alternatively, or in addition to glucose, nitrate can be added to the fermentation broth to serve as an electron acceptor and initiator of growth. Anaerobic growth of *E. coli* on fatty acids, which are ultimately metabolized to acetyl-CoA, has been demonstrated in the presence of nitrate (Campbell et al., *Mol. Microbiol.* 47:793-805 (2003)). Similar conditions can be employed by culturing the microbial organisms in the presence of an electron acceptor such as nitrate. Oxygen can also be provided as long as its intracellular levels are maintained below any inhibition threshold of the engineered enzymes. "Synthetic syngas" of a composition suitable for these experiments is employed along with methanol. $^{13}$C-labeled methanol or $^{13}$C-labeled CO are provided to the cells, and analytical mass spectrometry is employed to measure incorporation of the labeled carbon into acetate and cell mass, for example, proteinogenic amino acids.

Pyruvate ferredoxin oxidoreductase. The pyruvate ferredoxin oxidoreductase genes from *M. thermoacetica, D. africanus*, and *E. coli* are cloned and expressed in strains exhibiting MTR and ACS/CODH activities. Conditions, promoters, and the like, are described above. Given the large size of the PFOR genes and oxygen sensitivity of the corresponding enzymes, tests are performed using low or single-copy plasmid vectors or single-copy chromosomal integrations. Activity assays (as described in Furdui and Ragsdale, *J. Biol. Chem.* 275:28494-28499 (2000)) are applied to demonstrate activity. In addition, demonstration of growth on the gaseous carbon sources and methanol in the absence of an external electron acceptor provides further evidence for PFOR activity in vivo.

Hydrogenase. The endogenous hydrogen-utilizing hydrogenase activity of the host organism is tested by growing the cells as described above in the presence and absence of hydrogen. If a dramatic shift towards the formation of more reduced products during fermentation is observed (for example, increased ethanol as opposed to acetate), this indicates that endogenous hydrogenase activity is sufficiently active. In this case, no heterologous hydrogenases are cloned and expressed. If the native enzymes do not have sufficient activity or reduce the needed acceptor, the genes encoding an individual hydrogenase complex are cloned and expressed in strains exhibiting MTR, ACS/CODH, and PFOR activities. Conditions, promoters, and the like, are described above.

This example describes the cloning and expression of genes conferring a syngas and methanol utilization pathway and assay for appropriate activities.

Example XIII

Development and Optimization of Fermentation Process for Production of Acetyl-CoA from an Organism Engineered to Utilize Syngas and Methanol This example describes development and optimization of fermentation conditions for syngas and methanol utilizing organisms.

Important process considerations for a syngas fermentation are high biomass concentration and good gas-liquid mass transfer (Bredwell et al., *Biotechnol. Prog.* 15:834-844 (1999)). The solubility of CO in water is somewhat less than that of oxygen. Continuously gas-sparged fermentations can be performed in controlled fermenters with constant off-gas analysis by mass spectrometry and periodic liquid sampling and analysis by GC and HPLC. The liquid phase can function in batch mode. Fermentation products such as alcohols, organic acids, and residual glucose along with residual methanol are quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids. The growth rate is determined by measuring optical density using a spectrophotometer (600 nm). All piping in these systems is glass or metal to maintain anaerobic conditions. The gas sparging is performed with glass frits to decrease bubble size and improve mass transfer. Various sparging rates are tested, ranging from about 0.1 to 1 vvm (vapor volumes per minute). To obtain accurate measurements of gas uptake rates, periodic challenges are performed in which the gas flow is temporarily stopped, and the gas phase composition is monitored as a function of time.

In order to achieve the overall target productivity, methods of cell retention or recycle are employed. One method to increase the microbial concentration is to recycle cells via a tangential flow membrane from a sidestream. Repeated batch culture can also be used, as previously described for production of acetate by *Moorella* (Sakai et al., *J. Biosci. Bioeng.* 99:252-258 (2005)). Various other methods can also be used (Bredwell et al., *Biotechnol. Prog.* 15:834-844 (1999); Datar et al., *Biotechnol. Bioeng.* 86:587-594 (2004)). Additional optimization can be tested such as overpressure at 1.5 atm to improve mass transfer (Najafpour and Younesi, *Enzyme and Microbial Technology* 38:223-228 (2006)).

Once satisfactory performance is achieved using pure $H_2$/CO as the feed, synthetic gas mixtures are generated containing inhibitors likely to be present in commercial syngas. For example, a typical impurity profile is 4.5% $CH_4$, 0.1% $C_2H_2$, 0.35% $C_2H_6$, 1.4% $C_2H_4$, and 150 ppm nitric oxide (Datar et al., *Biotechnol. Bioeng.* 86:587-594 (2004)). Tars, represented by compounds such as benzene, toluene, ethylbenzene, p-xylene, o-xylene, and naphthalene, are added at ppm levels to test for any effect on production. For example, it has been shown that 40 ppm NO is inhibitory to *C. carboxidivorans* (Ahmed and Lewis, *Biotechnol. Bioeng.* 97:1080-1086 (2007)). Cultures are tested in shake-flask cultures before moving to a fermentor. Also, different levels of these potential inhibitory compounds are tested to quantify the effect they have on cell growth. This knowledge is used to develop specifications for syngas purity, which is utilized for scale up studies and production. If any particular component is found to be difficult to decrease or remove from syngas used for scale up, an adaptive evolution procedure is utilized to adapt cells to tolerate one or more impurities.

This example describes development and optimization of fermentation conditions for syngas and methanol utilizing organisms.

Example XIV

Methods for Handling CO and Anaerobic Cultures

This example describes methods for handling CO and anaerobic cultures.

Handling of CO in small quantities for assays and small cultures. CO is an odorless, colorless and tasteless gas that is a poison. Therefore, cultures and assays that utilize CO can require special handling. Several assays, including CO oxidation, acetyl-CoA synthesis, CO concentration using myoglobin, and CO tolerance/utilization in small batch cultures, call for small quantities of the CO gas that can be dispensed and handled within a fume hood. The biochemical assays called for saturating very small quantities (<2 ml) of the biochemical assay medium or buffer with CO and then performing the assay. All of the CO handling steps were performed in a fume hood with the sash set at the proper height and blower turned on; CO was dispensed from a compressed gas cylinder and the regulator connected to a Schlenk line. The latter ensures that equal concentrations of CO will be dispensed to each of several possible cuvettes or vials. The Schlenk line was set up containing an oxygen scrubber on the input side and an oil pressure release bubbler and vent on the other side. Alternatively, a cold trap can be used. Assay cuvettes were both anaerobic and CO-containing. Therefore, the assay cuvettes were tightly sealed with a rubber stopper and reagents added or removed using gas-tight needles and syringes. Secondly, small (~50 ml) cultures were grown with saturating CO in tightly stoppered serum bottles. As with the biochemical assays, the CO-saturated microbial cultures were equilibrated in the fume hood using the Schlenk line setup. Both the biochemical assays and microbial cultures were in portable, sealed containers and in small volumes making for safe handling outside of the fume hood. The compressed CO tank was adjacent to the fume hood.

Typically, a Schlenk line was used to dispense CO to cuvettes, each vented. Rubber stoppers on the cuvettes are pierced with 19 or 20 gage disposable syringe needles and are vented with the same. An oil bubbler is used with a CO tank and oxygen scrubber. The glass or quartz spectrophotometer cuvettes have a circular hole on top into which a Kontes stopper sleeve, Sz7 774250-0007 was fitted. The CO detector unit was positioned proximal to the fume hood.

Handling of CO in larger quantities fed to large-scale cultures. Fermentation cultures are fed either CO or a mixture of CO and $H_2$ to simulate syngas or syngas as a feedstock in fermentative production. Therefore, quantities of cells ranging from 1 liter to several liters can include the addition of CO gas to increase the dissolved concentration of CO in the medium. In these circumstances, fairly large and continuously administered quantities of CO gas will be added to the cultures. At different points, the cultures are harvested or samples removed. Alternatively, cells can be harvested with an integrated continuous flow centrifuge that is part of the fermenter.

The fermentative processes are generally carried out under anaerobic conditions. In some cases, it is uneconomical to pump oxygen or air into fermenters to ensure adequate oxygen saturation to provide a respiratory environment. In addition, the reducing power generated during anaerobic fermentation is likely to be needed in product formation rather than respiration. Furthermore, many of the enzymes being considered for various pathways are oxygen-sensitive to varying degrees. Classic acetogens such as M. thermoacetica are obligate anaerobes and the enzymes in the Wood-Ljungdahl pathway are highly sensitive to irreversible inactivation by molecular oxygen. While there are oxygen-tolerant acetogens, the repertoire of enzymes in the Wood-Ljungdahl pathway are likely to all have issues in the presence of oxygen because most are metallo-enzymes, key components are ferredoxins, and regulation may divert metabolism away from the Wood-Ljungdahl pathway to maximize energy acquisition. At the same time, cells in culture act as oxygen scavengers that moderate the need for extreme measures in the presence of large cell growth.

Anaerobic chamber and conditions. Exemplary anaerobic chambers are available commercially (see, for example, Vacuum Atmospheres Company, Hawthorne Calif.; MBraun, Newburyport Mass.). Exemplary conditions include an $O_2$ concentration of 1 ppm or less and 1 atm pure $N_2$. In one example, 3 oxygen scrubbers/catalyst regenerators can be used, and the chamber can include an $O_2$ electrode (such as Teledyne; City of Industry Calif.). Nearly all items and reagents are cycled 4× in the airlock of the chamber prior to opening the inner chamber door. Reagents with a volume >5 ml are sparged with pure $N_2$ prior to introduction into the chamber. Gloves are changed ~2 X/yr and the catalyst containers are regenerated periodically when the chamber displays increasingly sluggish response to changes in oxygen levels. The chamber's pressure is controlled through one-way valves activated by solenoids. This feature is very convenient because it allows setting the chamber pressure at a level higher than the surroundings to allow transfer of very small tubes through the purge valve.

The anaerobic chambers can achieve levels of $O_2$ that can be reached that are consistently very low and are needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release is controlled by a bubbler. Instead of using instrument-based O2 monitoring, test strips can be used instead. To improve the anaerobic conditions a few relatively simple changes in our system can be made; some are already in progress.

Anaerobic microbiology. Small cultures are handled as described above for CO handling. In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step; each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl can be added. This was made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle should be stoppered immediately as the sodium sulfide solution will generate hydrogen sulfide gas upon contact with the cysteine. When injecting into the culture, a syringe filter is used to sterilize the solution. Other components can be added through syringe needles, such as B12 (10 μM cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 μM—made as 100-1000× stock solution in anaerobic water in the chamber and sterilized by autoclaving or by using a syringe filter upon injection into the culture). To facilitate faster growth under anaerobic conditions, the 1 l bottles were inoculated with 50 ml of a preculture grown anaerobically. Induction of the pA1-lacO1 promoter in the vectors was performed by addition of isopropyl β-D-1-thiogalactopyranoside (IPTG) to a final concentration of 0.2 mM and was carried out for ~3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles can be incubated in an incubator in room air but with continuous nitrogen sparging into the bottles.

This example describes the handling of CO and anaerobic cultures.

Example XV

CO Oxidation (CODH) Assay

This example describes assay methods for measuring CO oxidation (CO dehydrogenase; CODH).

The 7 gene CODH/ACS operon of *Moorella thermoacetica* was cloned into *E. coli* expression vectors. The intact ~10 kbp DNA fragment was cloned, and it is likely that some of the genes in this region are expressed from their own endogenous promoters and all contain endogenous ribosomal binding sites. *M. thermoacetica* is Gram positive, and ribosome binding site elements are expected to work well in *E. coli*. These clones were assayed for CO oxidation, using an assay that quantitatively measures CODH activity. Antisera to the *M. thermoacetica* gene products was used for Western blots to estimate specific activity. This activity, described below in more detail, was estimated to be ~1/50th of the *M. thermoacetica* specific activity.

It is possible that CODH activity of recombinant *E. coli* cells could be limited by the fact that *M. thermoacetica* enzymes have temperature optima around 55° C. Therefore, a mesophilic CODH/ACS pathway could be advantageous such as the close relative of *Moorella* that is mesophilic and does have an apparently intact CODH/ACS operon and a Wood-Ljungdahl pathway, *Desulfitobacterium hafniense*. Acetogens as potential host organisms include, but are not limited to, *Rhodospirillum rubrum, Moorella thermoacetica* and *Desulfitobacterium hafniense*.

CO oxidation is both the most sensitive and most robust of the CODH/ACS assays. It is likely that an *E. coli*-based syngas using system will ultimately need to be about as anaerobic as *Clostridial* (i.e., *Moorella*) systems, especially for maximal activity. Improvement in CODH should be possible but will ultimately be limited by the solubility of CO gas in water.

Initially, each of the genes was cloned individually into expression vectors. Combined expression units for multiple subunits/1 complex were generated. Expression in *E. coli* at the protein level was determined. Both combined *M. thermoacetica* CODH/ACS operons and individual expression clones were made.

CO oxidation assay. This assay is one of the simpler, reliable, and more versatile assays of enzymatic activities within the Wood-Ljungdahl pathway and tests CODH (Seravalli et al., *Biochemistry* 43:3944-3955 (2004)). A typical activity of *M. thermoacetica* CODH specific activity is 500 U at 55° C. or ~60 U at 25° C. This assay employs reduction of methyl viologen in the presence of CO. This is measured at 578 nm in stoppered, anaerobic, glass cuvettes.

In more detail, glass rubber stoppered cuvettes were prepared after first washing the cuvette 4× in deionized water and 1× with acetone. A small amount of vacuum grease was smeared on the top of the rubber gasket. The cuvette was gassed with CO, dried 10 min with a 22 Ga. needle plus an exhaust needle. A volume of 0.98 ml of reaction buffer (50 mM Hepes, pH 8.5, 2 mM dithiothreitol (DTT) was added using a 22 Ga. needle, with exhaust needled, and 100% CO. Methyl viologen ($CH_3$ viologen) stock was 1 M in water. Each assay used 20 microliters for 20 mM final concentration. When methyl viologen was added, an 18 Ga needle (partial) was used as a jacket to facilitate use of a Hamilton syringe to withdraw the $CH_3$ viologen. 4-5 aliquots were drawn up and discarded to wash and gas equilibrate the syringe. A small amount of sodium dithionite (0.1 M stock) was added when making up the $CH_3$ viologen stock to slightly reduce the $CH_3$ viologen. The temperature was equilibrated to 55° C. in a heated Olis spectrophotometer (Bogart Ga.). A blank reaction ($CH_3$ viologen+buffer) was run first to measure the base rate of $CH_3$ viologen reduction. Crude *E. coli* cell extracts of ACS90 and ACS91 (CODH-ACS operon of *M. thermoacetica* with and without, respectively, the first cooC). 10 microliters of extract were added at a time, mixed and assayed. Reduced $CH_3$ viologen turns purple. The results of an assay are shown in Table X

TABLE 2

| Crude extract CO Oxidation Activities. | | | | |
|---|---|---|---|---|
| ACS90 | 7.7 mg/ml | ACS91 | | 11.8 mg/ml |
| Mta98 | 9.8 mg/ml | Mta99 | | 11.2 mg/ml |
| Extract | Vol | OD/ | U/ml | U/mg |
| ACS90 | 10 microliters | 0.073 | 0.376 | 0.049 |
| ACS91 | 10 microliters | 0.096 | 0.494 | 0.042 |
| Mta99 | 10 microliters | 0.0031 | 0.016 | 0.0014 |
| ACS90 | 10 microliters | 0.099 | 0.51 | 0.066 |
| Mta99 | 25 microliters | 0.012 | 0.025 | 0.0022 |
| ACS91 | 25 microliters | 0.215 | 0.443 | 0.037 |
| Mta98 | 25 microliters | 0.019 | 0.039 | 0.004 |
| ACS91 | 10 microliters | 0.129 | 0.66 | 0.056 |
| Averages | | | | |
| ACS90 | | 0.057 U/mg | | |
| ACS91 | | 0.045 U/mg | | |
| Mta99 | | 0.0018 U/mg | | |

Mta98/Mta99 are *E. coli* MG1655 strains that express methanol methyltransferase genes from *M. thermoacetia* and, therefore, are negative controls for the ACS90 ACS91 *E. coli* strains that contain *M. thermoacetica* CODH operons.

If ~1% of the cellular protein is CODH, then these figures would be approximately 100× less than the 500 U/mg activity of pure *M. thermoacetica* CODH. Actual estimates based on Western blots are 0.5% of the cellular protein, so the activity is about 50× less than for *M. thermoacetica* CODH. Nevertheless, this experiment did clearly demonstrate CO oxidation activity in recombinant *E. coli* with a much smaller amount in the negative controls. The small amount of CO oxidation ($CH_3$ viologen reduction) seen in the negative controls indicates that *E. coli* may have a limited ability to reduce $CH_3$ viologen.

Figure 9:
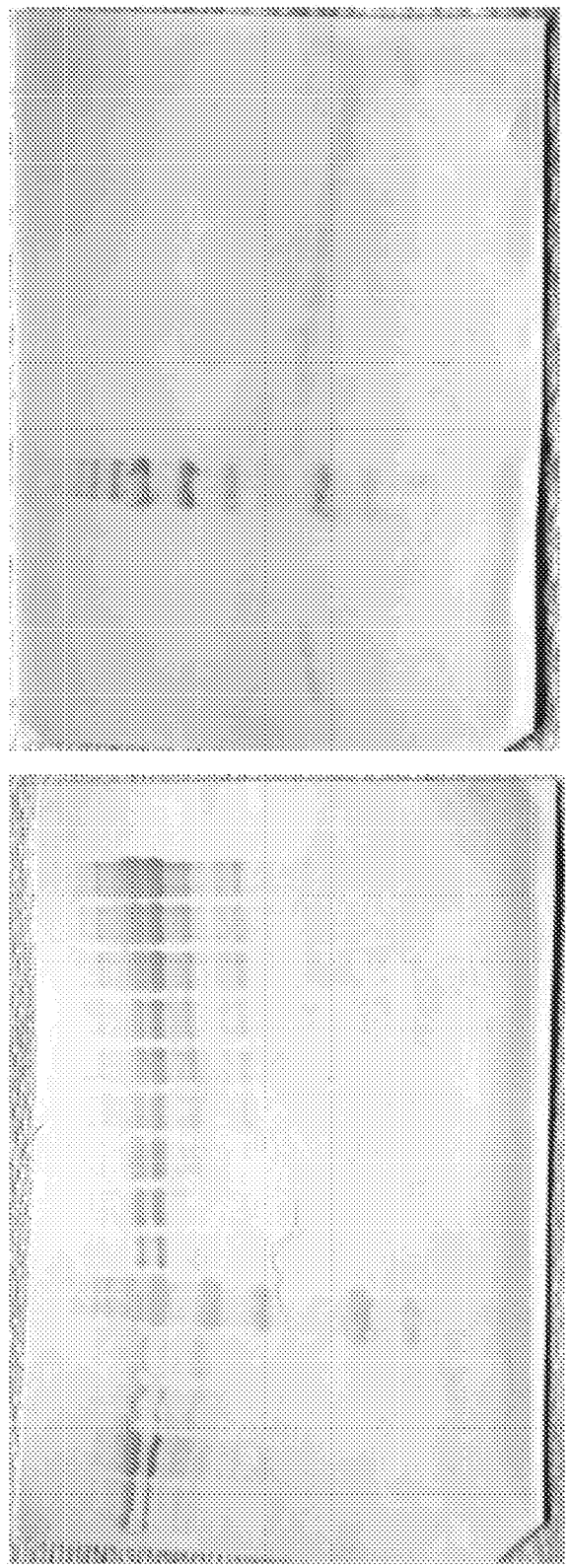
FIG. 9 shows Western blots of 10 micrograms ACS90 (lane 1), ACS91 (lane 2), Mta98/99 (lanes 3 and 4) cell extracts with size standards (lane 5) and controls of *M. thermoacetica* CODH (Moth_1202/1203) or Mtr (Moth_1197) proteins (50, 150, 250, 350, 450, 500, 750, 900, and 1000 ng).

To estimate the final concentrations of CODH and Mtr proteins, SDS-PAGE followed by Western blot analyses were performed on the same cell extracts used in the CO oxidation, ACS, methyltransferase, and corrinoid Fe—S assays. The antisera used were polyclonal to purified *M. thermoacetica* CODH-ACS and Mtr proteins and were visualized using an alkaline phosphatase-linked goat-anti-rabbit secondary antibody. The Westerns were performed and results are shown in FIGS. 9A and 9B. The amounts of CODH in ACS90 and ACS91 were estimated at 50 ng by comparison to the control lanes. Expression of CODH-ACS operon genes including 2 CODH subunits and the methyltransferase were confirmed via Western blot analysis. Therefore, the recombinant *E. coli* cells express multiple components of a 7 gene operon. In addition, both the methyltransferase and corrinoid iron sulfur protein were active in the same recombinant *E. coli* cells. These proteins are part of the same operon cloned into the same cells.

Figure 10:
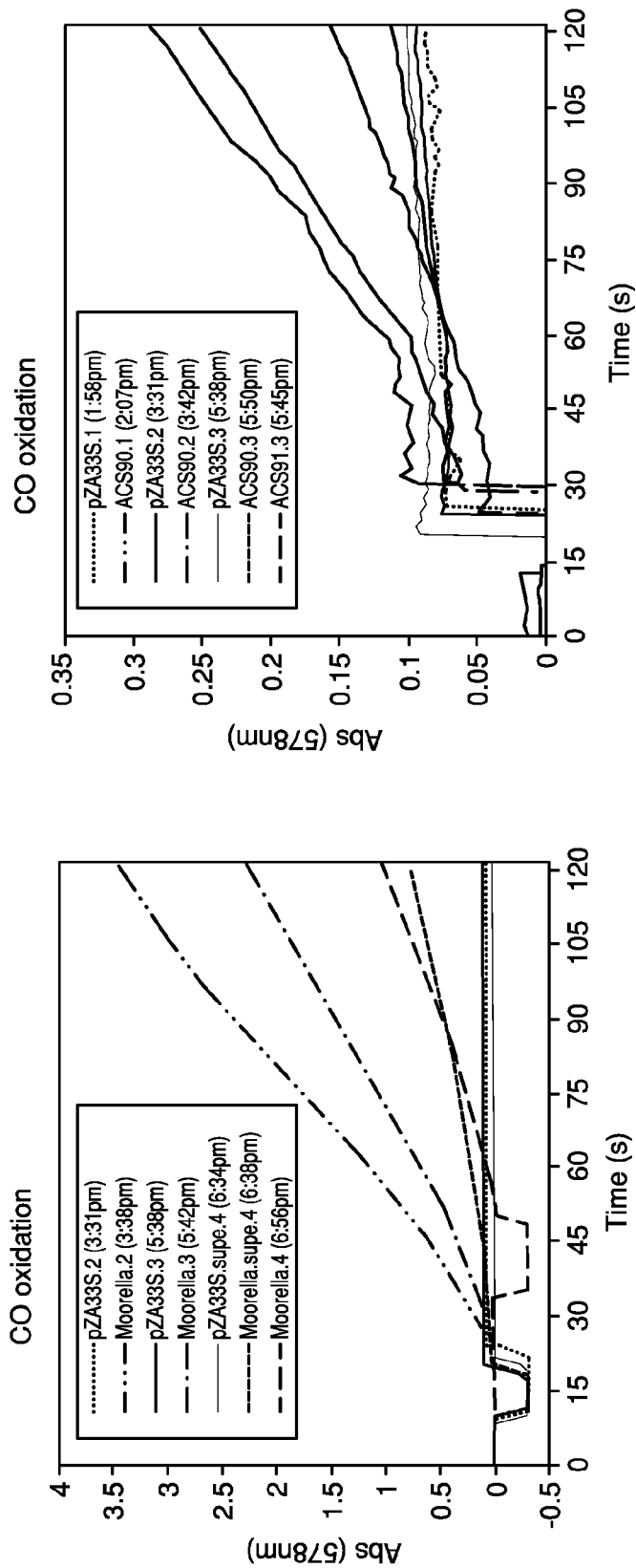
FIG. 10 shows CO oxidation assay results. Cells (*M. thermoacetica* or *E. coli* with the CODH/ACS operon; ACS90 or ACS91 or empty vector: pZA33S) were grown and extracts prepared. Assays were performed at 55° C. at various times on the day the extracts were prepared. Reduction of methylviologen was followed at 578 nm over a 120 sec time course.

The CO oxidation assays were repeated using extracts of *Moorella thermoacetica* cells for the positive controls. Though CODH activity in *E. coli* ACS90 and ACS91 was measurable, it was at about 130-150× lower than the *M. thermoacetica* control. The results of the assay are shown in FIG. 10. Briefly, cells (*M. thermoacetica* or *E. coli* with the CODH/ACS operon; ACS90 or ACS91 or empty vector: pZA33S) were grown and extracts prepared as described above. Assays were performed as described above at 55° C. at various times on the day the extracts were prepared. Reduction of methylviologen was followed at 578 nm over a 120 sec time course.

These results describe the CO oxidation (CODH) assay and results. Recombinant *E. coli* cells expressed CO oxidation activity as measured by the methyl viologen reduction assay.

Example XVI

Acetyl-CoA Synthase (ACS) Activity Assay (CO Exchange Assay)

This example describes an ACS assay method.

This assay measures the ACS-catalyzed exchange of the carbonyl group of acetyl-CoA with CO (Raybuck et al., *Biochemistry* 27:7698-7702 (1988)). ACS (as either a purified enzyme or part of a cell extract) is incubated with acetyl-CoA labeled with $^{14}C$ at the carbonyl carbon under a CO atmosphere. In the presence of active ACS, the radioactivity in the liquid phase of the reaction decreases exponentially until it reaches a minimum defined by the equilibrium between the levels of $^{14}C$-labeled acetyl-CoA and $^{14}C$-labeled CO. The same cell extracts of *E. coli* MG1655 expressing ACS90 and ACS91 employed in the other assays as well as control extracts were assayed by this method.

Briefly in more detail, in small assay vials under normal atmosphere, a solution of 0.2 mM acetyl-CoA, 0.1 mM methyl viologen, and 2 mM Ti(III)citrate in 0.3M MES buffer, pH 6.0, was made. The total reaction volume when all components are added was 500 µl. Vials were sealed with rubber stoppers (Bellco) and crimp aluminum seals (Bellco) to create a gas-tight reaction atmosphere. Each vial was sparged with 100% CO for several minutes, long enough to completely exchange the vials' atmosphere, and brought into an anaerobic chamber. The assay vials were placed in a 55° C. sand bath and allowed to equilibrate to that temperature. A total of 10 scintillation vials with 40 µl of 1M HCl were prepared for each assay vial. A gas-tight Hamilton syringe was used to add ACS to the assay vial and incubated for approximately 2-3 minutes for the reaction to come to equilibrium. A gas-tight Hamilton syringe was used to add 1 µl (0.36 nmoles) $^{14}C$-acetyl-CoA to start the assay (time=0 min). Time points were taken starting immediately. Samples (40 µl) were removed from the assay vials with a gas-tight Hamilton syringe. Each sample was added to the 40 µl of HCl in the prepared scintillation vials to quench the reaction. As the ACS enzyme transfers $^{14}C$ label to CO from acetyl-CoA, the concentration of the isotope decreases exponentially. Therefore, the assay was sampled frequently in the early time points. The precise time for each sample was recorded. The exact pace of the reaction depends on the ACS enzyme, but generally several samples are taken immediately and sampled over the initial 10-15 minutes. Samples are continued to be taken for 1-2 hours.

In a particular exemplary assay, four assay conditions were used: blank (no ACS), 12 µl of purified *E. coli* strains expressing *M. thermoacetica* ACS, 4 µl of purified *E. coli* ACS, and 3.7 µl of *M. thermoacetica* CODH/ACS. In another exemplary assay, four assay conditions were used: 108 µg CODH/ACS, 1 mg Mta99 cell extract, 1 mg ACS90 cell extract, and 1 mg ACS91 cell extract. The enzymes were added as 100 µl solutions (50 mM KPi, 0.1M NaCl, pH7.6). A more sensitive assay that can be used for most of the CODH-ACS activities is the synthesis assay described below.

This example describes the assay conditions for measuring ACS activity.

Example XVII

Acetyl-CoA Synthesis and Methyltransferase Assays

This example describes acetyl-CoA synthesis and methyltransferase assays.

Synthesis assay. This assay is an in vitro reaction that synthesizes acetyl-CoA from methyl-tetrahydrofolate, CO, and CoA using CODH/ACS, methyltransferase (MeTr), and corrinoid Fe—S protein (CFeSP) (Raybuck et al., Biochemistry 27:7698-7702 (1988)). By adding or leaving out each of the enzymes involved, this assay can be used for a wide range of experiments, from testing one or more purified enzymes or cell extracts for activity, to determining the kinetics of the reaction under various conditions or with limiting amounts of substrate or enzyme. Samples of the reaction taken at various time points are quenched with 1M HCl, which liberates acetate from the acetyl-CoA end product. After purification with Dowex columns, the acetate can be analyzed by chromatography, mass spectrometry, or by measuring radioactivity. The exact method will be determined by the specific substrates used in the reaction.

A $^{14}$C-labeled methyl-THF was utilized, and the radioactivity of the isolated acetate samples was measured. The primary purpose was to test CFeSP subunits. The assay also included +/− purified methyltransferase enzymes. The following 6 different conditions were assayed: (1) purified CODH/ACS, MeTr, and CFeSP as a positive control; (2) purified CODH/ACS with ACS90 cell extract; (3) purified CODH/ACS with ACS91 cell extract; (4) purified CODH/ACS, MeTr with ACS90 cell extract; (5) purified CODH/ACS, MeTr with ACS91 cell extract; (6) purified CODH/ACS, MeTr with as much ACS91 cell extract as possible (excluding the MES buffer).

The reaction is assembled in the anaerobic chamber in assay vials that are filled with CO. The total reaction volume is small compared to the vial volume, so the reagents can be added before or after the vial is filled with CO, so long as a gas-tight Hamilton syringe is used and the reagents are kept anaerobic. The reaction (~60 ul total) consisted of the cell extract (except assay #1), CoA, Ti(III)citrate, MES (except assay #6), purified CODH/ACS, $^{14}$C-methyl-tetrahydrofolate, methyl-viologen, and ferredoxin. Additionally, purified MeTr was added to assays #1 and #4-6, and purified CFeSP was added to assay #1.

The reaction was carried out in an anaerobic chamber in a sand bath at 55° C. The final reagent added was the $^{14}$C-methyl-tetrahydrofolate, which started the reaction (t=0s). An initial sample was taken immediately, followed by samples at 30 minutes, 1 hour, and 2 hours. These time points are not exact, as the 6 conditions were run concurrently (since this experiment was primarily a qualitative one). The 15 μl samples were added to 15 μl of 1M HCl in scintillation vials. For the last sample, if less than 15 μl was left in the reactions, the assay vials were rinsed with the 15 ul of HCl to take the remainder of the reaction. A volume of 10 μl of cell extract was used for assay #2-5, and 26.4 μl of cell extract was used for assay #6.

Typical amounts of purified enzyme to be used in the assays is as follows: CODH/ACS=~0.2 nmoles; MeTr=0.2 nmoles; CFeSP=0.05 nmoles. Typical assay concentrations are used as follows: CODH/ACS=1 uM; Me-CFeSP=0.4 uM; MeTr=1 uM; Ferredoxin=3 uM; CoA=0.26 mM; $^{14}$C methyl-THF=0.4 mM; methyl viologen=0.1 mM; and Ti(III)citrate=3 mM.

After counting the reaction mixtures, it was determined that the corrinoid Fe—S protein in ACS90 extracts was active with total activity approaching approximately ⅓ of the positive control and significantly above the negative control (no extract).

A non-radioactive synthesis assay can also be used. Optional non-radioactive assay conditions are as follows: Assay condition #1: 100 mM MES, pH 6.0; 1 mM CoA; 1 mM Me-THF; 0.33 mM Ti(III) citrate, volume to 950 ul, +50 ul of extract; incubated under a CO atmosphere (Ar for control), at 55° C. These reactions should be carried out in the dark, as the corrinoid methyl carrier is light sensitive. Assay condition #2: 100 mM MES, pH 6.0; 1 mM CoA; 1 mM Me-THF; 1 mM methyl viologen; volume to 950 ul, +50 ul of extract; incubated under a CO atmosphere, at 55° C., in the dark. The reaction was quenched with 10 μl of 10% formic acid, with samples taken at 1 hr, 3 hrs, and 6.5 hrs, and stored at −20°. Assay condition #3: 100 mM Tris, pH 7.6; 5 mM CoA; 7.5 mM Me-THF; 1 mM Me-viologen; volume to 90 μl, +10 μl extract; incubated under CO or Ar, at 55° C. in the dark for 1hr, quenched with 10 μl 10% formic acid, and stored at −20° C.

In Lu et al., (*J. Biol. Chem.* 265:3124-3133. (1990)), the pH optimum for the synthesis reaction was found to be between 7.2-7.5. Lu et al. also found that CoA concentrations above 10 mM were inhibitory. Lu et al. described using methyl iodide as the methyl donor instead of Me-THF, and used 5-7.5 mM concentrations. Lu et al. also determined that DTT or other reducing agents were not necessary, although they did use ferredoxin as an electron carrier. Methyl viologen was substituted in the above-described reactions. In addition, Maynard et al., *J. Biol. Inorg. Chem.* 9:316-322 (2004), has determined that the electron carrier was not strictly necessary, but that failure to include one resulted in a time lag of the synthesis. Maynard et al. used 1 mM methyl viologen as electron carrier when one was used.

Methyltransferase Assay. Within the CODH-ACS operon is encoded an essential methyltransferase activity that catalyzes the transfer of $CH_3$ from methyl-tetrahydrofolate to the ACS complex as part of the synthesis of acetyl-CoA. This is the step that the methyl and carbonyl pathways join together. Within the operon in *M. thermoacetica*, the Mtr-encoding gene is Moth_1197 and comes after the main CODH and ACS subunits. Therefore, Mtr activity would constitute indirect evidence that the more proximal genes can be expressed.

Mtr activity was assayed by spectroscopy. Specifically, methylated CFeSP, with Co(III), has a small absorption peak at ~450 nm, while non-methylated CFeSP, with Co(I), has a large peak at ~390 nm. This spectrum is due to both the cobalt and iron-sulfur cluster chromophores. Additionally, the CFeSP can spontaneously oxidize to Co(II), which creates a broad absorption peak at ~470 nm (Seravalli et al., *Biochemistry* 38:5728-5735 (1999)). Recombinant methyltransferase is tested using *E. coli* cell extracts, purified CFeSP from *M. thermoacetica*, and methyl-tetrahydrofolate. The methylation of the corrinoid protein is observed as a decrease in the absorption at 390 nm with a concurrent increase in the absorption at 450 nm, along with the absence of a dominant peak at 470 nm.

Non-radioactive assays are also being developed using $^{13}$C-methanol. This should transfer to tetrahydrofolate and create a MTHF of molecular mass +1. Alternatively, the methyltransferase is thought to also work by transfer of the methanol methyl group to homocysteine to form methionine. This assay is also useful because methionine +1 mass is more readily detectable than MTHF +1 or some other possibilities. In addition to using 13C, deuterium can also be used as a tracer, both of which can be measured using mass spectrometry. These tracers can also be used in in vivo labeling studies. Other assay methods can be used to determine various intermediates or products including, for example, electron paramagnetic resonance (EPR), Mossbauer spectroscopy, Electron-Nuclear DOuble Resonance (ENDOR), infrared, magnetic circular dichroism (MCD), crystallography, X-ray absorption, as well as kinetic methods, including stopped flow and freeze-quench EPR.

Figure 8:
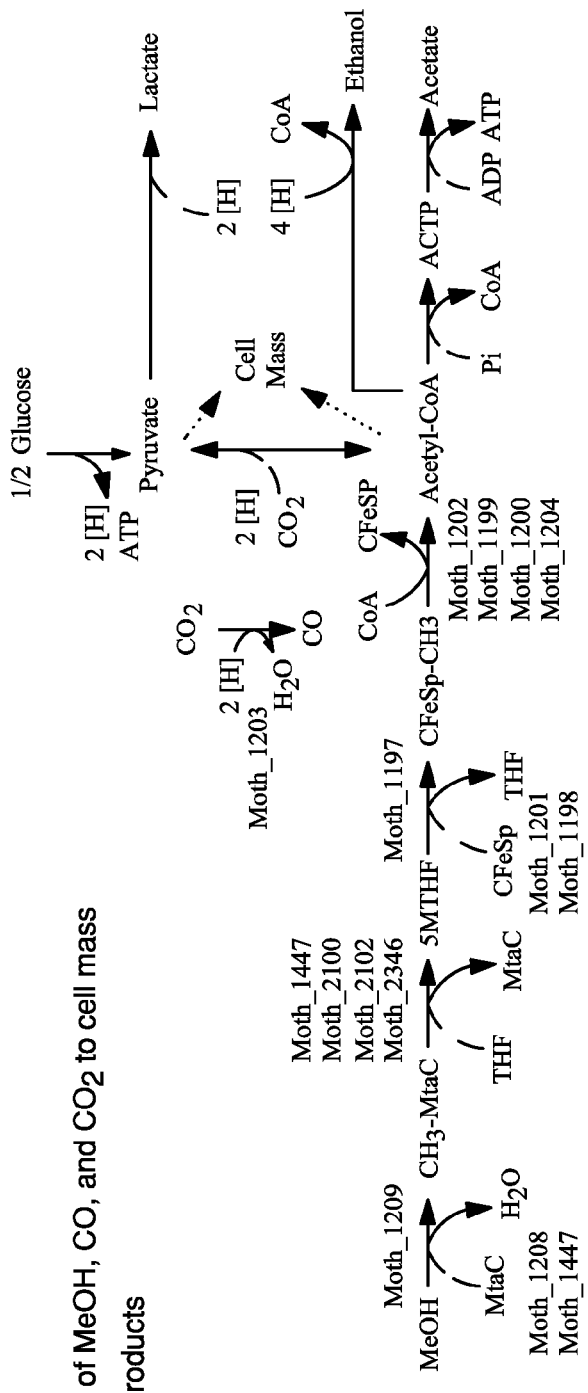
FIG. 8 shows a pathway for conversion of methanol, CO and $CO_2$ to cell mass and fermentation products.

FIG. 8 illustrates how methanol methyltransferase can be fitted into a CODH/ACS ('syngas') pathway. Essentially, the methyl group of methanol is transferred via a cobabalamin-dependent process to tetrahydrofolate and then to the corrinoid-FeS protein of CODH/ACS (also a cobalamin protein) and that, in turn, donates the methyl group to the ACS reaction that results in acetate synthesis. The methanol methyltransferase complex consists of three gene products; two of these, MtaB and MtaC, (Moth_1209 and Moth_1208) are adjacent and were readily cloned. The third, MtaA, may be encoded by three different genes (Moth_2100, Moth_2102, and Moth_2346), and it unclear whether all three genes are required or whether a subset of the three can function. All cloning in *E. coli* was performed using the Lutz-Bujard vectors (Lutz and Bujard, *Nucleic Acids Res.* 25:1203-1210 (1997)).

The following assay can be used to determine the activity of MtaB that encodes a methanol methyltransferase gene product. A positive control for the latter can be performed with vanillate o-demethylation.

Methanol Methyltransferase reaction. An examplary methanol methyl-transfer reaction has been described previously (Sauer and Thauer, Eur. J. Biochem. 249:280-285 (1997); Naidu and Ragsdale, J. Bacteriol. 183:3276-3281 (2001)). The reaction conditions are as follows: 50 mM MOPS/KOH, pH 7.0; 10 mM $MgCl_2$; 4 mM Ti(III) citrate; 0.2% dodecylmaltoside (replacing SDS, see Sauer and. Thauer, Eur. J. Biochem. 253:698-705 (1998)); 25 μM hydroxycobalamin; 1% MeOH or 1 mM vanillate (depending on the methyl transferase version).

These reactions are measured by spectrograph readings in the dark at 37° C. or 55° C. This assay tests the ability of MtaB or MtvB to transfer the methyl group to cobalamin from methanol or vanillate, respectively.

Example XVIII

E. coli CO Tolerance Experiment and CO Concentration Assay (Myoglobin Assay)

This example describes the tolerance of E. coli for high concentrations of CO.

To test whether or not E. coli can grow anaerobically in the presence of saturating amounts of CO, cultures were set up in 120 ml serum bottles with 50 ml of Terrific Broth medium (plus reducing solution, $NiCl_2$, $Fe(II)NH_4SO_4$, cyanocobalamin, IPTG, and chloramphenicol) as described above for anaerobic microbiology in small volumes. One half of these bottles were equilibrated with nitrogen gas for 30 min. and one half was equilibrated with CO gas for 30 min. An empty vector (pZA33) was used as a control, and cultures containing the pZA33 empty vector as well as both ACS90 and ACS91 were tested with both $N_2$ and CO. All were inoculated and grown for 36 hrs with shaking (250 rpm) at 37° C. At the end of the 36 hour period, examination of the flasks showed high amounts of growth in all. The bulk of the observed growth occurred overnight with a long lag.

Given that all cultures appeared to grow well in the presence of CO, the final CO concentrations were confirmed. This was performed using an assay of the spectral shift of myoglobin upon exposure to CO. Myoglobin reduced with sodium dithionite has an absorbance peak at 435 nm; this peak is shifted to 423 nm with CO. Due to the low wavelength and need to record a whole spectrum from 300 nm on upwards, quartz cuvettes must be used. CO concentration is measured against a standard curve and depends upon the Henry's Law constant for CO of maximum water solubility=970 micromolar at 20° C. and 1 atm.

For the myoglobin test of CO concentration, cuvettes were washed 10× with water, 1× with acetone, and then stoppered as with the CODH assay. $N_2$ was blown into the cuvettes for ~10 min. A volume of 1 ml of anaerobic buffer (HEPES, pH 8.0, 2 mM DTT) was added to the blank (not equilibrated with CO) with a Hamilton syringe. A volume of 10 microliter myoglobin (~1 mM—can be varied, just need a fairly large amount) and 1 microliter dithionite (20 mM stock) were added. A CO standard curve was made using CO saturated buffer added at 1 microliter increments. Peak height and shift was recorded for each increment. The cultures tested were pZA33/CO, ACS90/CO, and ACS91/CO. each of these was added in 1 microliter increments to the same cuvette. Midway through the experiment a second cuvette was set up and used. The results are shown in Table 3.

TABLE 3

| Carbon Monoxide Concentrations, 36 hrs. | |
|---|---|
| Strain and Growth Conditions | Final CO concentration (micromolar) |
| pZA33-CO | 930 |
| ACS90-CO | 638 |
|  | 494 |
|  | 734 |
|  | 883 |
| ave | 687 |
| SD | 164 |
| ACS91-CO | 728 |
|  | 812 |
|  | 760 |
|  | 611 |
| ave. | 728 |
| SD | 85 |

The results shown in Table 3 indicate that the cultures grew whether or not a strain was cultured in the presence of CO or not. These results indicate that E. coli can tolerate exposure to CO under anaerobic conditions and that E. coli cells expressing the CODH-ACS operon can metabolize some of the CO.

These results demonstrate that E. coli cells, whether expressing CODH/ACS or not, were able to grow in the presence of saturating amounts of CO. Furthermore, these grew equally well as the controls in nitrogen in place of CO. This experiment demonstrated that laboratory strains of E. coli are insensitive to CO at the levels achievable in a syngas project performed at normal atmospheric pressure. In addition, preliminary experiments indicated that the recombinant E. coli cells expressing CODH/ACS actually consumed some CO, probably by oxidation to carbon dioxide.

Example IXX

Exemplary Pathways for Production of 4-Hydroxybutyrate and 1,4-Butanediol

This example describes exemplary pathways for the production of 4-hydroxybutyrate and 1,4-butanediol from acetyl-CoA.

As disclosed herein, the combination of (1) pathways for the conversion of synthesis gases with and without methanol to acetyl-CoA and (2) pathways for the conversion of acetyl-CoA to 4-hydroxybutyrate, or 1,4-butanediol. As such, this invention provides production organisms and conversion routes with inherent yield advantages over organisms engineered to produce 4-hydroxybutyrate, or 1,4-butanediol from carbohydrate feedstocks. For example, the maximum theoretical yields of 4-hydroxybutyrate, and 1,4-butanediol from glucose are 1 mole per mole using the metabolic pathways proceeding from acetyl-CoA as described herein. Specifically, 2 moles of acetyl-CoA are derived per mole of glucose via glycolysis and 2 moles of acetyl-CoA are required per mole of 4-hydroxybutyrate, or 1,4-butanediol. The net conversions are described by the following stoichiometric equations:

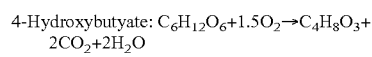
4-Hydroxybutyate: $C_6H_{12}O_6 + 1.5O_2 \rightarrow C_4H_8O_3 + 2CO_2 + 2H_2O$

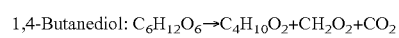
1,4-Butanediol: $C_6H_{12}O_6 \rightarrow C_4H_{10}O_2 + CH_2O_2 + CO_2$ On the other hand, gasification of glucose to its more simpler components, CO and $H_2$, followed by their conversion to 4-hydroxybutyrate, and 1,4-butanediol using the pathways described herein results in the following maximum theoretical yields:

4-Hydroxybutyate: $6CO+6H_2 \rightarrow 1.333C_4H_8O_3 + 0.667CO_2 + 0.667H_2O$ 1,4-Butanediol: $6CO+6H_2 \rightarrow 1.091C_4H_{10}O_2 + 1.636CO_2 + 0.545H_2O$ Note that the gasification of glucose can at best provide 6 moles of CO and 6 moles of $H_2$. The maximum theoretical yields of 4-hydroxybutyrate, and 1,4-butanediol from synthesis gases can be further enhanced by the addition of methanol as described below:

4-Hydroxybutyate: $CH_4O+6CO+6H_2 \rightarrow 1.667C_4H_8O_3 + 0.333CO_2 + 1.333H_2O$ 1,4-Butanediol: $CH_4O+6CO+6H_2 \rightarrow 1.364C_4H_{10}O_2 + 1.545CO_2 + 1.182H_2O$ 4-Hydroxybutyate: $2CH_4O+6CO+6H_2 \rightarrow 2C_4H_8O_3 + 2H_2O$ 1,4-Butanediol: $2CH_4O+6CO+6H_2 \rightarrow 1.636C_4H_{10}O_2 + 1.455CO_2 + 1.818H_2O$ Thus it is clear that the organisms and conversion routes described herein provide an efficient means of converting carbohydrates to 4-hydroxybutyrate, or 1,4-butanediol.

Acetoacetyl-CoA thiolase converts two molecules of acetyl-CoA into one molecule each of acetoacetyl-CoA and CoA. Exemplary acetoacetyl-CoA thiolase enzymes include the gene products of atoB from *E. coli* (Martin et al., *Nat. Biotechnol* 21:796-802 (2003)), thlA and thlB from *C. acetobutylicum* (Hanai et al., *Appl Environ Microbiol* 73:7814-7818 (2007); Winzer et al., *J. Mol. Microbiol Biotechnol* 2:531-541 (2000), and ERG10 from *S. cerevisiae* Hiser et al., *J. Biol. Chem.* 269:31383-31389 (1994)).

| Protein | GenBank ID | Organism |
|---------|------------|----------|
| AtoB | NP_416728 | *Escherichia coli* |
| ThlA | NP_349476.1 | *Clostridium acetobutylicum* |
| ThlB | NP_149242.1 | *Clostridium acetobutylicum* |
| ERG10 | NP_015297 | *Saccharomyces cerevisiae* |

Exemplary 3-hydroxyacyl dehydrogenases which convert acetoacetyl-CoA to 3-hydroxybutyryl-CoA include hbd from *C. acetobutylicum* (Boynton et al., Journal of Bacteriology 178:3015-3024 (1996)), hbd from *C. beijerinckii* (Colby and Chen et al., Appl Environ. Microbio 158:3297-3302 (1992)), and a number of similar enzymes from *Metallosphaera sedula* (Berg et al., 2007 Science 318:1782-1786 (2007)).

| Protein | GenBank ID | Organism |
|---------|------------|----------|
| hbd | NP_349314.1 | *Clostridium acetobutylicum* |
| hbd | AAM14586.1 | *Clostridium beijerinckii* |
| Msed_1423 | YP_001191505 | *Metallosphaera sedula* |
| Msed_0399 | YP_001190500 | *Metallosphaera sedula* |
| Msed_0389 | YP_001190490 | *Metallosphaera sedula* |
| Msed_1993 | YP_001192057 | *Metallosphaera sedula* |

The gene product of crt from *C. acetobutylicum* catalyzes the dehydration of 3-hydroxybutyryl-CoA to crotonyl-CoA (Atsumi et al., *Metab Eng* (2007); Boynton et al., *Journal of Bacteriology* 178:3015-3024 (1996)). Further, enoyl-CoA hydratases are reversible enzymes and thus suitable candidates for catalyzing the dehydration of 3-hydroxybutyryl-CoA to crotonyl-CoA. The enoyl-CoA hydratases, phaA and phaB, of *P. putida* are believed to carry out the hydroxylation of double bonds during phenylacetate catabolism (Olivera et al., *Proc Nat Acad Sci U.S.A.* 95:6419-6424 (1998)). The paaA and paaB from *P. fluorescens* catalyze analogous transformations (Olivera et al., *Proc Nat Acad Sci U.S.A.* 95:6419-6424 (1998)). Lastly, a number of *Escherichia coli* genes have been shown to demonstrate enoyl-CoA hydratase functionality including maoC, paaF, and paaG (Ismail et al., *European Journal of Biochemistry* 270:3047-3054 (2003); Park and Lee, *J Bacteriol.* 185:5391-5397 (2003); Park and Lee, *Appl Biochem. Biotechnol* 113-116:335-346 (2004); Park and Yup, *Biotechnol Bioeng* 86:681-686 (2004)).

| Protein | GenBank ID | Organism |
|---------|------------|----------|
| crt | NP_349318.1 | *Clostridium acetobutylicum* |
| paaA | NP_745427.1 | *Pseudomonas putida* |
| paaB | NP_745426.1 | *Pseudomonas putida* |
| phaA | ABF82233.1 | *Pseudomonas fluorescens* |
| phaB | ABF82234.1 | *Pseudomonas fluorescens* |
| maoC | NP_415905.1 | *Escherichia coli* |
| paaF | NP_415911.1 | *Escherichia coli* |
| paaG | NP_415912.1 | *Escherichia coli* |

Several enzymes that naturally catalyze the reverse reaction (i.e., the dehydration of 4-hydroxybutyryl-CoA to crotonoyl-CoA) in vivo have been identified in numerous species. This transformation is used for 4-aminobutyrate fermentation by *Clostridium aminobutyricum* (Scherf and Buckel, *Eur. J Biochem.* 215:421-429 (1993)) and succinate-ethanol fermentation by *Clostridium kluyveri* (Scherf et al., *Arch. Microbiol* 161:239-245 (1994)). The transformation is also a step in Archaea, for example, *Metallosphaera sedula*, as part of the 3-hydroxypropionate/4-hydroxybutyrate autotrophic carbon dioxide assimilation pathway (Berg et al., *Science* 318:1782-1786 (2007)). This pathway uses the hydration of crotonoyl-CoA to form 4-hydroxybutyryl-CoA. The reversibility of 4-hydroxybutyryl-CoA dehydratase is well-documented (Friedrich et al., *Angew. Chem. Int. Ed. Engl.* 47:3254-3257 (2008); Muh et al., *Eur. J. Biochem.* 248:380-384 (1997); Muh et al., *Biochemistry* 35:11710-11718 (1996)) and the equilibrium constant has been reported to be about 4 on the side of crotonoyl-CoA (Scherf and Buckel, *Eur. J Biochem.* 215:421-429 (1993)). This indicates that the downstream 4-hydroxybutyryl-CoA dehydrogenase keeps the 4-hydroxybutyryl-CoA concentration low so as to not create a thermodynamic bottleneck at crotonyl-CoA.

| Protein | GenBank ID | Organism |
|---------|------------|----------|
| AbfD | CAB60035 | *Clostridium aminobutyricum* |
| AbfD | YP_001396399 | *Clostridium kluyveri* |
| Msed_1321 | YP_001191403 | *Metallosphaera sedula* |
| Msed_1220 | YP_001191305 | *Metallosphaera sedula* |

4-Hydroxybutyryl-CoA transferase transfers the CoA moiety from 4-hydroxybutyryl-CoA to acetate, in turn, forming 4-hydroxybutyrate and acetyl-CoA. One exemplary 4-hydroxybutyryl-CoA transferase is encoded by the cat2 gene of *Clostridium kluyveri* (Seedorf et al., *Proc. Natl. Acad. Sci. U.S.A.* 105:2128-2133 (2008); Sohling and Gottschalk *J Bacteriol.* 178:871-880 (1996)). The abfT-2 gene from *Porphyromonas gingivalis* was also shown to exhibit 4-hydroxybutyryl-CoA transferase activity when implemented as part of a pathway to produce 4-hydroxybutyate and 1,4-butanediol (Burk, et al., WO/2008/115840 (2008)). An additional candidate enzyme, encoded by abfT-1, from *P. gingivalis* can be inferred by sequence homology. Another 4-hydroxybutyryl-CoA transferase is encoded by the gene product of abfT from *Clostridium aminobutyricum* (Gerhardt et al., *Arch. Microbiol* 174:189-199 (2000)).

| Protein | GenBank ID | Organism |
| --- | --- | --- |
| cat2 | YP_001396397 | *Clostridium kluyveri* |
| abfT-2 | NP_906037 | *Porphyromonas gingivalis* |
| abfT-1 | NP_904965.1 | *Porphyromonas gingivalis* |
| abfT | CAB60036 | *Clostridium aminobutyricum* |

Exemplary phosphate transferring acyltransferases include phosphotransacetylase, encoded by pta, and phosphotransbutyrylase, encoded by ptb. The pta gene from *E. coli* encodes an enzyme that can convert acetyl-CoA into acetyl-phosphate, and vice versa (Suzuki, T. 1969 *Biochim. Biophys. Acta* 191:559-569 (1969)). This enzyme can also utilize propionyl-CoA instead of acetyl-CoA forming propionate in the process (Hesslinger et al., *Mol. Microbiol* 27:477-492 (1998)). Similarly, the ptb gene from *C. acetobutylicum* encodes an enzyme that can convert butyryl-CoA into butyryl-phosphate (Huang et al., *J. Mol. Microbiol Biotechnol* 2:33-38 (2000); (Walter et al., *Gene* 134:107-111 (1993)). This same enzyme was shown to have activity on 4-hydroxybutyryl-CoA when implemented as part of a pathway to produce 1,4-butanediol WO/2008/115840 (2008). Additional ptb genes can be found in butyrate-producing bacterium L2-50 (Ljungdahl and Andreesen, *Methods Enzymol.* 53:360-372 (1978) and *Bacillus megaterium* (Vazquez et al., *Curr. Microbiol* 42:345-349 (2001)).

| Protein | GenBank ID | Organism |
| --- | --- | --- |
| pta | NP_416800.1 | *Escherichia coli* |
| ptb | NP_349676 | *Clostridium acetobutylicum* |
| ptb | AAR19757.1 | butyrate-producing bacterium L2-50 |
| ptb | CAC07932.1 | *Bacillus megaterium* |

Exemplary kinases include the *E. coli* acetate kinase, encoded by ackA (Skarstedt and Silverstein, *J. Biol. Chem.* 251:6775-6783 (1976)), the *C. acetobutylicum* butyrate kinases, encoded by buk1 and buk2 (Huang et al., 2000 *J. Mol. Microbiol Biotechnol* 2:33-38 (2000); Walter et al., *Gene* 134:107-111 (1993)), and the *E. coli* gamma-glutamyl kinase, encoded by proB (Smith et al., *J. Bacteriol.* 157:545-551 (1984)). These enzymes phosphorylate acetate, butyrate, and glutamate, respectively. The ackA gene product from *E. coli* also phosphorylates propionate (Hesslinger et al., *Mol. Microbiol* 27:477-492 (1998)). The gene product of buk1 from *C. acetobutylicum* was shown in Burk et al., WO/2008/115840 (2008) to have activity on 4-hydroxybutyryl-CoA when implemented as part of a pathway to produce 1,4-butanediol.

| Protein | GenBank ID | Organism |
| --- | --- | --- |
| ackA | NP_416799.1 | *Escherichia coli* |
| buk1 | NP_349675 | *Clostridium acetobutylicum* |
| buk2 | Q97II1 | *Clostridium acetobutylicum* |
| proB | NP_414777.1 | *Escherichia coli* |

Alcohol-forming 4-hydroxybutyryl-CoA reductase enzymes catalyze the 2 reduction steps required to form 1,4-butanediol from 4-hydroxybutyryl-CoA. Exemplary 2-step oxidoreductases that convert an acyl-CoA to alcohol include those that transform substrates such as acetyl-CoA to ethanol (e.g., adhE from *E. coli* (Kessler et al., FEBS. Lett. 281:59-63 (1991)) and butyryl-CoA to butanol (e.g. adhE2 from *C. acetobutylicum* (Fontaine et al., *J. Bacteriol.* 184:821-830 (2002)). The adhE2 enzyme from *C. acetobutylicum* was specifically shown in ref. Burk et al., WO/2008/115840 (2008). to produce BDO from 4-hydroxybutyryl-CoA. In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., *J. Gen. Appl. Microbiol.* 18:43-55 (1972); Koo et al., *Biotechnol Lett.* 27:505-510 (2005)).

| Protein | GenBank ID | Organism |
| --- | --- | --- |
| adhE | NP_415757.1 | *Escherichia coli* |
| adhE2 | AAK09379.1 | *Clostridium acetobutylicum* |
| adhE | AAV66076.1 | *Leuconostoc mesenteroides* |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol.* 184:2404-2410 (2000); Strauss and Fuchs, *Eur. J. Biochem.* 215:633-643 (1993)). This enzyme, with a mass of 300 kDa, is highly substrate-specific and shows little sequence similarity to other known oxidoreductases (Hugler et al., *J. Bacteriol.* 184:2404-2410 (2002)). No enzymes in other organisms have been shown to catalyze this specific reaction; however there is bioinformatic evidence that other organisms may have similar pathways (Klatt et al., *Environ. Microbiol.* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity.

| Protein | GenBank ID | Organism |
| --- | --- | --- |
| mcr | AAS20429.1 | *Chloroflexus aurantiacus* |
| Rcas_2929 | YP_001433009.1 | *Roseiflexus castenholzii* |
| NAP1_02720 | ZP_01039179.1 | *Erythrobacter* sp. NAP1 |
| MGP2080_00535 | ZP_01626393.1 | marine gamma proteobacterium HTCC2080 |

An alternative route to BDO from 4-hydroxybutyryl-CoA involves first reducing this compound to 4-hydroxybutanal. Several acyl-CoA dehydrogenases are capable of reducing an acyl-CoA to its corresponding aldehyde. Exemplary genes that encode such enzymes include the *Acinetobacter calcoaceticus* acyl encoding a fatty acyl-CoA reductase (Reiser and Somerville, *Journal of Bacteriology* 179:2969-2975 (1997)), the *Acinetobacter* sp. M-1 fatty acyl-CoA reductase (Ishige et al., *Appl. Environ. Microbiol.* 68:1192-1195 (2002)), and a CoA- and NADP-dependent succinate semialdehyde dehydrogenase encoded by the sucD gene in *Clostridium kluyveri* (Sohling and Gottschalk, *J Bacteriol.* 178:871-880 (1996)). SucD of *P. gingivalis* is another succinate semialdehyde dehydrogenase (Takahashi et al., *J. Bacteriol.* 182:4704-4710 (2000)). These succinate semialdehyde dehydrogenases were specifically shown in ref Burk et al., WO/2008/115840 (2008) to convert 4-hydroxybutyryl-CoA to 4-hydroxybutanal as part of a pathway to produce 1,4-butanediol. The enzyme acylating acetaldehyde dehydrogenase in *Pseudomonas* sp, encoded by bphG, is yet another capable enzyme as it has been demonstrated to oxidize and acylate acetaldehyde, propionaldehyde, butyraldehyde, isobutyraldehyde and formaldehyde (Powlowski et al., *J Bacteriol*. 175:377-385 (1993)).

| Protein | GenBank ID | Organism |
| --- | --- | --- |
| acr1 | YP_047869.1 | *Acinetobacter calcoaceticus* |
| acr1 | AAC45217 | *Acinetobacter baylyi* |
| acr1 | BAB85476.1 | *Acinetobacter* sp. Strain M-1 |
| sucD | P38947.1 | *Clostridium kluyveri* |
| sucD | NP_904963.1 | *Porphyromonas gingivalis* |
| bphG | BAA03892.1 | *Pseudomonas* sp |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., *Science* 318:1782-1786 (2007); Thauer, R. K. *Science* 318:1732-1733 (2007)). The enzyme utilizes NADPH as a cofactor and has been characterized in *Metallosphaera* and *Sulfolobus* spp (Alber et al., *J. Bacteriol* 1.188:8551-8559 (2006); Hugler et al., *J. Bacteriol*. 184:2404-2410 (2002)). The enzyme is encoded by Msed_0709 in *Metallosphaera sedula* (Alber et al., *J. Bacteriol*. 188:8551-8559 (2006); Berg et al., *Science* 318:1782-1786 (2007)). A gene encoding a malonyl-CoA reductase from *Sulfolobus tokodaii* was cloned and heterologously expressed in *E. coli* (Alber et al., *J. Bacteriol*. 188:8551-8559 (2006)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*.

| Protein | GenBank ID | Organism |
| --- | --- | --- |
| Msed_0709 | YP_001190808.1 | *Metallosphaera sedula* |
| mcr | NP_378167.1 | *Sulfolobus tokodaii* |
| asd-2 | NP_343563.1 | *Sulfolobus solfataricus* |
| Saci_2370 | YP_256941.1 | *Sulfolobus acidocaldarius* |

Enzymes exhibiting 1,4-butanediol dehydrogenase activity are capable of forming 1,4-butanediol from 4-hydroxybutanal. Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., Appl. Environ. Microbiol. 66:5231-5235 (2000)), ADH2 from *Saccharomyces cerevisiae* Atsumi et al. *Nature* 451:86-89 (2008)), yqhD from *E. coli* which has preference for molecules longer than C(3) (Sulzenbacher et al., *Journal of Molecular Biology* 342:489-502 (2004)), and bdh I and bdh II from *C. acetobutylicum* which converts butyryaldehyde into butanol (Walter et al., *Journal of Bacteriology* 174:7149-7158 (1992)).

| Protein | GenBank ID | Organism |
| --- | --- | --- |
| alrA | BAB12273.1 | *Acinetobacter* sp. Strain M-1 |
| ADH2 | NP_014032.1 | *Saccharymyces cerevisiae* |
| yqhD | NP_417484.1 | *Escherichia coli* |
| bdh I | NP_349892.1 | *Clostridium acetobutylicum* |
| bdh II | NP_349891.1 | *Clostridium acetobutylicum* |

Enzymes exhibiting 4-hydroxybutyrate dehydrogenase activity (EC 1.1.1.61) also fall into this category. Such enzymes have been characterized in *Ralstonia eutropha* (Bravo et al., J. Forensic Sci. 49:379-387 (2004)), *Clostridium kluyveri* (Wolff and Kenealy, Protein Expr. Purif. 6:206-212 (1995)) and *Arabidopsis thaliana* (Breitkreuz et al., *J. Biol. Chem.* 278:41552-41556 (2003)).

| Protein | GenBank ID | Organism |
| --- | --- | --- |
| 4hbd | YP_726053.1 | *Ralstonia eutropha* H16 |
| 4hbd | L21902.1 | *Clostridium kluyveri* DSM 555 |
| 4hbd | Q94B07 | *Arabidopsis thaliana* |

The nonnative genes needed for 4-hydroxybutyrate synthesis are cloned on expression plasmids as described previously. The host strain also expresses methanol methyltransferase activity, CODH/ACS activity, and possibly PFOR and hydrogenase activities. At this point, these (CODH/ACS, etc.) genes are integrated into the genome and expressed from promoters that can be used constitutively or with inducers (i.e., PA1-lacO1 is inducible in cells containing lacI or is otherwise constitutive). Once expression and yields of 4-hydroxybutyrate are optimized, the base strain is further modified by integration of a single copy of these genes at a neutral locus. Given the relatively limited number of genes (at minimum, 5, and at most, 6), an artificial operon encoding the required genes can be constructed. This operon is introduced using integrative plasmids and is coupled to counter-selection methods such as that allowed by the *Bacillus* sacB gene (Link et al., *J Bacteriol*. 179:6228-6237 (1997)). In this way, markerless and scar less insertions at any location in the *E. coli* chromosome can be generated. Optimization involves altering gene order as well as ribosomal binding sites and promoters.

The nonnative genes needed for 1,4-butanediol synthesis are cloned on expression plasmids as described previously. The host strain also expresses methanol methyltransferase activity, CODH/ACS activity, and possibly PFOR and hydrogenase activities. At this point, these (CODH/ACS, etc.) genes are integrated into the genome and expressed from promoters that can be used constitutively or with inducers (i.e., PA1-lacO1 is inducible in cells containing lacI or is otherwise constitutive). Once expression and yields of 1,4-butanediol are optimized, the base strain is further modified by integration of a single copy of these genes at a neutral locus. Given the relatively limited number of genes (at minimum, 5, and at most, 6), an artificial operon encoding the required genes can be constructed. This operon is introduced using integrative plasmids and is coupled to counter-selection methods such as that allowed by the *Bacillus* sacB gene (Link et al., *J Bacteriol*. 179:6228-6237 (1997)). In this way, markerless and scar less insertions at any location in the *E. coli* chromosome can be generated. Optimization involves altering gene order as well as ribosomal binding sites and promoters.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. An isolated microorganism, comprising a genetic modification, wherein said genetic modification comprises transformation of said microorganism with exogenous bacterial nucleic acid molecules encoding the proteins cobalamide corrinoid/iron-sulfur protein, methyltransferase, carbon monoxide dehydrogenase, acetyl-CoA synthase, acetyl-CoA synthase disulfide reductase and hydrogenase, whereby expression of said proteins increases the efficiency of producing acetyl-CoA from CO2, CO or H2, or a combination thereof.

2. The microorganism of claim 1, wherein said microorganism converts $CO_2$ to acetyl-CoA.

3. The microorganism of claim 1, wherein said microorganism converts CO to acetyl-CoA.

4. The microorganism of claim 1, wherein said microorganism converts $CO_2$ and $H_2$ to acetyl-CoA.

5. The microorganism of claim 1, wherein said microorganism converts CO and $H_2$ to acetyl-CoA.

6. The microorganism of claim 1, wherein said microorganism converts $CO_2$, CO and $H_2$ to acetyl-CoA.

7. The microorganism of claim 1, wherein said microorganism is in a substantially anaerobic culture medium.

8. A method for producing acetyl-CoA, comprising culturing the microorganism of claim 1 under conditions and for a sufficient period of time to produce acetyl-CoA.

9. The method of claim 8, wherein said microorganism is in a substantially anaerobic culture medium.

10. The method of claim 8, wherein said microorganism is cultured in the presence of $CO_2$, CO, or $H_2$, or a combination thereof.

11. The method of claim 8, wherein said microorganism converts $CO_2$ to acetyl-CoA.

12. The method of claim 11, wherein said microorganism is cultured in the presence of $CO_2$.

13. The method of claim 8, wherein said microorganism converts CO to acetyl-CoA.

14. The method of claim 13, wherein said microorganism is cultured in the presence of CO.

15. The method of claim 8, wherein said microorganism converts $CO_2$ and $H_2$ to acetyl-CoA.

16. The method of claim 15, wherein said microorganism is cultured in the presence of $CO_2$ and $H_2$.

17. The method of claim 8, wherein said microorganism converts CO and $H_2$ to acetyl-CoA.

18. The method of claim 17, wherein said microorganism is cultured in the presence of CO and $H_2$.

19. The method of claim 8, wherein said microorganism converts $CO_2$, CO and $H_2$ to acetyl-CoA.

20. The method of claim 19, wherein said microorganism is cultured in the presence of $CO_2$, CO and $H_2$.

* * * * *